United States Patent
Hawtin et al.

(10) Patent No.: US 9,459,246 B2
(45) Date of Patent: Oct. 4, 2016

(54) INDUCED INTERCELLULAR COMMUNICATION

(71) Applicant: Nodality, Inc., South San Francisco, CA (US)

(72) Inventors: Rachael Hawtin, San Carlos, CA (US); Drew Hotson, Menlo Park, CA (US); Alessandra Cesano, Redwood City, CA (US); Garry P. Nolan, San Francisco, CA (US)

(73) Assignee: NODALITY, INC., South San Francisco, CA (US)

( * ) Notice: Subject to any disclaimer, the term of this patent is extended or adjusted under 35 U.S.C. 154(b) by 13 days.

(21) Appl. No.: 14/073,692

(22) Filed: Nov. 6, 2013

(65) Prior Publication Data

US 2014/0134650 A1     May 15, 2014

Related U.S. Application Data

(63) Continuation-in-part of application No. 14/072,623, filed on Nov. 5, 2013, which is a continuation of application No. 13/821,539, filed as application No. PCT/US2011/001565 on Sep. 8, 2011, now
(Continued)

(51) Int. Cl.
*C12Q 1/68* (2006.01)
*G01N 33/50* (2006.01)
(Continued)

(52) U.S. Cl.
CPC ....... *G01N 33/5011* (2013.01); *G01N 33/5032* (2013.01); *G01N 33/5047* (2013.01);
(Continued)

(58) Field of Classification Search
CPC ............... G01N 33/5011; G01N 33/5032; G01N 33/5047; G01N 33/564; G01N 33/6866; G01N 33/6869
See application file for complete search history.

(56) References Cited

U.S. PATENT DOCUMENTS

| 4,469,863 A | 9/1984 | To's et al. |
| 4,568,649 A | 2/1986 | Bertoglio-Matte |

(Continued)

FOREIGN PATENT DOCUMENTS

| WO | WO 99/54494 A2 | 10/1999 |
| WO | WO 03/067210 A2 | 8/2003 |

(Continued)

OTHER PUBLICATIONS

Karakauer, Coordinate Suppression of Superantigen-Induced Cytokine Production and T-Cell Proliferation by a Small Nonpeptidic Inhibitor of Class II Major Histocompatibility Complex and CD4 Interaction, Antimicrobial Agents and Chemotherapy, Apr. 2000, p. 1067-1069.*

(Continued)

*Primary Examiner* — Reza Ghafoorian
(74) *Attorney, Agent, or Firm* — Wilson Sonsini Goodrich & Rosati

(57) ABSTRACT

The present invention provides an approach for the determination of the activation state of discrete cell populations and/or the state of one or more cellular networks in an individual, when modulated with a modulator that acts on one cell population to communicate with other cell populations in the network. The status of discrete cell populations and/or the state of one or more cellular networks can be correlated with the diagnosis, prognosis, choice or modification of treatment, and/or monitoring of a condition, and with screening of agents.

38 Claims, 30 Drawing Sheets

Related U.S. Application Data abandoned, said application No. 14/072,623 is a continuation-in-part of application No. 12/877,998, filed on Sep. 8, 2010.

(60) Provisional application No. 61/240,613, filed on Sep. 8, 2009, provisional application No. 61/381,067, filed on Sep. 8, 2010, provisional application No. 61/440,523, filed on Feb. 8, 2011, provisional application No. 61/469,812, filed on Mar. 31, 2011, provisional application No. 61/499,127, filed on Jun. 20, 2011, provisional application No. 61/722,976, filed on Nov. 6, 2012.

(51) Int. Cl.

| | | |
|---|---|---|
| *G01N 33/564* | (2006.01) | |
| *G01N 33/68* | (2006.01) | |
| *C12Q 1/02* | (2006.01) | |
| *C40B 30/06* | (2006.01) | |
| *G01N 27/26* | (2006.01) | |
| *G01N 33/53* | (2006.01) | |
| *G06F 19/00* | (2011.01) | |
| *G06F 17/10* | (2006.01) | |
| *G06F 19/12* | (2011.01) | |
| *G06F 19/24* | (2011.01) | |

(52) U.S. Cl.
CPC ........ *G01N33/564* (2013.01); *G01N 33/6866* (2013.01); *G01N 33/6869* (2013.01); *G01N 2333/525* (2013.01); *G06F 19/12* (2013.01); *G06F 19/24* (2013.01)

(56) References Cited

U.S. PATENT DOCUMENTS

| | | |
|---|---|---|
| 5,216,141 A | 6/1993 | Benner |
| 5,386,023 A | 1/1995 | Sanghvi et al. |
| 5,602,240 A | 2/1997 | De Mesmaeker et al. |
| 5,637,684 A | 6/1997 | Cook et al. |
| 5,644,048 A | 7/1997 | Yau |
| 5,744,934 A | 4/1998 | Wu |
| 5,968,738 A | 10/1999 | Anderson et al. |
| 6,190,870 B1 | 2/2001 | Schmitz et al. |
| 6,495,333 B1 | 12/2002 | Willmann et al. |
| 6,733,743 B2 | 5/2004 | Jordan |
| 7,018,850 B2 | 3/2006 | Raymond et al. |
| 7,082,426 B2 | 7/2006 | Musgrove et al. |
| 7,316,897 B2 | 1/2008 | Bisconte de Saint Julien et al. |
| 7,381,535 B2 | 6/2008 | Perez et al. |
| 7,393,656 B2 | 7/2008 | Perez et al. |
| 7,563,584 B2 | 7/2009 | Perez et al. |
| 7,695,924 B2 | 4/2010 | Perez et al. |
| 7,695,926 B2 | 4/2010 | Perez et al. |
| 7,714,933 B2 | 5/2010 | Park |
| 7,939,278 B2 | 5/2011 | Perez et al. |
| 8,148,094 B2 | 4/2012 | Perez et al. |
| 8,187,885 B2 | 5/2012 | Purvis, Jr. |
| 8,198,037 B2 | 6/2012 | Perez et al. |
| 8,206,939 B2 | 6/2012 | Perez et al. |
| 8,214,157 B2 | 7/2012 | Moser et al. |
| 8,227,202 B2 | 7/2012 | Fantl et al. |
| 8,242,248 B2 | 8/2012 | Soper et al. |
| 8,273,544 B2 | 9/2012 | Fantl et al. |
| 8,309,306 B2 | 11/2012 | Nolan et al. |
| 8,309,316 B2 | 11/2012 | Perez et al. |
| 8,394,599 B2 | 3/2013 | Perez et al. |
| 8,399,206 B2 | 3/2013 | Fantl et al. |
| 8,778,620 B2 | 7/2014 | Fantl et al. |
| 9,034,257 B2 | 5/2015 | Covey et al. |
| 2001/0006787 A1 | 7/2001 | Payan |
| 2003/0100995 A1 | 5/2003 | Loraine et al. |
| 2005/0009078 A1 | 1/2005 | Craford et al. |
| 2006/0046272 A1 | 3/2006 | Chow et al. |
| 2006/0134599 A1 | 6/2006 | Toner et al. |
| 2006/0292618 A1 | 12/2006 | Mellor et al. |
| 2007/0009923 A1 | 1/2007 | Nolan et al. |
| 2007/0196869 A1 | 8/2007 | Perez et al. |
| 2008/0254489 A1 | 10/2008 | Perez et al. |
| 2009/0068681 A1 | 3/2009 | Perez et al. |
| 2009/0081699 A1 | 3/2009 | Perez et al. |
| 2009/0098594 A1 | 4/2009 | Fantl et al. |
| 2009/0269773 A1 | 10/2009 | Fantl et al. |
| 2009/0269800 A1 | 10/2009 | Covey et al. |
| 2009/0291458 A1 | 11/2009 | Cohen et al. |
| 2010/0014741 A1 | 1/2010 | Banville et al. |
| 2010/0030719 A1 | 2/2010 | Covey et al. |
| 2010/0042351 A1 | 2/2010 | Covey et al. |
| 2010/0086951 A1 | 4/2010 | Hedley et al. |
| 2010/0099109 A1 | 4/2010 | Fantl et al. |
| 2010/0105074 A1 | 4/2010 | Covey et al. |
| 2010/0184092 A1 | 7/2010 | Perez et al. |
| 2010/0204973 A1 | 8/2010 | Parkinson et al. |
| 2010/0209929 A1 | 8/2010 | Fantl et al. |
| 2010/0215644 A1 | 8/2010 | Fantl et al. |
| 2010/0233733 A1 | 9/2010 | Fantl et al. |
| 2010/0297676 A1 | 11/2010 | Fantl et al. |
| 2011/0059861 A1 | 3/2011 | Nolan et al. |
| 2011/0207145 A1 | 8/2011 | Perez et al. |
| 2011/0207146 A1 | 8/2011 | Perez et al. |
| 2011/0250614 A1 | 10/2011 | Perez et al. |
| 2011/0262468 A1 | 10/2011 | Fantl et al. |
| 2011/0269634 A1 | 11/2011 | Perez et al. |
| 2012/0070849 A1 | 3/2012 | Perez et al. |
| 2012/0157340 A1 | 6/2012 | Cesano et al. |
| 2012/0215487 A1 | 8/2012 | Banville et al. |
| 2012/0276558 A1 | 11/2012 | Soper et al. |
| 2012/0309026 A1 | 12/2012 | Perez et al. |
| 2012/0309029 A1 | 12/2012 | Fantl et al. |
| 2013/0024177 A1 | 1/2013 | Nolan |
| 2013/0034862 A1 | 2/2013 | Fantl et al. |
| 2013/0035253 A1 | 2/2013 | Rosen et al. |
| 2013/0071860 A1 | 3/2013 | Hale et al. |
| 2013/0078621 A1 | 3/2013 | Nolan et al. |
| 2013/0096948 A1 | 4/2013 | Parkinson et al. |
| 2013/0109050 A1 | 5/2013 | Purvis, Jr. |
| 2013/0122524 A1 | 5/2013 | Fantl et al. |
| 2013/0123131 A1 | 5/2013 | Purvis et al. |
| 2013/0124522 A1 | 5/2013 | Moser et al. |
| 2013/0129681 A1 | 5/2013 | Covey et al. |
| 2013/0130279 A1 | 5/2013 | Fantl et al. |
| 2013/0177970 A1 | 7/2013 | Perez et al. |
| 2013/0218474 A1 | 8/2013 | Longo |
| 2014/0011222 A1 | 1/2014 | Fantl |
| 2014/0017678 A1 | 1/2014 | Cesano et al. |
| 2014/0031308 A1 | 1/2014 | Diane et al. |
| 2014/0040265 A1 | 2/2014 | Moser et al. |
| 2014/0057865 A1 | 2/2014 | Fantl et al. |
| 2014/0065633 A1 | 3/2014 | Fantl et al. |
| 2014/0093903 A1 | 4/2014 | Ptacek et al. |
| 2014/0120122 A1 | 5/2014 | Fantl et al. |
| 2014/0127716 A1 | 5/2014 | Longo |
| 2014/0134648 A1 | 5/2014 | Fantl et al. |
| 2014/0147857 A1 | 5/2014 | Fantl et al. |
| 2014/0170698 A1 | 6/2014 | Purvis, Jr. |
| 2014/0199273 A1 | 7/2014 | Cesano et al. |
| 2014/0255393 A1 | 9/2014 | Ptacek et al. |
| 2015/0017119 A1 | 1/2015 | Fantl et al. |
| 2015/0110736 A1 | 4/2015 | Fantl et al. |
| 2015/0118247 A1 | 4/2015 | Hotson et al. |
| 2015/0119288 A1 | 4/2015 | Soper et al. |
| 2015/0241427 A1 | 8/2015 | Fantl et al. |
| 2015/0241442 A1 | 8/2015 | Nolan et al. |
| 2015/0276745 A1 | 10/2015 | Fantl et al. |

FOREIGN PATENT DOCUMENTS

| | | |
|---|---|---|
| WO | WO 03/067210 A3 | 12/2003 |
| WO | WO 2006/012507 A2 | 2/2006 |
| WO | WO 2006/079092 A2 | 7/2006 |
| WO | WO 2007/117423 A2 | 10/2007 |
| WO | WO 2008/088857 A2 | 7/2008 |

(56) References Cited

FOREIGN PATENT DOCUMENTS

| WO | WO 2009/025847 A2 | 2/2009 | |
|---|---|---|---|
| WO | PCT/US2009/042187 | * 11/2009 | ............ G01N 33/50 |
| WO | WO 2009/134944 A2 | 11/2009 | |
| WO | WO 2010/006291 A1 | 1/2010 | |
| WO | WO 2010/006303 A2 | 1/2010 | |
| WO | WO 2010/028277 A1 | 3/2010 | |
| WO | WO 2010/045651 A1 | 4/2010 | |
| WO | WO 2010/135608 A1 | 11/2010 | |
| WO | WO 2011/031803 A1 | 3/2011 | |
| WO | WO 2011/106558 A1 | 9/2011 | |
| WO | WO 2011/119868 A2 | 9/2011 | |
| WO | WO 2011/156654 A2 | 12/2011 | |
| WO | WO 2012/024546 A2 | 2/2012 | |
| WO | WO 2012/033537 A1 | 3/2012 | |
| WO | WO 2012/083274 A2 | 6/2012 | |
| WO | WO 2012/109484 A1 | 8/2012 | |
| WO | PCT/US2013/045273 | 6/2013 | |
| WO | WO 2013/112948 A1 | 8/2013 | |
| WO | PCT/US2013/068815 | 11/2013 | |
| WO | PCT/US2013/071354 | 11/2013 | |
| WO | WO 2013/188469 A2 | 12/2013 | |
| WO | WO 2014/074646 A2 | 5/2014 | |
| WO | WO 2014/081987 A1 | 5/2014 | |
| WO | WO 2014/134570 A1 | 9/2014 | |

OTHER PUBLICATIONS

U.S. Appl. No. 13/801,420, filed Mar. 13, 2013, Cesano et al.
U.S. Appl. No. 13/821,539, filed Mar. 7, 2013, Longo.
U.S. Appl. No. 13/900,170, filed May 22, 2013, Fantl.
U.S. Appl. No. 13/913,029, filed Jun. 7, 2013, Fantl et al.
U.S. Appl. No. 13/958,285, filed Aug. 2, 2013, Fantl et al.
U.S. Appl. No. 14/011,715, filed Aug. 27, 2013, Ptacek et al.
U.S. Appl. No. 14/013,567, filed Aug. 29, 2013, Purvis, Jr.
U.S. Appl. No. 14/014,110, filed Aug. 29, 2013, Moser et al.
U.S. Appl. No. 14/036,216, filed Sep. 25, 2013, Fantl et al.
U.S. Appl. No. 14/045,548, filed Oct. 3, 2013, Fantl et al.
U.S. Appl. No. 14/049,624, filed Oct. 9, 2013, Fantl et al.
U.S. Appl. No. 14/072,623, filed Nov. 5, 2013, Longo.
U.S. Appl. No. 14/086,922, filed Nov. 21, 2013, Cesano et al.
Amico, et al. Differential response of human acute myeloid leukemia cells to gemtuzumab ozogamicin in vitro: role of Chk1 and Chik2 phosphorylation and caspase 3. Blood. Jun. 1, 2003;101(11):4589-97.
Baker, et al. Superantigens: structure-function relationships. Int J Med Microbiol. Apr. 2004;293(7-8):529-37.
Balaban, et al. Staphylococcal enterotoxins. Int J Food Microbiol. Oct. 1, 2000;61(1):1-10.
Barn, et al. Design and synthesis of a maximally diverse and druglike screening library using REM resin methodology. J Comb Chem. 2001;3(6):534-41.
Beaucage, et al. The functionalization of oligonucleotides via phosphoramidite derivative. Tetrahedron. 1993;49(10):1925-63.
Benekli, et al. Signal transducer and activator of transcription proteins in leukemias. Blood. Apr. 15, 2003;101(8):2940-54.
Bienz. APC: the plot thickens. Curr Opin Genet Dev. 1999; 9(5): 595-603.
Birkenkamp, et al. Regulation of constitutive STAT5 phosphorylation in acute myeloid leukemia blasts. Leukemia. 2001; 15(12):1923-31.
Blume-Jensen, et al. Oncogenic kinase signalling. Nature. May 17, 2001;411(6835):355-65.
Boer, et al. Prostaglandin-E2 enhances EPO-mediated STAT5 transcriptional activity by serine phosphorylation of CREB. Blood. 2002;100(2):467-73.
Brill, et al. Synthesis of oligodeoxynucleoside phosphorodithioates via thioamidites. J. Am. Chem. Soc. 1989;111:2321-2322.
Burks, et al. IRS proteins and beta-cell function. Diabetes. 2001. S140-S145, Suppl 1:S140-5.

Carlsson, et al. Screening for genetic mutations. Nature. 1996;380(6571):207.
Chattopadhyay, et al. Quantum dot semiconductor nanocrystals for immunophenotyping by polychromatic flow cytometry. Nat Med. 2006;12(8):972-7.
Chow, et al. Constitutive phosphorylation of the S6 ribosomal protein via mTOR and ERK signaling in the peripheral blasts of acute leukemia patients. Experimental hematology. 2006; 34(9):1182-1190.
Chow, et al. Measurement of MAP kinase activation by flow cytometry using phospho-specific antibodies to MEK and ERK: potential for pharmacodynamic monitoring of signal transduction inhibitors. Cytometry. Apr. 15, 2001;46(2):72-8.
Cochran, et al. A minimal peptide scaffold for beta-turn display: optimizing a strand position in disulfide-cyclized beta-hairpins. J Am Chem Soc. 2001;123(4):625-32.
Crans-Vargas, et al. CREB as a prognostic marker in acute leukemia. Abstract. Blood. 2001; 98(11), part 1, p. 316a.
D'Ambrosio, et al. Chemokine receptors in inflammation: an overview. J Immunol Methods. 2003. 273(1-2):3-13.
Dempcy, et al. Synthesis of a thymidyl pentamer of deoxyribonucleic guanidine and binding studies with DNA homopolynucleotides. Proc Natl Acad Sci USA. 1995;92(13):6097-101.
Denis, et al. Detection of disseminated tumor cells in peripheral blood of colorectal cancer patients. Int J Cancer. Oct. 21, 1997;74(5):540-4.
Egholm, et al. Peptide nucleic acids (PNA) oligonucleotide analogues with an achiral peptide backbone. J. Am. Chem. Soc. 1992;114:1895-1897.
Egholm, et al. PNA hybridizes to complementary oligonucleotides obeying the Watson-Crick hydrogen-bonding rules. Nature. 1993;365(6446):566-8.
Emmert-Buck, et al. Laser capture microdissection. Science. Nov. 8, 1996;274(5289):998-1001.
European search report and search opinion dated Feb. 22, 2011 for Application No. 10180167.8.
Evan, et al. Isolation of monoclonal antibodies specific for human c-myc proto-oncogene product. Mol Cell Biol. Dec. 1985;5(12):3610-6.
Field, et al. Purification of a RAS-responsive adenylyl cyclase complex from Saccharomyces cerevisiae by use of an epitope addition method. Mol Cell Biol. May 1988;8(5):2159-65.
Goldman, et al. Avidin: a natural bridge for quantum dot-antibody conjugates. J Am Chem Soc. 2002;124(22):6378-82.
Golub, et al. Molecular classification of cancer: class discovery and class prediction by gene expression monitoring. Science. Oct. 15, 1999;286(5439):531-7.
Gualillo, et al. Leptin promotes the tyrosine phosphorylation of SHC proteins and SHC association with GRB2. Mol Cell Endocrinol. 2002;190(1-2):83-9.
Gururaja, et al. A novel artificial loop scaffold for the noncovalent constraint of peptides. Chem. Biol. 2000;7:515-27.
Hanahan, et al. The Hallmarks of Cancer. Cell. 2000;100(1):57-70.
Hopp, et al. A short polypeptide marker sequence useful for recombinant protein identification and purification. Nature Biotechnology. 1988; 6:1204-1210.
Houimel, et al. Functional inhibition of CCR3-dependent responses by peptides derived from phage libraries. Eur. J. Immunol 2001;31:3535-45.
Houimel, et al. Selection of peptides and synthesis of pentameric peptabody molecules reacting specifically with ErbB-2 receptor. 2001;92(5):748-55.
Hunter. Signaling—2000 and beyond. Cell. 2000. 100(1):113-27.
Irish, et al. Single cell profiling of potentiated phospho-protein networks in cancer cells. Cell. Jul. 23, 2004;118(2):217-28.
Jenkins, et al. The biosynthesis of carbocyclic nucleosides. Chem. Soc. Rev. 1995;169-176.
Ju, et al. Imprinted polymers as tools for the recovery of secondary metabolites produced by fermentation. Biotechnol Bioeng. 1999;64(2):232-9.
Kindler, et al. Identification of a novel activating mutation (Y842C) within the activation loop of FLT3 in a patient with AML.

(56) References Cited

OTHER PUBLICATIONS

Abstract 4681. Blood. 2003; 102(11):239B-240B and 45th Annual Meeting of the American Society of Hematology. San Diego, CA, USA. Dec. 6-9, 2003.
Kornblau, et al. Dynamic single-cell network profiles in acute myelogenous leukemia are associated with patient response to standard induction therapy. Clin Cancer Res. Jul. 15, 2010;16(14):3721-33. (abstract).
Krutzik, et al. High-content single-cell drug screening with phosphospecific flow cytometry. Natural Chemical Biology. 2008. 4(2):132-42.
Krutzik, et al. Intracellular phospho-protein staining techniques for flow cytometry: monitoring single cell signaling events. Cytometry A. 2003; 55(2): 61-70.
Krutzik, et al. Analysis of protein phosphorylation and cellular signaling events by flow cytometry: techniques and clinical applications. Clinical Immunology. 2004; 110: 206-21.
Krutzik, et al. Coordinate analysis of murine immune cell surface markers and intracellular phosphoproteins by flow cytometry. J Immunol. 2005. 175(4):2357-65.
Krutzik. Characterization of the murine immunological signaling network with phosphospecific flow cytometry. J Immunol. 2005. 175(4): 2366-73.
Kumar, et al. 2-methoxyestradiol blocks cell-cycle progression at G(2)/M phase and inhibits growth of human prostate cancer cells. Mol Carcinog. Jul. 2001;31(3):111-24.
Letsinger, et al. Cationic oligonucletides. J. Am Chem. Soc. 1988; 110:4470-4471.
Letsinger, et al. Effects of pendant groups at phosphorus on binding properties of d-ApA analogues. Nucleic Acids Res. 1986;14(8):3487-99.
Letsinger, et al. Phosphoramidate analogs of oligonucleotides. J Org Chem. 1970;35(11):3800-3.
Lutz-Freyermuth, et al. Quantitative determination that one of two potential RNA-binding domains of the A protein component of the U1 small nuclear ribonucleoprotein complex binds with high affinity to stem-loop II of U1 RNA. Proc Natl Acad Sci U S A. Aug. 1990;87(16):6393-7.
Mack, et al. Detection of caspase-activation in intact lymphoid cells using standard caspase substrates and inhibitors. J Immunol Methods. Jul. 31, 2000;241(1-2):19-31.
Mag, et al. Synthesis and selective cleavage of an oligodeoxynucleotide containing a bridged internucleotide 5'-phosphorothioate linkage. Nucleic Acids Res. 1991;19(7):1437-41.
Malhotra, et al. Molecular biology of protein kinase C signaling in cardiac myocytes. Mol Cell Biochem. 2001. 225(1-):97-107.
Martin, et al. GAP domains responsible for ras p21-dependent inhibition of muscarinic atrial K+ channel currents. Science. Jan. 10, 1992;255(5041):192-4.
Marvin et al. Normal bone marrow signal transduction profiles: a requisite for enhanced detection of signaling dysregulations in AML. Blood. Jan. 13, 2011. doi:10.1182/blood-2010-10-316026 [Epub ahead of print].
Meier, et al. Peptide nuclieic acids (PNAs)—Unusual properties of nonionic oligonucleotide analogues. Chem. Int. Ed. Engl. 1992;31:1008-1010.
Menard, et al. Biologic and therapeutic role of HER2 in cancer. Oncogene. 2003. 22(42): 6570-8.
Monroe. Ligand-independent tonic signaling in B-cell receptor function. Current opinion in Immunology. 2004; 16:288-295.
Nagrath, et al. Isolation of rare circulating tumour cells in cancer patients by microchip technology. Nature. Dec. 20, 2007;450(7173):1235-9.
Paborsky, et al. Mammalian cell transient expression of tissue factor for the production of antigen. Protein Eng. May 1990;3(6):547-53.
Pathak, et al. Hydroxylated quantum dots as luminescent probes for in situ hybridization. J Am Chem Soc. 2001;123(17):4103-4.
Pauwels, et al. Biological activity of new 2-5A analogues. Chemica Scripta. 1986;26:141-9.

Perez, et al. LFA-1 signaling through p44/42 is coupled to perforin degranulation in CD56+CD8+ natural killer cells. Blood. Aug. 15, 2004;104(4):1083-93.
Perez, et al. Simultaneous measurement of multiple active kinase states using polychromatic flow cytometry. Nat Biotechnol. 2002; 20: 155-62.
Rawls, R. Optimistic about antisense. Promising clinical results and chemical strategies for further improvements delight antisense drug researchers. C & E News. Jun. 2, 1997; 35-59.
Remacle, et al. Architecture with designer atoms: simple theoretical considerations. Proc Natl Acad Sci U S A. Jan. 18, 2000;97(2):553-8.
Rosen, et al. Functional characterization of FLT3 receptor signaling deregulation in acute myeloid leukemia by single cell network profiling (SCNP). PLoS One. Oct. 27, 2010;5(10):e13543.
Sanghvi, et al. ed. Chapters 2 and 3, ASC Symposium Series 580—Carbohydrates Modifications in Antisense Research. American Chemical Society. Washington, DC. 1994.
Sanghvi, et al. ed. Chapters 6 and 7, ASC Symposium Series 580—Carbohydrates Modifications in Antisense Research. American Chemical Society. Washington, DC. 1994.
Sanz, et al. Single-chain antibody-based gene therapy inhibition of tumor growth by in situ production of phage-derived human antibody fragments blocking functionally active sites of cell-associated matrices. Gene Therapy. 2002;9(15):1049-53.
Sawai, et al. Synthesis and properties of oligoadenylic acids containing 2'-5' phosphoramide linkage. Chem. Lett. 1984; 805-808.
Schaefer, et al. IGF-I and Prostate Cancer. Science. 1998; 282:199a.
Schulz. Single-cell phospho-protein analysis by flow cytometry. Current Protocols in Immunology. 2007;78:8.17.1-20.
Shankar, et al. CREB is amplified in AML blasts and is associated with an increased risk of relapse and decreased event-free survival. Abstract. Blood. 2004; 104(11), Part 1, p. 166A.
Shankar, et al. Role of cyclic AMP response element binding protein in human leukemias. Cancer. Nov. 1, 2005;104(9):1819-24.
Shankar, et al. The role of CREB as a proto-oncogene in hematopoiesis and in acute myeloid leukemia. Cancer Cell. Apr. 2005;7(4):351-62.
Shevach. Mechanisms of foxp3+ T regulatory cell-mediated suppression. Immunity. May 2009;30(5):636-45. doi: 10.1016/j.immuni.2009.04.010.
Singh. A rapid method for the preparation of single-cell suspensions from solid tissues. Cytometry. Mar. 1, 1998;31(3):229-32.
Skinner, et al. Use of the Glu-Glu-Phe C-terminal Epitope for Rapid Purification of the Catalytic Domain of Normal and Mutant ras GTPase-activating Proteins. J. Biol. Chem. 1991; 266:15163-15166.
Soini, et al. Lanthanide chelates as new fluorochrome labels for cytochemistry. J Histochem Cytochem. Nov. 1988;36(11):1449-51.
Solanki, et al. Superantigens: a brief review with special emphasis on dermatologic diseases. Dermatol Online J. Feb. 28, 2008;14(2):3.
Spiekermann, et al. Overexpression and constitutive activation of FLT3 induces STAT5 activation in primary acute myeloid leukemia blast cells. Clinical Cancer Research. Jun. 2003; 9:2140-2150.
Sprinzel, et al. Enzymatic incorporation of ATP and CTP analogues into the 3' end of tRNA. Eur J Biochem. 1977;81(3):579-89.
Stelzer, et al. Use of Multiparameter Flow Cytometry and Immunophenotyping for the Diagnosis and Classfication of Acute Myeloid Leukemia. In Immunophenotyping. New York, NY: Wiley-Liss, 2000.
Sun, et al. A microfluidic platform for systems pathology: multiparameter single-cell signaling measurements of clinical brain tumor specimens. Cancer Res. Aug. 1, 2010;70(15):6128-38. doi: 10.1158/0008-5472.CAN-10-0076. Epub Jul. 14, 2010.
Tanner, et al. Multiplex bio-assay with inductively coupled plasma mass spectrometry: Towards a massively multivariate single-cell technology. Spectrochimia Acta Part B. 2007; 62(3):188-95.
Thomas, et al. Spontaneous activation and signaling by overexpressed epidermal growth factor receptors in glioblastoma cells. Int J Cancer. 2003; 104(1): 19-27.

(56) References Cited

OTHER PUBLICATIONS

Tse, et al. Intracellular antibody capture technology: application to selection of intracellular antibodies recognising the BCR-ABL oncogenic protein. J Mol Biol. 2002;317(1):85-94.
UK office action and search report dated Feb. 22, 2011 for GB Application No. 1017857.2.
Van Hest, et al. Efficient introduction of alkene functionality into proteins in vivo. FEBS Lett. May 22, 1998;428(1-2):68-70.
Whang, et al. Inactivation of the tumor suppressor PTEN/MMAC1 in advanced human prostate cancer through loss of expression. Proc Natl Acad Sci USA. 1998; 95(9): 5246-50.
Wolters, et al. An analysis of the role of collagenase and protease in the enzymatic dissociation of the rat pancreas for islet isolation. Diabetologia. Aug. 1992;35(8):735-42.
Young. An improved method for the detection of peroxidase-conjugated antibodies on immunoblots. J Virol Methods. Apr.-May 1989;24(1-2):227-35.
Zheng, et al. Regulation of STAT3 and STAT5 in the differentiation of FLT3/ITD expressing 32Dc13 cells induced by G-CSF and CEP-701. Abstract 2935.Blood. 2002; 100(11) and 44th Annual Meeting of the American Society of Hematology. Philadelphia, PA, USA. Dec. 6-10, 2002.
Zieglschmid, et al. Detection of disseminated tumor cells in peripheral blood. Crit Rev Clin Lab Sci. 2005;42(2):155-96.
U.S. Appl. No. 14/667,388, filed Mar. 24, 2015, Covey et al.
U.S. Appl. No. 14/525,013, filed Oct. 27, 2014, Hotson et al.
U.S. Appl. No. 14/572,317, filed Dec. 16, 2014, Fantl et al.
U.S. Appl. No. 14/574,277, filed Dec. 17, 2014, Fantl et al.
U.S. Appl. No. 14/193,746, filed Feb. 28, 2014, Ptacek et al.
U.S. Appl. No. 14/279,905, filed May 16, 2014, Fantl et al.
U.S. Appl. No. 14/294,592, filed Jun. 3, 2014, Fantl et al.
He, et al. Toll-like receptors activate programmed necrosis in macrophages through a receptor-interacting kinase-3-mediated pathway. Proc Natl Acad Sci U S A. Dec. 13, 2011;108(50):20054-9. doi: 10.1073/pnas.1116302108. Epub Nov. 28, 2011.
International search report and written opinion dated Apr. 24, 2014 for PCT/US2013/068815.
Rolfe, et al. Pulmonary fibroblast expression of interleukin-8: a model for alveolar macrophage-derived cytokine networking. Am J Respir Cell Mol Biol. Nov. 1991;5(5):493-501.
Sims, et al. Analysis of single mammalian cells on-chip. Lab Chip. Apr. 2007;7(4):423-40. Epub Mar. 6, 2007.
Underwood, et al. SB 239063, a p38 MAPK inhibitor, reduces neutrophilia, inflammatory cytokines, MMP-9, and fibrosis in lung. Am J Physiol Lung Cell Mol Physiol. Nov. 2000;279(5):L895-902.
Wang, et al. TNFα induced IL-8 production through p38 MAPK-NF-KB pathway in human hepatocellular carcinoma cells. Zhonghua Gan Zang Bing Za Zhi. Dec. 2011;19(12):912-6. doi: 10.3760/cma.j.issn.1007-3418.2011.12.008.
Xu, et al. Macrophages induce differentiation of plasma cells through CXCL10/IP-10. J Exp Med. Sep. 24, 2012;209(10):1813-23, S1-2. Epub Sep. 17, 2012.
U.S. Appl. No. 14/814,398, filed Jul. 30, 2015, Parkinson et al.
U.S. Appl. No. 14/825,486, filed Aug. 13, 2015, Fantl et al.
U.S. Appl. No. 14/837,902, filed Aug. 27, 2015, Hawtin et al.
U.S. Appl. No. 14/843,801, filed Sep. 2, 2015, Cesano et al.
U.S. Appl. No. 14/450,639, filed Aug. 4, 2014, Soper et al.

\* cited by examiner

Figure 17

| Modulator | Inhibitor | Mono IL2 | Mono IL6 | Mono TNF | B cell IL2 | B cell IL6 | B cell TNF | CD4 IL2 | CD4 IL6 | CD4 TNF | CD8 IL2 | CD8 IL6 |
|---|---|---|---|---|---|---|---|---|---|---|---|---|
| CON 402 | | | | | | | | | | | | |
| Unstim | None | 0.993 | 0.621 | 0.897 | 0.365 | 1.39 | 0.877 | 0.112 | 1.15 | 0.202 | 0.268 | 0.692 |
| SAg | None | 11.1 | 0.304 | 0.768 | 0.251 | 5.14 | 5.64 | 6.65 | 2.8 | 20.1 | 1.21 | 1.78 |
| LPS | None | 5.41 | 16.2 | 5.11 | 0.675 | 0.759 | 2.87 | 0.382 | 0.518 | 0.436 | 0.757 | 0.235 |
| Unstim | ant-IL2 | 3.88 | 1.17 | 1.17 | 0.577 | 0.961 | 3.55 | 1.67 | 1.82 | 4.45 | 0.469 | 0.531 |
| SAg | ant-IL2 | 12.1 | 0.54 | 1.26 | 0.796 | 3.18 | 4.88 | 5.57 | 2.14 | 14.5 | 0.831 | 1.06 |
| LPS | ant-IL2 | 5.41 | 31.8 | 4.42 | 0.374 | 0.312 | 2.56 | 0.666 | 0.826 | 0.367 | 0.882 | 0.495 |
| Unstim | ant-IL6 | 0.674 | 1.01 | 0.459 | 0.228 | 2.22 | 1.37 | 0.129 | 1.64 | 0.129 | 0.429 | 0.51 |
| SAg | ant-IL6 | 14.5 | 0.337 | 0.675 | 1.2 | 4.69 | 5.49 | 6.79 | 2.6 | 37.4 | 0.955 | 1.56 |
| LPS | ant-IL6 | 5.46 | 35.9 | 3.71 | 0.955 | 0.896 | 3.64 | 1.17 | 0.793 | 0.419 | 1.51 | 0.277 |
| Unstim | ant-TNFa | 0.65 | 0.335 | 1.06 | 0.734 | 1.32 | 0.979 | 0.351 | 1.98 | 0.454 | 0.606 | 0.551 |
| SAg | ant-TNFa | 10.3 | 0.224 | 0.897 | 1.12 | 4.3 | 6.07 | 6.41 | 2.5 | 22.6 | 1.86 | 1.33 |
| LPS | ant-TNFa | 4.93 | 35.2 | 9.85 | 0.669 | 1.23 | 3.01 | 1.02 | 0.958 | 0.49 | 1.14 | 0.379 |
| Unstim | Anti IL2/IL6/TNF | 0.449 | 0.349 | 0.948 | 1.15 | 1.88 | 1.1 | 0.867 | 1.65 | 1.19 | 1.18 | 0.699 |
| SAg | Anti IL2/IL6/TNF | 11.5 | 0.256 | 1.41 | 1.54 | 3.18 | 6.36 | 6.88 | 2.99 | 38 | 2.17 | 0.914 |
| LPS | Anti IL2/IL6/TNF | 4.03 | 20.9 | 11.1 | 0.148 | 1.48 | 3.32 | 0.703 | 0.9 | 0.253 | 0.74 | 0.396 |
| Unstim | CAL101 | 1.65 | 1.83 | 0.459 | 0.629 | 0.858 | 0.572 | 0.21 | 1.95 | 0.229 | 0.474 | 0.768 |
| SAg | CAL101 | 8.08 | 0.836 | 0.65 | 0.423 | 0.403 | 0.846 | 0.635 | 1.71 | 0.953 | 0.498 | 0.997 |
| LPS | CAL101 | 5.25 | 27.1 | 2.04 | 0.54 | 0.3 | 0.6 | 0.242 | 1.82 | 0.0744 | 0.463 | 0.498 |
| Unstim | Tofactinib | 2.49 | 38.8 | 1.29 | 1.23 | 0.759 | 2.1 | 1.1 | 2.12 | 1.18 | 1.4 | 0.663 |
| SAg | Tofactinib | 4.23 | 26.1 | 0.785 | 0.483 | 0.322 | 1.21 | 0.633 | 2.23 | 0.7 | 0.579 | 0.641 |
| LPS | Tofactinib | 7.43 | 35.1 | 1.33 | 0.704 | 0.646 | 0.998 | 0.455 | 1.45 | 0.352 | 0.935 | 0.348 |
| CON 403 | | | | | | | | | | | | |
| Unstim | None | 0.997 | 0.562 | 0.613 | 0.15 | 2.05 | 0.751 | 0.084 | 7.92 | 0.126 | 0.189 | 1.89 |
| SAg | None | 8.35 | 0.716 | 1.67 | 1.34 | 5.64 | 3.75 | 10 | 7.69 | 39.8 | 2.29 | 6.03 |
| LPS | None | 3.61 | 38.8 | 2.68 | 0.565 | 0.919 | 2.4 | 0.194 | 7.69 | 0.167 | 0.0642 | 1.51 |
| Unstim | ant-IL2 | 0.436 | 1.02 | 0.657 | 0.2 | 2.38 | 0.479 | 0.0727 | 7.24 | 0.0545 | 0.161 | 1.49 |
| SAg | ant-IL2 | 10.3 | 1.91 | 1.2 | 3.02 | 5.25 | 8.03 | 11.1 | 6.63 | 20.1 | 3.37 | 4.87 |
| LPS | ant-IL2 | 2.05 | 29.9 | 2.96 | 0.485 | 1.02 | 2.37 | 0.0459 | 7.38 | 0.0229 | 0.294 | 1.29 |
| Unstim | ant-IL6 | 0.997 | 1.26 | 0.376 | 0.105 | 3.9 | 0.843 | 0.0657 | 7.38 | 0.131 | 0.223 | 1.58 |
| SAg | ant-IL6 | 10.3 | 1.99 | 0.855 | 1.2 | 4.65 | 3.75 | 8.73 | 6.65 | 38.2 | 1.08 | 5.28 |
| LPS | ant-IL6 | 3.1 | 32.8 | 2.89 | 0.654 | 1.87 | 2.43 | 0.0854 | 6.24 | 0.149 | 0.409 | 1.44 |
| Unstim | ant-TNFa | 0.959 | 0.0405 | 0.446 | 0.42 | 1.44 | 0.526 | 0.195 | 7.32 | 0.162 | 0.312 | 1.15 |
| SAg | ant-TNFa | 7.57 | 0.299 | 1.1 | 0.693 | 4.16 | 4.23 | 7.01 | 7.41 | 35.5 | 2.19 | 2.99 |
| LPS | ant-TNFa | 2.07 | 39.5 | 3.5 | 0.614 | 3.63 | 3.59 | 0.349 | 6.94 | 0.41 | 0.427 | 1.09 |
| Unstim | Anti IL2/IL6/TNF | 0.749 | 0.0936 | 0.749 | 1.19 | 1.61 | 1.45 | 1.81 | 7.71 | 2.73 | 1.5 | 1.64 |
| SAg | Anti IL2/IL6/TNF | 7.81 | 0.377 | 0.743 | 1.01 | 3.14 | 3.65 | 5.2 | 7.02 | 13.2 | 1.67 | 3.84 |
| LPS | Anti IL2/IL6/TNF | 3.63 | 39.2 | 14.6 | 1.47 | 2.12 | 4.03 | 0.596 | 7.13 | 0.549 | 0.77 | 2.02 |
| Unstim | CAL101 | 1.85 | 0.364 | 0.221 | 1.23 | 1.98 | 2.2 | 1.11 | 7.71 | 0.817 | 1.08 | 1.84 |
| SAg | CAL101 | 10.1 | 0.0704 | 0.141 | 0.495 | 0.405 | 0.765 | 0.657 | 7.83 | 1.18 | 0.488 | 2.46 |
| LPS | CAL101 | 5.28 | 22.8 | 1.83 | 0.871 | 1.13 | 1.52 | 0.257 | 7.77 | 0.342 | 0.322 | 2.22 |
| Unstim | Tofactinib | 2.42 | 26.1 | 1.16 | 0.854 | 2.39 | 1.34 | 0.899 | 7.78 | 0.882 | 0.918 | 1.91 |
| SAg | Tofactinib | 4.24 | 17.5 | 0.825 | 0.543 | 0.483 | 0.844 | 0.508 | 8.3 | 0.395 | 0.646 | 2.42 |
| LPS | Tofactinib | 8.33 | 38.8 | 1.44 | 0.312 | 1.07 | 0.847 | 0.193 | 8.52 | 0.298 | 0.357 | 1.6 |

Figure 23

Figure 25A
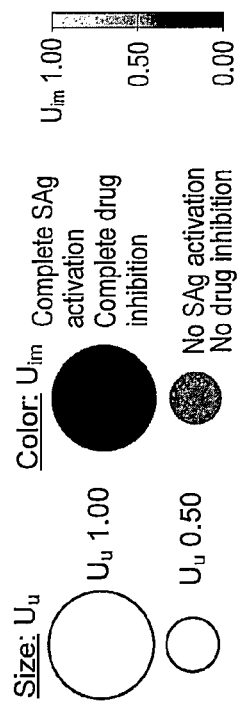
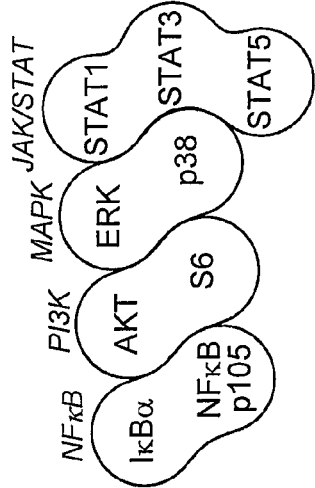
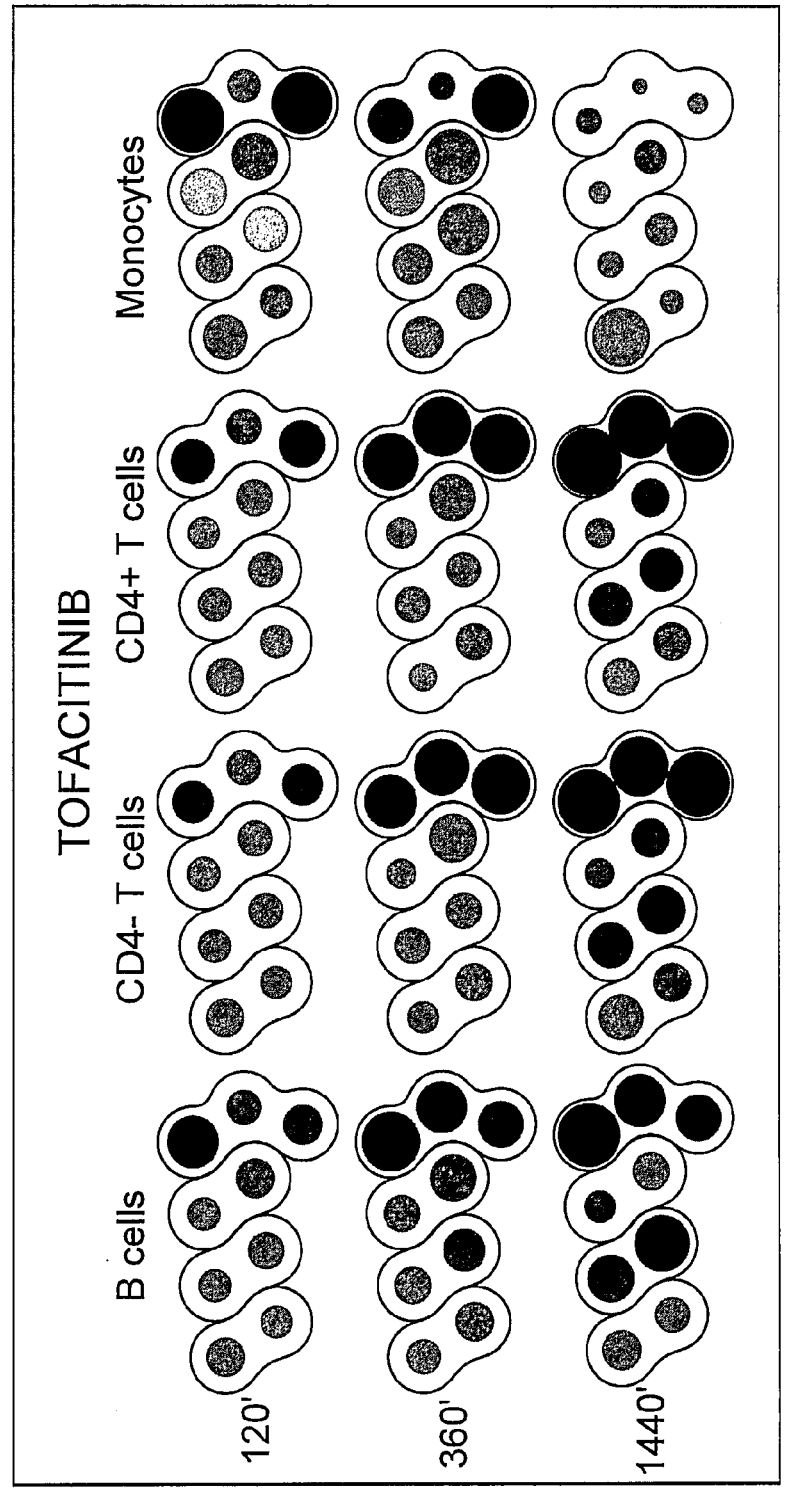

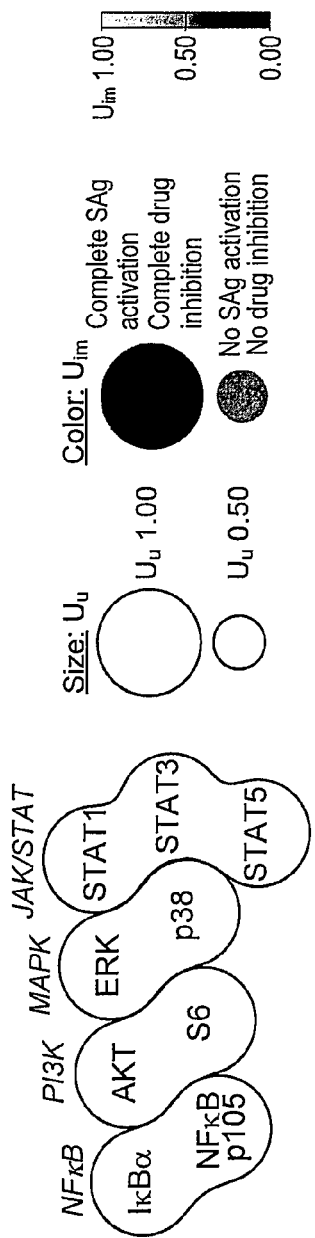
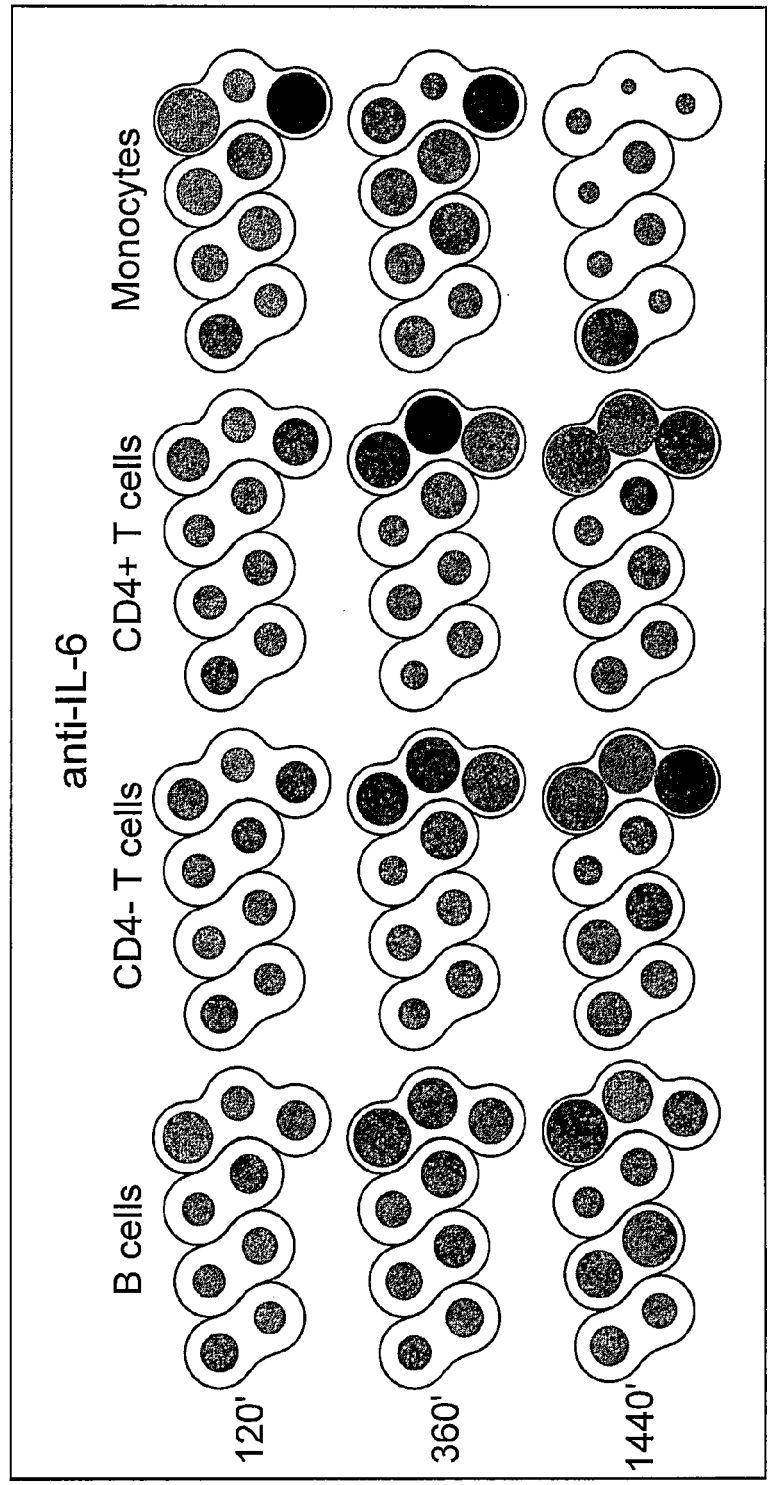
Figure 25B

INDUCED INTERCELLULAR COMMUNICATION

PRIORITY CLAIM

This application claims the benefit of U.S. Ser. No. 61/722,976, filed Nov. 6, 2012 which application is incorporated by reference in its entirety. This application is a continuation-in part of U.S. patent application Ser. No. 14/072,623, filed Nov. 5, 2013, which is a continuation of U.S. patent application Ser. No. 13/821,539, filed Oct. 2, 2013, which is a national stage of PCT Patent Application No. US2011/01565 filed Sep. 8, 2011, which claims the benefit of U.S. Patent Application No. 61/381,067 filed Sep. 8, 2010, 61/440,523 filed Feb. 8, 2011, 61/469,812 filed Mar. 31, 2011, and 61/499,127 filed Jun. 20, 2011. U.S. patent application Ser. No. 14/072,623 is also a continuation-in-part of U.S. patent application Ser. No. 12/877,998, filed Sep. 8, 2010, which claims the benefit of U.S. Patent Application No. 61/240,613, filed Sep. 8, 2009, all of which are incorporated by reference in their entireties.

BACKGROUND OF THE INVENTION

Many conditions are characterized by disruptions in cellular pathways that lead, for example, to aberrant control of cellular processes, with uncontrolled growth and increased cell survival. These disruptions are often caused by changes in the activity of molecules participating in cellular pathways. For example, alterations in specific signaling pathways have been described for many cancers.

Conditions today are diagnosed by analyzing these disruptions in a single homogenous population of cells. However, different types of cells co-exist with other different types of cells in a complex environment milieu which might affect the pathology of a condition. Thus, the successful diagnosis of a condition and use of therapies may require knowledge of the cellular events that are responsible for the condition pathology in a variety of cells and/or cellular networks.

Accordingly, there is a need for a biologically based clinically relevant analysis of condition disorders that can diagnose or predict the disease course for an individual. This analysis, based upon the status of different discrete cell populations will provide a more complete depiction of the pathology of a condition, thus, aiding clinicians in both more reliable prognosis and therapeutic selection at the individual patient level.

Therefore, cross-talk between cells (malignant, immune, bystanders, and others) tissues and biological systems contributes to the ability to diagnose, treat, and select and design drugs for a given disease state.

SUMMARY OF THE INVENTION

In certain embodiments, the invention provides methods, compositions, and systems directed to modulation of a culture containing a plurality of discrete cell populations in communication, and evaluation of one or more elements in single cells of the populations.

In one aspect, the invention provides methods.

In certain embodiments of this aspect, the invention provides a method of evaluating the effects of a modulator on a plurality of discrete cell populations in communication, comprising (i) preparing a culture from a sample that has been removed from an individual, wherein the culture comprises a plurality of discrete cell populations in communication; (ii) contacting a first cell from a first discrete cell population in the culture with a modulator, wherein the modulator interacts with the first cell population but does not substantially interact with a second discrete cell population in the culture; (iii) incubating the culture for a period of time; and (iv) after the incubation, determining an activation level of a first activatable element in single cells from the second cell population. The individual can be a mammal, e.g., a human, such as a human known or suspected of suffering from a condition, for example an autoimmune condition or cancer. The sample can be a blood sample. In certain embodiments, the blood sample is treated to remove certain classes of cells before being used for the culture, to create a modified sample not found in the individual, such as a peripheral blood mononuclear cell (PBMC) sample. Potential communication between the first and second cell populations can be evaluated based, at least in part, on the activation level of the first activatable element in single cells from the second cell population. The culture can be placed in an artificial environment. The method can further comprise determining an activation level of a second activatable element in single cells from a third discrete cell population; the second activatable element can be the same as the first activatable element or different, and the third discrete cell population can be the same as the first discrete cell population or different. The method can further comprise determining an intracellular level of an intercellular communication messenger in single cells from a fourth discrete cell population, e.g. where the fourth discrete cell population is the same as the second discrete cell population, or is different from the second discrete cell population. The intercellular communication messenger can be a growth factor, cytokine, hormone, or exosome. In certain embodiments, the intercellular communication messenger is a cytokine, such as IL1, IL2, IL3, IL4, IL5, IL6, IL8, IL9, IL10, IL12, IL15, IL17A, IL17F, IL21, IL23, TNF☐, TNF☐, IFN☐, IFN☐, or IFN☐☐ In certain embodiments the culture is sampled at a plurality of time periods and step (iv) is performed on a sample from each of the time periods, or steps (i)-(iv) are performed on a plurality of cell cultures under substantially the same conditions except the cell cultures are incubated for different periods of time. In these embodiments, the activation levels of the first activatable element in cultures incubated for different periods of time can be compared in a kinetic analysis, for example a kinetic analysis used to produce an intercellular communication profile for the second discrete cell type. In certain embodiments steps (i)-(iv) are performed on a second cell culture under substantially the same conditions except that no modulator is added to the second cell culture, and the activation level of the first activatable element in the first cell culture is compared to the activation level of the first activatable element in the second cell culture. In all embodiments, the activation levels of the first activatable element can be determined on a single cell-by-cell basis in a plurality of cells in the second cell population. The method can further comprise adding an agent that affects one or more intercellular communication messengers to the culture, which can be added at the same time as the modulator or substantially at the same time. The agent can be an agent being screened for potential therapeutic use for a condition, such as by comparing the agent with an agent of known efficacy for treating the condition. The method can further comprise preparing a report of the results, or based at least in part on the results of A(iv) or on information derived from the results of A(iv). The method can further comprise determining a status for the individual, based at least in part on a metric for the individual derived at least in part from the result of step (iv), such as a health status, for example, presence or absence of a condition, status of a condition, prognosis of a condition, or responsiveness to therapy for a condition, or a combination thereof. In these embodiments, the determination of the status of the individual, can be based at least in part on a comparison of the individual metric with a standard metric, wherein the standard metric is derived, at least in part, from the activation level or levels of the first activatable element in a second cell population in a plurality of cultures each comprising a plurality of discrete cell populations in communication, each culture being derived from samples removed from a plurality of healthy individuals and treated substantially as in steps (i)-(iv). The standard metric can be further derived, at least in part, from the activation level or levels of the first activatable element in a second cell population in a plurality of cultures comprising a plurality of discrete cell populations in communication, each derived from samples removed from a plurality of individuals having a status that is a status to be determined for the individual of step (i). The modulator can be a modulator that acts as a toll-like receptor (TLR) modulator, a superantigen, a costimulatory, a T cell modulator, a B cell modulator, a cytokine, a growth factor, or a modulator of Fc receptor signaling on natural killer (NK) cells and/or monocytes, or a combination thereof. The activatable element can be an activatable element in a signaling pathway, such as a NFkB pathway, a PI3K/Akt pathway, a MAPK pathway, a JAK/STAT pathway, a DNA damage repair pathway, an apoptosis pathway, a PKC pathway, a cell cycle pathway, a phosphatase regulation pathway, a FLT3L signaling pathway, a TCR pathway, a BCR pathway, or a combination thereof. In certain embodiments, the pathway is a NFkB pathway, a PI3K/Akt pathway, a MAPK pathway, a JAK/STAT pathway, or a combination thereof. In certain embodiments, the single cells of the second cell population are gated to remove unhealthy cells, such as by a process that included elimination of dead cells, cells committed to apoptosis, or a combination thereof. The gating can comprise eliminating cells committed to apoptosis by applying a threshold level for an apoptosis element, e.g., cleaved PARP (cPARP).

In other certain embodiments of this aspect, the invention provides a method for evaluating a chemical or biological agent comprising (i) contacting a first cell from a first discrete cell population with a modulator in a first culture containing a plurality of discrete cell populations in communication, wherein the modulator interacts with the first discrete cell population in the culture but does not substantially interact with a second discrete cell population in the culture; (ii) contacting the culture with the agent; (iii) incubating the first culture for a period of time; (iv) after the incubation, determining an activation level of a first activatable element in single cells from the second cell population; and (v) evaluating the effect of the agent based at least in part on the activation level of the first activatable element determined in (iv). The culture can be prepared from a sample that has been removed from an individual, such as a mammal, e.g., a human, such as a human suffering from or suspected of suffering from a condition. The method can further comprise evaluating the potential efficacy of the agent in treating a condition based at least in part on the evaluation of step (v). The method can further comprise comparing the activation level of the first activatable element with an activation level of the same element obtained in a second culture to which the agent has not been added but which is otherwise treated substantially the same as the first culture. In certain embodiments of the method, either the first culture is sampled at a plurality of time periods and step (v) is performed on a sample from each of the time periods, or steps (i)-(v) are performed on a plurality of cell cultures under substantially the same conditions except the cell cultures are incubated for different periods of time. The method can further comprise determining a level of an intercellular communication messenger in single cells from a discrete cell population in the culture, such as a growth factor, hormone, exosome, or cytokine. In certain embodiments, the intercellular communication messenger is a cytokine, such as IL1, IL2, IL3, IL4, IL5, IL6, IL8, IL9, IL10, IL12, IL15, IL17A, IL17F, IL21, IL23, TNF☐, TNF☐, IFN☐, IFN☐, or IFN☐☐ In certain embodiments, the method further comprises determining the activation level of a second activatable element in single cells in a third discrete cell population in the culture after the incubation; the first and second activatable elements can be the same activatable element, or the first and second activatable elements can be different activatable elements; and the third discrete cell population can be the same as or different from the first discrete cell population. In certain embodiments of the method the agent comprises an agent that affects one or more intercellular communication messengers, or for which it is desired to test its effect on one or more intercellular communication messengers, such as a growth factor, hormone, exosome, or cytokine, e.g., a cytokine. In certain embodiments the agent is a cytokine inhibitor or an agent desired to be tested as a cytokine inhibitor, e.g., an antibody directed against a cytokine, for example, IL1, IL2, IL3, IL4, IL5, IL6, IL8, IL9, IL10, IL12, IL15, IL17A, IL17F, IL21, IL23, TNF☐, TNF☐, IFN☐, IFN☐, or IFN☐☐☐ or, for example, IL-2, IL-6, IL-7, IL-15, IL-17, IL-23, or TNF☐☐☐ or for example IL6 and TNF☐☐ In certain embodiments the agent is an agent that affects an intracellular pathway involved in intercellular communication, or for which it is desired to examine the effect on an intracellular pathway involved in intercellular communication, such as an inhibitor of the intracellular pathway. The pathway can be selected from the JAK/STAT pathway, PI3K pathway, or BCR pathway. The agent can be added at the same time as the modulator, or at substantially the same time as the modulator. The method can further comprise comparing the agent with an agent of known efficacy for treating a condition. The method can further comprise preparing a report of the results, or based at least in part on the results, of (iv), or information derived therefrom.

In another aspect, the invention provides systems.

In certain embodiments of this aspect, the invention provides a system for informing a decision by a subject and/or healthcare provider for the subject involving diagnosing, prognosing, evaluating status of, or determining a method of treatment for a condition from which the subject is suffering or is suspected of suffering, wherein the system comprises (i) the subject and the healthcare provider; (ii) a sample removed from the subject; (ii) a unit configured to analyze a culture derived from the sample, wherein the culture comprises a plurality of discrete cell populations in communication, wherein the unit is configured to (a) contact a first cell from a first discrete cell population in the culture with a modulator, wherein the modulator interacts with the first cell population but does not substantially interact with a second discrete cell population in the culture; (b) incubate the culture for a period of time; and (c) after the incubation, determine an activation level of a first activatable element in single cells from the second cell population, in the form of raw data; (iii) a unit configured to communicate the raw data or information derived at least in part from the raw data to the subject and/or healthcare provider so that a decision may be made regarding diagnosis, prognosis, state of, or treatment of the condition that the subject suffers from or is suspected of suffering from. The condition can be a pathological condition selected from the group consisting of cancer and autoimmune conditions. The system can further comprise a unit configured to treat the sample for transport to to the analysis unit. In certain embodiments of the system, the analysis unit comprises a flow cytometer or mass spectrometer configured to determine on a single cell basis the levels of a detectable binding element in the cell, wherein the detectable binding element is an element that binds to a form of the activatable element, such an activated form, and where the activatable element is activated by cleavage or phosphorylation. The analytical unit can be configured to gate data from healthy vs. unhealthy cells, such as by determining cPARP levels in cells and gating the cells at least in part based on their cPARP levels.

In another certain embodiment of this aspect, the invention provides a system for informing a decision by a decision-making entity regarding a chemical or biological agent comprising (i) the decision-making entity; (ii) a unit configured to analyze a culture derived from a sample obtained from an individual wherein the culture comprises a plurality of discrete cell populations in communication, wherein the unit is configured to (a) contact a first cell from a first discrete cell population in the culture with a modulator, wherein the modulator interacts with the first cell population but does not substantially interact with a second discrete cell population in the culture; (b) contact the culture with the agent, (c) incubate the culture for a period of time; and (d) after the incubation, determine an activation level of a first activatable element in single cells from the second cell population, in the form of raw data; and (iii) a unit configured to communicate the raw data, or information derived at least in part from the raw data, to the decision-making entity so that a decision may be made regarding the agent. The agent can be an agent to be evaluated for efficacy in affecting an intercellular communication messenger, such as a growth factor, hormone, exosome, or cytokine, e.g., a cytokine. In certain embodiments the system further comprises a unit configured to treat the sample for transport to to the analysis unit. The analysis unit can comprise a flow cytometer or mass spectrometer configured to determine on a single cell basis the levels of a detectable binding element in the cell, wherein the detectable binding element is an element that binds to a form of the activatable element, such as an activated form, for example where the activatable element is activated by cleavage or phosphorylation. The analytical unit can be configured to gate data from healthy vs. unhealthy cells, for example by a gating that comprises determining cPARP levels in cells and gating the cells at least in part based on their cPARP levels. In certain embodiments, the decision-making entity comprises a computer. In certain embodiments, the decision-making entity comprises a human being.

In another aspect, the invention provides compositions.

In certain embodiments of this aspect, the invention provides a report comprising data regarding an activation level of an activatable element in a single cell in a culture comprising a plurality of discrete cell populations, wherein the cell is a member of a first discrete cell population and wherein the culture has been contacted for a period of time with a modulator that interacts with a second cell population in the culture, but does not substantially interact with the first cell population, or information derived at least in part from the data. The report can further comprise data, or information derived from data regarding an activation level of an activatable element in a plurality of single cells, obtained on a cell-by-cell basis, in a culture comprising a plurality of discrete cell populations, wherein the cells are members of the first discrete cell population and wherein the culture has been contacted for a period of time with a modulator that interacts with a second cell population in the culture but does not substantially interact with the first cell population. The report can be an electronic report, a hard copy, or a combination of an electronic report and a hard copy.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 17 shows inhibitors affect intracellular cytokine production.

FIG. 23 shows the effects of inhibitors on LPS modulation effects on intracellular readouts at various time points in B cells, CD4− cells, CD4+ cells, and monocytes. Metric is Uim (proportion of cells inhibited compared to modulator, see FIG. 27 for explanation), shown as 5-color heat map and as numbers within cells. PBMC from two healthy volunteers, values averaged.

DETAILED DESCRIPTION OF THE INVENTION

Figure 1:
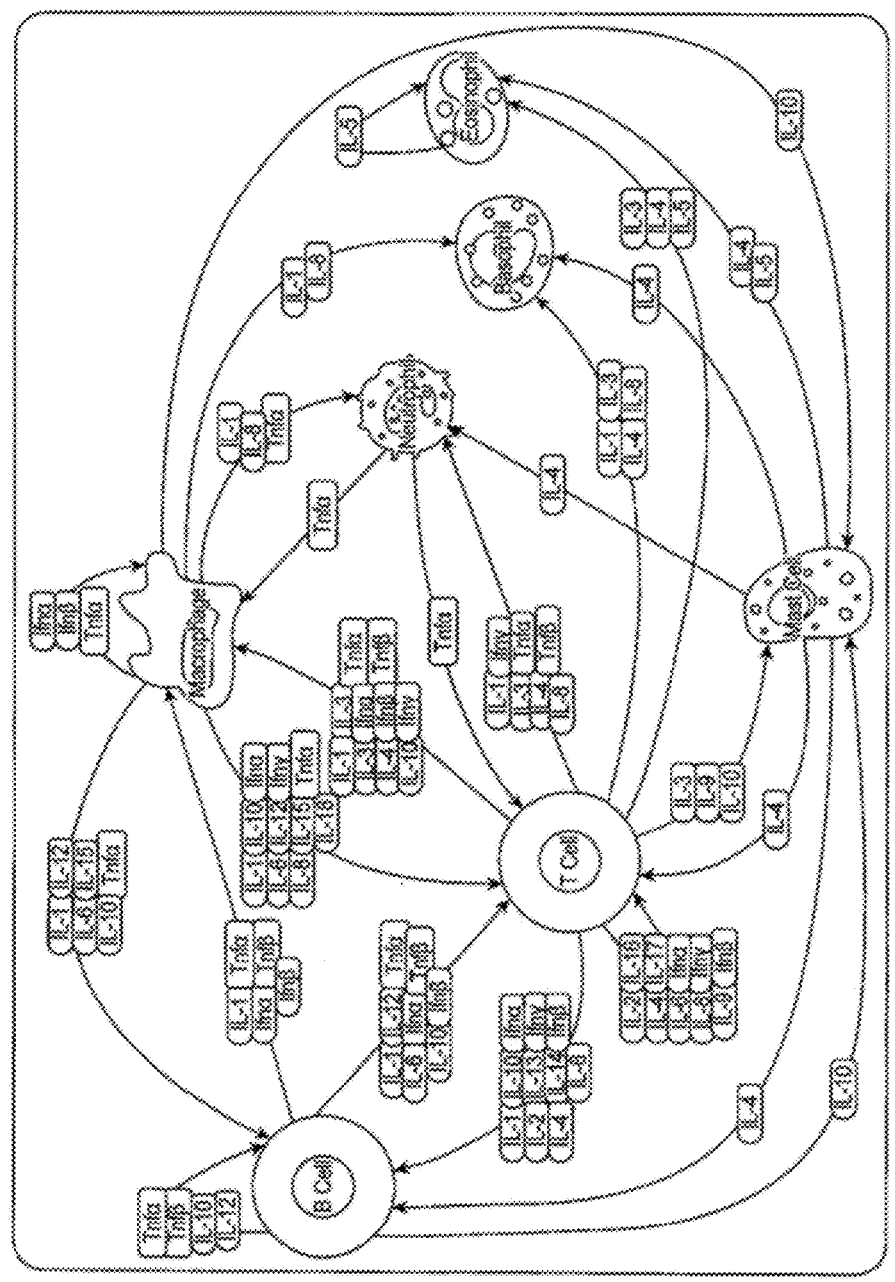
FIG. 1 depicts an example of the immune system cell communication network.

I. Introduction
II. A plurality of discrete cell populations in communication
III. Samples, sampling, and cultures
IV. Modulators
V. Intercellular communication messengers
VI. Agents affecting one or more intercellular communication messengers
VII. Agents that affect one or more intracellular pathways involved in intercellular communication
VIII. Time period of incubation of the culture
IX. Activation levels of activatable elements
   A. Activatable elements
   B. Additional elements
   C. Signaling Pathways
   D. Detection of levels of activatable elements and/or additional elements
      1. Binding elements
      2. Labels
      3. Alternative activation state indicators
      4. Detection
   E. Data analysis and presentation
X. Determination of activation state of a discrete cell population
XI. Classifying and Characterizing Cell Networks Based on Activation State Data Associated With Discrete Populations of Cells
XII. Methods
   A. Methods of evaluating the effects of a modulator on a plurality of discrete cell populations in communication
   B. Methods of evaluating chemical or biological agents
   C. Methods of determining the status of an individual
   D. Methods of evaluating a condition that affects a group of individuals
   E. Methods of generating a report
XIII. Compositions
   A. Reports
   B. Kits
XIV. Systems
   A. System for informing a decision by a subject and/or healthcare provider for the subject
   B. System for informing a decision by a decision-making entity regarding a chemical or biological agent The present invention incorporates information disclosed in other applications and texts. The following patent and other publications are hereby incorporated by reference in their entireties: Haskell et al, Cancer Treatment, 5th Ed., W.B. Saunders and Co., 2001; Alberts et al., The Cell, 4th Ed., Garland Science, 2002; Vogelstein and Kinzler, The Genetic Basis of Human Cancer, 2d Ed., McGraw Hill, 2002; Michael, Biochemical Pathways, John Wiley and Sons, 1999; Weinberg, The Biology of Cancer, 2007; Immunobiology, Janeway et al. 7th Ed., Garland, and Leroith and Bondy, Growth Factors and Cytokines in Health and Disease, A Multi Volume Treatise, Volumes 1A and 1B, Growth Factors, 1996. Other conventional techniques and descriptions can be found in standard laboratory manuals such as Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press), Stryer, L. (1995) Biochemistry (4th Ed.) Freeman, New York, Gait, "Oligonucleotide Synthesis: A Practical Approach" 1984, IRL Press, London, Nelson and Cox (2000), Lehninger, Principles of Biochemistry 3rd Ed., W. H. Freeman Pub., New York, N.Y. and Berg et al. (2002) Biochemistry, 5th Ed., W. H. Freeman Pub., New York, N.Y.; and Sambrook, Fritsche and Maniatis. "Molecular Cloning A laboratory Manual" 3rd Ed. Cold Spring Harbor Press (2001), all of which are herein incorporated in their entirety by reference for all purposes.

Also, patents and applications that are incorporated by reference include U.S. Pat. Nos. 7,381,535, 7,393,656, 7,563,584, 7,695,924, 7,695,926, 7,939,278, 8,148,094, 8,187,885, 8,198,037, 8,206,939, 8,214,157, 8,227,202, 8,242,248; U.S. patent application Ser. Nos. 11/338,957, 11/655,789, 12/061,565, 12/125,759, 12/125,763, 12/229,476, 12/432,239, 12/432,720, 12/471,158, 12/501,274, 12/501,295, 12/538,643, 12/551,333, 12/581,536, 12/606,869, 12/617,438, 12/687,873, 12/688,851, 12/703,741, 12/713,165, 12/730,170, 12/778,847, 12/784,478, 12/877,998, 12/910,769, 13/082,306, 13/091,971, 13/094,731, 13/094,735, 13/094,737, 13/098,902, 13/098,923, 13/098,932, 13/098,939, 13/384,181; International Applications Nos. PCT/US2011/001565, PCT/US2011/065675, PCT/US2011/026117, PCT/US2011/029845, PCT/US2011/048332; and U.S. Provisional Applications Ser. Nos. 60/304,434, 60/310,141, 60/646,757, 60/787,908, 60/957,160, 61/048,657, 61/048,886, 61/048,920, 61/055,362, 61/079,537, 61/079,551, 61/079,579, 61/079,766, 61/085,789, 61/087,555, 61/104,666, 61/106,462, 61/108,803, 61/113,823, 61/120,320, 61/144,68, 61/144,955, 61/146,276, 61/151,387, 61/153,627, 61/155,373, 61/156,754, 61/157,900, 61/162,598, 61/162,673, 61/170,348, 61/176,420, 61/177,935, 61/181,211, 61/182,518, 61/182,638, 61/186,619, 61/216,825, 61/218,718, 61/226,878, 61/236,281, 61/240,193, 61/240,613, 61/241,773, 61/245,000, 61/254,131, 61/263,281, 61/265,585, 61/265,743, 61/306,665, 61/306,872, 61/307,829, 61/317,187, 61/327,347, 61/350,864, 61/353,155, 61/373,199, 61/374,613, 61/381,067, 61/382,793, 61/423,918, 61/436,534, 61/440,523, 61/469,812, 61/499,127, 61/515,660, 61/521,221, 61/542,910, 61/557,831, 61/558,343, 61/565,391, 61/565,929, 61/565,935, 61/591,122, 61/640,794, 61/658,092, 61/664,426, 61/693,429, and 61/713,260.

Some commercial reagents, protocols, software and instruments that are useful in some embodiments of the present invention are available at the Becton Dickinson Website and the Beckman Coulter websites. Relevant articles include High-content single-cell drug screening with phosphospecific flow cytometry, Krutzik et al., Nature Chemical Biology, 23 December (2007); Irish et al., FLt3 ligand Y591 duplication and Bcl-2 over expression are detected in acute myeloid leukemia cells with high levels of phosphorylated wild-type p53, Neoplasia, (2007), Irish et al. Mapping normal and cancer cell signaling networks: towards single-cell proteomics, Nature (2006) 6:146-155; and Irish et al., Single cell profiling of potentiated phospho-protein networks in cancer cells, Cell, (2004) 118, 1-20; Schulz, K. R., et al., Single-cell phospho-protein analysis by flow cytometry, Curr Protoc Immunol, (2007) 78:8 8.17.1-20; Krutzik, P. O., et al., Coordinate analysis of murine immune cell surface markers and intracellular phosphoproteins by flow cytometry, J Immunol. (2005) 175(4):2357-65; Krutzik, P. O., et al., Characterization of the murine immunological signaling network with phosphospecific flow cytometry, J Immunol. (2005) 175(4):2366-73; Shulz et al., Current Protocols in Immunology (2007) 78:8.17.1-20; Stelzer et al. Use of Multiparameter Flow Cytometry and Immunophenotyping for the Diagnosis and Classification of Acute Myeloid Leukemia, Immunophenotyping, Wiley, 2000; and Krutzik, P. O. and Nolan, G. P., Intracellular phospho-protein staining techniques for flow cytometry: monitoring single cell signaling events, Cytometry A. (2003) 55(2):61-70; Hanahan D., Weinberg, The Hallmarks of Cancer, CELL (2000) 100:57-70; Krutzik et al, High content single cell drug screening with phosphospecific flow cytometry, Nat Chem Biol. (2008) 4:132-42; and Monroe, J. G., Ligand independent tonic signaling in B-cell receptor function, Current Opinion in Immunology 2004, 16:288-295. Experimental and process protocols and other helpful information can be found at the website for the NHLBI Proteomics Center for Systems Immunology at Stanford University. The articles and other references cited below are also incorporated by reference in their entireties for all purposes.

I. Introduction

In certain embodiments, the present invention provides methods, compositions, and systems related to evaluation of cells belonging to a plurality of discrete cell populations that are in communication with each other in a culture, where the cells are contacted with a modulator that interacts with a first discrete cell population in the culture but that does not interact with, or does not substantially interact with, a second discrete cell population in the culture, and after a period of time one or more characteristics of the second discrete cell population is measured, on a cell-by-cell basis. Without being bound by theory, it is believed that contacting the culture with the modulate induces events in the first cell population, often in combination with another cell population, that causes intercellular communication with the second cell population, inducing events in the second cell population that become measurable over time.

The culture may be a culture derived from a sample from an individual, e.g., a culture derived from a blood sample. The plurality of discrete cell populations may be immune cell populations. Alternatively, or in addition to, the measurement of intracellular levels of an activatable element, intracellular levels of one or more intercellular communication messengers, such as cytokines, may be determined in single cells of one or more discrete cell populations. In certain embodiments, an agent that affects one or more intercellular communication messengers, or an agent that affects one or more intracellular pathways involved in intercellular communication may be added to the cell culture in addition to the modulator, and the effects of the agent on various characteristics in various discrete cell populations may be measured. In some of these embodiments, the modulator need not necessarily be a modulator that interacts with one discrete cell population in the culture but that does not interact, or does not substantially interact, with a second discrete cell population in the culture.

In certain embodiments, the invention also provides methods of evaluating chemical or biological elements, methods of determining the status of an individual, methods of evaluating a condition that affects a group of individuals, and method of generating a report, all of which are based on the technique of the above paragraphs or some modification of the technique. The invention further provides reports, kits, systems for informing a decision by a subject and/or healthcare provider for the subject, and systems for informing a decision by a decision-making entity regarding a chemical or biological agent, all of which are based on the technique of the above paragraphs or some modification of the technique.

Without being bound by theory, in certain embodiments, intercellular communication is induced using a modulator or modulators that interacts with, e.g., activates or inhibits, at least a first discrete cell population in the culture but that does not interact with, or does not substantially interact with, a second cell population in the culture. The modulator or modulators causes modulation of one or more intracellular pathways in the first cell population, leading to an alteration (increase or decrease) in release of one or more intercellular communication messengers by the first cell population, which interact with the second cell population to cause modulation of one or more intracellular pathways in the second cell population. It will be appreciated that in some cultures there will be many discrete cell populations, some or all of which are affected by the increase or decrease of intercellular communication messenger or messengers released by the first discrete cell population. It will also be appreciated that the discrete cell populations that are affected by the intercellular modulators may themselves be induced to increase or decrease release of intercellular communication messengers, which affect other cell populations, possibly including the first cell population. See FIG. 1 as an example of such intercellular communication. In addition, intercellular communication messengers released by a given discrete cell population may act in an autocrine fashion on that cell population in a feedback loop, which is often a negative feedback loop.

The modulation of the intracellular pathways is manifested as an alteration in the activation level of one or more activatable elements in the cells that are members of the pathway, e.g., phosphorylation of phosphorylatable proteins, or protein cleavage. The levels of a given activatable elements can be measured in single cells of discrete cell populations in the culture, for example in the first discrete cell population and/or in the second discrete cell population, e.g., as a means of evaluating intercellular communication due to the modulator or modulators. The modulation of the intercellular pathway or pathways is often also manifested as an alteration in the intracellular levels of one or more intercellular communication messengers in cells, and thus, alternatively, or in addition, the intracellular levels of one or more intercellular communication messengers, e.g., cytokines, may also be measured in single cells of discrete cell populations in the culture, e.g., the first and/or second cell population.

Single cells may be analyzed by any means described herein, and cells may be gated to place them in discrete cell populations so that data from single cells in a given discrete cell population may be pooled for analysis, e.g., comparison to an unmodulated culture, or comparison to a culture derived from a sample from another individual, or comparison to a modulated culture also treated with an agent that affects one or more intercellular communication messengers or an agent that affects one or more intracellular pathways involved in intercellular communication, and the like. Cells may also be gated so that only data from healthy cells is used in the analysis. Other gating, as described herein, may be used.

An exemplary culture comprising a plurality of discrete cell populations in communication is a culture derived from whole blood that has been removed from an individual, where the discrete cell populations are immune cells, e.g., monocytes and monocyte-derived cells, T cells, and B cells, that communicate via intercellular communication messengers, e.g., cytokines. The culture is not in the natural whole body environment when treated with modulator. In certain embodiments, the culture has been treated to modify it substantially from it's state even in the sample removed from the individual, e.g. a culture that comprises PBMCs derived from a blood sample, where entire classes of cells have been removed from the sample.

II. A Plurality of Discrete Cell Populations in Communication

The methods and compositions of the invention relate to modulation of cells in culture where the culture contains a plurality of discrete cell populations in communication.

Discrete Cell Populations

Figure 2:
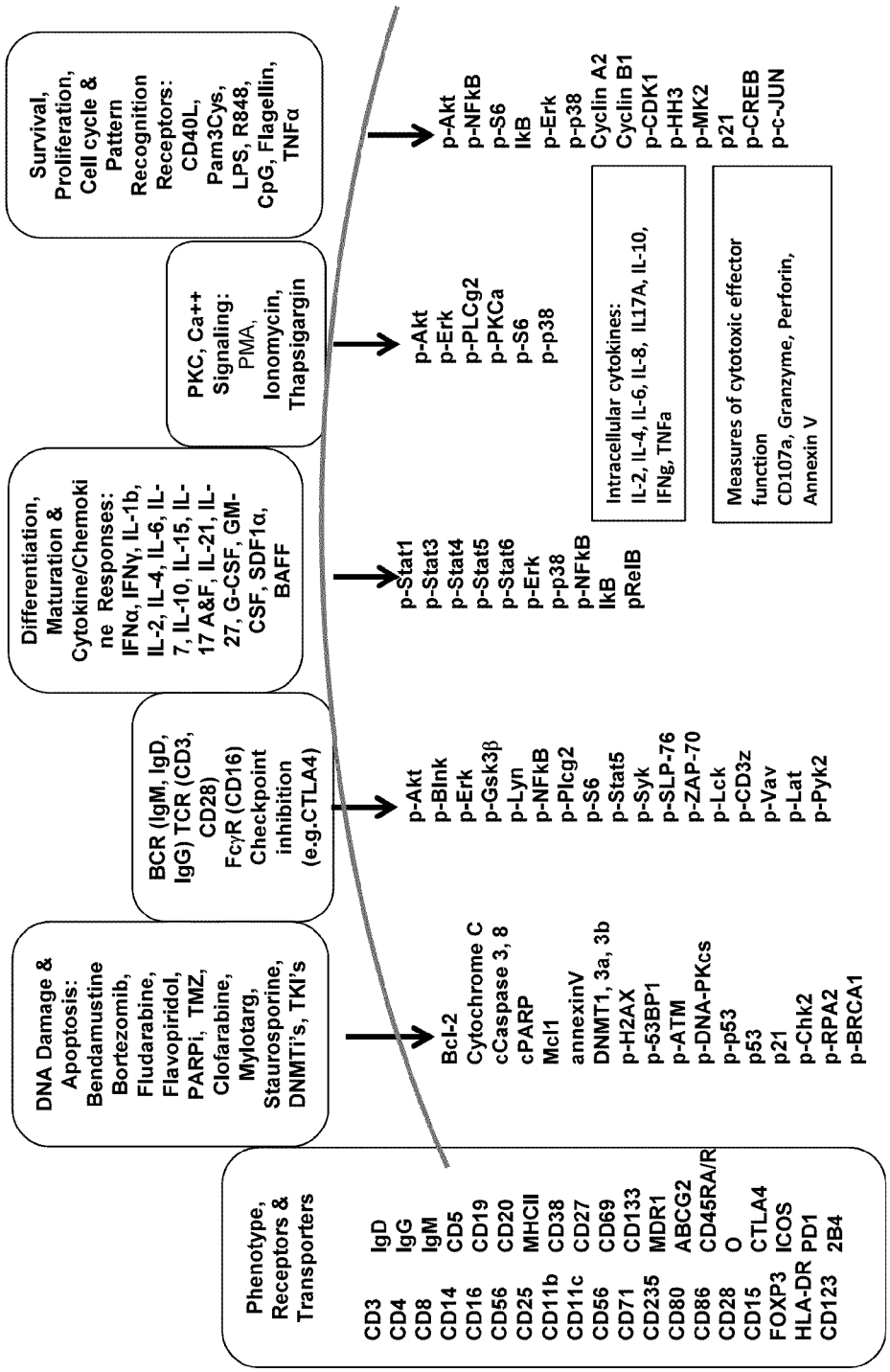
FIG. 2 shows an exemplary modulators that modulate cells and some corresponding downstream readouts induced by various modulators. A variety of modulators is shown. Modulators shown in this Figure include physiological signals, e.g., cytokines such as the interleukins, and non-physiologic signals, e.g., araC and Daunorubicin. In addition, various exemplary readouts downstream of the modulators are shown, most of which are activatable element readouts, as well as phenotype, etc., markers, and exemplary intracellular cytokines and measures of cytotoxic effector function that may be measured.

A "discrete cell population," as used herein, includes a population of cells in which the majority of cells is of a same cell type or has a same characteristic. Unless otherwise indicated, a "culture containing a plurality of discrete cell populations," and similar expressions, refers to discrete cell populations in communication. One convenient way to class single cells as part of a discrete cell population is to determine the level of a surface marker characteristic of a given discrete population of cells on the single cell. The term "surface marke" and "extracellular marker" are used interchangeably herein. For example, T cells can be identified and classed based on the presence or absence, or relative abundance, of the CD4 marker; thus one set of discrete cell populations in a plurality of discrete immune cell populations could be CD4+ T cells and another set could be CD4− T cells. Further subgroupings can be achieved in a similar manner; thus, for example, CD4+ T cells can be further classified according to the presence or absence or relative abundance of the CD8 marker. Such markers and classifications are well-known in the art and any suitable method of classification may be used. Some exemplary surface markers are shown in FIG. 2 and classification of cells into discrete cell populations is discussed in more detail below.

Thus, in certain embodiments, a discrete population of cells is a population of cells wherein every cell has the same or substantially the same of a set of surface markers or range of surface markers that are used to identify the discrete cell population, where the set can be one or more surface markers. Such sets of surface markers are well-known in the art. For example, "stem cell populations" are characterized by $CD34^+$ $CD38^-$ or $CD34^+$ $CD33^-$ expressing cells, or regulatory CD4 T lymphocytes; e.g. CD4+ CD25+Foxp3+ cells, or memory CD4 T lymphocytes by $CD4^+$ $CD45RA^+$ $CD29^{low}$ cells, and multiple leukemic subclones can be identified based on CD33, CD45, HLA-DR, CD11b. These examples are merely illustrative.

Thus, the discrete cell populations can be gated according to markers that are known to segregate different cell types or cell sub-types. The division into discrete cell populations can be relatively broad or quite narrow, or anything in between, depending on the level of information desired. For example, at one extreme, cells in a culture containing mainly hematopoietic-derived cells can be gated as myelod cells and lymphocytes. A further narrowing would be to gat CD4+ T cells, CD4− T cells, B cells, and monocytes and monocyte-derived cells. See, e.g., Examples 8-14. The cells can be even further subdivided into more finely defined populations, for example: CD4 and CD8 T cell subsets can be gated as naïve, effector, memory, using markers: CD45RA, CD27, CD28, CCR7, CD57; B cells subsets can be gated as naïve, non-class switched memory, class switched memory, plasma cell, using markers: CD19, CD20, CD27, CD38, IgD; myeloid cells can be gated as granulocytes, monocytes, conventional dendritic cells, plasmacytoid dendritic, myeloid derived suppressor cells, markers CD14, CD15, CD16, CD11b, CD11c, CD33, CD123, HLA-DR. Any suitable classification and gating scheme for examining discrete cell populations in a culture containing a plurality of discrete cell populations may be used.

Alternatively, or in addition, a user may identify discrete cell populations/subpopulations based on intracellular markers, such as transcription factors or other intracellular proteins; based on a functional assay (e.g., dye efflux assay to determine drug transporter+cells or fluorescent glucose uptake) or based on other markers, e.g., fluorescent markers. Other biological processes that affect the status of a cellular constituent may also be used to identify a cell population. Examples include the translocation of biomolecules or changes in their turnover rates and the formation and disassociation of complexes of biomolecule. Such complexes can include multi-protein complexes, multi-lipid complexes, homo- or hetero-dimers or oligomers, and combinations thereof. Other characteristics include proteolytic cleavage, e.g. from exposure of a cell to an extracellular protease or from the intracellular proteolytic cleavage of a biomolecule.

In some embodiments, gates are used to identify the presence of specific discrete populations and/or subpopulations in existing independent data. The existing independent data can be data stored in a computer from a previous patient, or data from independent studies using different patients.

In certain embodiments of the invention, the plurality of discrete cell populations in communication in the culture are immune cell populations. FIG. 1 shows an example of a plurality of discrete cell populations in the immune system and present in the blood, and some of the factors by which they communicate. For example, without intending to be limited to any theory, several different cell types participate as part of the immune system, including B cells, T cells, macrophages, neutrophils, basophils and eosinophils. Each of these cell types has a distinct role in the immune system, and communicates with other immune cells, e.g., using secreted cytokines, including interleukins, TNF, and the interferons. Macrophages, derived from monocytes, phagocytose self and foreign bodies and are antigen-presenting cells (APCs), using cytokines to stimulate specific antigen dependent responses by B and T cells and non-specific responses by other cell types. Dendritic cells, also derived from monocytes, can also serve as APCs. Cell signaling is also initiated directly by cell-cell contact at the immunological synapse formed between APCs and T cells. T cells secrete a variety of factors to coordinate and stimulate immune responses to specific antigen, such as the role of helper T cells in B cell activation in response to antigen. The proliferation and activation of eosinophils, neutrophils and basophils respond to cytokines as well. Each of the cytokines is secreted by one set of cells and provokes a response in another target set of cells, often including the cell that secretes the cytokine. In a PBMC sample the system is further simplified in that erythrocytes and polymorphonuclear cells have been removed.

In certain embodiments the different discrete cell populations are hematopoietic cell populations. Examples of hematopoietic populations include, but are not limited to, pluripotent hematopoietic stem cells, B-lymphocyte lineage progenitor or derived cells, T-lymphocyte lineage progenitor or derived cells, NK cell lineage progenitor or derived cells, granulocyte lineage progenitor or derived cells, monocyte lineage progenitor or derived cells, megakaryocyte lineage progenitor or derived cells and erythroid lineage progenitor or derived cells.

In Communication.

Cells communicate by a variety of means that are well-known in the art. These include release of intracellular communication messengers by cells of one or more discrete cell populations that interact with cells of another discrete cell population, and cell-cell interaction. Intracellular communication messengers include cytokines, growth factors, exosomes, and hormones. In embodiments of the invention in which the discrete cell populations in communication are immune cells, a typical intercellular communication messenger is a cytokine, e.g., interleukins, tumor necrosis factors (TNFs), interferons (IFNs), and the like. Cytokines of interest in the invention are discussed more fully elsewhere herein. Growth factors of interest can include EPO, G-CSF, GM-CSF, FLT3 ligand, TPO, TGF-b, and/or VEGF. In general, hematopoietic-derived cells are not thought to make hormones, but can be influenced by hormones or neurotransmitters from other cell types, such as epinephrine and norepinephrine, which in certain embodiments may be present in the culture and/or added to the culture.

The methods and compositions of the invention are used with a sample that has been removed from the body of an individual, e.g., a blood sample or a peripheral blood mononuclear (PBMC) sample. Thus, the plurality of discrete cell populations has been isolated from the whole body and the overall communication in the system is not necessarily the same as would occur in the milieu of the body—e.g., for a whole blood sample, contact with non-blood tissue is not present, hormonal signals from non-blood cells will not influence the communication, factors released from tissue such as muscle tissue, liver tissue, and the like during the time course of incubation are not present, and the like. In this sense, the assays used in the invention are performed on a simplified, non-natural sample, outside of its natural environment under artificial, controlled conditions. In the case of a PBMC sample, entire classes of cells normally present in the blood have been removed and, in many cases, the sample has been cryopreserved and thawed before use in the invention.

More generally regarding intercellular communication, in response to tissue injury, a multifactorial network of chemical signals initiate and maintain a host response designed to heal the afflicted tissue. When a condition such as cancer is present in an individual the homeostasis in, e.g., tissue, organ and/or microenvironment is perturbed. For example, there can be signaling effects in circulating immune cells, such as T cells that indirectly indicate a disease stated. Also, neoplasia-associated angiogenesis and lymphangiogenesis produces a chaotic vascular organization of blood vessels and lymphatics where neoplastic cells interact with other cell types (mesenchymal, haematopoietic and lymphoid) and a remodelled extracellular matrix. Neoplastic cells produce an array of cytokines and chemokines that are mitogenic and/or chemoattractants for granulocytes, mast cells, monocytes/macrophages, fibroblasts and endothelial cells. In addition, activated fibroblasts and infiltrating inflammatory cells secrete proteolytic enzymes, cytokines and chemokines, which are mitogenic for neoplastic cells, as well as endothelial cells involved in neoangiogenesis and lymphangiogenesis. Other factors include IDO, which is produced by antigen presenting cells, to decrease T cell response. See Ethan Shevach, Immunity, 30, May 22, 2009, pages 636-645 and U.S. Pat. Pub. 2006/0292618. These factors can potentiate tumor growth, stimulate angiogenesis, induce fibroblast migration and maturation, and enable metastatic spread via engagement with either the venous or lymphatic networks. Thus, determining the activation state data of various cell populations in culture derived from a sample from an individual provides a better picture of the status of the individual and/or the state of the cellular network, and the cultures of the invention provide a simplified and artificial environment, e.g., not in contact with the tumor itself or indeed with any other tissues of the body, in which to examine partial cellular networks, removed from the overall cellular network milieu of the body.

Similarly, in autoimmune conditions, much attention has recently been focused on the use of biologics, which are molecules that affect intercellular communication in the immune cell network. In a condition like rheumatoid arthritis (RA) contributions made by interactions between dendritic cells, T cells and other immune cells, and local production of cytokines and chemokines may contribute to the pathogenesis of RA. These cells further interact with local cells (e.g. synoviocytes). In response to local inflammation and production of proinflammatory cytokines, after an unknown event, dendritic cells, T cells and other immune cells are attracted to the synovium in response to local production of cytokines and chemokines. In some patients with rheumatoid arthritis, chronic inflammation leads to the destruction of the cartilage, bone, and ligaments, causing deformity of the joints. Damage to the joints can occur early in the disease and be progressive. As with cancer, the cultures of the invention provide a simplified and artificial environment in which to examine partial cellular networks, e.g., not in contact with the synovium and all the other tissues of the body.

In some disease states (e.g. cancer) the tumor escapes eradication by the immune system by creating an immune-suppressive environment. Therefore, determining the activation state of cells in the immune compartment by stimulation of intercellular immune cell communication by use of a modulator that acts on certain discrete cell population or populations in a sample can provide valuable information to, e.g., reveal the mechanism by which the tumor evades an immune response, in an artificial culture removed from the complex natural milieu of the body as a whole. This information can be used to guide all phases of immunotherapy development, ranging from discovery of drug targets, to drug development in both the laboratory and clinical trials, to patient diagnosis and treatment selection. In other disease states, such as autoimmune disease, the intercellular communication itself may be abnormal, and stimulation of such communication by use of a modulator that acts on certain discrete cell population or populations in a sample can provide valuable information to inform, e.g., from discovery of drug targets, to drug development in both the laboratory and clinical trials, to patient diagnosis and treatment selection. In the present invention, a simplified, artificial sample condition is used which, though it does not match the natural in vivo condition, and in which the exact natural interactions, far more complex than the interactions in the simplified culture of the invention, nonetheless can provide information useful in determining the status of an individual, selecting potential therapeutics, and the like. In addition, many of the modulators used in the present invention are not naturally present in the body, either under normal circumstances or under any circumstances, but nonetheless provide useful information by stimulating intercellular communication in a network of discrete cell populations.

In some embodiments, the activation state data of one or a plurality of populations of cells is determined by analyzing multiple single cells in each population (e.g. by flow cytometry). Measuring multiple single cells in each discrete cell population in an individual provides multiple data points that in turn allows for the determination of the network boundaries in the individual. Measuring modulated networks at a single cell level provides the level of biologic resolution that allows the assessment of intrapatient clonal heterogeneity ultimately relevant to disease management and outcome. The network boundaries and/or the state of the network might change when the individual is suffering from a pathological condition or if the individual is responding or not responding to treatment. Thus, the determination of network boundaries and/or the state of the network can be used for diagnosis, prognosis of a condition or determination of outcome after administering a therapeutic to treat the condition.

III. Samples, Sampling, and Cultures

The invention involves analysis of cultures containing a plurality of discrete cell populations, where the cultures are derived from one or more samples removed from an individual or individuals. An individual or a patient is any multi-cellular organism; in some embodiments, the individual is an animal, e.g., a mammal. In some embodiments, the individual is a human. In all cases, the culture is derived from a sample that has been removed from the individual and placed in an environment in which it is no longer in contact with, and interacting with, the body as a whole, and any cells and cell populations involved in events in the culture are thus removed from interactions with cells, tissues, and organs of the body, and any factors produced by the cells, tissues, and organs, that would normally and naturally occur in a natural, i.e., whole-body, setting.

The sample may be any suitable type that allows for the derivation of a culture for the analysis of different discrete populations of cells. Samples may be obtained once or multiple times from an individual. Multiple samples may be obtained from different locations in the individual (e.g., blood samples, bone marrow samples and/or lymph node samples), at different times from the individual (e.g., a series of samples taken to monitor response to treatment or to monitor for return of a pathological condition), or any combination thereof. These and other possible sampling combinations based on the sample type, location and time of sampling allows for the detection of the presence of pre-pathological or pathological cells, the measurement treatment response and also the monitoring for disease.

When samples are obtained as a series, e.g., a series of blood samples obtained after treatment, the samples may be obtained at fixed intervals, at intervals determined by the status of the most recent sample or samples or by other characteristics of the individual, or some combination thereof. For example, samples may be obtained at intervals of approximately 1, 2, 3, or 4 weeks, at intervals of approximately 1, 2, 3, 4, 5, 6, 7, 8, 9, 10, or 11 months, at intervals of approximately 1, 2, 3, 4, 5, or more than 5 years, or some combination thereof. It will be appreciated that an interval may not be exact, according to an individual's availability for sampling and the availability of sampling facilities, thus approximate intervals corresponding to an intended interval scheme are encompassed by the invention. As an example, an individual who has undergone treatment for a cancer may be sampled (e.g., by blood draw) relatively frequently (e.g., every month or every three months) for the first six months to a year after treatment, then, if no abnormality is found, less frequently (e.g., at times between six months and a year) thereafter. If, however, any abnormalities or other circumstances are found in any of the intervening times, or during the sampling, sampling intervals may be modified.

Generally, the most easily obtained samples are fluid samples. Fluid samples include normal and pathologic bodily fluids and aspirates of those fluids. Fluid samples also comprise rinses of organs and cavities (lavage and perfusions). Bodily fluids include whole blood, samples derived from whole blood such as peripheral blood mononuclear cells (PBMCs), bone marrow aspirate, synovial fluid, cerebrospinal fluid, saliva, sweat, tears, semen, sputum, mucus, menstrual blood, breast milk, urine, lymphatic fluid, amniotic fluid, placental fluid and effusions such as cardiac effusion, joint effusion, pleural effusion, and peritoneal cavity effusion (ascites). Rinses can be obtained from numerous organs, body cavities, passage ways, ducts and glands. Sites that can be rinsed include lungs (bronchial lavage), stomach (gastric lavage), gastrointestinal track (gastrointestinal lavage), colon (colonic lavage), vagina, bladder (bladder irrigation), breast duct (ductal lavage), oral, nasal, sinus cavities, and peritoneal cavity (peritoneal cavity perfusion).

In certain embodiments the sample from which a culture containing a plurality of discrete cell populations is derived is blood. The blood may be untreated or minimally treated, beyond having been removed from the natural and more complex milieu of the body of the individual. In certain embodiments, the sample is treated by methods well-known in the art to contain only, or substantially only, PBMC.

Solid tissue samples may also be used, either alone or in conjunction with fluid samples. Solid samples may be derived from individuals by any method known in the art including surgical specimens, biopsies, and tissue scrapings, including cheek scrapings. Surgical specimens include samples obtained during exploratory, cosmetic, reconstructive, or therapeutic surgery. Biopsy specimens can be obtained through numerous methods including bite, brush, cone, core, cytological, aspiration, endoscopic, excisional, exploratory, fine needle aspiration, incisional, percutaneous, punch, stereotactic, and surface biopsy.

Samples may include circulating tumor cells (CTC). Methods for isolating CTC are known in the art. See for example: Toner M et al. Nature 450, 1235-1239 (20 Dec. 2007); Lustenberger P et al. Int J Cancer. 1997 Oct. 21; 74(5):540-4; Reviews in Clinical Laboratory Sciences, Volume 42, Issue 2 Mar. 2005, pages 155-196; and Biotechno, pp. 109-113, 2008 International Conference on Biocomputation, Bioinformatics, and Biomedical Technologies, 2008.

In some embodiments, the sample is a blood or PMBC sample. In some embodiments, the sample is a bone marrow sample. In some embodiments, the sample is a lymph node sample. In some embodiments, the sample is cerebrospinal fluid. In some embodiments, combinations of one or more of a blood, bone marrow, cerebrospinal fluid, and lymph node sample are used.

Certain fluid samples can be analyzed in their native state, though isolated and removed from the natural milieu of the whole body, with or without the addition of a diluent or buffer. Alternatively, fluid samples may be further processed to obtain enriched or purified discrete cell populations prior to analysis. Numerous enrichment and purification methodologies for bodily fluids are known in the art. A common method to separate cells from plasma in whole blood is through centrifugation using heparinized tubes. By incorporating a density gradient, further separation of the lymphocytes from the red blood cells can be achieved. A variety of density gradient media are known in the art including sucrose, dextran, bovine serum albumin (BSA), FICOLL diatrizoate (Pharmacia), FICOLL metrizoate (Nycomed), PERCOLL (Pharmacia), metrizamide, and heavy salts such as cesium chloride. Alternatively, red blood cells can be removed through lysis with an agent such as ammonium chloride prior to centrifugation.

Whole blood can also be applied to filters that are engineered to contain pore sizes that select for the desired cell type or class. For example, rare pathogenic cells can be filtered out of diluted, whole blood following the lysis of red blood cells by using filters with pore sizes between 5 to 10 µm, as disclosed in U.S. patent application Ser. No. 09/790,673. Alternatively, whole blood can be separated into its constituent cells based on size, shape, deformability or surface receptors or surface antigens by the use of a microfluidic device as disclosed in U.S. patent application Ser. No. 10/529,453.

Select cell populations can also be enriched for or isolated from whole blood through positive or negative selection based on the binding of antibodies or other entities that recognize cell surface or cytoplasmic constituents. For example, U.S. Pat. No. 6,190,870 to Schmitz et al. discloses the enrichment of tumor cells from peripheral blood by magnetic sorting of tumor cells that are magnetically labeled with antibodies directed to tissue specific antigens.

Solid tissue samples may require the disruption of the extracellular matrix or tissue stroma and the release of single cells for analysis. Various techniques are known in the art including enzymatic and mechanical degradation employed separately or in combination. An example of enzymatic dissociation using collagenase and protease can be found in Wolters G H J et al. An analysis of the role of collagenase and protease in the enzymatic dissociation of the rat pancrease for islet isolation. Diabetologia 35:735-742, 1992. Examples of mechanical dissociation can be found in Singh, N P. Technical Note: A rapid method for the preparation of single-cell suspensions from solid tissues. Cytometry 31:229-232 (1998). Alternately, single cells may be removed from solid tissue through microdissection including laser capture microdissection as disclosed in Laser Capture Microdissection, Emmert-Buck, M. R. et al. Science, 274 (8):998-1001, 1996.

The cells can be separated from body samples by centrifugation, elutriation, density gradient separation, apheresis, affinity selection, panning, FACS, centrifugation with Hypaque, solid supports (magnetic beads, beads in columns, or other surfaces) with attached antibodies, etc. By using antibodies specific for markers identified with particular cell types, a relatively homogeneous population of cells may be obtained. Alternatively, a heterogeneous cell population can be used. Cells can also be separated by using filters. Once a sample is obtained, it can be used directly, frozen, or maintained in appropriate culture medium for short periods of time. Methods to isolate one or more cells for use according to the methods of this invention are performed according to standard techniques and protocols well-established in the art. See also U.S. Ser. Nos. 12/432,720 and 13/493,857 and U.S. Pat. No. 8,227,202. See also, the commercial products from companies such as BD and BCI. See also U.S. Pat. Nos. 7,381,535 and 7,393,656.

In some embodiments, the cells are cultured post collection in a media suitable for revealing the activation level of an activatable element (e.g. RPMI, DMEM) in the presence, or absence, of serum such as fetal bovine serum, bovine serum, human serum, porcine serum, horse serum, or goat serum. When serum is present in the media it could be present at a level ranging from 0.0001% to 30%.

IV. Modulators

A characteristic of certain embodiments of the invention is contacting a first cell from a first discrete cell population with a modulator in a culture containing a plurality of discrete cell populations in communication, where the modulator induces intercellular communication between the first discrete cell population and the second discrete cell population. In certain embodiments, the modulator interacts with the first discrete cell population but does not interact with a second discrete cell population in the culture, or does not substantially interact with the second discrete cell population. By "interact" is meant direct interaction, and does not include indirect interaction such as an effect on the second cell population mediated by an intercellular communication messenger released by the first cell population in response to the modulator. "Does not substantially interact," as used herein, encompasses either no interaction, or interaction that does not alter the second cell population in such a way as to alter intracellular events within the second discrete cell population to the same degree as the alteration of the first discrete cell population when it interacts with the modulator, such as less than 50%, 40%, 30%, 20%, 10%, 5%, or 1% of the alteration of the first discrete cell population, e.g., activation levels of one or more activatable elements within the cells of the second population attributable to the modulator are less than 50%, or less than 40%, or less than 30%, or less than 20%, or less than 10%, or less than 5%, or less than 1% of activation levels of the same elements in the first cell population, on average, at a given time point that is chosen so that an increase in intercellular communication messengers released by the first discrete cell population have not had a chance to significantly affect the second population, e.g, 1, 5, 10, 15, 20, 25, 30, 35, 40, 45, 50, 60, 70, 80, or 90 minutes after the culture is contacted with the modulator. Without being bound by theory, it is thought that the modulator induces intracellular events in the first discrete cell population that lead to intercellular communication with other discrete cell populations in the culture, including, directly or indirectly, the second discrete cell population. Direct communication could include, e.g., modulation of the second discrete cell population by intercellular communication messengers, e.g., cytokines released by the first discrete cell population in response to the modulator. Indirect communication could include, e.g., modulation of the second discrete cell population by intercellular communication messengers, e.g., cytokines released by a third discrete cell population in response to intercellular communication messengers, e.g., cytokines released by the first discrete cell population in response to the modulator, or in response to cell-cell contact between the first and third cell populations, or a combination thereof.

In certain embodiments the culture is a culture derived from a blood sample, such as whole blood or PBMC, and the plurality of discrete cell populations in communication are immune cells, and may include, e.g., monocytes and monocyte derivative cells (such as dendritic cells and/or macrophages), T cells, and B cells.

In certain of these embodiments, a modulator or modulators may be used that interacts with monocytes or monocyte derivatives, e.g., antigen presenting cells (APC) such as dendritic cells or macrophages, but that does not interact, or does not substantially interact, with at least one other discrete population of immune cells in the culture, e.g., T cells or B cells, or a subclass of T or B cells. An example is a TLR4 agonist, such as LPS or R848. These are merely exemplary and those of skill in the art are aware of many such modulators that stimulate monocytes and/or monocyte derivatives such as APCs preferentially while not interacting, or not substantially interacting, with at least one other class of immune cells present in the culture. Without being bound by theory, it is thought that in this case the modulator or modulators stimulate the monocytes or monocyte derivative, e.g. APC such as macrophages and/or dendritic cells, to produce intercellular communication messenger or messengers, e.g., cytokines, that modulate other immune cells, such as T cells and B cells, which can be followed over time. In addition one or more of the intercellular communication messengers may act on one or more of the originally modulated cells in a feedback loop which can be followed over time.

Alternatively, or in addition, a modulator or modulators may be used that interacts with T cells or a class of T cells, such as T helper (CD4+) cells, but that does not interact, or does not substantially interact, with at least one other discrete immune cell population present in the culture, e.g., monocytes or monocyte-derived cells, or B cells, or subclasses thereof. Examples include a T cell activator, or a TCR activator in combination with a costimulatory molecule, such as a CD3/CD28 agonist combination. These are merely exemplary and those of skill in the art are aware of many such modulators and modulator combinations that stimulate T cells or a class of T cells such as CD4+ T cells, without interacting or substantially interacting with at least one other class of immune cells present in a blood-derived culture, such as a PBMC culture. Without being bound by theory, it is thought that the stimulated T cells produce one or more intercellular communication messengers, such as cytokines, that that modulate other immune cells, such as B cells and/or other classes of T cells, which can be followed over time. In addition one or more of the intercellular communication messengers may act on one or more of the originally modulated cells in a feedback loop which can be followed over time.

In certain cases, a modulator is used that both stimulates monocytes or monocyte derivatives and that causes activation of a class of T cells, such as CD4+ cells, without interacting or without substantially interacting with at least one other class of immune cells in the culture, e.g., B cells. An example is Superantigen, discussed more fully below. Without being bound by theory, it is thought that the stimulated monocytes and/or monocyte derivatives and the stimulated T cell produce one or more intercellular communication messengers, e.g., cytokines, that then modulate other classes of immune cells in the culture, such as B cells, which can be followed over time. In addition one or more of the intercellular communication messengers may act on one or more of the originally modulated cells in a feedback loop which can be followed over time.

More generally, any suitable modulator may be used that interacts with one discrete cell population in the culture but that does not interact or does not substantially interact with at least one other discrete cell population in the culture, where the discrete cell populations in the culture are in communication.

Thus, classes of modulators useful in the invention include toll-like receptor (TLR) modulators; Superantigens; T cell modulators; B cell modulators; costimulatory modulators that can be used in conjunction with other modulators; and modulators that affect Fc Receptor signaling on NK cells and monocytes.

It will be appreciated that combinations of modulators may be used, e.g., LPS and CD3/CD28 agonists.

In certain embodiments, the modulator is a TLR modulator. In certain of these embodiments, the modulator is a TLR agonist. TLR agonists are well-known in the art, and any such suitable agonist may be used, provided that it interacts with one discrete cell population in the culture that is a population expressing a TLR but does not interact, or does not substantially interact, with another discrete cell population in the culture. Exemplary agonists include LPS (acts on TLR4), R848 (acts on TLR7/8), Pam3CSK4 (acts on TLR1/2), and CpG DNA and ODNs (act on TLR9). Other potential modulators of TLR are known in the art, see, e.g., modulators available from Invivogen at http://www.invivogen.com/index.php. A sample of modulators is listed in Table 1. In certain embodiments, the modulator is LPS. See Example 14. Without being bound by theory, LPS mediated signaling (PI3K, MAPK, NF-KB) induces cytokine secretion (IL1b, IL-6, TNFα) by APCs. Then, T cells respond to cytokines with activation of STAT and other pathways. In certain embodiments, the modulator is R848. In certain embodiments, the modulator is Pam3CSK4. In certain embodiments, the modulator is CpG DNA or ODN.

TABLE 1

| TLR | Immune Cell Expresion | Pathogen-associated microbial patterns (PAMP) | Danger-associated molecular patterns (DAMP) |
| --- | --- | --- | --- |
| TLR1 + TLR2 | Cell surface Mo, MΦ, DC, B | Triacylated lipoproteins (Pam3CSK4) Peptidoglycans, Lipopolysaccharides | (TLR2 DAMPs listed below) |
| TLR2 + TLR6 | Cell surface Mo, MΦ, MC, B | Diacylated lipoproteins (FSL-1) | Heat Shock Proteins (HSP 60, 70, Gp96) High mobility group proteins (HMGB1) Proteoglycans (Versican, Hyaluronic Acid fragments) |

TABLE 1-continued

| TLR | Immune Cell Expresion | Pathogen-associated microbial patterns (PAMP) | Danger-associated molecular patterns (DAMP) |
|---|---|---|---|
| TLR3 | Endosomes B, T, NK, DC | dsRNA (poly (I:C)) tRNA, siRNA | mRNA tRNA |
| TLR4 | Cell surface/ endosomes Mo, MΦ, DC, MC, IE | Lipopolysaccharides (LPS) Paclitaxel | Heat Shock Proteins (HSP22, 60, 70, 72, Gp96) High mobility group proteins (HMGB1) Proteoglycans (Versican, Heparin sulfate, Hyaluronic Acid fragments) Fibronectin, Tenascin-C |
| TLR5 | Cell surface Mo, MΦ, DC, IE | Flagellin | |
| TLR7 | Endosomes Mo, MΦ, DC, B | ssRNA Imidazoquinolines (R848) Guanosine analogs (Loxoribine) | ssRNA |
| TLR8 | Endosomes Mo, MΦ, DC, MC | ssRNA, Imidazoquinolines (R848) | ssRNA |
| TLR9 | Endosomes Mo, MΦ, DC, B, T | CpG DNA CpG ODNs | Chromatin IgG complex |
| TLR10 | Endosomes Mo, MΦ, DC | profilin-like proteins | |

Mo: monocytes,
MΦ: macrophages,
DC: dendritic cells,
MC: Mast cells,
B: B cells,
T: T cells,
IE: Intestinal epithelium,
IC: Inflammatory cytokines In certain embodiments, the modulator is a Superantigen (SAg) or a combination of Superantigens. Superantigens are well-known in the art, and any suitable SAg or combination of Sags may be used, provided that it interacts with one or more discrete cell population in the culture but does not interact, or does not substantially interact, with another discrete cell population in the culture.

Superantigens are microbial or viral toxins that are potent immunostimulatory molecules. They bind the MHC class-II molecules and cause non-specific activation of T-cells resulting in polyclonal T cell activation and massive cytokine release. SAgs can be produced by pathogenic microbes (including viruses, mycoplasma, and bacteria) as a defense mechanism against the immune system. Compared to a normal antigen-induced T-cell response where 0.001-0.0001% of the body's T-cells are activated, these SAgs are capable of activating up to 83% of the body's T-cells. These properties are based on their ability to cross link MHC class-II and the T Cell receptor.

The large number of activated T-cells secrete large amounts of cytokines. See FIG. 1 for cytokines that are released by immune system cells, and FIG. 3 for a model of Superantigen action on APCs and T cells (B cells not shown in the Figure).

SAg stimulation of antigen presenting cells and T-cells elicits a response that is mainly inflammatory, focused on the action of Th1 T-helper cells. Some of the major products are IL-1, IL-2, IL-6, TNF-α, gamma interferon, macrophage inflammatory protein 1α (MIP-1α), MIP-1β, and monocyte chemoattractant protein 1 (MCP-1).

Superantigens can be broadly divided into the following families: Endogenous; exogenous, and B-cell. Endogenous SAgs are encoded by viruses into the genome, such as MMTV and EBV.

In certain embodiments the modulator comprises one or more exogenous Sags. Exogenous SAgs are secreted by bacteria, and include Staphylococcal enterotoxins (SEs): A, B, C1 to C3, D, E, G to Q; Saphylococcal toxic shock syndrome toxin-1 (TSST-1); Staphylococcal exfoliative toxins: exoliatin A, exfoliatin B; Staphylococcal enterotoxin-like toxins formed due to recombination within enterotoxin gene cluster: U2, V; Streptococcal pyrogenic exotoxins (SPEs): A1 to A4, C, G to M; Streptococcal mitogenic exotoxins: SMEZ; Streptococcal superantigen: SSA; *Yersinia pseudotuberculosis:* Yersinia pseudotuberculosis-derived mitogen (YAM); *Mycoplasma* species: *Mycoplasma arthritidis*-derived mitogen (MAM); Cholera toxin: subunit A of cholera toxin; *Prevotella intermedia; Mycobacterium tuberculosis;* Viral superantigens: (a) Mouse leukemia virus; (b) IDDMK1222-Ppol-ENV-U3; (c) HIV-Nef; and (d) Rabies virus-nucleoside protein. One or more of these Superantigens may be used as a modulator in certain embodiments of the invention.

In certain embodiments, the modulator comprises one or more of Staphylococcal enterotoxin A (SEA), Staphylococcal enterotoxin B (SEB), and/or Staphylococcal exotoxin TSST. Staphylococcal enterotoxins are reviewed in Balaban and Rasooly International Journal of Food Microbiology, Vol. 61, Issue 1, Oct. 1, 2000, pages 1-10. See also Solanki, et. Al., Dermatology Online Journal 14 (2):3. They are commercially available from Toxin Technologies in Sarasota, Fla. In certain embodiments, the Superantigen is a combination of SEA, SEB, and TSST. See, e.g., Examples 8-13.

As stated above, Staphylococcal enterotoxins A and B are enterotoxins produced by the bacterium *Staphylococcus aureus*. Toxic shock syndrome toxin (TSST) is a superantigen with a size of 22 KDa produced by 5 to 25% of

*Staphylococcus aureus* isolates. It causes toxic shock syndrome (TSS) by stimulating the release of large amounts of interleukin-1, interleukin-2 and tumor necrosis factor.

In certain embodiments, the modulator comprises one or more B-Cell Superantigens. The B-cell superantigens are those superantigens which stimulate predominantly B cells. Examples include staphylococcal protein A and protein Fv. See generally Acharya K R, Baker M D. Superantigen: structure-function relationships. Int J Med Microbiol 2004; 293: 529-37; and Ware R E. Immune abnormalities secondary to infectious diseases. In: Rich R R, Fleisher T A, Shearer W T, Kotzin B L, Schroeder H W, editors. Textbook of clinical immunology: principles and practice. New York: Mosby; 2001. pp. 43.1-43.7. B cell Sags include Staphylococcal protein A and Protein Fv (PFv).

When a SAg such as SEA or SEB is added to a cell culture, such as a culture derived from whole blood, e.g., PBMC culture, they cross link MHC II and other potentially costimulatory molecules on an APC, such as a macrophage or a dendritic cell. MHC II signaling induces antigen presenting cell (APC) activation and maturation, and cytokines are produced like IL1 beta and TNF alpha. Thus, without being bound by theory, one effect of Superantigens like SEA and SEB appears to be on the APC itself, and this alone induced intercellular communication with other cells in the culture. In addition, the Superantigen (e.g., SEA)/MHC II complex engages the T cell receptor (TCR) on T cells, leading to non-specific T cell activation. The T cell produces cytokines such as IL-2, IFN gamma, and TNF alpha, leading to further intercellular communication. When LPS is added to immune cells, APCs detect it via the toll like receptor 4 (TLR4).

In certain embodiments, the modulator is a T cell modulator, e.g. a T cell activator. T cell modulators, e.g., T cell activators are well-known in the art, and any such suitable modulator or combination of modulators may be used, provided that it interacts with one discrete cell population in the culture that is a T cell population but does not interact, or does not substantially interact, with another discrete cell population in the culture, to modulate the activity of the T cells, e.g., to activate the T cells. Examples include TCR crosslinkers, and certain anti-CD3 antibodies, certain anti-CD28 antibodies (such as TGN1412, also known as CD28-SuperMAB), which even used singly can cause massive activation of T cells to cause intercellular communication with other cells. In certain embodiments, T cell activation is achieved by use of a CD3/CD28 agonist combination. See, e.g., Example 18. In certain cases, cytokines are known to preferentially interact with T cells, or subclasses of T cells, e.g., IL-12, which acts mainly on activated, TH1 biased CD4+ T cells, IL-23, which acts mainly on memory CD4+ T cells, or IL2, which activates T cells. Many other T cell activators are known in the art.

B cell modulators, such as B cell activators are well-known in the art, and any such suitable modulator or combination of modulators may be used, provided that it interacts with one discrete cell population in the culture that is a B cell population but does not interact, or does not substantially interact, with another discrete cell population in the culture, to modulate the activity of the B cells, e.g., to activate the B cells. Examples include BCR crosslinkers, IgM, IgD, or IgG crosslinkers, such as F(Ab)$_2$IgM. Activators include antibodies or molecular binding entities that recognize cell surface markers or receptors including B cell receptor complex, B cell co-receptor complex or surface immunoglobulins. In one embodiment, cell surface markers, receptors or immunoglobulins are crosslinked by the activators. In a further embodiment, the crosslinking activator is a polyclonal IgM antibody, a monoclonal IgM antibody, F(ab)$_2$IgM, biotinylated F(ab)$_2$IgM, biotinylated polyclonal anti-IgM, or biotinylated monoclonal anti-IgM. In some embodiments, the modulator is a B cell receptor modulator. In some embodiments, the B cell receptor modulator is a B cell receptor activator.

An example of B cell receptor activator is a cross-linker of the B cell receptor complex or the B-cell co-receptor complex. In some embodiments, cross-linker is an antibody or molecular binding entity. In some embodiments, the cross-linker is an antibody. In some embodiments, the antibody is a multivalent antibody. In some embodiments, the antibody is a monovalent, bivalent, or multivalent antibody made more multivalent by attachment to a solid surface or tethered on a nanoparticle surface to increase the local valency of the epitope binding domain.

In some embodiments, the cross-linker is a molecular binding entity. In some embodiments, the molecular binding entity acts upon or binds the B cell receptor complex via carbohydrates or an epitope in the complex. In some embodiments, the molecular is a monovalent, bivalent, or multivalent is made more multivalent by attachment to a solid surface or tethered on a nanoparticle surface to increase the local valency of the epitope binding domain.

In some embodiments, the cross-linking of the B cell receptor complex or the B-cell co-receptor complex comprises binding of an antibody or molecular binding entity to the cell and then causing its crosslinking via interaction of the cell with a solid surface that causes crosslinking of the BCR complex via antibody or molecular binding entity.

In some embodiments, the crosslinker is F(ab)$_2$IgM, IgG, IgD, polyclonal BCR antibodies, monoclonal BCR antibodies, or Fc receptor derived binding elements. In some embodiments, the Ig is derived from a species selected from the group consisting of mouse, goat, rabbit, pig, rat, horse, cow, shark, chicken, or llama. In some embodiments, the crosslinker is F(ab)$_2$IgM, Polyclonal anti-IgM, Monoclonal anti-IgM, Biotinylated F(ab)$_2$IgM, Biotinylated Polyclonal anti-IgM, or Biotinylated Monoclonal anti-IgM.

Costimulatory modulators are modulators that can be used in conjunction with other modulators, such as agonists of costimulation activators (e.g., CD28 agonists) or antagonists of costimulation inhibitors (e.g., CTLA4 antagonists).

Modulators that affect Fc Receptor signaling on NK cells and monocytes are illustrated by the following example: 1) Add antibody to bind the FcR and then crosslink that antibody. 2) Add antibody against CD16 and then crosslink it 3) Add Rituximab, which binds CD20 on B cells and FcR on NK cells and induces NK cell signaling/killing.

Modulation can be performed in a variety of environments. In all cases, the environment is a non-natural environment that is not the same as the environment in which the cells are naturally found, i.e., in the body of the individual. The methods of the invention involve modulating the culture, then evaluating the culture or a sample from the culture at a later time. Thus, the environment, for example, lacks certain factors found in the natural environment over the time course of the assays (e.g., entire classes of cells in the case of a PBMC sample, or factors secreted or absorbed by non-blood cells over the course of the assay) and/or includes factors not found in the normal environment, such as buffers and the like, or, e.g. in the case of some PBMC samples, cryopreservation followed by thawing. In some embodiments, cells comprising discrete cell populations are exposed to a modulator immediately after collection. In some embodiments where there is a mixed population of cells, purification of cells is performed after modulation. In some embodiments, whole blood is collected to which a modulator is added. In some embodiments, cells are modulated after processing for single cells or purified fractions of single cells. As an illustrative example, whole blood can be collected and processed for an enriched fraction of lymphocytes that is then exposed to a modulator. Modulation can include exposing cells to more than one modulator. For instance, in some embodiments, cells comprising discrete cell populations are exposed to at least 2, 3, 4, 5, 6, 7, 8, 9, or 10 modulators. See U.S. patent application Ser. No. 12/432,239 which is incorporated by reference.

In some embodiments, cells comprising discrete cells populations are cultured post collection in a suitable media before exposure to a modulator or modulators. In some embodiments, the media is a growth media. In some embodiments, the growth media is a complex media that may include serum. In some embodiments, the growth media comprises serum. In some embodiments, the serum is selected from the group consisting of fetal bovine serum, bovine serum, human serum, porcine serum, horse serum, and goat serum. In some embodiments, the serum level ranges from 0.0001% to 30%. In some embodiments, the growth media is a chemically defined minimal media and is without serum. In some embodiments, cells are cultured in a differentiating media.

More generally, modulators include chemical and biological entities, and physical or environmental stimuli. Modulators can act extracellularly or intracellularly. Chemical and biological modulators include growth factors, cytokines, drugs (such as anticancer drugs), immune modulators, ions, neurotransmitters, adhesion molecules, hormones, small molecules, inorganic compounds, polynucleotides, antibodies, natural compounds, lectins, lactones, chemotherapeutic agents, biological response modifiers, carbohydrate, proteases and free radicals. Modulators include complex and undefined biologic compositions that may comprise cellular or botanical extracts, cellular or glandular secretions, physiologic fluids such as serum, amniotic fluid, or venom. Physical and environmental stimuli include electromagnetic, ultraviolet, infrared or particulate radiation, redox potential and pH, the presence or absences of nutrients, changes in temperature, changes in oxygen partial pressure, changes in ion concentrations and the application of oxidative stress. Modulators can be endogenous or exogenous and may produce different effects depending on the concentration and duration of exposure to the single cells or whether they are used in combination or sequentially with other modulators. Modulators can act directly on the activatable elements or indirectly through the interaction with one or more intermediary biomolecule. Indirect modulation includes alterations of gene expression wherein the expressed gene product is the activatable element or is a modulator of the activatable element.

In some embodiments the modulator is selected from the group consisting of growth factors, cytokines, adhesion molecules, drugs, hormones, small molecules, polynucleotides, antibodies, natural compounds, lactones, chemotherapeutic agents, immune modulators, carbohydrates, proteases, ions, reactive oxygen species, peptides, and protein fragments, either alone or in the context of cells, cells themselves, viruses, and biological and non-biological complexes (e.g. beads, plates, viral envelopes, antigen presentation molecules such as major histocompatibility complex). In some embodiments, the modulator is a physical stimuli such as heat, cold, UV radiation, and radiation. Examples of modulators include the SAgs listed and discussed below.

Other modulators include, but are not limited to IFN-α, IFN-γ, IL-10, IL-6, IL-27, G-CSF, FLT-3L, IGF-1, M-CSF, SCF, PMA, Il-15, anti-IgM, anti CTLA-4, anti-CD3, anti-CD28, R848, Il-21, PD-L1.fc, anti PD-1, IL-3, IL-4, GM-CSF, EPO, LPS, TNF-α, and CD40L.

In some embodiments, the modulator is an activator. In some embodiments the modulator is an inhibitor. In some embodiments, cells are exposed to one or more modulator. In some embodiments, cells comprising discrete cell populations are exposed to at least 2, 3, 4, 5, 6, 7, 8, 9, or 10 modulators. In some embodiments, cells comprising discrete cell populations are exposed to at least two modulators, wherein one modulator can be an activator and one modulator can be an inhibitor. In some embodiments, cells comprising discrete cell populations are exposed to at least 2, 3, 4, 5, 6, 7, 8, 9, or 10 modulators, where at least one of the modulators can be an inhibitor. In some embodiments, the different discrete cell populations are exposed to the same modulators. In some embodiments, the different discrete cell populations are exposed to different modulators. For example, in some embodiments, the different discrete cell populations are exposed to the one or more modulators, where the one or more modulators are the same between the different discrete cell populations. In other embodiments, the different discrete cell populations are exposed to the one or more modulators, where the one or more modulators are different between the different discrete cell populations.

In some embodiments, the cross-linker is a molecular binding entity. In some embodiments, the molecular binding entity is a monovalent, bivalent, or multivalent is made more multivalent by attachment to a solid surface or tethered on a nanoparticle surface to increase the local valency of the epitope binding domain.

In some embodiments, the inhibitor is an inhibitor of a cellular factor or a plurality of factors that participates in a cellular pathway (e.g. signaling cascade) in the cell. In some embodiments, the inhibitor is a phosphatase inhibitor. Examples of phosphatase inhibitors include, but are not limited to H2O2, siRNA, miRNA, Cantharidin, (−)-p-Bromotetramisole, Microcystin LR, Sodium Orthovanadate, Sodium Pervanadate, Vanadyl sulfate, Sodium oxodiperoxo (1,10-phenanthroline)vanadate, bis(maltolato)oxovanadium (IV), Sodium Molybdate, Sodium Perm olybdate, Sodium Tartrate, Imidazole, Sodium Fluoride, β-Glycerophosphate, Sodium Pyrophosphate Decahydrate, Calyculin A, Discodermia calyx, bpV(phen), mpV(pic), DMHV, Cypermethrin, Dephostatin, Okadaic Acid, NIPP-1, N-(9,10-Dioxo-9,10-dihydro-phenanthren-2-yl)-2,2-dimethyl-propionamide, α-Bromo-4-hydroxyacetophenone, 4-Hydroxyphenacyl Br, α-Bromo-4-methoxyacetophenone, 4-Methoxyphenacyl Br, α-Bromo-4-(carboxymethoxy)acetophenone, 4-(Carboxymethoxy)phenacyl Br, and bis(4-Trifluoromethylsulfonamidophenyl)-1,4-diisopropylbenzene, phenylarsine oxide, Pyrrolidine Dithiocarbamate, and Aluminium fluoride. In some embodiments, the phosphatase inhibitor is H2O2.

In some embodiments, the activation level of an activatable element in a discrete cell population is determined by contacting the discrete cell population with at least 2, 3, 4, 5, 6, 7, 8, 9, or 10 modulators. In some embodiments, the activation level of an activatable element in a discrete cell population is determined by contacting the discrete cell population with at least 2, 3, 4, 5, 6, 7, 8, 9, or 10 modulators where at least one of the modulators is an inhibitor. In some embodiments, the activation level of an activatable element in a discrete cell population is determined by contacting the discrete cell population with an inhibitor and a modulator, where the modulator can be an inhibitor or an activator. In some embodiments, the activation level of an activatable element in a discrete cell population is determined by contacting the discrete cell population with an inhibitor and an activator. In some embodiments, the activation level of an activatable element in a discrete cell population is determined by contacting the discrete cell population with two or more modulators. In some embodiments, the activation level of the same activatable element(s) is determined in different discrete cell populations. In some embodiments, the activation level of a different activatable element(s) is determined in different discrete cell populations. For example, in some embodiments, the activation level of the same activatable element(s) is determined in different discrete cell populations when the different discrete cells populations are exposed to one or more modulators, where the one or more modulators are the same between the different discrete cell populations. In some embodiments, the activation level of the same activatable element(s) is determined in different discrete cell populations when the different discrete cells populations are exposed to one or more modulators, where the one or more modulators are different between the different discrete cell populations. In some embodiments, the activation level of different activatable element(s) is determined in different discrete cell populations when the different discrete cells populations are exposed to one or more modulators, where the one or more modulators are the same between the different discrete cell populations. In some embodiments, the activation level of different activatable element(s) is determined in different discrete cell populations when the different discrete cells populations are exposed to one or more modulators, where the one or more modulators are different between the different discrete cell populations.

In some embodiments, the activation state a discrete cell population is determined by measuring the activation level of an activatable element when the population of cells is exposed to one or more modulators. The population of cells can be divided into a plurality of samples, and the activation state of the discrete cell population is determined by measuring the activation level of at least one activatable element in the samples after the samples have been exposed to one or more modulators. In some embodiments, the activation state different discrete cell populations are determined by measuring the activation level of an activatable element in each population of cells when each of the populations of cells is exposed to a modulator. The different populations of cells can be exposed to the same or different modulators. In some embodiments, the physiological status of different cell discrete populations is used to determine the status of an individual as described herein.

V. Intercellular Communication Messengers

Intercellular communication messengers are substances released by cells of a first discrete cell population that interact with a second discrete cell population (and which may also interact with the first discrete cell population in an autocrine loop) in such a way as to modulate the activity of the second discrete cell population, e.g., by modulating one or more intracellular pathways in the second cell population. In certain embodiments of the invention, activation levels of one or more activatable elements in one or more intracellular pathways of the second discrete cell population (and in some cases of the first discrete cell population) are measured in single cells of the population. In certain embodiments, levels of intercellular communication messengers are measured in single cells of the second discrete cell population (and in some cases of the first discrete cell population).

Intercellular communication messengers among cells of the immune system include cytokines, growth factors, hormones, and exosomes, and in certain embodiments of the invention, one or more of these types of intercellular communication messengers may be used. Exosomes are cell-derived vesicles that may express molecules that initiate signaling in other cells, for example, Dendritic cell-derived exosomes express MHC I, MHC II, and costimulatory molecules and have been proven to be able to induce and enhance antigen-specific T cell responses in vivo.

In certain embodiments, the intercellular communication messenger is a cytokine. Cytokines of interest include IL1, IL2, IL3, IL4, IL5, IL6, IL8, IL9, IL10, IL12, IL15, IL17A, IL17F, IL21, IL23, TNF☐, TNF☐, IFN☐, IFN☐, and IFN☐☐☐ In certain embodiments, the intercellular communication messenger is selected from the group consisting of IL-2, IL-6, and TNFα. However, cytokines are well-known in the art and any suitable cytokine or group of cytokines may be measured as appropriate to the response of the discrete cell population of interest.

In certain embodiments, intracellular levels of cytokines in single cells of one or more discrete cell populations are measured at one or more time points after modulation of the cells in culture. In addition, or alternatively, levels of one or more cytokines in a non-cellular fraction of the culture may be measured.

VI. Agents that Affect One or More Intracellular Communication Messengers

In certain embodiments of the invention, there is added to the culture, in addition to a modulator or modulators, a chemical or biological agent affecting one or more intercellular communication messengers and/or an agent or agents that affects one or more intracellular pathways involved in intercellular communication. An intracellular pathway may affect intercellular communication by affecting the expression and/or secretion of one or more intercellular communication messengers, or by affecting the proliferation of cells that produce one or more intercellular messengers, or by affecting cell-cell contact, or some combination of these. In some of these embodiments, the modulator or modulators need not necessarily be a modulator or modulators that interacts with a first discrete cell population in the culture but does not interact, or does not substantially interact, with a second discrete cell population of the culture. In other embodiments, the modulator or modulators interacts with a first discrete cell population in the culture but does not interact, or does not substantially interact, with a second discrete cell population of the culture.

In the case of agents that affect one or more intercellular communication messengers, any suitable agent may be used so long as it targets one, or a distinct group, of intercellular messengers and acts to alter the activity of the messenger. In some cases, the agent or agents is being screened for potential ability to affect one or more intercellular communication messengers, and in these cases, the approach is more empirical, with effects being tested and a determination made as to the potential usefulness of the agent (see Methods of Screening, below). The agent may be an agonist or antagonist of the intercellular communication messenger. In certain embodiments, the agent is an antagonist of an intercellular communication messenger, or an agent to be screened as a potential antagonist of an intercellular communication messenger. In particular, many anti-cytokine biologics of use, or suspected to be of use, as biologics in autoimmune conditions are of interest in certain embodiments of the invention. Such agents are well-known in the art, and any such agent, or any newly-developed agent or agent useful for another purpose whose use as a biologic in autoimmune disease is desired to be investigated, may be used. In certain embodiments, the agent is an antagonist of a cytokine or group of cytokines, or an agent to be screened as a potential antagonist of cytokine or group of cytokines. Examples include anti-cytokine antibodies, such as an antibody directed against a cytokine selected from the group consisting of IL1, IL2, IL3, IL4, IL5, IL6, IL8, IL9, IL10, IL12, IL15, IL17A, IL17F, IL21, IL23, TNF□, TNF□, IFN□, IFN□, and IFN□ In certain embodiments, the agent affecting an intercellular communication messenger is an antibody directed against a cytokine selected from the group consisting of IL-2, IL-6, IL-7, 11-15, IL-17, IL-23, and TNF□□□ In certain embodiments, the agent affecting an intercellular communication messenger is an antibody directed against a cytokine selected from the group consisting of IL-2, IL-6, and TNF□□□ In certain embodiments, the agent affecting an intercellular communication messenger is an antibody directed against a cytokine selected from the group consisting of IL-6 and TNF□□□ The Examples provide illustrations of the use of various agents that affect intercellular communication messengers.

Agents can also include antibodies to the cytokines, such as anti-TNFα therapeutic agents, such as infliximab (Remicade), adalimumab (Humira), certolizumab pegol (Cimzia), and golimumab (Simponi), or to a circulating receptor fusion protein such as etanercept (Enbrel). Other potential agents include an anti-IL-6 chimeric monoclonal antibody (CNTO 328), ALD518/BMS-945429, CNTO 136, CPSI-2364, and CDP6038. An anti-IL-17 compound includes ixekizumab (Lilly) and an anti-CTLA-4 includes Abatacept.

VII. Agents that Affect One or More Intracellular Pathways Involved in Intercellular Communication In addition to, or alternatively, in certain embodiments a chemical or biological agent is added to the culture that affects one or more intracellular pathways involved in intercellular communication. The intercellular pathway may be any pathway known in the art to be involved in intercellular communication, e.g., pathways involved in the alteration of expression and/or secretion of cytokines. In certain embodiments, the pathway may be a pathway not known to be involved in intercellular communication. Examples of intracellular pathways are described elsewhere herein, see, e.g., Signaling Pathways, and include the JAK/STAT pathway, the PI3 kinase pathway, the NFkB pathway, the MAPK pathway, and others as described herein.

In particular, agents that affect intracellular pathways thought to be involved in a condition for which a therapy is sought are useful in certain embodiments of the invention, and any such pathway, as known in the art or as discovered, can be the target of an agent. Exemplary conditions are cancer and autoimmune disease, and much research is focused on, e.g., costimulation modifiers in cancer (e.g., ipilimumab), as well as pathway modifiers such as CAL-101 and GDC-0941. Similar agents are of interest and under active development in autoimmune disease. Any existing or suspected agent that modifies one or more pathways involved in a condition may be used in the invention.

In certain embodiments, the agent is an agent that affects a pathway selected from the group consisting of a JAK/STAT pathway, an NFkB pathway, a MAPK pathway, and a PI3K pathway. In certain embodiments, the agent affects the JAK/STAT pathway, for example, a JAK inhibitor. Other inhibitors may be found in U.S. patent application Ser. No. 12/687,873, filed Jan. 14, 2000. An exemplary JAK inhibitor is Tofacitinib. In certain embodiments, the agent affects the PI3K pathway, for example, a PI3K inhibitor. Exemplary PI3K inhibitors include GDC-0941 and CAL-101. Other inhibitors may be found in U.S. patent application Ser. No. 12/703,741, filed Feb. 10, 2010.

In certain embodiments, the agent is a kinase inhibitor.

VIII. Time Period of Incubation of the Culture

The invention involves modulation of a culture containing a plurality of discrete cell populations in communication, then measuring characteristics of single cells of at least one discrete cell population in the culture at some time after modulation, e.g., the activation level of an activatable element. In general, the characteristic, e.g., activation level of an activated element, is compared to the characteristic measured at an earlier timepoint, and/or measured in a culture that has not been contacted with a modulator and/or not been contacted with an agent. Because it is desired to measure the effects of intercellular communication, sufficient time must be allowed so that such communication takes place. Though time periods as short as minutes, e.g., 45 min, may be used, in general such short time periods will not allow examination of the effects of modulation of one discrete cell population on another discrete cell population, though they will allow examination of effects of the modulator on the cell population with which it preferentially interacts. Thus, for example, in cells stimulated with LPS or with SAg, activation of monocytes is seen in a time period as short as 45 min. See Examples. In general, a time period of hours or even days may be used. In certain embodiments, a series of measurements is taken over a time period of hours to days, thus kinetic analysis may be performed.

In certain embodiments, the time period after addition of modulator for at least one measurement is in the range of 30 min to 96 hours, or 45 min to 96 hours, or 1 hr to 96 hours, or 2 hours to 96 hours, or 3 hours to 96 hours, or 4 hours to 96 hours, or 5 hours to 96 hours, or 6 hours to 96 hours, or 7 hours to 96 hours, or 8 hours to 96 hours, or 9 hours to 96 hours, or 10 hours to 96 hours, or 12 hours to 96 hours, or 14 hours to 96 hours, or 16 hours to 96 hours, or 18 hours to 96 hours, or 20 hours to 96 hours, or 22 hours to 96 hours, or 24 hours to 96 hours, or 30 min to 72 hours, or 45 min to 72 hours, or 1 hr to 72 hours, or 2 hours to 72 hours, or 3 hours to 72 hours, or 4 hours to 72 hours, or 5 hours to 72 hours, or 6 hours to 72 hours, or 7 hours to 72 hours, or 8 hours to 72 hours, or 9 hours to 72 hours, or 10 hours to 72 hours, or 12 hours to 72 hours, or 14 hours to 72 hours, or 16 hours to 72 hours, or 18 hours to 72 hours, or 20 hours to 72 hours, or 22 hours to 72 hours, or 24 hours to 72 hours, or 30 min to 48, or 45 min to 48 hours, or 1 hr to 48 hours, or 2 hours to 48 hours, or 3 hours to 48 hours, or 4 hours to 48 hours, or 5 hours to 48 hours, or 6 hours to 48 hours, or 7 hours to 48 hours, or 8 hours to 48 hours, or 9 hours to 48 hours, or 10 hours to 48 hours, or 12 hours to 48 hours, or 14 hours to 48 hours, or 16 hours to 48 hours, or 18 hours to 48 hours, or 20 hours to 48 hours, or 22 hours to 48 hours, or 24 hours to 48 hours, or 30 min to 36 hours, or 45 min to 36 hours, or 1 hr to 36 hours, or 2 hours to 36 hours, or 3 hours to 36 hours, or 4 hours to 36 hours, or 5 hours to 36 hours, or 6 hours to 36 hours, or 7 hours to 36 hours, or 8 hours to 36 hours, or 9 hours to 36 hours, or 10 hours to 36 hours, or 12 hours to 36 hours, or 14 hours to 36 hours, or 16 hours to 36 hours, or 18 hours to 36 hours, or 20 hours to 36 hours, or 22 hours to 36 hours, or 24 hours to 36 hours, or 30 min to 30 hours, or 45 min to 30 hours, or 1 hr to 30 hours, or 2 hours to 30 hours, or 3 hours to 30 hours, or 4 hours to 30 hours, or 5 hours to 30 hours, or 6 hours to 30 hours, or 7 hours to 30 hours, or 8 hours to 30 hours, or 9 hours to 30 hours, or 10 hours to 30 hours, or 12 hours to 30 hours, or 14 hours to 30 hours, or 16 hours to 30 hours, or 18 hours to 30 hours, or 20 hours to 30 hours, or 22 hours to 30 hours, or 24 hours to 30 hours, or 30 min to 28 hours, or 45 min to 28 hours, or 1 hr to 28 hours, or 2 hours to 28 hours, or 3 hours to 28 hours, or 4 hours to 28 hours, or 5 hours to 28 hours, or 6 hours to 28 hours, or 7 hours to 28 hours, or 8 hours to 28 hours, or 9 hours to 28 hours, or 10 hours to 28 hours, or 12 hours to 28 hours, or 14 hours to 28 hours, or 16 hours to 28 hours, or 18 hours to 28 hours, or 20 hours to 28 hours, or 22 hours to 28 hours, or 24 hours to 28 hours. In certain embodiments, the time period after addition of modulator for at least one measurement is in the range of 2 hours to 96 hours, or 2 hours to 72 hours, or 2 hours to 48 hours, or 2 hours to 36 hours, or 2 hours to 30 hours, or 2 hours to 24 hours. In certain embodiments, the time period after addition of modulator for at least one measurement is in the range of 4 hours to 96 hours, or 4 hours to 74 hours, or 4 hours to 48 hours, or 4 hours to 36 hours, or 4 hours to 30 hours, or 4 hours to 24 hours. In certain embodiments, the time period after addition of modulator for at least one measurement is in the range of 6 hours to 96 hours, or 6 hours to 76 hours, or 6 hours to 48 hours, or 6 hours to 36 hours, or 6 hours to 30 hours, or 6 hours to 24 hours. In certain embodiments, the time period after addition of modulator for at least one measurement is in the range of 8 hours to 96 hours, or 8 hours to 78 hours, or 8 hours to 48 hours, or 8 hours to 36 hours, or 8 hours to 30 hours, or 8 hours to 24 hours. In certain embodiments, the time period after addition of modulator for at least one measurement is in the range of 12 hours to 96 hours, or 12 hours to 72 hours, or 12 hours to 48 hours, or 12 hours to 36 hours, or 12 hours to 30 hours, or 12 hours to 24 hours.

In certain embodiments, the invention includes at least one measurement taken at or after at least 1, 1.5, 2, 2.5, 3, 3.5, 4, 4.5, 5, 5.5, 6, 6.5, 7, 7.5, 8, 9, 10, 11, 12, 13, 14, 15, 16, 17, 18, 19, 20, 21, 22, 23, 24, 26, 28, 30, 36, 42, 48, 54, 60, 66, or 72 hours from addition of modulator or modulators. In certain embodiments, the invention includes at least one measurement taken at or after at least 2, 4, 6, 8, 10, 12, 14, 18, 24, 30, 42, 60, or 72 hours from the addition of modulator.

In certain embodiments, measurements are taken at a plurality of time periods after addition of modulator, wherein the plurality of time periods includes at least one measurement taken at or after at least 1, 1.5, 2, 2.5, 3, 3.5, 4, 4.5, 5, 5.5, 6, 6.5, 7, 7.5, 8, 9, 10, 11, 12, 13, 14, 15, 16, 17, 18, 19, 20, 21, 22, 23, 24, 26, 28, 30, 36, 42, 48, 54, 60, 66, or 72 hours from addition of modulator or modulators. In certain embodiments, measurements are taken at a plurality of time periods after addition of modulator, wherein the plurality of time periods includes at least one measurement taken at or after at least 2, 4, 6, 8, 10, 12, 14, 18, 24, 30, 42, 60, or 72 hours from addition of modulator or modulators.

In some embodiments, the activation levels of a discrete cell population or a discrete subpopulation of cells may be measured at multiple time intervals following treatment with a modulator to generate "dynamic activation state data" (also referred to herein as kinetic activation state data). In these embodiments, a sample or sub-sample (e.g. patient sample) is divided into aliquots which are then treated with one or more modulators. The different aliquots are then subject to treatment with a fixing agent at different time intervals. For instance, an aliquot that is to be measured at 5 minutes will be treated with one or more modulators and then subject to a treatment with a fixing agent after 5 minutes. The time intervals can vary greatly and will range from minutes (e.g. 5, 10, 15, 20, 25, 30, 35, 40, 45, 50, 55 minutes) to hours (e.g. 1, 2, 3, 4, 5, 6, 7, 8, 9, 10, 11, 12, 13, 14, 15, 6, 17 18, 19, 20, 21, 22, 23 hours) to days (e.g. 24 hours, 48 hours, 72 hours, 96 hours, 120 hours) or any combination thereof. Cells may also be treated with different concentrations of the modulator.

Figure 3:
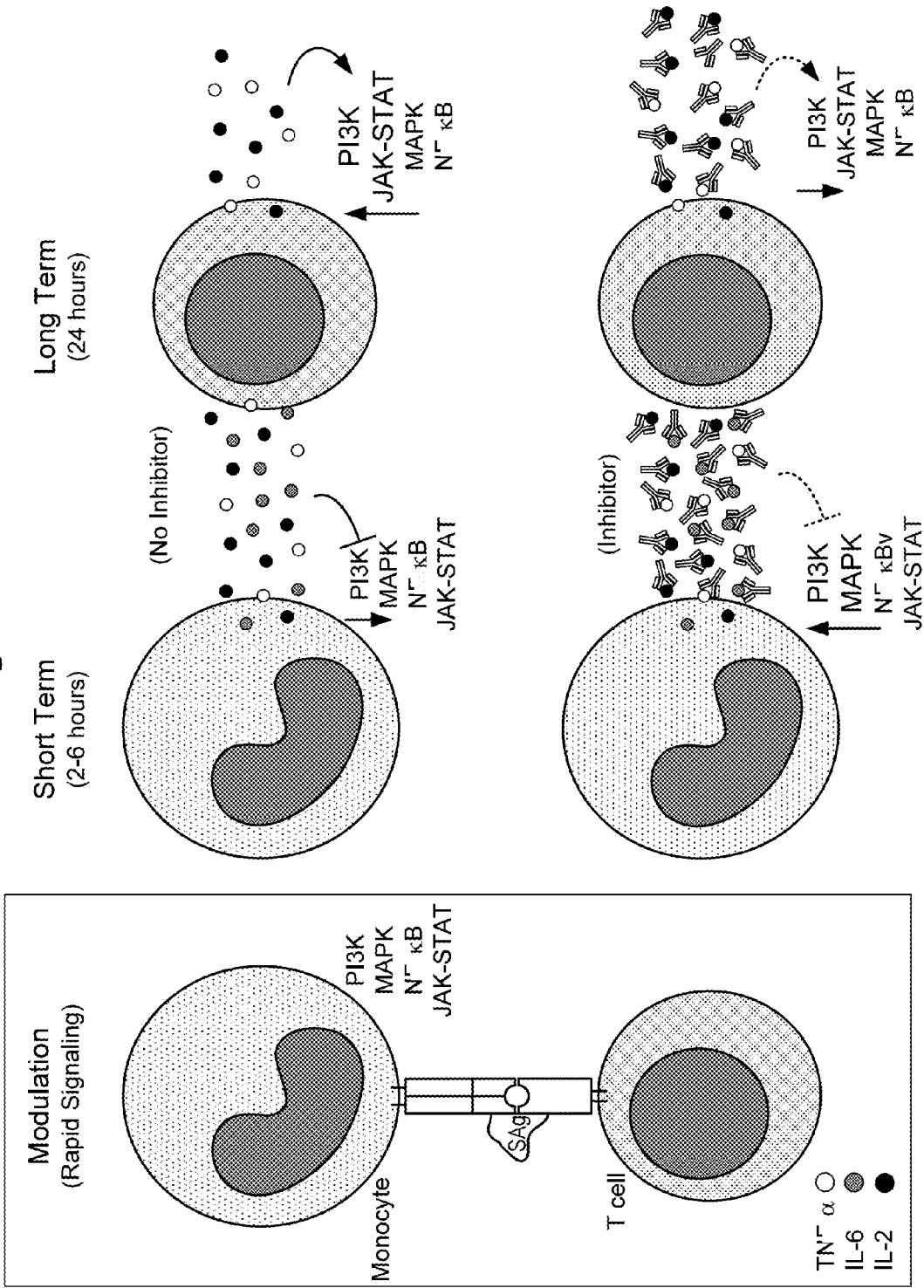
FIG. 3 shows a model for induced intercellular communication, and the potential effects of inhibitors on monocytes and T cells.

In these embodiments, the activation state data may be analyzed to identify discrete cell populations and then further analyzed to characterize the response of the different discrete cell populations to a modulator over time. The activation state data may be temporally modeled to characterize the dynamic response of the activatable elements to the stimulation with the modulator. Modeling the dynamic response to modulation can provide better understanding of the pathophysiology of a disease or prognostic status or a response to treatment. An example of modeling the dynamic response of normal cells to a modulator is shown in FIG. 3 and Example 6 of U.S. Ser. No. 12/877,998. Additionally, the modulator-induced activation levels of a discrete population of cells over time associated may be compared of other samples, e.g., samples with no modulator, or samples with modulator+agent, to identify activation levels that represent a response to a modulator and/or agent at specific time points. Response to a modulator, in some cases in the presence or absence of an agent may be associated with, e.g., status of an individual, such as a diagnostic or a prognostic status, or a cytogenetic status, or predicted therapeutic response, or, in the case of an agent, potential usefulness of the agent in treating a condition. Having activation levels at different time points is beneficial because the maximal differential response between samples associated with different statuses may be observed as early as 5 minutes after treatment with a modulator, in some cases in the presence or absence of an agent, and as late as 5 days after treatment with a modulator, in some cases in the presence or absence of an agent.

The modulator-induced response of the different discrete cell populations may be modeled to further understand communication between the discrete cell populations that are associated with disease. For example, an increased phosphorylation of an activatable element in a first cell population at an earlier time point may have a causal effect on the activation (phosphorylation) or expression of a second activatable element in a second cell population at a later time point. These causal associations may be modeled using Bayesian Networks or temporal models. (See U.S. Ser. Nos. 11/338,957 and 13/636,627). Alternatively, these causal associations may be identified using unsupervised learning techniques such as principle components analysis and/or clustering. Causal relationships may also be identified by addition of molecules that inhibit the signaling network (e.g. kinase inhibitors, cytokine neutralizing antibodies). Causal associations between activation levels in different discrete cell populations may represent communications between cellular networks over time. These communications may provide insight into, e.g., the mechanism of drug response, autoimmune disease, cancer progression and carcinogenesis. Therefore, the identification and characterization of these communications allows for the development of diagnostics which can accurately predict drug response, therapeutic and early stage detection. In addition, it may be used for identification of drug targets as well as drug development. In certain embodiments, such relationships are determined, at least in part, by examining the activation levels of one or more activatable elements in one discrete cell population that does not itself interact with the modulator, or does not substantially interact with the modulator.

In some embodiments, the activation state data at a first time point is computationally analyzed (e.g. through binning or gating as described elsewhere) to determine discrete populations of cells. The discrete populations of cells are subsequently analyzed individually over the remaining time points to identify sub-populations of cells with different response to a modulator. Differential response over time within a same population of cells may be modeled using methods such as temporal modeling or hyper-spatial modeling as described in U.S. patent application Ser. No. 13/636,627 and below. Also, adjusting to analyze non-apoptotic cell populations is important as described in PCT/US2011/048332. These methods may allow the modeling of a single discrete cell population over time or multiple discrete cell populations over time.

In another embodiment, the activation state data is computationally analyzed at all of the time points to determine discrete populations of cells. The discrete populations of cells are then modeled in order to determine consistent membership in a discrete population of cells over time. In this way, the populations of cells are not characterized by the activation levels of modulators at a single time point, but rather are determined based on the activation levels of modulators at multiple time points. Both gating and binning may be used to first segregate the activation state data for cell populations at all of the time points. Based on the segregated cell populations at the various time points, discrete cell populations may be identified. Although this technique works well using gating or semi-supervised identification of discrete cell populations, this technique is ideal for use with unsupervised identification of discrete cell populations such as the methods described in U.S. Publication No. 2009/0307248 and below.

VIII. Activation Levels of Activatable Elements in Intracellular Pathways

In certain embodiments, the activation level of an activatable element of an intracellular pathway or pathways is measured in single cells of one or more discrete cell populations in the culture. If the culture has been contacted with modulator or modulators for a period of time, the modulation is stopped, typically by fixing the cells. In general, cells are fixed and permeabilized, and contacted with one or more detectable binding elements specific to an activated form of an activatable element, and detected on a single cell basis.

A. Activatable Elements

An "activatable element," as that term is used herein, is an element that exists in at least two states that are distinct and that are distinguishable. The activation state of an individual activatable element is either in the on or off state. An activatable element is generally a part of a cellular protein or other constituent. In some cases the term "activatable element" is used synonomously with the term "protein or constituent with an activatable element," which is clear from context. As an illustrative example, and without intending to be limited to any theory, an individual phosphorylatable site on a protein will either be phosphorylated and then be in the "on" state or it will not be phosphorylated and hence, it will be in the "off" state. See Blume-Jensen and Hunter, Nature, vol 411, 17 May 2001, p 355-365. The terms "on" and "off," when applied to an activatable element that is a part of a cellular constituent, are used here to describe the state of the activatable element (e.g., phosphorylated is "on" and non-phosphorylated is "off"), and not the overall state of the cellular constituent of which it is a part. Typically, a cell possesses a plurality of a particular protein or other constituent with a particular activatable element and this plurality of proteins or constituents usually has some proteins or constituents whose individual activatable element is in the on state and other proteins or constituents whose individual activatable element is in the off state. Since the activation state of each activatable element is typically measured through the use of a binding element that recognizes a specific activation state, only those activatable elements in the specific activation state recognized by the binding element, representing some fraction of the total number of activatable elements, will be bound by the binding element to generate a measurable signal.

The measurable signal corresponding to the summation of individual activatable elements of a particular type that are activated in a single cell is the "activation level" for that activatable element in that cell.

At the next level of data aggregation, activation levels for a particular activatable element may vary among individual cells so that when a plurality of cells is analyzed, the activation levels follow a distribution. The distribution may be a normal distribution, also known as a Gaussian distribution, or it may be of another type. Different populations of cells may have different distributions of activation levels that can then serve to distinguish between the populations. See FIG. 25D for an example of distributions of activation levels in discrete cell populations under various conditions.

In some embodiments, the basis determining the activation levels of one or more activatable elements in cells may use the distribution of activation levels for one or more specific activatable elements which will differ among different conditions. A certain activation level, or more typically a range of activation levels for one or more activatable elements seen in a cell or a population of cells, is indicative that that cell or population of cells belongs to a certain condition. Other measurements, such as cellular levels (e.g., expression levels) of biomolecules that may not contain activatable elements, may also be used to determine the activation state data of a cell in addition to activation levels of activatable elements; it will be appreciated that these levels also will follow a distribution, similar to activatable elements. Thus, the activation level or levels of one or more activatable elements, alternatively or in addition, with levels of one or more of biomolecules that may not contain activatable elements, of one or more cells in a discrete population of cells may be used to determine the activation state data of the discrete cell population.

In some embodiments, the basis for determining the activation state data of a discrete cell population may use the position of a cell in a contour or density plot. The contour or density plot represents the number of cells that share a characteristic such as the activation level of activatable proteins in response to a modulator. For example, when referring to activation levels of activatable elements in response to one or more modulators, normal individuals and patients with a condition might show populations with increased activation levels in response to the one or more modulators. However, the number of cells that have a specific activation level (e.g. specific amount of an activatable element) might be different between normal individuals and patients with a condition. Thus, the activation state data of a cell can be determined according to its location within a given region in the contour or density plot.

B. Additional Elements

Instead of, or in addition to activation levels of intracellular activatable elements, expression levels of intracellular or extracellular biomolecules, e.g., proteins may be used alone or in combination with activation states of activatable elements when evaluating a discrete cell population. Further, additional cellular elements, e.g., biomolecules or molecular complexes such as RNA, DNA, carbohydrates, metabolites, and the like, may be used instead of, or in addition to activatable states, expression levels or any combination of activatable states and expression levels in the determination of the physiological status of a population of cells encompassed here.

In certain embodiments, intracellular levels of one or more intercellular communication messengers are measured in individual cells of a discrete cell population. In certain embodiments, the intercellular communication messenger is a cytokine, as further described herein. The intracellular level of the intercellular communication messenger may be used instead of, or in addition to, activation levels of activatable elements.

In some embodiments, other characteristics that affect the status of a cellular constituent may also be used to determine the activation state data of a discrete cell population. Examples include the translocation of biomolecules or changes in their turnover rates and the formation and disassociation of complexes of biomolecule. Such complexes can include multi-protein complexes, multi-lipid complexes, homo- or hetero-dimers or oligomers, and combinations thereof. Other characteristics include proteolytic cleavage, e.g. from exposure of a cell to an extracellular protease or from the intracellular proteolytic cleavage of a biomolecule.

Additional elements may also be used to determine the activation state data of a discrete cell population, such as the expression level of extracellular or intracellular markers, nuclear antigens, enzymatic activity, protein expression and localization, cell cycle analysis, chromosomal analysis, cell volume, and morphological characteristics like granularity and size of nucleus or other distinguishing characteristics. For example, myeloid lineage cells can be further subdivided based on the expression of cell surface markers such as CD14, CD15, or CD33, CD34 and CD45.

Alternatively, populations of cells can be aggregated based upon shared characteristics that may include inclusion in one or more additional cell populations or the presence of extracellular or intracellular markers, similar gene expression profile, nuclear antigens, enzymatic activity, protein expression and localization, cell cycle analysis, chromosomal analysis, cell volume, and morphological characteristics like granularity and size of nucleus or other distinguishing characteristics.

In some embodiments, the activation state data of one or more cells is determined by examining and profiling the activation level of one or more activatable elements in a cellular pathway. In some embodiments, the activation levels of one or more activatable elements of a cell from a first discrete cell population and the activation levels of one or more activatable elements of cell from a second discrete cell population are correlated with a condition. In some embodiments, the first discrete cell population and second discrete cell population are hematopoietic cell populations. In some embodiments, the activation levels of one or more activatable elements of a cell from a first discrete cell population of hematopoietic cells and the activation levels of one or more activatable elements of cell from a second discrete cell population of hematopoietic cells are correlated with a neoplastic, autoimmune or hematopoietic condition as described herein. Examples of different discrete populations of hematopoietic cells include, but are not limited to, pluripotent hematopoietic stem cells, B-lymphocyte lineage progenitor or derived cells, T-lymphocyte lineage progenitor or derived cells, NK cell lineage progenitor or derived cells, granulocyte lineage progenitor or derived cells, monocyte lineage progenitor or derived cells, megakaryocyte lineage progenitor or derived cells and erythroid lineage progenitor or derived cells.

The activation level of one or more activatable elements in single cells in the sample is determined. Cellular constituents that may include activatable elements include without limitation proteins, carbohydrates, lipids, nucleic acids and metabolites. In some cases, the constituent is itself referred to as the "activatable element," which is clear from context. The activatable element may be a portion of the cellular constituent, for example, an amino acid residue in a protein that may undergo phosphorylation, or it may be the cellular constituent itself, for example, a protein that is activated by translocation, change in conformation (due to, e.g., change in pH or ion concentration), by proteolytic cleavage, and the like. Upon activation, a change occurs to the activatable element, such as covalent modification of the activatable element (e.g., binding of a molecule or group to the activatable element, such as phosphorylation) or a conformational change. Such changes generally contribute to changes in particular biological, biochemical, or physical properties of the cellular constituent that contains the activatable element. The state of the cellular constituent that contains the activatable element is determined to some degree, though not necessarily completely, by the state of a particular activatable element of the cellular constituent. For example, a protein may have multiple activatable elements, and the particular activation states of these elements may overall determine the activation state of the protein; the state of a single activatable element is not necessarily determinative. Additional factors, such as the binding of other proteins, pH, ion concentration, interaction with other cellular constituents, and the like, can also affect the state of the cellular constituent.

In some embodiments, the activation levels of a plurality of intracellular activatable elements in single cells are determined. The term "plurality" as used herein refers to two or more. In some embodiments, the activation levels of at least 2, 3, 4, 5, 6, 7, 8, 9, 10, or more than 10 intracellular activatable elements are determined in single cells of a discrete cell population. The activation levels may be determined in the same cell, or different cells of the same population.

Activation states of activatable elements may result from chemical additions or modifications of biomolecules and include biochemical processes such as glycosylation, phosphorylation, acetylation, methylation, biotinylation, glutamylation, glycylation, hydroxylation, isomerization, prenylation, myristoylation, lipoylation, phosphopantetheinylation, sulfation, ISGylation, nitrosylation, palmitoylation, SUMOylation, ubiquitination, neddylation, citrullination, amidation, and disulfide bond formation, disulfide bond reduction. Other possible chemical additions or modifications of biomolecules include the formation of protein carbonyls, direct modifications of protein side chains, such as o-tyrosine, chloro-, nitrotyrosine, and dityrosine, and protein adducts derived from reactions with carbohydrate and lipid derivatives. Other modifications may be non-covalent, such as binding of a ligand or binding of an allosteric modulator.

In certain embodiments, the activatable element is an element that undergoes phosphorylation or dephosphorylation, or an element that undergoes cleavage.

In some embodiments, the activatable element is a protein. Examples of proteins that may include activatable elements include, but are not limited to kinases, phosphatases, lipid signaling molecules, adaptor/scaffold proteins, cytokines, cytokine regulators, ubiquitination enzymes, adhesion molecules, cytoskeletal/contractile proteins, heterotrimeric G proteins, small molecular weight GTPases, guanine nucleotide exchange factors, GTPase activating proteins, caspases, proteins involved in apoptosis, cell cycle regulators, molecular chaperones, metabolic enzymes, vesicular transport proteins, hydroxylases, isomerases, deacetylases, methylases, demethylases, tumor suppressor genes, proteases, ion channels, molecular transporters, transcription factors/DNA binding factors, regulators of transcription, and regulators of translation. Examples of activatable elements, activation states and methods of determining the activation level of activatable elements are described in US Publication Number 20060073474 entitled "Methods and compositions for detecting the activation state of multiple proteins in single cells" and US Publication Number 20050112700 entitled "Methods and compositions for risk stratification" the content of which are incorporate here by reference. See U.S. Ser. Nos. 12/432,720 and 13/493,857 and U.S. Pat. No. 8,227,202 and Shulz et al., Current Protocols in Immunology 2007, 7:8.17.1-20.

In some embodiments, the protein that may be activated is selected from the group consisting of HER receptors, PDGF receptors, FLT3 receptor, Kit receptor, FGF receptors, Eph receptors, Trk receptors, IGF receptors, Insulin receptor, Met receptor, Ret, VEGF receptors, erythropoetin receptor, thromobopoetin receptor, CD114, CD116, TIE1, TIE2, FAK, Jak1, Jak2, Jak3, Tyk2, Src, Lyn, Fyn, Lck, Fgr, Yes, Csk, Abl, Btk, ZAP70, Syk, IRAKs, cRaf, ARaf, BRAF, Mos, Lim kinase, ILK, Tpl, ALK, TGFβ receptors, BMP receptors, MEKKs, ASK, MLKs, DLK, PAKs, Mek 1, Mek 2, MKK3/6, MKK4/7, ASK1, Cot, NIK, Bub, Myt 1, Weel, Casein kinases, PDK1, SGK1, SGK2, SGK3, Akt1, Akt2, Akt3, p90Rsks, p70S6Kinase, Prks, PKCs, PKAs, ROCK 1, ROCK 2, Auroras, CaMKs, MNKs, AMPKs, MELK, MARKs, Chk1, Chk2, LKB-1, MAPKAPKs, Pim1, Pim2, Pim3, IKKs, Cdks, Jnks, Erks, IKKs, GSK3α, GSK3β, Cdks, CLKs, PKR, PI3-Kinase class 1, class 2, class 3, mTor, SAPK/JNK1,2,3, p38s, PKR, DNA-PK, ATM, ATR, Receptor protein tyrosine phosphatases (RPTPs), LAR phosphatase, CD45, Non receptor tyrosine phosphatases (NPRTPs), SHPs, MAP kinase phosphatases (MKPs), Dual Specificity phosphatases (DUSPs), CDC25 phosphatases, Low molecular weight tyrosine phosphatase, Eyes absent (EYA) tyrosine phosphatases, Slingshot phosphatases (SSH), serine phosphatases, PP2A, PP2B, PP2C, PP1, PP5, inositol phosphatases, PTEN, SHIPs, myotubularins, phosphoinositide kinases, phopsholipases, prostaglandin synthases, 5-lipoxygenase, sphingosine kinases, sphingomyelinases, adaptor/scaffold proteins, Shc, Grb2, BLNK, LAT, B cell adaptor for PI3-kinase (BCAP), SLAP, Dok, KSR, MyD88, Crk, CrkL, GAD, Nck, Grb2 associated binder (GAB), Fas associated death domain (FADD), TRADD, TRAF2, RIP, T-Cell leukemia family, IL-2, IL-4, IL-8, IL-6, interferon γ, interferon α, suppressors of cytokine signaling (SOCs), Cbl, SCF ubiquitination ligase complex, APC/C, adhesion molecules, integrins, Immunoglobulin-like adhesion molecules, selectins, cadherins, catenins, focal adhesion kinase, p130CAS, fodrin, actin, paxillin, myosin, myosin binding proteins, tubulin, eg5/KSP, CENPs, β-adrenergic receptors, muscarinic receptors, adenylyl cyclase receptors, small molecular weight GTPases, H-Ras, K-Ras, N-Ras, Ran, Rac, Rho, Cdc42, Arfs, RABs, RHEB, Vav, Tiam, Sos, Dbl, PRK, TSC1,2, Ras-GAP, Arf-GAPs, Rho-GAPs, caspases, Caspase 2, Caspase 3, Caspase 6, Caspase 7, Caspase 8, Caspase 9, Bcl-2, Mcl-1, Bcl-XL, Bcl-w, Bcl-B, Al, Bax, Bak, Bok, Bik, Bad, Bid, Bim, Bmf, Hrk, Noxa, Puma, IAPB, XIAP, Smac, Cdk4, Cdk 6, Cdk 2, Cdk1, Cdk 7, Cyclin D, Cyclin E, Cyclin A, Cyclin B, Rb, p16, p14Arf, p27KIP, p21CIP, molecular chaperones, Hsp90s, Hsp70, Hsp27, metabolic enzymes, Acetyl-CoAa Carboxylase, ATP citrate lyase, nitric oxide synthase, caveolins, endosomal sorting complex required for transport (ESCRT) proteins, vesicular protein sorting (Vsps), hydroxylases, prolyl-hydroxylases PHD-1, 2 and 3, asparagine hydroxylase FIH transferases, Pin1 prolyl isomerase, topoisomerases, deacetylases, Histone deacetylases, sirtuins, histone acetylases, CBP/P300 family, MYST family, ATF2, DNA methyl transferases, Histone H3K4 demethylases, H3K27, JHDM2A, UTX, VHL, WT-1, p53, Hdm, PTEN, ubiquitin proteases, urokinase-type plasminogen activator (uPA) and uPA receptor (uPAR) system, cathepsins, metalloproteinases, esterases, hydrolases, separase, potassium channels, sodium channels, multi-drug resistance proteins, P-Gycoprotein, nucleoside transporters, Ets, Elk, SMADs, Rel-A (p65-NFKB), CREB, NFAT, ATF-2, AFT, Myc, Fos, Spl, Egr-1, T-bet, HIFs, FOXOs, E2Fs, SRFs, TCFs, Egr-1, β-catenin, FOXO STAT1, STAT 3, STAT 4, STAT 5, STAT 6, p53, WT-1, HMGA, pS6, 4EPB-1, eIF4E-binding protein, RNA polymerase, initiation factors, elongation factors. In one embodiment, the activatable element is a phosphorylated protein such as p-IkB, p-Akt, p-S6, p-NFκB proteins, p-IkK a/b, p-p38, p-Lck, P-Zap70, p-SRC Y418, p-Syk, or p-Erk 1/2.

In some embodiments of the invention, the methods described herein are employed to determine the activation level of an activatable element, e.g., in an intracellular pathway. Methods and compositions are provided for the determination of the activation state data of a cell according to the activation level of an activatable element in a cellular pathway. Methods and compositions are provided for the determination of the activation state data of a cell in a first discrete cell population and a cell in a second discrete cell population according to the activation level of an activatable element in a cellular pathway in each cell. The cells can be a hematopoietic cell and examples are shown herein.

C. Signaling Pathways

In some embodiments, the methods of the invention are employed to determine the activation level of an activatable element in a signaling pathway in single cells in a discrete cell population. In some embodiments, the activation state data of a cell is determined, as described herein, according to the activation level of one or more activatable elements in one or more signaling pathways. Signaling pathways and their members have been extensively described. See (Hunter T. Cell Jan. 7, 2000; 100(1): 13-27; Weinberg, 2007; Blume-Jensen and Hunter, Nature, vol 411, 17 May 2001, p 355-365 cited above) and U.S. Pat. No. 8,227,202. Exemplary signaling pathways include the following pathways and their members: the JAK-STAT pathway including JAKs, STATs 2, 3 4 and 5, the FLT3L signaling pathway, the MAP kinase pathway including Ras, Raf, MEK, ERK p38, and elk; the PI3K/Akt pathway including PI-3-kinase, PDK1, Akt, s6 and Bad; the NF-κB pathway including IKKs, IkB, e.g., IkB☐ and NF-κB, the Wnt pathway including frizzled receptors, beta-catenin, APC and other co-factors and TCF (see Cell Signaling Technology, Inc. 2002 Catalog pages 231-279 and Hunter T., supra.), one or more DNA damage, DNA damage repair and apoptosis repair pathways.

In some embodiments of the invention, the correlated activatable elements being assayed (or the signaling proteins being examined) are members of the MAP kinase, Akt, NFκB, WNT, STAT and/or PKC signaling pathways. In an alternative embodiment, the activation level of an activatable elements in one or more pathways as shown in FIG. 2 is measured. Individual elements (in their activated forms) are shown in FIG. 2, e.g., p-Stat1, p-Stat3, p-Stat4, p-Stat5, p-Stat6, p-ERK, p-p38, pNFkB, IkB, and PRelB in pathways involved in differentiation, maturation, and cytokine/chemokine responses.

In certain embodiments, the intracellular pathway involved in intercellular communication is a pathway selected from the group consisting of NFkB pathway, PI3K pathway, MAPK pathway, JAK/STAT pathway, and combinations thereof. Activatable elements in the NFkB pathway include IkBa and NFkBP105. Activatable elements in the PI3K pathway include AKT, e.g., Akt1, Akt2, Akt3, and s6. Activatable elements in the MAPK pathway include ERK and p38. Activatable elements in the JAK/STAT pathway include STAT1, STAT3, STAT4, STAT5, STATE, JAK1 and JAK2.

In some embodiments, the methods of the invention are employed to determine the activation level of a signaling protein in a signaling pathway known in the art including those described herein. Exemplary types of signaling proteins within the scope of the present invention include, but are not limited to, kinases, kinase substrates (i.e. phosphorylated substrates), phosphatases, phosphatase substrates, binding proteins (such as 14-3-3), receptor ligands and receptors (cell surface receptor tyrosine kinases and nuclear receptors)). Kinases and protein binding domains, for example, have been well described (see, e.g., Cell Signaling Technology, Inc., 2002 Catalogue "The Human Protein Kinases" and "Protein Interaction Domains" pgs. 254-279).

Exemplary signaling proteins include, but are not limited to, kinases, HER receptors, PDGF receptors, Kit receptor, FGF receptors, Eph receptors, Trk receptors, IGF receptors, Insulin receptor, Met receptor, Ret, VEGF receptors, TIE1, TIE2, FAK, Jak1, Jak2, Jak3, Tyk2, Src, Lyn, Fyn, Lck, Fgr, Yes, Csk, Abl, Btk, ZAP70, Syk, IRAKs, cRaf, ARaf, BRAF, Mos, Lim kinase, ILK, Tpl, ALK, TGFβ receptors, BMP receptors, MEKKs, ASK, MLKs, DLK, PAKs, Mek 1, Mek 2, MKK3/6, MKK4/7, ASK1, Cot, NIK, Bub, Myt 1, Wee1, Casein kinases, PDK1, SGK1, SGK2, SGK3, Akt1, Akt2, Akt3, p90Rsks, p70S6Kinase, Prks, PKCs, PKAs, ROCK 1, ROCK 2, Auroras, CaMKs, MNKs, AMPKs, MELK, MARKs, Chk1, Chk2, LKB-1, MAPKAPKs, Pim1, Pim2, Pim3, IKKs, Cdks, Jnks, Erks, IKKs, GSK3α, GSK3β, Cdks, CLKs, PKR, PI3-Kinase class 1, class 2, class 3, mTor, SAPK/JNK1,2,3, p38s, PKR, DNA-PK, ATM, ATR, phosphatases, Receptor protein tyrosine phosphatases (RPTPs), LAR phosphatase, CD45, Non receptor tyrosine phosphatases (NPRTPs), SHPs, MAP kinase phosphatases (MKPs), Dual Specificity phosphatases (DUSPs), CDC25 phosphatases, low molecular weight tyrosine phosphatase, Eyes absent (EYA) tyrosine phosphatases, Slingshot phosphatases (SSH), serine phosphatases, PP2A, PP2B, PP2C, PP1, PP5, inositol phosphatases, PTEN, SHIPs, myotubularins, lipid signaling, phosphoinositide kinases, phospholipases, prostaglandin synthases, 5-lipoxygenase, sphingosine kinases, sphingomyelinases, adaptor/scaffold proteins, Shc, Grb2, BLNK, LAT, B cell adaptor for PI3-kinase (BCAP), SLAP, Dok, KSR, MyD88, Crk, CrkL, GAD, Nck, Grb2 associated binder (GAB), Fas associated death domain (FADD), TRADD, TRAF2, RIP, T-Cell leukemia family, cytokines, IL-2, IL-4, IL-8, IL-6, interferon γ, interferon α, cytokine regulators, suppressors of cytokine signaling (SOCs), ubiquitination enzymes, Cbl, SCF ubiquitination ligase complex, APC/C, adhesion molecules, integrins, Immunoglobulin-like adhesion molecules, selectins, cadherins, catenins, focal adhesion kinase, p130CAS, cytoskeletal/contractile proteins, fodrin, actin, paxillin, myosin, myosin binding proteins, tubulin, eg5/KSP, CENPs, heterotrimeric G proteins, β-adrenergic receptors, muscarinic receptors, adenylyl cyclase receptors, small molecular weight GTPases, H-Ras, K-Ras, N-Ras, Ran, Rac, Rho, Cdc42, Arfs, RABs, RHEB, guanine nucleotide exchange factors, Vav, Tiam, Sos, Dbl, PRK, TSC1,2, GTPase activating proteins, Ras-GAP, Arf-GAPs, Rho-GAPs, caspases, Caspase 2, Caspase 3, Caspase 6, Caspase 7, Caspase 8, Caspase 9, proteins involved in apoptosis, Bcl-2, Mcl-1, Bcl-XL, Bcl-w, Bcl-B, Al, Bax, Bak, Bok, Bik, Bad, Bid, Bim, Bmf, Hrk, Noxa, Puma, IAPs, XIAP, Smac, cell cycle regulators, Cdk4, Cdk 6, Cdk 2, Cdk1, Cdk 7, Cyclin D, Cyclin E, Cyclin A, Cyclin B, Rb, p16, p14Arf, p27KIP, p21CIP, molecular chaperones, Hsp90s, Hsp70, Hsp27, metabolic enzymes, Acetyl-CoAa Carboxylase, ATP citrate lyase, nitric oxide synthase, vesicular transport proteins, caveolins, endosomal sorting complex required for transport (ESCRT) proteins, vesicular protein sorting (Vsps), hydroxylases, prolyl-hydroxylases PHD-1, 2 and 3, asparagine hydroxylase FIH transferases, isomerases, Pin1 prolyl isomerase, topoisomerases, deacetylases, Histone deacetylases, sirtuins, acetylases, histone acetylases, CBP/P300 family, MYST family, ATF2, methylases, DNA methyl transferases, demethylases, Histone H3K4 demethylases, H3K27, JHDM2A, UTX, tumor suppressor genes, VHL, WT-1, p53, Hdm, PTEN, proteases, ubiquitin proteases, urokinase-type plasminogen activator (uPA) and uPA receptor (uPAR) system, cathepsins, metalloproteinases, esterases, hydrolases, separase, ion channels, potassium channels, sodium channels, molecular transporters, multidrug resistance proteins, P-Gycoprotein, nucleoside transporters, transcription factors/DNA binding proteins, Ets, Elk, SMADs, Rel-A (p65-NFKB), CREB, NFAT, ATF-2, AFT, Myc, Fos, Spl, Egr-1, T-bet, β-catenin, HIFs, FOXOs, E2Fs, SRFs, TCFs, Egr-1, β-catenin, FOXO STAT1, STAT 3, STAT 4, STAT 5, STAT 6, p53, WT-1, HMGA, regulators of translation, pS6, 4EPB-1, eIF4E-binding protein, regulators of transcription, RNA polymerase, initiation factors, and elongation factors. In some embodiments the protein expression may be affected by activation. Exemplary proteins include, but are not limited to, intracellular cytokines including TNF☐, IFN☐, IFN☐, IL-2, IL-4, IL-6 and IL-17, transcription factors such Foxp3, Tbet and ROR☐T, activation markers such as CD25 and CD69, the proliferation marker Ki67, and T cell-Antigen Presenting Cell co-stimulation agonists and antagonists such as CD28, CTLA-4, PD-1, ICOS, CD80, CD86, PD-L1, PD-L2 and L-ICOS.

In some embodiments the protein is selected from the group consisting of PI3-Kinase (p85, p110a, p110b, p110d), Jak1, Jak2, SOCs, Rac, Rho, Cdc42, Ras-GAP, Vav, Tiam, Sos, Dbl, Nck, Gab, PRK, SHP1, and SHP2, SHIP1, SHIP2, sSHIP, PTEN, Shc, Grb2, PDK1, SGK, Akt1, Akt2, Akt3, TSC1,2, Rheb, mTor, 4EBP-1, p70S6Kinase, S6, LKB-1, AMPK, PFK, Acetyl-CoAa Carboxylase, DokS, Rafs, Mos, Tp12, MEK1/2, MLK3, TAK, DLK, MKK3/6, MEKK1,4, MLK3, ASK1, MKK4/7, SAPK/JNK1,2,3, p38s, Erk1/2, Syk, Btk, BLNK, LAT, ZAP70, Lck, Cbl, SLP-76, PLCyi, PLCy 2, STAT1, STAT 3, STAT 4, STAT 5, STAT 6, FAK, p130CAS, PAKs, LIMK1/2, Hsp90, Hsp70, Hsp27, SMADs, Rel-A (p65-NFKB), CREB, Histone H2B, HATs, HDACs, PKR, Rb, Cyclin D, Cyclin E, Cyclin A, Cyclin B, P16, p14Arf, p27KIP, p21CIP, Cdk4, Cdk6, Cdk7, Cdk1, Cdk2, Cdk9, Cdc25, A/B/C, Abl, E2F, FADD, TRADD, TRAF2, RIP, Myd88, BAD, Bcl-2, Mcl-1, Bcl-XL, Caspase 2, Caspase 3, Caspase 6, Caspase 7, Caspase 8, Caspase 9, IAPB, Smac, Fodrin, Actin, Src, Lyn, Fyn, Lck, NIK, IκB, p65(RelA), IKKα, PKA, PKCα, PKC β, PKCθ, PKCδ, CAMK, Elk, AFT, Myc, Egr-1, NFAT, ATF-2, Mdm2, p53, DNA-PK, Chk1, Chk2, ATM, ATR, βcatenin, CrkL, GSK3α, GSK3β, and FOXO.

In some embodiments of the invention, the methods described herein are employed to determine the activation level of an activatable element in a signaling pathway. See U.S. Ser. Nos. 12/432,720 and 13/493,857 and U.S. Pat. No. 8,227,202. Methods and compositions are provided for the determination of an activation state data of a cell according to the status of an activatable element in a signaling pathway. Methods and compositions are provided for the determination of a physiological status of cells in different populations of cells according to the status of an activatable element in a signaling pathway. The cells can be hematopoietic cells. Examples of hematopoietic cells are shown herein.

In some embodiments, the determination of an activation state data of cells in different populations of cells according to the activation level of an activatable element in a signaling pathway comprises classifying the cell populations as cells that are correlated with a clinical outcome. Examples of clinical outcome, staging, patient responses and classifications are shown above.

D. Detection of Levels of Activatable Elements and/or Additional Elements

In certain embodiments of the invention, the level of an activatable element and/or additional element is determined using a detectable binding element that binds to one form of the activatable element, and detecting the element. Generally, the binding element is rendered detectable by being labeled, or susceptible to labeling.

1. Binding Elements

In some embodiments of the invention, the activation level of an activatable element is determined. One embodiment makes this determination by contacting a cell from a cell population with a binding element that is specific for an activation state of the activatable element. The term "Binding element" includes any molecule, e.g., peptide, nucleic acid, small organic molecule which is capable of detecting an activation state of an activatable element over another activation state of the activatable element. Binding elements and labels for binding elements are shown in U.S. Ser. Nos. 12/432,720 and 13/493,857 and U.S. Pat. No. 8,227,202 and the other applications incorporated above.

In some embodiments, the binding element is a peptide, polypeptide, oligopeptide or a protein. The peptide, polypeptide, oligopeptide or protein may be made up of naturally occurring amino acids and peptide bonds, or synthetic peptidomimetic structures. Thus "amino acid", or "peptide residue", as used herein include both naturally occurring and synthetic amino acids. For example, homo-phenylalanine, citrulline and norleucine are considered amino acids for the purposes of the invention. The side chains may be in either the (R) or the (S) configuration. In some embodiments, the amino acids are in the (S) or L-configuration. If non-naturally occurring side chains are used, non-amino acid substituents may be used, for example to prevent or retard in vivo degradation. Proteins including non-naturally occurring amino acids may be synthesized or in some cases, made recombinantly; see van Hest et al., FEBS Lett 428:(1-2) 68-70 May 22, 1998 and Tang et al., Abstr. Pap Am. Chem. S218: U138 Part 2 Aug. 22, 1999, both of which are expressly incorporated by reference herein.

Methods of the present invention may be used to detect any particular activatable element in a sample that is antigenically detectable and antigenically distinguishable from other activatable element which is present in the sample. For example, the activation state-specific antibodies of the present invention can be used in the present methods to identify distinct signaling cascades of a subset or subpopulation of complex cell populations; and the ordering of protein activation (e.g., kinase activation) in potential signaling hierarchies. Hence, in some embodiments the expression and phosphorylation of one or more polypeptides are detected and quantified using methods of the present invention. In some embodiments, the expression and phosphorylation of one or more polypeptides that are cellular components of a cellular pathway are detected and quantified using methods of the present invention. As used herein, the term "activation state-specific antibody" or "activation state antibody" or grammatical equivalents thereof, refer to an antibody that specifically binds to a corresponding and specific antigen. Preferably, the corresponding and specific antigen is a specific form of an activatable element. Also preferably, the binding of the activation state-specific antibody is indicative of a specific activation state of a specific activatable element.

In some embodiments, the binding element is an antibody. In some embodiment, the binding element is an activation state-specific antibody.

The term "antibody" includes full length antibodies and antibody fragments, and may refer to a natural antibody from any organism, an engineered antibody, or an antibody generated recombinantly for experimental, therapeutic, or other purposes as further defined below. Examples of antibody fragments, as are known in the art, such as Fab, Fab', F(ab')2, Fv, scFv, or other antigen-binding subsequences of antibodies, either produced by the modification of whole antibodies or those synthesized de novo using recombinant DNA technologies. The term "antibody" comprises monoclonal and polyclonal antibodies. Antibodies can be antagonists, agonists, neutralizing, inhibitory, or stimulatory. They can be humanized, glycosylated, bound to solid supports, and posses other variations. See U.S. Ser. Nos. 12/432,720 and 13/493,857 and U.S. Pat. No. 8,227,202 for more information about antibodies as binding elements.

Activation state specific antibodies can be used to detect kinase activity, however additional means for determining kinase activation are provided by the present invention. For example, substrates that are specifically recognized by protein kinases and phosphorylated thereby are known. Antibodies that specifically bind to such phosphorylated substrates but do not bind to such non-phosphorylated substrates (phospho-substrate antibodies) may be used to determine the presence of activated kinase in a sample.

The antigenicity of an activated isoform of an activatable element is distinguishable from the antigenicity of non-activated isoform of an activatable element or from the antigenicity of an isoform of a different activation state. In some embodiments, an activated isoform of an element possesses an epitope that is absent in a non-activated isoform of an element, or vice versa. In some embodiments, this difference is due to covalent addition of moieties to an element, such as phosphate moieties, or due to a structural change in an element, as through protein cleavage, or due to an otherwise induced conformational change in an element which causes the element to present the same sequence in an antigenically distinguishable way. In some embodiments, such a conformational change causes an activated isoform of an element to present at least one epitope that is not present in a non-activated isoform, or to not present at least one epitope that is presented by a non-activated isoform of the element. In some embodiments, the epitopes for the distinguishing antibodies are centered around the active site of the element, although as is known in the art, conformational changes in one area of an element may cause alterations in different areas of the element as well.

Many antibodies, many of which are commercially available (for example, see the websites of Cell Signaling Technology or Becton Dickinson) have been produced which specifically bind to the phosphorylated isoform of a protein but do not specifically bind to a non-phosphorylated isoform of a protein. Many such antibodies have been produced for the study of signal transducing proteins which are reversibly phosphorylated. Particularly, many such antibodies have been produced which specifically bind to phosphorylated, activated isoforms of protein. Examples of proteins that can be analyzed with the methods described herein include, but are not limited to, kinases, HER receptors, PDGF receptors, FLT3 receptor, Kit receptor, FGF receptors, Eph receptors, Trk receptors, IGF receptors, Insulin receptor, Met receptor, Ret, VEGF receptors, TIE1, TIE2, erythropoetin receptor, thromobopoetin receptor, CD114, CD116, FAK, Jak1, Jak2, Jak3, Tyk2, Src, Lyn, Fyn, Lck, Fgr, Yes, Csk, Abl, Btk, ZAP70, Syk, IRAKs, cRaf, ARaf, BRAF, Mos, Lim kinase, ILK, Tpl, ALK, TGFβ receptors, BMP receptors, MEKKs, ASK, MLKs, DLK, PAKs, Mek 1, Mek 2, MKK3/6, MKK4/7, ASK1, Cot, NIK, Bub, Myt 1, Weel, Casein kinases, PDK1, SGK1, SGK2, SGK3, Akt1, Akt2, Akt3, p90Rsks, p70S6Kinase, Prks, PKCs, PKAs, ROCK 1, ROCK 2, Auroras, CaMKs, MNKs, AMPKs, MELK, MARKs, Chk1, Chk2, LKB-1, MAPKAPKs, Pim1, Pim2, Pim3, IKKs, Cdks, Jnks, Erks, IKKs, GSK3α, GSK3β, Cdks, CLKs, PKR, PI3-Kinase class 1, class 2, class 3, mTor, SAPK/JNK1,2,3, p38s, PKR, DNA-PK, ATM, ATR, phosphatases, Receptor protein tyrosine phosphatases (RPTPs), LAR phosphatase, CD45, Non receptor tyrosine phosphatases (NPRTPs), SHPs, MAP kinase phosphatases (MKPs), Dual Specificity phosphatases (DUSPs), CDC25 phosphatases, Low molecular weight tyrosine phosphatase, Eyes absent (EYA) tyrosine phosphatases, Slingshot phosphatases (SSH), serine phosphatases, PP2A, PP2B, PP2C, PP1, PPS, inositol phosphatases, PTEN, SHIPs, myotubularins, lipid signaling, phosphoinositide kinases, phopsholipases, prostaglandin synthases, 5-lipoxygenase, sphingosine kinases, sphingomyelinases, adaptor/scaffold proteins, Shc, Grb2, BLNK, LAT, B cell adaptor for PI3-kinase (BCAP), SLAP, Dok, KSR, MyD88, Crk, CrkL, GAD, Nck, Grb2 associated binder (GAB), Fas associated death domain (FADD), TRADD, TRAF2, RIP, T-Cell leukemia family, cytokines, IL-2, IL-4, IL-8, IL-6, interferon γ, interferon α, cytokine regulators, suppressors of cytokine signaling (SOCs), ubiquitination enzymes, Cbl, SCF ubiquitination ligase complex, APC/C, adhesion molecules, integrins, Immunoglobulin-like adhesion molecules, selectins, cadherins, catenins, focal adhesion kinase, p130CAS, cytoskeletal/contractile proteins, fodrin, actin, paxillin, myosin, myosin binding proteins, tubulin, eg5/KSP, CENPs, heterotrimeric G proteins, β-adrenergic receptors, muscarinic receptors, adenylyl cyclase receptors, small molecular weight GTPases, H-Ras, K-Ras, N-Ras, Ran, Rac, Rho, Cdc42, Arfs, RABs, RHEB, guanine nucleotide exchange factors, Vav, Tiam, Sos, Dbl, PRK, TSC1,2, GTPase activating proteins, Ras-GAP, Arf-GAPs, Rho-GAPs, caspases, Caspase 2, Caspase 3, Caspase 6, Caspase 7, Caspase 8, Caspase 9, proteins involved in apoptosis, Bcl-2, Mcl-1, Bcl-XL, Bcl-w, Bcl-B, Al, Bax, Bak, Bok, Bik, Bad, Bid, Bim, Bmf, Hrk, Noxa, Puma, IAPB, XIAP, Smac, cell cycle regulators, Cdk4, Cdk 6, Cdk 2, Cdk1, Cdk 7, Cyclin D, Cyclin E, Cyclin A, Cyclin B, Rb, p16, p14Arf, p27KIP, p21CIP, molecular chaperones, Hsp90s, Hsp70, Hsp27, metabolic enzymes, Acetyl-CoAa Carboxylase, ATP citrate lyase, nitric oxide synthase, vesicular transport proteins, caveolins, endosomal sorting complex required for transport (ESCRT) proteins, vesicular protein sorting (Vsps), hydroxylases, prolyl-hydroxylases PHD-1, 2 and 3, asparagine hydroxylase FIH transferases, isomerases, Pin1 prolyl isomerase, topoisomerases, deacetylases, Histone deacetylases, sirtuins, acetylases, histone acetylases, CBP/P300 family, MYST family, ATF2, methylases, DNA methyl transferases, demethylases, Histone H3K4 demethylases, H3K27, JHDM2A, UTX, tumor suppressor genes, VHL, WT-1, p53, Hdm, PTEN, proteases, ubiquitin proteases, urokinase-type plasminogen activator (uPA) and uPA receptor (uPAR) system, cathepsins, metalloproteinases, esterases, hydrolases, separase, ion channels, potassium channels, sodium channels, molecular transporters, multi-drug resistance proteins, P-Gycoprotein, nucleoside transporters, transcription factors/DNA binding proteins, Ets, Elk, SMADs, Rel-A (p65-NFKB), CREB, NFAT, ATF-2, AFT, Myc, Fos, Spl, Egr-1, T-bet, β-catenin, HIFs, FOXOs, E2Fs, SRFs, TCFs, Egr-1, β-FOXO STAT1, STAT 3, STAT 4, STAT 5, STAT 6, p53, WT-1, HMGA, regulators of translation, pS6, 4EPB-1, eIF4E-binding protein, regulators of transcription, RNA polymerase, initiation factors, elongation factors. In some embodiments, the protein is S6. See also the proteins listed in the examples below.

In some embodiments, an epitope-recognizing fragment of an activation state antibody rather than the whole antibody is used. In some embodiments, the epitope-recognizing fragment is immobilized. In some embodiments, the antibody light chain that recognizes an epitope is used. A recombinant nucleic acid encoding a light chain gene product that recognizes an epitope may be used to produce such an antibody fragment by recombinant means well known in the art.

In alternative embodiments of the instant invention, aromatic amino acids of protein binding elements may be replaced with other molecules. See U.S. Ser. Nos. 12/432,720 and 13/493,857 and U.S. Pat. No. 8,227,202.

In some embodiments, the activation state-specific binding element is a peptide comprising a recognition structure that binds to a target structure on an activatable protein. A variety of recognition structures are well known in the art and can be made using methods known in the art, including by phage display libraries (see e.g., Gururaja et al. Chem. Biol. (2000) 7:515-27; Houimel et al., Eur. J. Immunol. (2001) 31:3535-45; Cochran et al. J. Am. Chem. Soc. (2001) 123:625-32; Houimel et al. Int. J. Cancer (2001) 92:748-55, each incorporated herein by reference). Further, fluorophores can be attached to such antibodies for use in the methods of the present invention.

A variety of recognitions structures are known in the art (e.g., Cochran et al., J. Am. Chem. Soc. (2001) 123:625-32; Boer et al., Blood (2002) 100:467-73, each expressly incorporated herein by reference)) and can be produced using methods known in the art (see e.g., Boer et al., Blood (2002) 100:467-73; Gualillo et al., Mol. Cell Endocrinol. (2002) 190:83-9, each expressly incorporated herein by reference)), including for example combinatorial chemistry methods for producing recognition structures such as polymers with affinity for a target structure on an activatable protein (see e.g., Barn et al., J. Comb. Chem. (2001) 3:534-41; Ju et al., Biotechnol. (1999) 64:232-9, each expressly incorporated herein by reference). In another embodiment, the activation state-specific antibody is a protein that only binds to an isoform of a specific activatable protein that is phosphorylated and does not bind to the isoform of this activatable protein when it is not phosphorylated or nonphosphorylated. In another embodiment the activation state-specific antibody is a protein that only binds to an isoform of an activatable protein that is intracellular and not extracellular, or vice versa. In a some embodiment, the recognition structure is an anti-laminin single-chain antibody fragment (scFv) (see e.g., Sanz et al., Gene Therapy (2002) 9:1049-53; Tse et al., J. Mol. Biol. (2002) 317:85-94, each expressly incorporated herein by reference).

In some embodiments the binding element is a nucleic acid. The term "nucleic acid" include nucleic acid analogs, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphosphoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169-176). Several nucleic acid analogs are described in Rawls, C & E News Jun. 2, 1997 page 35. All of these references are hereby expressly incorporated by reference. These modifications of the ribose-phosphate backbone may be done to facilitate the addition of additional moieties such as labels, or to increase the stability and half-life of such molecules in physiological environments.

In some embodiment the binding element is a small organic compound. Binding elements can be synthesized from a series of substrates that can be chemically modified. "Chemically modified" herein includes traditional chemical reactions as well as enzymatic reactions. These substrates generally include, but are not limited to, alkyl groups (including alkanes, alkenes, alkynes and heteroalkyl), aryl groups (including arenes and heteroaryl), alcohols, ethers, amines, aldehydes, ketones, acids, esters, amides, cyclic compounds, heterocyclic compounds (including purines, pyrimidines, benzodiazepins, beta-lactams, tetracylines, cephalosporins, and carbohydrates), steroids (including estrogens, androgens, cortisone, ecodysone, etc.), alkaloids (including ergots, vinca, curare, pyrollizdine, and mitomycines), organometallic compounds, hetero-atom bearing compounds, amino acids, and nucleosides. Chemical (including enzymatic) reactions may be done on the moieties to form new substrates or binding elements that can then be used in the present invention.

In some embodiments the binding element is a carbohydrate. As used herein the term carbohydrate is meant to include any compound with the general formula $(CH_2O)_n$. Examples of carbohydrates are di-, tri- and oligosaccharides, as well polysaccharides such as glycogen, cellulose, and starches.

In some embodiments the binding element is a lipid. As used herein the term lipid herein is meant to include any water insoluble organic molecule that is soluble in nonpolar organic solvents. Examples of lipids are steroids, such as cholesterol, and phospholipids such as sphingomeylin.

In some embodiments, the binding elements are used to isolated the activatable elements prior to its detection, e.g. using mass spectrometry.

Examples of activatable elements, activation states and methods of determining the activation level of activatable elements are described in US publication number 20060073474 entitled "Methods and compositions for detecting the activation state of multiple proteins in single cells" and US publication number 20050112700 entitled "Methods and compositions for risk stratification" the content of which are incorporate here by reference.

2. Labels

The methods and compositions of the instant invention provide detectable binding elements, e.g., binding elements comprising a label or tag. By label is meant a molecule that can be directly (i.e., a primary label) or indirectly (i.e., a secondary label) detected; for example a label can be visualized and/or measured or otherwise identified so that its presence or absence can be known. Binding elements and labels for binding elements are shown in See U.S. Ser. Nos. 12/432,720 and 13/493,857 and U.S. Pat. No. 8,227,202 and the other applications incorporated above.

A compound can be directly or indirectly conjugated to a label which provides a detectable signal, e.g. radioisotopes, fluorescers, enzymes, antibodies, particles such as magnetic particles, chemiluminescers, molecules that can be detected by mass spec, or specific binding molecules, etc. Specific binding molecules include pairs, such as biotin and streptavidin, digoxin and antidigoxin etc. Examples of labels include, but are not limited to, optical fluorescent and chromogenic dyes including labels, label enzymes and radioisotopes. In some embodiments of the invention, these labels may be conjugated to the binding elements.

In some embodiments, one or more binding elements are uniquely labeled. Using the example of two activation state specific antibodies, by "uniquely labeled" is meant that a first activation state antibody recognizing a first activated element comprises a first label, and second activation state antibody recognizing a second activated element comprises a second label, wherein the first and second labels are detectable and distinguishable, making the first antibody and the second antibody uniquely labeled.

In general, labels fall into four classes: a) isotopic labels, which may be radioactive or heavy isotopes; b) magnetic, electrical, thermal labels; c) colored, optical labels including luminescent, phosphorous and fluorescent dyes or moieties; and d) binding partners. Labels can also include enzymes (horseradish peroxidase, etc.) and magnetic particles. In some embodiments, the detection label is a primary label. A primary label is one that can be directly detected, such as a fluorophore.

Labels include optical labels such as fluorescent dyes or moieties. Fluorophores can be either "small molecule" fluors, or proteinaceous fluors (e.g. green fluorescent proteins and all variants thereof).

In some embodiments, activation state-specific antibodies are labeled with quantum dots as disclosed by Chattopadhyay, P. K. et al. Quantum dot semiconductor nanocrystals for immunophenotyping by polychromatic flow cytometry. Nat. Med. 12, 972-977 (2006). Quantum dot labels are commercially available through Invitrogen, <<http://probes.invitrogen.com/products/qdot/>>.

Quantum dot labeled antibodies can be used alone or they can be employed in conjunction with organic fluorochrome-conjugated antibodies to increase the total number of labels available. As the number of labeled antibodies increase so does the ability for subtyping known cell populations. Additionally, activation state-specific antibodies can be labeled using chelated or caged lanthanides as disclosed by Erkki, J. et al. Lanthanide chelates as new fluorochrome labels for cytochemistry. J. Histochemistry Cytochemistry, 36:1449-1451, 1988, and U.S. Pat. No. 7,018,850, entitled Salicylamide-Lanthanide Complexes for Use as Luminescent Markers. Other methods of detecting fluorescence may also be used, e.g., Quantum dot methods (see, e.g., Goldman et al., J. Am. Chem. Soc. (2002) 124:6378-82; Pathak et al. J. Am. Chem. Soc. (2001) 123:4103-4; and Remade et al., Proc. Natl. Sci. USA (2000) 18:553-8, each expressly incorporated herein by reference) as well as confocal microscopy.

In some embodiments, the activatable elements are labeled with tags suitable for Inductively Coupled Plasma Mass Spectrometer (ICP-MS) as disclosed in Tanner et al. Spectrochimica Acta Part B: Atomic Spectroscopy, 2007 March; 62(3):188-195.

Alternatively, detection systems based on FRET, discussed in detail below, may be used. FRET finds use in the instant invention, for example, in detecting activation states that involve clustering or multimerization wherein the proximity of two FRET labels is altered due to activation. In some embodiments, at least two fluorescent labels are used which are members of a fluorescence resonance energy transfer (FRET) pair.

The methods and composition of the present invention may also make use of label enzymes. By label enzyme is meant an enzyme that may be reacted in the presence of a label enzyme substrate that produces a detectable product. Suitable label enzymes for use in the present invention include but are not limited to, horseradish peroxidase, alkaline phosphatase and glucose oxidase. Methods for the use of such substrates are well known in the art. The presence of the label enzyme is generally revealed through the enzyme's catalysis of a reaction with a label enzyme substrate, producing an identifiable product. Such products may be opaque, such as the reaction of horseradish peroxidase with tetramethyl benzedine, and may have a variety of colors. Other label enzyme substrates, such as Luminol (available from Pierce Chemical Co.), have been developed that produce fluorescent reaction products. Methods for identifying label enzymes with label enzyme substrates are well known in the art and many commercial kits are available. Examples and methods for the use of various label enzymes are described in Savage et al., Previews 247:6-9 (1998), Young, J. Virol. Methods 24:227-236 (1989), which are each hereby incorporated by reference in their entirety.

By radioisotope is meant any radioactive molecule. Suitable radioisotopes for use in the invention include, but are not limited to 14C, 3H, 32P, 33P, 35S, 125I and 131I. The use of radioisotopes as labels is well known in the art.

As mentioned, labels may be indirectly detected, that is, the tag is a partner of a binding pair. By "partner of a binding pair" is meant one of a first and a second moiety, wherein the first and the second moiety have a specific binding affinity for each other. Suitable binding pairs for use in the invention include, but are not limited to, antigens/antibodies (for example, digoxigenin/anti-digoxigenin, dinitrophenyl (DNP)/anti-DNP, dansyl-X-anti-dansyl, Fluorescein/anti-fluorescein, lucifer yellow/anti-lucifer yellow, and rhodamine anti-rhodamine), biotin/avidin (or biotin/streptavidin) and calmodulin binding protein (CBP)/calmodulin. Other suitable binding pairs include polypeptides such as the FLAG-peptide [Hopp et al., BioTechnology, 6:1204-1210 (1988)]; the KT3 epitope peptide [Martin et al., Science, 255: 192-194 (1992)]; tubulin epitope peptide [Skinner et al., J. Biol. Chem., 266:15163-15166 (1991)]; and the T7 gene 10 protein peptide tag [Lutz-Freyermuth et al., Proc. Natl. Acad. Sci. USA, 87:6393-6397 (1990)] and the antibodies each thereto. As will be appreciated by those in the art, binding pair partners may be used in applications other than for labeling, as is described herein.

As will be appreciated by those in the art, a partner of one binding pair may also be a partner of another binding pair. For example, an antigen (first moiety) may bind to a first antibody (second moiety) that may, in turn, be an antigen for a second antibody (third moiety). It will be further appreciated that such a circumstance allows indirect binding of a first moiety and a third moiety via an intermediary second moiety that is a binding pair partner to each.

As will be appreciated by those in the art, a partner of a binding pair may comprise a label, as described above. It will further be appreciated that this allows for a tag to be indirectly labeled upon the binding of a binding partner comprising a label. Attaching a label to a tag that is a partner of a binding pair, as just described, is referred to herein as "indirect labeling".

By "surface substrate binding molecule" or "attachment tag" and grammatical equivalents thereof is meant a molecule have binding affinity for a specific surface substrate, which substrate is generally a member of a binding pair applied, incorporated or otherwise attached to a surface. Suitable surface substrate binding molecules and their surface substrates include, but are not limited to poly-histidine (poly-his) or poly-histidine-glycine (poly-his-gly) tags and Nickel substrate; the Glutathione-S Transferase tag and its antibody substrate (available from Pierce Chemical); the flu HA tag polypeptide and its antibody 12CA5 substrate [Field et al., Mol. Cell. Biol., 8:2159-2165 (1988)]; the c-myc tag and the 8F9, 3C7, 6E10, G4, B7 and 9E10 antibody substrates thereto [Evan et al., Molecular and Cellular Biology, 5:3610-3616 (1985)]; and the Herpes Simplex virus glycoprotein D (gD) tag and its antibody substrate [Paborsky et al., Protein Engineering, 3(6):547-553 (1990)]. In general, surface binding substrate molecules useful in the present invention include, but are not limited to, polyhistidine structures (His-tags) that bind nickel substrates, antigens that bind to surface substrates comprising antibody, haptens that bind to avidin substrate (e.g., biotin) and CBP that binds to surface substrate comprising calmodulin.

In some embodiments, the activatable elements are labeled by incorporating a label as describing herein within the activatable element. For example, an activatable element can be labeled in a cell by culturing the cell with amino acids comprising radioisotopes. The labeled activatable element can be measured using, for example, mass spectrometry.

3. Alternative Activation State Indicators

An alternative activation state indicator useful with the instant invention is one that allows for the detection of activation by indicating the result of such activation. For example, phosphorylation of a substrate can be used to detect the activation of the kinase responsible for phosphorylating that substrate. Similarly, cleavage of a substrate can be used as an indicator of the activation of a protease responsible for such cleavage. Methods are well known in the art that allow coupling of such indications to detectable signals, such as the labels and tags described above in connection with binding elements. For example, cleavage of a substrate can result in the removal of a quenching moiety and thus allowing for a detectable signal being produced from a previously quenched label. In addition, binding elements can be used in the isolation of labeled activatable elements which can then be detected using techniques known in the art such as mass spectrometry.

4. Detection

In practicing the methods of this invention, the detection of the status of the one or more activatable elements can be carried out by a person, such as a technician in the laboratory. Alternatively, the detection of the status of the one or more activatable elements can be carried out using automated systems. In either case, the detection of the status of the one or more activatable elements for use according to the methods of this invention is performed according to standard techniques and protocols well-established in the art. See U.S. Pat. Nos. 8,227,202 and 8,206,939 for some basic procedures and U.S. Ser. No. 12/606,869 for automation systems and procedures.

One or more activatable elements can be detected and/or quantified by any method that detect and/or quantitates the presence of the activatable element of interest. Such methods may include radioimmunoassay (RIA) or enzyme linked immunoabsorbance assay (ELISA), immunohistochemistry, immunofluorescent histochemistry with or without confocal microscopy, reversed phase assays, homogeneous enzyme immunoassays, and related non-enzymatic techniques, Western blots, whole cell staining, immunoelectronmicroscopy, nucleic acid amplification, gene array, protein array, mass spectrometry, patch clamp, 2-dimensional gel electrophoresis, differential display gel electrophoresis, microsphere-based multiplex protein assays, label-free cellular assays and flow cytometry, etc. U.S. Pat. No. 4,568,649 describes ligand detection systems, which employ scintillation counting. These techniques are particularly useful for modified protein parameters. Cell readouts for proteins and other cell determinants can be obtained using fluorescent or otherwise tagged reporter molecules. Flow cytometry methods are useful for measuring intracellular parameters. See U.S. Pat. No. 7,393,656 and Shulz et al., Current Protocols in Immunology, 2007, 78:8.17.1-20 which are incorporated by reference in their entireties.

In certain embodiments, the method of detection is flow cytometry or mass spectrometry. In certain embodiments, the method of detection is flow cytometry. In certain embodiments, the method of detection is mass spectrometry.

In some embodiments, the present invention provides methods for determining the activation level on an activatable element for a single cell. The methods may comprise analyzing cells by flow cytometry on the basis of the activation level of at least two activatable elements. Binding elements (e.g. activation state-specific antibodies) are used to analyze cells on the basis of activatable element activation level, and can be detected as described below. Binding elements can also be used to isolate activatable elements which can then be analyzed by methods known in the art. Alternatively, non-binding elements systems as described above can be used in any system described herein.

When using fluorescent labeled components in the methods and compositions of the present invention, it will recognize that different types of fluorescent monitoring systems, e.g., Cytometric measurement device systems, can be used to practice the invention. In some embodiments, flow cytometric systems are used or systems dedicated to high throughput screening, e.g. 96 well or greater microtiter plates. Methods of performing assays on fluorescent materials are well known in the art and are described in, e.g., Lakowicz, J. R., Principles of Fluorescence Spectroscopy, New York: Plenum Press (1983); Herman, B., Resonance energy transfer microscopy, in: Fluorescence Microscopy of Living Cells in Culture, Part B, Methods in Cell Biology, vol. 30, ed. Taylor, D. L. & Wang, Y.-L., San Diego: Academic Press (1989), pp. 219-243; Turro, N. J., Modern Molecular Photochemistry, Menlo Park: Benjamin/Cummings Publishing Col, Inc. (1978), pp. 296-361.

Fluorescence in a sample can be measured using a fluorimeter. In general, excitation radiation, from an excitation source having a first wavelength, passes through excitation optics. The excitation optics cause the excitation radiation to excite the sample. In response, fluorescent proteins in the sample emit radiation that has a wavelength that is different from the excitation wavelength. Collection optics then collect the emission from the sample. The device can include a temperature controller to maintain the sample at a specific temperature while it is being scanned. According to one embodiment, a multi-axis translation stage moves a microtiter plate holding a plurality of samples in order to position different wells to be exposed. The multi-axis translation stage, temperature controller, auto-focusing feature, and electronics associated with imaging and data collection can be managed by an appropriately programmed digital computer. The computer also can transform the data collected during the assay into another format for presentation. In general, known robotic systems and components can be used.

Other methods of detecting fluorescence may also be used, e.g., Quantum dot methods (see, e.g., Goldman et al., J. Am. Chem. Soc. (2002) 124:6378-82; Pathak et al. J. Am. Chem. Soc. (2001) 123:4103-4; and Remade et al., Proc. Natl. Sci. USA (2000) 18:553-8, each expressly incorporated herein by reference) as well as confocal microscopy. In general, flow cytometry involves the passage of individual cells through the path of a laser beam. The scattering the beam and excitation of any fluorescent molecules attached to, or found within, the cell is detected by photomultiplier tubes to create a readable output, e.g. size, granularity, or fluorescent intensity.

The detecting, sorting, or isolating step of the methods of the present invention can entail fluorescence-activated cell sorting (FACS) techniques, where FACS is used to select cells from the population containing a particular surface marker, or the selection step can entail the use of magnetically responsive particles as retrievable supports for target cell capture and/or background removal. A variety of FACS systems are known in the art and can be used in the methods of the invention (see e.g., WO99/54494, filed Apr. 16, 1999; U.S. Ser. No. 20010006787, filed Jul. 5, 2001, each expressly incorporated herein by reference).

In some embodiments, a FACS cell sorter (e.g. a FACSVantage™ Cell Sorter, Becton Dickinson Immunocytometry Systems, San Jose, Calif.) is used to sort and collect cells that may used as a modulator or as a population of reference cells. In some embodiments, the modulator or reference cells are first contacted with fluorescent-labeled binding elements (e.g. antibodies) directed against specific elements. In such an embodiment, the amount of bound binding element on each cell can be measured by passing droplets containing the cells through the cell sorter. By imparting an electromagnetic charge to droplets containing the positive cells, the cells can be separated from other cells. The positively selected cells can then be harvested in sterile collection vessels. These cell-sorting procedures are described in detail, for example, in the FACSVantage™. Training Manual, with particular reference to sections 3-11 to 3-28 and 10-1 to 10-17, which is hereby incorporated by reference in its entirety.

In another embodiment, positive cells can be sorted using magnetic separation of cells based on the presence of an isoform of an activatable element. In such separation techniques, cells to be positively selected are first contacted with specific binding element (e.g., an antibody or reagent that binds an isoform of an activatable element). The cells are then contacted with retrievable particles (e.g., magnetically responsive particles) that are coupled with a reagent that binds the specific element. The cell-binding element-particle complex can then be physically separated from non-positive or non-labeled cells, for example, using a magnetic field. When using magnetically responsive particles, the positive or labeled cells can be retained in a container using a magnetic filed while the negative cells are removed. These and similar separation procedures are described, for example, in the Baxter Immunotherapy Isolex training manual which is hereby incorporated in its entirety.

In some embodiments, methods for the determination of a receptor element activation state profile for a single cell are provided. The methods comprise providing a population of cells and analyze the population of cells by flow cytometry. Preferably, cells are analyzed on the basis of the activation level of at least one activatable element. In some embodiments, cells are analyzed on the basis of the activation level of at least two activatable elements.

In some embodiments, a multiplicity of activatable element activation-state antibodies is used to simultaneously determine the activation level of a multiplicity of elements.

In some embodiment, cell analysis by flow cytometry on the basis of the activation level of at least two elements is combined with a determination of other flow cytometry readable outputs, such as the presence of surface markers, granularity and cell size to provide a correlation between the activation level of a multiplicity of elements and other cell qualities measurable by flow cytometry for single cells.

As will be appreciated, the present invention also provides for the ordering of element clustering events in signal transduction. Particularly, the present invention allows the artisan to construct an element clustering and activation hierarchy based on the correlation of levels of clustering and activation of a multiplicity of elements within single cells. Ordering can be accomplished by comparing the activation level of a cell or cell population with a control at a single time point, or by comparing cells at multiple time points to observe subpopulations arising out of the others.

As will be appreciated, these methods provide for the identification of distinct signaling cascades for both artificial and stimulatory conditions in cell populations, such a peripheral blood mononuclear cells, or naive and memory lymphocytes.

When necessary, cells are dispersed into a single cell suspension, e.g. by enzymatic digestion with a suitable protease, e.g. collagenase, dispase, etc; and the like. An appropriate solution is used for dispersion or suspension. Such solution will generally be a balanced salt solution, e.g. normal saline, PBS, Hanks balanced salt solution, etc., conveniently supplemented with fetal calf serum or other naturally occurring factors, in conjunction with an acceptable buffer at low concentration, generally from 5-25 mM. Convenient buffers include HEPES1 phosphate buffers, lactate buffers, etc. The cells may be fixed, e.g. with 3% paraformaldehyde, and are usually permeabilized, e.g. with ice cold methanol; HEPES-buffered PBS containing 0.1% saponin, 3% BSA; covering for 2 min in acetone at −200 C; and the like as known in the art and according to the methods described herein.

In some embodiments, one or more cells are contained in a well of a 96 well plate or other commercially available multiwell plate. In an alternate embodiment, the reaction mixture or cells are in a cytometric measurement device. Other multiwell plates useful in the present invention include, but are not limited to 384 well plates and 1536 well plates. Still other vessels for containing the reaction mixture or cells and useful in the present invention will be apparent to the skilled artisan.

The addition of the components of the assay for detecting the activation level or activity of an activatable element, or modulation of such activation level or activity, may be sequential or in a predetermined order or grouping under conditions appropriate for the activity that is assayed for. Such conditions are described here and known in the art. Moreover, further guidance is provided below (see, e.g., in the Examples).

In some embodiments, the activation level of an activatable element is measured using Inductively Coupled Plasma Mass Spectrometer (ICP-MS). A binding element that has been labeled with a specific element binds to the activatable. When the cell is introduced into the ICP, it is atomized and ionized. The elemental composition of the cell, including the labeled binding element that is bound to the activatable element, is measured. The presence and intensity of the signals corresponding to the labels on the binding element indicates the level of the activatable element on that cell (Tanner et al. Spectrochimica Acta Part B: Atomic Spectroscopy, 2007 March; 62(3):188-195). See also Bodenmiller et al, Nature Biotechnology, published online Aug. 19, 2012, doi:10.1038/nbt.2317.

As will be appreciated by one of skill in the art, the instant methods and compositions find use in a variety of other assay formats in addition to flow cytometry analysis. For example, a chip analogous to a DNA chip can be used in the methods of the present invention. Arrayers and methods for spotting nucleic acids on a chip in a prefigured array are known. In addition, protein chips and methods for synthesis are known. These methods and materials may be adapted for the purpose of affixing activation state binding elements to a chip in a prefigured array. In some embodiments, such a chip comprises a multiplicity of element activation state binding elements, and is used to determine an element activation state profile for elements present on the surface of a cell. See U.S. Pat. No. 5,744,934. In some embodiments, a microfluidic image cytometry is used (Sun et al. Cancer Res; 70(15) Aug. 1, 2010)

In some embodiments confocal microscopy can be used to detect activation profiles for individual cells. Confocal microscopy relies on the serial collection of light from spatially filtered individual specimen points, which is then electronically processed to render a magnified image of the specimen. The signal processing involved confocal microscopy has the additional capability of detecting labeled binding elements within single cells, accordingly in this embodiment the cells can be labeled with one or more binding elements. In some embodiments the binding elements used in connection with confocal microscopy are antibodies conjugated to fluorescent labels, however other binding elements, such as other proteins or nucleic acids are also possible.

In some embodiments, the methods and compositions of the instant invention can be used in conjunction with an "In-Cell Western Assay." In such an assay, cells are initially grown in standard tissue culture flasks using standard tissue culture techniques. Once grown to optimum confluency, the growth media is removed and cells are washed and trypsinized. The cells can then be counted and volumes sufficient to transfer the appropriate number of cells are aliquoted into microwell plates (e.g., Nunc TM 96 Microwell TM plates). The individual wells are then grown to optimum confluency in complete media whereupon the media is replaced with serum-free media. At this point controls are untouched, but experimental wells are incubated with a modulator, e.g. EGF. After incubation with the modulator cells are fixed and stained with labeled antibodies to the activation elements being investigated. Once the cells are labeled, the plates can be scanned using an imager such as the Odyssey Imager (LiCor, Lincoln Nebr.) using techniques described in the Odyssey Operator's Manual v1.2, which is hereby incorporated in its entirety. Data obtained by scanning of the multiwell plate can be analyzed and activation profiles determined as described below.

In some embodiments, the detecting is by high pressure liquid chromatography (HPLC), for example, reverse phase HPLC, and in a further aspect, the detecting is by mass spectrometry.

These instruments can fit in a sterile laminar flow or fume hood, or are enclosed, self-contained systems, for cell culture growth and transformation in multi-well plates or tubes and for hazardous operations. The living cells may be grown under controlled growth conditions, with controls for temperature, humidity, and gas for time series of the live cell assays. Automated transformation of cells and automated colony pickers may facilitate rapid screening of desired cells.

Flow cytometry or capillary electrophoresis formats can be used for individual capture of magnetic and other beads, particles, cells, and organisms.

Flexible hardware and software allow instrument adaptability for multiple applications. The software program modules allow creation, modification, and running of methods. The system diagnostic modules allow instrument alignment, correct connections, and motor operations. Customized tools, labware, and liquid, particle, cell and organism transfer patterns allow different applications to be performed. Databases allow method and parameter storage. Robotic and computer interfaces allow communication between instruments.

In some embodiments, the methods of the invention include the use of liquid handling components. The liquid handling systems can include robotic systems comprising any number of components. In addition, any or all of the steps outlined herein may be automated; thus, for example, the systems may be completely or partially automated.

As will be appreciated by those in the art, there are a wide variety of components which can be used, including, but not limited to, one or more robotic arms; plate handlers for the positioning of microplates; automated lid or cap handlers to remove and replace lids for wells on non-cross contamination plates; tip assemblies for sample distribution with disposable tips; washable tip assemblies for sample distribution; 96 well loading blocks; cooled reagent racks; microtiter plate pipette positions (optionally cooled); stacking towers for plates and tips; and computer systems. See U.S. Ser. No. 12/606,869 which is incorporated by reference in its entirety.

Fully robotic or micro fluidic systems include automated liquid-, particle-, cell- and organism-handling including high throughput pipetting to perform all steps of screening applications. This includes liquid, particle, cell, and organism manipulations such as aspiration, dispensing, mixing, diluting, washing, accurate volumetric transfers; retrieving, and discarding of pipet tips; and repetitive pipetting of identical volumes for multiple deliveries from a single sample aspiration. These manipulations are cross-contamination-free liquid, particle, cell, and organism transfers. This instrument performs automated replication of microplate samples to filters, membranes, and/or daughter plates, high-density transfers, full-plate serial dilutions, and high capacity operation.

In some embodiments, chemically derivatized particles, plates, cartridges, tubes, magnetic particles, or other solid phase matrix with specificity to the assay components are used. The binding surfaces of microplates, tubes or any solid phase matrices include non-polar surfaces, highly polar surfaces, modified dextran coating to promote covalent binding, antibody coating, affinity media to bind fusion proteins or peptides, surface-fixed proteins such as recombinant protein A or G, nucleotide resins or coatings, and other affinity matrix are useful in this invention.

In some embodiments, platforms for multi-well plates, multi-tubes, holders, cartridges, minitubes, deep-well plates, microfuge tubes, cryovials, square well plates, filters, chips, optic fibers, beads, and other solid-phase matrices or platform with various volumes are accommodated on an upgradable modular platform for additional capacity. This modular platform includes a variable speed orbital shaker, and multi-position work decks for source samples, sample and reagent dilution, assay plates, sample and reagent reservoirs, pipette tips, and an active wash station. In some embodiments, the methods of the invention include the use of a plate reader. See U.S. Ser. No. 12/606,869.

In some embodiments, thermocycler and thermoregulating systems are used for stabilizing the temperature of heat exchangers such as controlled blocks or platforms to provide accurate temperature control of incubating samples from 0° C. to 100° C.

In some embodiments, interchangeable pipet heads (single or multi-channel) with single or multiple magnetic probes, affinity probes, or pipetters robotically manipulate the liquid, particles, cells, and organisms. Multi-well or multi-tube magnetic separators or platforms manipulate liquid, particles, cells, and organisms in single or multiple sample formats.

In some embodiments, the instrumentation will include a detector, which can be a wide variety of different detectors, depending on the labels and assay. In some embodiments, useful detectors include a microscope(s) with multiple channels of fluorescence; plate readers to provide fluorescent, ultraviolet and visible spectrophotometric detection with single and dual wavelength endpoint and kinetics capability, fluorescence resonance energy transfer (FRET), luminescence, quenching, two-photon excitation, and intensity redistribution; CCD cameras to capture and transform data and images into quantifiable formats; and a computer workstation.

In some embodiments, the robotic apparatus includes a central processing unit which communicates with a memory and a set of input/output devices (e.g., keyboard, mouse, monitor, printer, etc.) through a bus. Again, as outlined below, this may be in addition to or in place of the CPU for the multiplexing devices of the invention. The general interaction between a central processing unit, a memory, input/output devices, and a bus is known in the art. Thus, a variety of different procedures, depending on the experiments to be run, are stored in the CPU memory. See U.S. Ser. No. 12/606,869 which is incorporated by reference in its entirety.

These robotic fluid handling systems can utilize any number of different reagents, including buffers, reagents, samples, washes, assay components such as label probes, etc.

Any of the steps above can be performed by a computer program product that comprises a computer executable logic that is recorded on a computer readable medium. For example, the computer program can execute some or all of the following functions: (i) exposing different population of cells to one or more modulators, (ii) exposing different population of cells to one or more binding elements, (iii) detecting the activation levels of one or more activatable elements, and (iv) making a diagnosis or prognosis based on the activation level of one or more activatable elements in the different populations.

The computer executable logic can work in any computer that may be any of a variety of types of general-purpose computers such as a personal computer, network server, workstation, or other computer platform now or later developed. In some embodiments, a computer program product is described comprising a computer usable medium having the computer executable logic (computer software program, including program code) stored therein. The computer executable logic can be executed by a processor, causing the processor to perform functions described herein. In other embodiments, some functions are implemented primarily in hardware using, for example, a hardware state machine. Implementation of the hardware state machine so as to perform the functions described herein will be apparent to those skilled in the relevant arts.

The program can provide a method of determining the status of an individual by accessing data that reflects the activation level of one or more activatable elements in the reference population of cells.

E. Data Analysis and Presentation

In some embodiments, the activation state data of a cell population is determined by contacting the cell population with one or more modulators, generating activation state data for the cell population and using computational techniques to identify one or more discrete cell populations based on the data. These techniques are implemented using computers comprising memory and hardware. In one embodiment, algorithms for generating metrics based on raw activation state data are stored in the memory of a computer and executed by a processor of a computer. These algorithms are used in conjunction with gating and binning algorithms, which are also stored and executed by a computer, to identify the discrete cell populations.

Gating can be used in different ways to identify discrete cell populations. For example, "Outside-in" comparison of activation state data for individual samples or subset (e.g., patients in a trial) is used to identify discrete cell populations. In this embodiment, cell populations are homogenous or lineage gated in such a way as to create discrete sets of cells considered to be homogenous based on a characteristic (e.g. cell type, expression, subtype, etc.). An example of sample-level comparison in an AML patient would be the identification of signaling profiles in lymphocytes (e.g., CD4 T cells, CD8 T cells and/or B cells), monocytes+granulocytes and leukemic blast and correlating the activation state data of these populations with non-random distribution of clinical responses. This is considered an outside-in approach because the discrete cell population of interest is pre-defined prior to the mapping and comparison of its profile to, e.g., a clinical outcome or the profile of the populations in normal individuals.

In another example, "Inside-out" comparison of activation state data at the level of individual cells in a heterogeneous population is used to identify discrete cell populations. An example of this would be the signal transduction state mapping of mixed hematopoietic cells under certain conditions and subsequent comparison of computationally identified cell clusters with lineage specific markers. This could be considered an inside-out approach to single cell studies as it does not presume the existence of specific discrete cell populations prior to classification. Suitable methods for inside-out identification of discrete cell populations include the multi-resolution binning algorithm described above. A major drawback of this approach is that it creates discrete cell populations which, at least initially, require multiple transient markers to enumerate and may never be accessible with a single cell surface epitope. As a result, the biological significance of such discrete cell populations can be difficult to determine. The main advantage of this unconventional approach is the unbiased tracking of discrete cell populations without drawing potentially arbitrary distinctions between lineages or cell types and the potential of using the activation state data of the different populations to determine the status of an individual.

Each of these techniques capitalizes on the ability of flow cytometry or other single cell detection techniques such as mass spectrometry to deliver large amounts of multi-parametric data at the single cell level. For discrete cell populations associated with a condition (e.g. neoplastic or hematopoetic condition), a third "meta-level" of data exists because cells associated with a condition (e.g. cancer cells) are generally treated as a single entity and classified according to historical techniques. These techniques have included organ or tissue of origin, degree of differentiation, proliferation index, metastatic spread, and genetic or metabolic data regarding the patient.

The data can be analyzed using various metrics, which apply not only to determining discrete cell populations, but also activatable elements, effects of modulators, agents, etc. For example, the median fluorescence intensity (MFI) is computed for each activatable element from the intensity levels for the cells in the cell population gate. The MFI values are then used to compute a variety of metrics by comparing them to the various baseline or background values, e.g. the unstimulated condition, autofluorescence, and isotype control. The following metrics are examples of metrics that can be used in the methods described herein: 1) a metric that measures the difference in the log of the median fluorescence value between an unstimulated fluorochrome-antibody stained sample and a sample that has not been treated with a stimulant or stained (log(MFIUnstimulated Stained)−log(MFIGated Unstained)), 2) a metric that measures the difference in the log of the median fluorescence value between a stimulated fluorochrome-antibody stained sample and a sample that has not been treated with a stimulant or stained (log(MFIStimulated Stained)−log(MFIGated Unstained)), 3) a metric that measures the change between the stimulated fluorochrome-antibody stained sample and the unstimulated fluorochrome-antibody stained sample log(MFIStimulated Stained)−log(MFIUnstimulated Stained), also called "fold change in median fluorescence intensity", 4) a metric that measures the percentage of cells in a Quadrant Gate of a contour plot which measures multiple populations in one or more dimension 5) a metric that measures MFI of phosphor positive population to obtain percentage positivity above the background and 6) use of multimodality and spread metrics for large sample population and for subpopulation analysis.

In certain embodiments, the equivalent number of reference fluorophores value (ERF) is generated. The ERF is a transformed value of the median fluorescent intensity values. The ERF value is computed using a calibration line determined by fitting observations of a standardized set of 8-peak rainbow beads for all fluorescent channels to standardized values assigned by the manufacturer. The ERF values for different samples can be combined in any way to generate different activation state metric. Different metrics can include: 1) a fold value based on ERF values for samples that have been treated with a modulator (ERFm) and samples that have not been treated with a modulator (ERFu), log 2 (ERFm/ERFu); 2) a total phospho value based on ERF values for samples that have been treated with a modulator (ERFm) and samples from autofluorecsent wells (ERFa), log 2 (ERFm/ERFa); 3) a basal value based on ERF values for samples that have not been treated with a modulator (ERFu) and samples from autofluorescent wells (ERFa), log 2 (ERFu/ERFa); 4) A Mann-Whitney statistic Uu comparing the ERFm and ERFu values that has been scaled down to a unit interval (0,1) allowing inter-sample comparisons; 5) A Mann-Whitney statistic Uu comparing the ERFm and ERFu values that has been scaled down to a unit interval (0,1) allowing inter-sample comparisons; 5) a Mann-Whitney statistic Ua comparing the ERFa and ERFm values that has been scaled down to a unit interval (0,1); and 6) A Mann-Whitney statistic U75. U75 is a linear rank statistic designed to identify a shift in the upper quartile of the distribution of ERFm and ERFu values. ERF values at or below the 75th percentile of the ERFm and ERFu values are assigned a score of 0. The remaining ERFm and ERFu values are assigned values between 0 and 1 as in the Uu statistic. For activatable elements that are surface markers on cells, the following metrics may be further generated: 1) a relative protein expression metric log 2(ERFstain)−log 2(ERFcontrol) based on the ERF value for a stained sample (ERFstain) and the ERF value for a control sample (ERFcontrol); and 2) A Mann-Whitney statistic Ui comparing the ERFm and ERFi values that has been scaled down to a unit interval (0,1), where the ERFi values are derived from an isotype control. Also, the "percent positive," or percentage of a cell population positive for staining for a given measurement in a flow cytometry experiment, may be used.

To put it more succinctly, the log 2Fold metric measures the magnitude of the responsiveness of a cell population to modulation relative to the same cell population in the reference well (e.g., isotype or unmodulated) by comparing the median fluorescence values of the responsive cell population to that of the reference population on a log 2 scale. A value of zero would indicate overlapping populations and a value different from zero indicates the responsive population has shifted to higher fluorescence (positive values) or to lower fluorescence (negative values). The log 2Fold metric is calculated as log 2(ERF modulated/ERF unmodulated). The Uu metric is the Mann-Whitney U statistic that compares the ERF values of the modulated and unmodulated wells that have been scaled to the unit interval (0,1) for a given donor and quantifies the fraction of cells responding to a specific modulation. In addition, when a modulator has been combined with an agent (e.g., a cytokine inhibitor), the Uim metric is the Mann-Whitney U statistic that compares the ERF values of the modulated−agent and modulated+agent wells that have been scaled to the unit interval (0,1) for a given donor and quantifies the fraction of cells responding to a specific modulation. See FIG. 25 for actual data for unmodulated, modulated−agent, and modulated+agent showing peak shifts involved in Uu and Uim. See FIG. 27 for a general representation of Uu and Uim.

When combined, a node-metric is a quantified change in signal and is used to interpret the functionality and biology of each signaling node. It is annotated as "node|metric", e.g. "anti-IgM→p-ERK|log 2Fold".

The activation state data for the different markers is "gated" in order to identify discrete subpopulations of cells within the data. In gating, activation state data is used to identify discrete sub-populations of cells with distinct activation levels of an activatable element. These discrete sub-populations of cells can correspond to cell types, cell sub-types, cells in a disease or other physiological state and/or a population of cells having any characteristic in common.

Adjustments to Account for Unhealthy Cells in Analysis

Gating may be performed so that only data from healthy cells is used in analyses. In some embodiments, the health of the cells is determined by using cell markers that indicate cell health. In some embodiments, cells that are dead or undergoing apoptosis are removed from the analysis. In some embodiments, cells are stained with apoptosis and/or cell death markers such as labeled anti-cPARP antibodies or Aqua dyes. Scatter characteristics may also be used. Cells undergoing apoptosis and/or cells that are dead can be gated out of the analysis. In other embodiments, apoptosis is monitored over time before and after treatment. For example, in some embodiments, the percentage of healthy cells can be measured at time zero and then at later time points and conditions such as, for example: 24 h with no modulator, and 24 h with treatment with an agent, such as fludarabine or bendamustine. In some embodiments, the measurements of activatable elements are adjusted by measurements of sample quality for the individual sample, such as the percent of healthy cells present.

Thus, in certain of these embodiments in which samples are gated for healthy cells, the gating criteria may include one or more of scatter data, Amine aqua dye staining data, and data from an indicator of apoptosis, for example an activated form of an activatable element involved in the apoptosis pathway, such as cPARP. In the case of an indicator of apoptosis, such as cPARP, cells may be exposed to not only labeled binding element, e.g., antibody, specific for at least one intracellular activatable element, but an additional labeled binding element, e.g., antibody, specific for the indicator of apoptosis, such as cPARP (in the case of cPARP, it is itself an additional activatable element). A cutoff for the indicator of apoptosis may be established and only data from cells on the side of the cutoff indicating no apoptosis or apoptosis not progressed beyond a certain point may be used. Similar cutoffs may be established for scatter data and/or Amine aqua blue staining intensity.

In certain embodiments, the one or more cell health markers comprise one or more of a caspase, protein caspase substrate, cytochrome C, apoptosis inducing factor (AIF), Inhibitor of Apoptosis (IAP) family member, Annexin-V, Bcl-2 family, BH3-only apoptotic sensitizer, pro-apoptotic protein, APO-1/Fas/CD95, growth stimulating gene, tumor suppressor gene, or a dye. In another embodiment, the protein caspase substrate is PARP or cytokeratin 18. In another embodiment, the one or more cell health markers is cleaved PARP or cleaved cytokeratin 18. In another embodiment, the one or more cell health markers is cleaved PARP. In another embodiment, the dye is a fluorescent dye or fluorogenic caspase substrate dye. In another embodiment, the tumor suppressor gene is p53. In another embodiment, the growth stimulating gene is c-myc proto-oncogene. In another embodiment, the Bcl-2 family member is MCL-1, BCL-2, or BCL-XL. In another embodiment, the BH3-only apoptosis sensitizer is PUMA, NOXA, Bim, or Bad. In another embodiment, the protein caspase substrate is caspase 3. In another embodiment, the pro-apoptotic proteins comprise Bad, Bak or Bax.

In some embodiments, a regression equation will be used to adjust raw node readout scores for the percentage of healthy cells at 24 hours post-thaw. In some embodiments, means and standard deviations will be used to standardize the adjusted node readout scores.

Before applying the SCNP classifier, raw node-metric signal readouts (measurements) for samples can adjusted for the percentage of healthy cells and then standardized. The adjustment for the percentage of healthy cells and the subsequent standardization of adjusted measurements is applied separately for each of the node-metrics in the SCNP classifier.

The following formula can be used to calculate the adjusted, normalized node-metric measurement (z) for each of the node-metrics of each sample. $z=((x-(b_0+b_1.times.pcthealthy))-residual\_mean)/residual\_sd$, where x is the raw node-metric signal readout, $b_0$ and $b_1$ are the coefficients from the regression equation used to adjust for the percentage of healthy cells (pcthealthy), and residual_mean and residual_sd are the mean and standard deviation, respectively, for the adjusted signal readouts in the training set data. The values of $b_0$, $b_1$, residual_mean, and residual_sd for each node-metric are included in the embedded object below, with values of the latter two parameters stored in variables by the same name. The values of the $b_0$ and $b_1$ parameters are contained on separate records in the variable named "estimate". The value for $b_0$ is contained on the record where the variable "parameter" is equal to "Intercept" and the value for $b_1$ is contained on the record where the variable "parameter" is equal to "percenthealthy24 Hrs". The value of pcthealthy will be obtained for each sample as part of the standard assay output. The SCNP classifier will be applied to the z values for the node-metrics to calculate the continuous SCNP classifier score and the binary induction response assignment (pNR or pCR) for each sample.

Further description of parameters that may be used to determine whether a cell should or should not be included in the analysis is provided in PCT Publication No. 2012/024546, incorporated herein in its entirety.

In some embodiments, the measurements of activatable elements are adjusted by measurements of sample quality for the individual cell populations or individual cells, based on markers of cell health in the cell populations or individual cells. Examples of analysis of healthy cells can be found in U.S. application Ser. No. 61/374,613 filed Aug. 18, 2010, the content of which is incorporated herein by reference in its entirety for all purposes.

In some embodiments, the activation state data is displayed as a two-dimensional scatter-plot and the discrete subpopulations are "gated" or demarcated within the scatter-plot. According to the embodiment, the discrete subpopulations may be gated automatically, manually or using some combination of automatic and manual gating methods. In some embodiments, a user can create or manually adjust the demarcations or "gates" to generate new discrete sub-populations of cells. Suitable methods of gating discrete subpopulations of cells are described in U.S. patent application Ser. No. 12/501,295, the entirety of which is incorporated by reference herein, for all purposes.

The discrete cell populations/subpopulations may be automatically gated according to activation state data that segregates the cells into discrete populations. For example, an activatable element that is "on" or "off" in cells may be used to segregate the cell population into two discrete subpopulations. In embodiments where the discrete cell subpopulations are automatically identified, different algorithm may be used to identify discrete cell subpopulations based on the activation state data. For example, a multi-resolution binning algorithm is used to iteratively identify discrete subpopulations of cell by partitioning the activation state data. This algorithm is outlined in detail in U.S. Publication No. 2009/0307248, which is incorporated herein in its entirety, for all purposes. In one embodiment, the multi-resolution binning algorithm is used to identify rare or uniquely discrete cell populations by iteratively identifying vectors or "hyperplanes" that partition activation state data into finer resolution bins. Using iterative algorithms such as multi-resolution binning algorithms, fine resolution bins containing rare populations of cells may be identified. For example, activation state data for one or more markers may be iteratively binned to identify a small number of cells with an unusually high expression of a marker. Normally, these cells would be discarded as "outlier" data or during normalization of the data. However, multi-resolution binning allows the identification of activation state data corresponding to rare populations of cells.

As another example, the present invention may use variance mapping techniques for mapping condition signaling space. These methods represent a significant advance in the study of condition biology because it enables comparison of conditions independent of a putative normal control. Traditional differential state analysis methods (e.g., DNA microarrays, subtractive Northern blotting) generally rely on the comparison of cells associated with a condition from each patient sample with a normal control, generally adjacent and theoretically untransformed tissue. Alternatively, they rely on multiple clusterings and reclusterings to group and then further stratify patient samples according to phenotype. In contrast, variance mapping of condition states compares condition samples first with themselves and then against the parent condition population. As a result, activation states with the most diversity among conditions provide the core parameters in the differential state analysis. Given a pool of diverse conditions, this technique allows a researcher to identify the molecular events that underlie differential condition pathology (e.g., cancer responses to chemotherapy), as opposed to differences between conditions and a proposed normal control.

In some embodiments, when variance mapping is used to profile the signaling space of patient samples, conditions whose signaling response to modulators is similar are grouped together, regardless of tissue or cell type of origin. Similarly, two conditions (e.g. two tumors) that are thought to be relatively alike based on lineage markers or tissue of origin could have vastly different abilities to interpret environmental stimuli and would be profiled in two different categories.

X. Determination of Activation State of a Discrete Cell Population

After treatment with one or more modulators, in some embodiments the sample is analyzed to determine the activation state of different discrete cell populations. This generates activation state data of different discrete cell populations. In some embodiments, the activation state data of a discrete cell population is determined by contacting the cell population with one or more modulators and determining the activation state or activation level of an activatable element of at least one cell in the cell population. Different modulators suitable for use are outlined in the section entitled "Modulators" and the Examples. The activation level is determined by quantifying a relative amount of the activatable element in the cell (e.g. using antibodies to quantify the activatable element). As outlined in the section entitled "Detection", any suitable form of analysis that allows a determination of cell activation level(s) may be used. Activatable elements are described in the section entitled "Activatable Elements." Determination of the activation level may be achieved by the use of activation state-specific binding elements, such as antibodies, as described below in the sections entitled "Binding Elements" and "Alternative Activation State Indicators." A plurality of activatable elements may be examined in one or more of the different discrete cell populations.

The population of cells can be divided into a plurality of samples, and the activation state data of the population is determined by measuring the activation level of at least one activatable element in the samples after the samples have been exposed to one or more modulators. In some embodiments, the analysis is performed in single cells. Any suitable analysis that allows determination of the activation level of an activatable element within single cells, which provides information useful for determining the activation state data of a discrete cell population from whom the sample was taken, may be used. Examples include flow cytometry, immunohistochemistry, immunofluorescent histochemistry with or without confocal microscopy, immunoelectronmicroscopy, nucleic acid amplification, gene array, protein array, mass spectrometry, patch clamp, 2-dimensional gel electrophoresis, differential display gel electrophoresis, microsphere-based multiplex protein assays, ELISA, Inductively Coupled Plasma Mass Spectrometer (ICP-MS) and label-free cellular assays. Additional information for the further discrimination between single cells can be obtained by many methods known in the art including the determination of the presence of absence of extracellular and/or intracellular markers, the presence of metabolites, gene expression profiles, DNA sequence analysis, and karyotyping.

The activation state data of the different discrete cell populations can be used to understand communication between the discrete cell populations that are associated with disease. The communications can occur between the immune cells in FIG. 1, or between one or more immune cells and a disease cell. These causal associations may be determined using any suitable method known in the art, such as simple statistical test and/or classification algorithms. These causal associations may be modeled using Bayesian Networks or temporal models. Alternatively, these causal associations may be identified using unsupervised learning techniques such as principle components analysis and/or clustering. Causal association can be determined using activators or inhibitors that might affect one or more discrete cell populations. For example, an inhibitor that inhibits phosphorylation of an activatable element in a first cell population may have a causal effect on the phosphorylation of a second activatable element in a second cell population. In some embodiments, the causal association between discrete cell populations is already known in the art. Thus, in some embodiments, determining a causal association between discrete cell populations involves using associations already predetermined in the art. Causal associations between activation levels in different discrete cell populations may represent communications between cellular networks and can be used to determine the state of a cellular network. The state of a cellular network can be associated, for example, with drug response and disease progression.

XI. Classifying and Characterizing Cell Networks Based on Activation State Data Associated with Discrete Populations of Cells When the activation state data associated with a plurality of discrete cell populations has been identified, it is frequently useful to determine whether activation state data is non-randomly distributed within the categories such as disease status, therapeutic response, clinical responses, presence of gene mutations, and protein expression levels. Activation state data that are strongly associated with one or more discrete cell populations with a specific characteristic (e.g. gene mutation, disease status) can be used both to classify a cell according to the characteristic and to further characterize and understand the cell network communications underlying the pathophysiology of the characteristic. Activation state data that uniquely identifies a discrete cell populations associated with a cell network can serve to re-enforce or complement other activation state data that uniquely identifies another discrete cell population associated with the cell network.

If activation state data is available for many discrete cell populations, activation state data that uniquely identifies a discrete cell population may be identified using simple statistical tests, such as the Student's t-test and the X2 test. Similarly, if the activation state data of two discrete cell populations within the experiment is thought to be related, the r2 correlation coefficient from a linear regression can used to represent the degree of this relationship. Other methods include Pearson and Spearman rank correlation. In some embodiments, correlation and statistical test algorithms will be stored in the memory of a computer and executed by a processor associated with the computer.

In some embodiments, the invention provides methods for determining whether the activation state data of different discrete cell populations is associated with a cellular network and/or a characteristic that can potentially complement each other to improve the accuracy of classification. In these embodiments, the activation state data of the discrete cell populations may be used generate a classifier for one or more characteristics associated with the discrete cell populations including, but not limited to: therapeutic response, disease status and disease prognosis. A classifier, as defined herein, is any type of statistical model that can be used to characterize a similarity between a sample and a class of samples. Classifiers can comprise binary and multi-class classifiers as in the traditional use of the term classifier. Classifiers can also comprise statistical models of activation levels and variance in only one class of samples (e.g. normal individuals). These single-class classifiers may be applied to data, e.g., from undiagnosed samples, to produce a similarity value, which can be used to determine whether the undiagnosed sample belongs to the class of samples (e.g. by using a threshold similarity value). Any suitable method known in the art can be used to generate the classifier. For example, simple statistical tests can be used to generate a classifier.

Examples, of classification algorithms that can be used to generate a classifier include, but are not limited to, Linear classifiers, Fisher's linear discriminant, ANOVA, Logistic regression, Naive Bayes classifier, Perceptron, Support vector machines, Quadratic classifiers, Kernel estimation, k-nearest neighbor, Boosting. Decision trees, Random forests, Neural networks, Bayesian networks, Hidden Markov models, and Learning vector quantization. Thus, in some embodiments, different types of classification algorithms may be used to generate the classifier including but not limited to: neural networks, support vector machines (SVMs), bagging, boosting and logistic regression. In some embodiments, the activation state data for different discrete populations associated with a same network and/or characteristic may be pooled before generating a classifier that specifies which combinations of activation state data associated with discrete cell populations can be used to uniquely identify and classify cells according to the activatable element.

In a specific embodiment, if the size of the activation state data associated with the discrete populations of cells is small, a straightforward corner classifier approach for picking combinations of activation state data that uniquely identifies the different discrete cell populations can be adopted. Combinations of discrete cell populations' activation state data can also be tested for their stability via a bootstrapping approach described below. In this embodiment, a corners classification algorithm with be applied to the data. The corners classifier is a rules-based algorithm for dividing subjects into two classes (e.g. dichotomized response to a treatment) using one or more numeric variables (e.g. population/node combination). This method works by setting a threshold on each variable, and then combining the resulting intervals (e.g., X<10, or Y>50) with the conjunction (and) operator (reference). This creates a rectangular region that is expected to hold most members of the class previously identified as the target (e.g. responders or non-responders of treatment). Threshold values are chosen by minimizing an error criterion based on the logit-transformed misclassification rate within each class. The method assumes only that the two classes (e.g. response or lack of response to treatment) tend to have different locations along the variables used, and is invariant under monotone transformations of those variables.

In some embodiments, computational methods of cross-validation are used during classifier generation to measure the accuracy of the classifier and prevent over-fitting of the classifier to the data. In a specific embodiment, bagging techniques, aka bootstrapped aggregation, are used to internally cross-validate the results of the above statistical model. In this embodiment, re-samples are iteratively drawn from the original data and used to validate the classifier. Each classifier, e.g. combination of population/node, is fit to the resample, and used to predict the class membership of those patients who were excluded from the resample. The accuracy of false positive and false negative classifications is determined for each classifier.

After iteratively re-sampling the original data, each patient acquires a list of predicted class memberships based on classifiers that were fit using other patients. Each patient's list is reduced to the fraction of target class predictions; members of the target class should have fractions near 1, unlike members of the other class. The set of such fractions, along with the patient's true class membership, is used to create a Receiver Operator Curve and to calculate the area under the ROC curve (herein referred to as the "AUC").

In some embodiments, the invention provides methods for determining a status of an individual such a disease status, therapeutic response, and/or clinical responses wherein the positive predictive value (PPV) is higher than 60, 70, 80, 90, 95, or 99.9%. In some embodiments, the invention provides methods for determining a status of an individual such a disease status, therapeutic response, and/or clinical responses, wherein the PPV is equal or higher than 95%. In some embodiments, the invention provides methods determining a status of an individual such a disease status, therapeutic response, and/or clinical responses, wherein the negative predictive value (NPV) is higher than 60, 70, 80, 90, 95, or 99.9%. In some embodiments, the invention provides methods for determining a status of an individual such a disease status, therapeutic response, and/or clinical responses, wherein the NPV is higher than 85%.

In some embodiments, the invention provides methods for predicting risk of relapse at 2 years, wherein the PPV is higher than 60, 70, 80, 90, 95, or 99.9%. In some embodiments, the invention provides methods for predicting risk of relapse at 2 years, wherein the PPV is equal or higher than 95%. In some embodiments, the invention provides methods for predicting risk of relapse at 2 years, wherein the NPV is higher than 60, 70, 80, 90, 95, or 99.9%. In some embodiments, the invention provides methods for predicting risk of relapse at 2 years, wherein the NPV is higher than 80%. In some embodiments, the invention provides methods for predicting risk of relapse at 5 years, wherein the PPV is higher than 60, 70, 80, 90, 95, or 99.9%. In some embodiments, the invention provides methods for predicting risk of relapse at 5 years, wherein the PPV is equal or higher than 95%. In some embodiments, the invention provides methods for predicting risk of relapse at 5 years, wherein the NPV is higher than 60, 70, 80, 90, 95, or 99.9%. In some embodiments, the invention provides methods for predicting risk of relapse at 5 years, wherein the NPV is higher than 80%. In some embodiments, the invention provides methods for predicting risk of relapse at 10 years, wherein the PPV is higher than 60, 70, 80, 90, 95, or 99.9%. In some embodiments, the invention provides methods for predicting risk of relapse at 10 years, wherein the PPV is equal or higher than 95%. In some embodiments, the invention provides methods for predicting risk of relapse at 10 years, wherein the NPV is higher than 60, 70, 80, 90, 95, or 99.9%. In some embodiments, the invention provides methods for predicting risk of relapse at 10 years, wherein the NPV is higher than 80%.

In some embodiments, the p value in the analysis of the methods described herein is below 0.05, 04, 0.03, 0.02, 0.01, 0.009, 0.005, or 0.001. In some embodiments, the p value is below 0.001. Thus in some embodiments, the invention provides methods for determining a status of an individual such a disease status, therapeutic response, and/or clinical responses, wherein the p value is below 0.05, 04, 0.03, 0.02, 0.01, 0.009, 0.005, or 0.001. In some embodiments, the p value is below 0.001. In some embodiments, the invention provides methods for determining a status of an individual such a disease status, therapeutic response, and/or clinical responses, wherein the AUC value is higher than 0.5, 0.6, 07, 0.8 or 0.9. In some embodiments, the invention provides methods for determining a status of an individual such a disease status, therapeutic response, and/or clinical responses, wherein the AUC value is higher than 0.7. In some embodiments, the invention provides methods for determining a status of an individual such a disease status, therapeutic response, and/or clinical responses, wherein the AUC value is higher than 0.8. In some embodiments, the invention provides methods for determining a status of an individual such a disease status, therapeutic response, and/or clinical responses, wherein the AUC value is higher than 0.9.

In another embodiment, activation state data generated for a cellular network over a series of time points may be used to identify activation state data that represents unique communications within the cellular network over time. The activation state data that represents unique communications within the cellular network can be used to classify other activation state data associated with cell populations to determine whether they are associated with a same characteristic as the cellular network or determine if there are in a specific stage or phase in time that is unique to a cellular network. For example, different discrete populations of cells in a cellular network may be treated with a same modulator and sub-sampled over a series of time points to determine communications between the discrete populations of cells that are unique to the stimulation with the modulator. Similarly, samples of different discrete cell populations may be derived from patients over the course of treatment and used to identify communications between the discrete populations of cells that are unique to the course of treatment.

In one embodiment, the activation state data for the discrete cell populations at different time points may be modeled to represent dynamic interactions between the discrete cell populations in a cell networks over time. The activation state data may be modeled using temporal models, Bayesian networks or some combination therefore. Suitable methods of generating Bayesian networks are described in Ser. No. 11/338,957, the entirety of which is incorporated herein, for all purposes. Suitable methods of generating temporal models of activation state data are described in U.S. patent application Ser. No. 13/636,627, the entirety of which is incorporated herein by reference. Analysis of non-apoptotic cells is shown in PCT/US2011/048332, which is also incorporated by reference in its entirety. Different metrics may be generated to describe the dynamic interactions including: derivatives, integrals, rate-of-change metrics, splines, state representations of activation state data and Boolean representations of activation state data.

In embodiments where metrics and other values describing dynamic interactions are generated, these values and metrics are used to generate a classifier. As outlined above, any suitable classification algorithm can be used to determine metrics and values that uniquely identify cellular network data that shares a same characteristic. In some embodiments, the descriptive values and metrics will be generated based on two distinct data sets: 1) activation state data that is associated with a characteristic and 2) activation state data that is not association with a characteristic. For example: activation state data generated from discrete cell populations after stimulation with a modulator and activation state data generated from un-stimulated discrete cell populations. In these embodiments, the descriptive values and metrics will be used to generate a two-class classifier. In other embodiments, descriptive values and metrics will be generated from a large number of activation state data sets associated with different characteristics and a multi-class classifier will be generated. The resulting classifier will be used to determine whether a cellular network is part of the data set.

In some embodiments, the above classifiers are used to characterize activation state data derived from an individual such as a patient. In these embodiments, activation state data associated with a cellular network of one or more discrete cell populations is derived from a patient. In some embodiments, the activation state data associated with the different discrete cell populations from a patient may be identified by obtaining patient samples with different characteristics (e.g. blood cells and tumor samples). In some embodiments, the activation state data associated with the different discrete cell populations may be identified computationally based on activation state data for activatable elements that are known to differentiate discrete cell populations. A classifier that specifies activation state data from different discrete cell populations used to determine whether the cells have a common characteristic is applied to the activation state data associated with the individual in order to generate a classification value that specifies the probability that the individual (or the cells derived from the individual) is associated with the characteristic. In most embodiments, the classifier is stored in computer memory or computer-readable storage media as a set of values or executable code and applying the classifier comprises executing code that applies the classifier to the activation state data associated with the individual. The classification value may be output to a user, transmit to an entity requesting the classification value and/or stored in memory associated with a computer. The classification value may represent information related to or representing the physiological status of the individual such as a diagnosis, a prognosis or a predicted response to treatment.

In some embodiments, the present invention includes method for evaluating cells that may indirectly reflect the presence or absence of disease cells, such as cancerous cells. For example, certain immune system cells, such as T cells (see FIG. 1), e.g. Tregs, can be affected by diseased cells to change their level of activation. Analysis of the Tregs for example, can indication an increase or decrease in signaling levels which show the affect of the diseased cells. Additionally, the immune cells may be affected by cancerous cells which may increase the signaling in Tregs.

The presence of a heterogeneous population of cells may indicate that therapy is needed. The outcome of the therapy can be monitored by reference to the graph. A change from a more heterogeneous population to a population that is more tightly grouped on the chart may indicate that the cell population is returning to a normal state. The lack of change may indicate that the therapy is not working and the cell population is refractory or resistant to therapy. It may also indicate that a different discrete cell population has changed over to the cancerous phenotype. Lack of change back to normal is indicative of a negative correlation to therapy. These changes may be genetic or epigenetic.

One embodiment of the present invention is to conduct the methods described herein by analyzing a population of normal cells to create a pattern or a database that can be compared in a graphical way to a cell population that is potentially cancerous. The analysis can be by many methods, but one preferred method is the use of flow cytometry.

In all these embodiments, the activation state data may be generated at a central laboratory and the classifier may be applied to the data at the central laboratory. Alternately, the activation state data may be generate by a third party and transmitted, for example, via a secure network to a central laboratory for classification. Methods of transmitting data for classification and analysis are outlined in U.S. patent application Ser. No. 12/688,851, the entirety of which is incorporated herein by reference, for all purposes.

Comparison to Normal, Unaffected Individuals

In some embodiments, the activation state data of a plurality of cell populations is determined in normal individuals or individual not suffering or not suspected of suffering from a condition. This activation state data can be used to create statistical model of the ranges of activation levels observed in cell populations derived from samples obtained from normal patients (e.g. regression model, variance model). This ranges and/or models may be used to determine whether samples from undiagnosed individuals exhibit the range of activation state data observed in normal samples (e.g., range of normal activation levels). This can be used to create a classifier for normal individuals. In some embodiments, the models may be used to generate a similarity value that indicates the similarity of the activation state data associated with the undiagnosed individual to the range of normal activation levels (e.g. correlation coefficient, fitting metric) and/or a probability value that indicates the probability that the activation state data would be similar to the range of normal activation levels by chance (i.e. probability value and/or associated confidence value). In other embodiments, activation state data from normal patients may be combined with activation state data from patients that are known to have a disease to create a binary or multi-class classifier. In some embodiments, the activation state data from an undiagnosed individual will be displayed graphically with the range of activation states observed in normal cells. This allows for a person, for example a physician, to visually assess the similarity of the activation state data associated with the undiagnosed patient to that range of activation states observed in samples from normal individuals. Examples of how to create statistical models or profiles of the ranges of activation levels observed in cell populations derived from samples obtained from normal patients and their uses in classifying individual are described in PCT/US2011/01565, the entirety of which is incorporated by reference herein for all purposes.

In one aspect of the invention, a method is provided comprising: a) measuring an activation level of one or more activatable elements from cells from a test sample from a subject; b) comparing the activation level of the one or more activatable elements from cells from the test sample to a model, wherein the model is derived from determining a range of activation levels of one or more activatable elements from samples of cells from a plurality of normal individuals; and c) preparing a report displaying the activation level of the one or activatable elements from the samples of cells from the plurality of normal individuals to the activation level of the one or more activatable elements from cells from the test sample from the subject.

In one embodiment, the samples of cells from the plurality of normal individuals are gated to separate populations of cells. In another embodiment, the method further comprises gating the sample of cells from the test sample from the subject into separate populations of cells. In another embodiment, the gating is based on one or more cell surface markers. In another embodiment, the samples of cells from a plurality of normal individuals were contacted with one or more modulators. In another embodiment, the method further comprises contacting the plurality of samples of cells from the test sample from the subject with the one or more modulators. In another embodiment, the normal individuals and the subject have the same gender, race, or ethnicity. In another embodiment, the method further comprises normalizing the activation level of the one or more activatable elements from cells form the test sample based on a sample characteristic. In another embodiment, the sample characteristic comprises race, ethnicity, gender or age. In another embodiment, the normal individuals are selected based on the age of the test subject. In another embodiment, the measuring the activation level of the one or more activatable elements comprises flow cytometry. In another embodiment, the displaying comprises a scatterplot, a line graph with error bars, a histogram, a bar and whisker plot, a circle plot, a radar plot, a heat map, and/or a bar graph.

The activation level of a cell in the individual, such as a T cell, can be plotted against a normal cell and if the activation levels are below a threshold, then a determination can be made that cell signaling is inhibited. The threshold can be 5, 10, 15, 20, or 25% lower than the level shown for the normal cell. The threshold can be even lower, such as 30, 40, 50 or more % lower than that shown for the normal cells.

XII. Methods

A. Methods of Evaluating the Effects of a Modulator on a Plurality of Discrete Cell Populations in Communication In one aspect, the invention provides methods of evaluating the effects of a modulator on a plurality of discrete cell populations in communication.

In certain embodiments of this aspect, methods are provided for evaluating the effects of a modulator on a plurality of discrete cell populations in communication, comprising
(i) preparing a culture from a sample that has been removed from an individual, wherein the culture comprises a plurality of discrete cell populations in communication;
(ii) contacting a first cell from a first discrete cell population in the culture with a modulator, wherein the modulator interacts with the first cell population but does not substantially interact with a second discrete cell population in the culture;
(iii) incubating the culture for a period of time; and
(iv) after the incubation, determining an activation level of a first activatable element in single cells from the second cell population.

The culture is prepared as described herein, in all cases from a sample removed from an individual, e.g., a mammal, such as a human, so as to no longer be part of the normal biology of the entire individual. The individual, e.g. human, may be a normal (healthy) individual. The individual, e.g., human, may suffer from, or be suspected of suffering from, a condition, such as a health condition, e.g., an autoimmune condition or cancer. The culture can be placed in an artificial environment. In certain embodiments, the culture is prepared from a fluid sample. The culture may be prepared from blood, e.g., a whole blood culture placed in an environment suitable for performing the steps of the method, e.g., a well in a multiwall plate. The culture may be prepared from blood by processing the blood, e.g., to remove one or more cell types. In certain embodiments, the culture is a PBMC culture placed in an environment suitable for performing the steps of the method, e.g., a well in a multiwall plate.

The modulator may be any modulator as described herein, so long as it interacts with a first discrete cell population in the culture but does not substantially interact with a second discrete cell population in the culture, as those terms are described herein. See the section entitled "Modulators" In certain embodiments, a modulator or modulators may be used that interacts with monocytes or monocyte derivatives, e.g., antigen presenting cells (APC) such as dendritic cells or macrophages, but that does not interact, or does not substantially interact, with at least one other discrete population of immune cells in the culture, e.g., T cells or B cells, or a subclass of T or B cells. An example is a TLR4 agonist, such as LPS or R848. Alternatively, or in addition, a modulator or modulators may be used that interacts with T cells or a class of T cells, such as T helper (CD4+) cells, but that does not interact, or does not substantially interact, with at least one other discrete immune cell population present in the culture, e.g., monocytes or monocyte-derived cells, or B cells, or subclasses thereof. Examples include a T cell activator, or a TCR activator in combination with a costimulatory molecule, such as a CD3/CD28 agonist combination. In certain cases, a modulator is used that both stimulates monocytes or monocyte derivatives and that causes activation of a class of T cells, such as CD4+ cells, without interacting or without substantially interacting with at least one other class of immune cells in the culture, e.g., B cells. An example is Superantigen.

In certain embodiments, the modulator is a toll-like receptor (TLR) modulator; a Superantigens; a T cell modulator; a B cell modulator; a costimulatory modulator that can be used in conjunction with other modulators; or a modulator that affect Fc Receptor signaling on NK cells and monocytes, or combinations thereof. Further description of these classes, and exemplary modulators in each of these classes useful in certain embodiments may be found in the section entitled "Modulators."

The period of time for which the culture is incubated may be any period as described herein; e.g., as described in the section entitled "Time period of incubation of the culture." In certain embodiments, multiple time periods are used, e.g., to provide a kinetic analysis. The kinetic analysis may provide information regarding the time course and causality of effects of the modulator on the second discrete cell group, on feedback effects on the first discrete cell group, and the like, as will be apparent to one of skill in the art. Thus, for example, in certain embodiments, either the culture is sampled at a plurality of time periods and step (iv) is performed on a sample from each of the time periods, or steps (i)-(iv) are performed on a plurality of cell cultures under substantially the same conditions except the cell cultures are incubated for different periods of time. The method of claim The activation levels of the first activatable element in cultures incubated for different periods of time may be compared in a kinetic analysis, which can be used, e.g., to produce an intercellular communication profile for the second discrete cell population. Other kinetic profiles for other activatable elements, discrete cell populations, and for intracellular communication messengers may also be produced.

After the incubation period, the activation level of a first activatable element in single cells from the second cell population is determined. Typically the incubation is stopped by fixing the cells, and the cells are permeabilized. In certain embodiments the activation level is determined by contacting the cell with a detectable (labeled) binding element and determining the signal from the label on a single cell basis, as described elsewhere herein. In certain embodiments, the detectable binding element is an antibody, e.g. a fluorescently labeled antibody for detection by flow cytometry, or a mass-tag-labeled antibody for detection by mass spectrometry. In certain embodiments, the process, from culture preparation through detection, is partially or completely automated.

The activation levels of the first activatable element may be determined on a single cell-by-cell basis in a plurality of cells in the second cell population, allowing data analysis techniques as described herein to be applied to determine the effects of the modulator, or other combinations, on the first activatable element and/or other activatable elements also analyzed. Similarly, if additional activatable elements and/or discrete cell populations are used they too may be determined on a cell-by-cell basis in a plurality of cells in the additional discrete cell populations and techniques as described herein applied to determine the effects of the modulator, or other combinations.

Additional activatable elements in single cells of discrete cell populations may be analyzed, limited only by the detection capabilities of the detector, the number of cells in the culture, the number of detectable binding elements available, and the desire to obtain information from the analysis. For example, the method may further comprise determining an activation level of a second activatable element in single cells from a third discrete cell population. The second activatable element can be the same as or different from the first activatable element. The method can further comprise determining an activation level of a second activatable element in single cells from a third discrete cell population. The third discrete cell population can the same as, or different from the first discrete cell population. Similarly, the activation level of a third, fourth, fifth, sixth, seventh, eighth, ninth, tenth, etc., activatable element can be determined in any one of a fourth, fifth, sixth, seventh, eighth, ninth, tenth, etc. discrete cell population. Examples involving detection of activations levels of multiple activatable elements in multiple cell types are shown in Examples 8-18.

The activatable element may be any suitable activatable element, as described herein. The activatable element may be, e.g., an activatable element as shown in FIG. 2 (activatable elements are shown in activated form in FIG. 2). In certain embodiments, the activatable element is an an element in a signaling pathway. The signaling pathway may be of a NFkB pathway, a PI3K/Akt pathway, a MAPK pathway, a JAK/STAT pathway, a DNA damage repair pathway, an apoptosis pathway, a PKC pathway, a cell cycle pathway, a phosphatase regulation pathway, a FLT3L signaling pathway, a TCR pathway, a BCR pathway, or a combination thereof. The signaling pathway may be an NFkB pathway, a PI3K/Akt pathway, a MAPK pathway, a JAK/STAT pathway, or a combination thereof. The activatable element may be an element in the NFkB pathway that is IkBa or NFkB p105. The activatable element may be an element in the PI3K pathway that is AKT or s6. The activatable element may be an element in the MAPK pathway that is ERK or p38. The activatable element may be an activatable element in the JAK/STAT pathway that is STAT1, STAT3, or STAT5. Descriptions of the measurement of activation levels of activatable elements in single cells, especially in cultures comprising a plurality of discrete cell populations in communication exposed to modulator and, in some cases, to an agent, may be found in Examples 8-17.

Cells for analysis may be gated so that only healthy cells are used. Gating criteria can include one or more of scatter characteristics, Amine Aqua dye staining intensity, and levels of indicators of apoptosis, such as cPARP.

In certain embodiments of the method, steps (i)-(iv) are performed on a second cell culture under substantially the same conditions except that no modulator is added to the second cell culture, and the activation level of the first activatable element in the first cell culture is compared to the activation level of the first activatable element in the second cell culture. Additional activatable elements, intracellular communication messengers, and discrete cell populations may also be compared. Similar cultures may be used in the case of analyses where a modulator is used in the presence of an agent, where the control culture does not contain the agent. Other controls will be apparent to those of skill in the art.

By performing such analyses, potential communication between the first and second cell populations can be evaluated based, at least in part, on the activation level of the first activatable element in single cells from the second cell population, or, more typically, on a plurality of activation levels as described herein.

In addition to determining the activation level of an activatable element or elements, or alternatively, the method can comprise comprising determining an intracellular level of an intercellular communication messenger in single cells from a discrete cell population in the culture, e.g., the second discrete cell population and/or any other cell population. The intercellular communication messenger can be a cytokine, growth factor, hormone, or exosome. In certain embodiments, the intercellular communication messenger is a cytokine, such as IL1, IL2, IL3, IL4, IL5, IL6, IL8, IL9, IL10, IL12, IL15, IL17A, IL17F, IL21, IL23, TNF☐, TNF☐, IFN☐, IFN☐, or IFN☐☐☐ In certain embodiments, the cytokine is IL2, IL6, or TNF☐☐☐ See Examples for descriptions of measuring levels of intracellular cytokines in single cells in the presence or absence of modulator.

In certain embodiments, an agent that affects one or more intercellular communication messengers is added to the culture, and measurements and analyses as described are performed. In certain embodiments, an agent that affects one or more intracellular pathways involved in intercellular communication to the cell culture, and measurements and analyses as described are performed. Typically, the agent is a chemical agent, e.g., a small molecule, or a biological agent, e.g., an antibody.

In these embodiments, the agent may be a known agent with known effects on known modulator-induced signaling in certain groups of individuals, e.g., healthy individuals or individuals suffering from a condition. Data regarding such effects may be available, e.g., in a database, or may be translated into a classifier. In this case, the effect of the agent on cells from an individual from whom the sample was removed can be compared to the known effect, e.g., database or classifier, e.g., to help determine the status of the individual.

In other of these embodiments, the agent may be an agent whose potential efficacy for a use, such as for treating a condition, is desired to be evaluated. For example, the agent may be a chemical agent or a biological agent that is a potential drug for treatment of a condition, e.g. an autoimmune condition or a cancer. In this case, the individual from whom the sample was removed may be a healthy individual or an individual suffering from the condition, and the results of the addition of the agent may be evaluated based on effects on certain pathways or activatable elements within pathways known or suspected of playing a role in the condition (drug target effects), or based on comparison with the effects of an agent or agents of known efficacy for the condition. The agent may also be evaluated for effects on pathways not known or suspected of playing a role in the condition (off target effects).

The agent may be an agent affecting, or potentially affecting (e.g., in the case of drug screening) an intracellular communication messenger that is a growth factor, hormone, cytokine, or exosome. In certain embodiments, the agent is an agent that affects a cytokine. In certain embodiments, the cytokine is as IL1, IL2, IL3, IL4, IL5, IL6, IL8, IL9, IL10, IL12, IL15, IL17A, IL17F, IL21, IL23, TNF☐, TNF☐, IFN☐, IFN☐, or IFN☐☐☐ In certain embodiments, the cytokine is IL2, IL6, or TNF☐☐☐ See Examples for the use of various agents affecting various cytokines.

The agent may be an agent affecting, or potentially affecting (e.g., in the case of drug screening) one or more intracellular pathways involved in intercellular communication, such as the JAK/STAT pathway, the PI3K pathway, the MAPK pathway, or the NFkB pathway. Other pathways that may be affected by the agent are as described herein. See Examples for the use of an agent affecting an intracellular pathway involved in intercellular signaling.

In certain embodiments, the method further comprises determining a status for the individual from whom the sample, based at least in part on a metric for the individual derived at least in part from the result of step (iv). The determination of the status of the individual, may be further based at least in part on a comparison of the individual metric with a standard metric, wherein the standard metric is derived, at least in part, from the activation level or levels of the first activatable element in a second cell population in a plurality of cultures each comprising a plurality of discrete cell populations in communication, each culture being derived from samples removed from a plurality of healthy individuals and treated substantially as in steps (i)-(iv). The standard metric may alternatively, or additionally, be derived, at least in part, from the activation level or levels of the first activatable element in a second cell population in a plurality of cultures comprising a plurality of discrete cell populations in communication, each derived from samples removed from a plurality of individuals having a status that is a status to be determined for the individual of step (i). The status can be a health status. The health status can be presence or absence of a condition, status of a condition, prognosis of a condition, or responsiveness to therapy for a condition, or a combination thereof. The condition can be an autoimmune condition or cancer.

Figure 27:
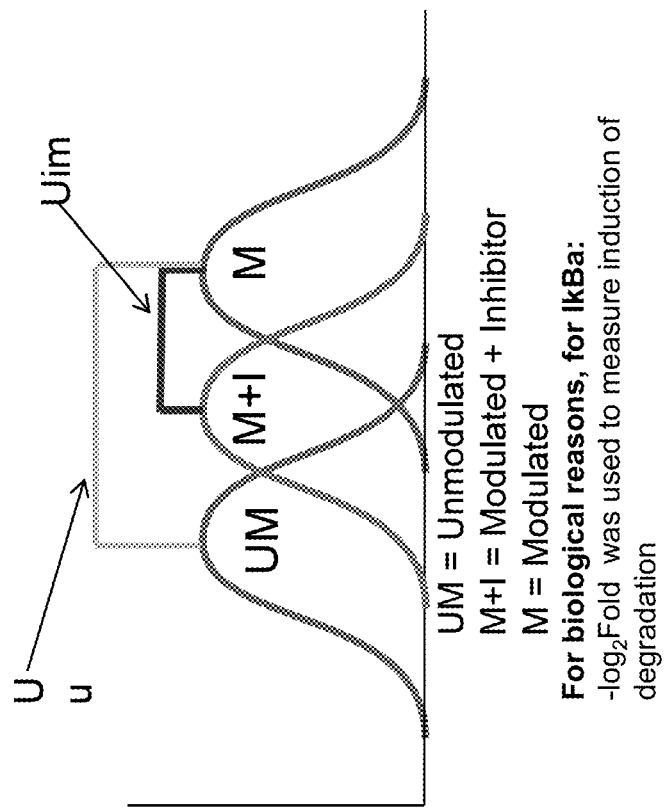
FIG. 27 shows how Uu and Uim are calculated. Separation of peaks between unmodulated and modulated (–inhibitor) is designated Uu. Separation of peaks between modulated (–inhibitor) and modulated (+inhibitor) is designated Uim.

In certain embodiments, the method includes generating a report based, at least in part, on the activation level measured in step (iv), or information derived therefrom. The report can be prepared with no data analysis, such as a report containing raw data for the activation level of an activatable element in a single cell from the second cell population, or it can be prepared with extensive data analysis and other analysis, such as a report containing a treatment recommendation, or anything in between these two extremes, e.g., the preparation of the report may include collections of data for activation levels of an activatable data from a plurality of cells, data for different discrete cell populations, information derived using algorithms to manipulate raw data, such as Uu, log 2 values, or Uim values, graphical representations of data, such as shown in FIGS. 25D and 27, and the like.

In another embodiment of this aspect, the invention provides a method comprising
(i) contacting a culture derived from a sample from an individual with a SuperAntigen, wherein the sample comprises a plurality of discrete cell populations in communication;
(ii) incubating the culture for a period of time; and
(iii) after the incubating, measuring the activation level of an activatable element in cells in single cells of a discrete cell population in the culture.

In certain embodiments, the Superantigen is SEA, SEB, or TSST. In certain embodiments, the Superantigen is SEA. In certain embodiments, the Superantigen is SEB. In certain embodiment, the Superantigen is TSST. In certain embodiments, the superantigen is a combination of SEA, SEB, and TSST. Examples 8-17 provide description for the use of Superantigen in this manner.

B. Methods of Evaluating Chemical or Biological Agents

In another aspect, the invention provides methods of evaluating chemical or biological agents.

In certain embodiments of this aspect, the invention provides a method for evaluating a chemical or biological agent comprising (i) contacting a first cell from a first discrete cell population with a modulator in a first culture containing a plurality of discrete cell populations in communication, wherein the modulator interacts with the first discrete cell population in the culture but does not substantially interact with a second discrete cell population in the culture; (ii) contacting the culture with the agent; (iii) incubating the first culture for a period of time; (iv) after the incubation, determining an activation level of a first activatable element in single cells from the second cell population; and (v) evaluating the effect of the agent based at least in part on the activation level of the first activatable element determined in (iv).

Description of samples, cultures, discrete cell populations in communication, modulators, activatable elements and determination of activation levels of activatable elements, and evaluating the effect of the agent suitable for use in this method may be found elsewhere in this application, see, e.g., the section entitled "Methods of evaluating the effects of a modulator on a plurality of discrete cell populations in communication."

The evaluation of the agent can include comparing the activation level of the first activatable element with an activation level of the same element obtained in a second culture to which the agent has not been added but which is otherwise treated substantially the same as the first culture. The evaluation of the effect of the agent can include comparison to the effects of an agent with known effects, e.g., known effects on a drug target and/or known off-target effects, or known effects on a condition, e.g., a health condition such as an autoimmune condition or cancer. Alternatively, the effects of the agent may be evaluated based on its effect on a known drug target, or on its off-target effects, or a combination thereof. The method can further evaluating the potential efficacy of the agent in treating a condition based at least in part on the evaluation of step (v), e.g., in the treatment of an autoimmune disease or cancer.

In addition to, or instead of, determining the activation level of an activatable element in cells from the second cell population, the method may include determining the intracellular level of an intercellular communication messenger, as described herein. The intercellular communication messenger may be a cytokine, growth factor, hormone, or exosome. In certain embodiments, the intercellular communication messenger is a cytokine, such as IL1, IL2, IL3, IL4, IL5, IL6, IL8, IL9, IL10, IL12, IL15, IL17A, IL17F, IL21, IL23, TNF□, TNF□, IFN□, IFN□, or IFN□□.

The agent to be evaluated may be a chemical or biological agent. In certain embodiments, the agent comprises an agent that affects, or is suspected of affecting, one or more intercellular communication messengers, such as a cytokine, a growth factor, a hormone, or an exosome. In certain embodiments the agent affects, or is suspected of affecting, a cytokine. In certain embodiments the agent inhibits, or is suspected of inhibiting, a cytokine, such as an agent that is an antibody directed against a cytokine. The cytokine that the agent affects or is suspected of affecting may be IL1, IL2, IL3, IL4, IL5, IL6, IL8, IL9, IL10, IL12, IL15, IL17A, IL17F, IL21, IL23, TNF□, TNF□, IFN□, IFN□, or IFN□□ In certain embodiments, the cytokine is IL-2, IL-6, IL-7, IL-15, IL-17, IL-23, or TNF□□ In certain embodiments, the cytokine is IL6 or TNF□□

The method of claim G wherein the agent is an agent that affects, or is suspected of affecting, an intracellular pathway involved in intercellular communication, such as inhibiting the intracellular pathway. The intracellular pathway may be any suitable pathway as described herein. In certain embodi- ments, the pathway is JAK/STAT pathway, PI3K pathway, or BCR pathway. In certain embodiments, the agent is a known or suspected kinase inhibitor, such as a JAK inhibitor, or a PI3K inhibitor. The Examples describe methods using a JAK inhibitor as an agent. The method can further include preparing a report of the results of (iv) or (v), or information derived therefrom. Methods of preparing a report are described elsewhere herein.

In certain embodiments the invention provides a method for evaluating a potential cytokine-modulating agent comprising i) contacting a culture comprising a plurality of discrete cell populations in communication with a modulator, wherein the modulator induces intercellular communication between the cell populations via one or more cytokines; ii) contacting the culture with the agent; iii) incubating the culture for a period of time; iv) after the incubation, determining in single cells of a first discrete cell population in the culture an activation level of an activatable element, wherein the first discrete cell population is a population involved in the communication between the cell populations; and v) evaluating the agent based at least in part on the activation level of iii). The agent can be evaluated for potential usefulness as a cytokine inhibitor. The agent can be evaluated for potential usefulness in treating a condition, for example by evaluating its effects on a drug target for which the activatable element of step iv) provides information, or evaluating its off-target effects for which the activatable element of step iv) provides information, or comparing the activation level, or information derived from the activation level observed in step iv), with an activation level, or information derived from the activation level observed in step iv) in a culture treated substantially the same as the culture exposed to the agent, except the second culture is exposed to an agent of known efficacy in treating the condition.

In certain embodiments, the method, in addition to or alternative to step iv), further comprises determining in single cells of a second discrete cell population in the culture after the incubation an intracellular level of a cytokine, wherein the second discrete cell population is a population involved in the communication between cell populations. The second discrete cell population may be the same as or different from the first cell population.

The method may further comprise preparing a report based on the results of the method. Methods of preparing reports are provided elsewhere herein.

C. Methods of Determining the Status of an Individual

The invention also provides methods of determining the status of an individual.

Typically, the status of an individual will be a status related to the health of the individual (referred to herein as "health status" or "disease status"), but any type of status can be determined if it can be correlated to the status of cells (e.g. single cells) from one or more discrete populations of cells from the individual. In some embodiments, the invention provides methods for determining the status of an individual by creating a response panel using two or more discrete cell populations. In some embodiments, the status of an individual is determined by a method comprising: a) contacting a first cell from a first discrete cell population from said individual with at least a first modulator; b) determining an activation level of at least one activatable element in said first cell; and c) correlating the activation level of the first cell to a disease stated in a second cell. In another embodiment of the invention, immune system cells are measure as an indirect indication of disease due to the communication between the immune cells and the diseased cells.

The status of an individual may be associated with a diagnosis, prognosis, choice or modification of treatment, and/or monitoring of a disease, disorder, or condition. Through the determination of the status of an individual, a health care practitioner can assess whether the individual is in the normal range for a particular condition or whether the individual has a pre-pathological or pathological condition warranting monitoring and/or treatment. Thus, in some embodiments, the status of an individual involves the classification, diagnosis, prognosis of a condition or outcome after administering a therapeutic to treat the condition.

In certain embodiments, the invention provides a method of determining the status of an individual comprising (i) preparing a culture from a sample that has been removed from the individual, wherein the culture comprises a plurality of discrete cell populations in communication; (ii) contacting a first cell from a first discrete cell population in the culture with a modulator, wherein the modulator interacts with the first cell population but does not substantially interact with a second discrete cell population in the culture; (iii) incubating the culture for a period of time; (iv) after the incubation, determining an activation level of a first activatable element in single cells from the second cell population; (v) deriving a metric for the individual based, at least in part, on the activation level of the first activatable element; and (vi) determining the status of the individual based, at least in part, on the metric of step (v). The status can be a health status, for example, a health status comprising presence or absence of a condition, status of a condition, prognosis of a condition, or responsiveness to therapy for a condition, or a combination thereof.

In certain embodiments, activation levels of the first activatable element are determined on a single cell-by-cell basis in a plurality of cells in the second cell population, and the individual metric of step (v) is derived, at least in part, from the activation levels of the first activatable element in the plurality of cells.

The metric of (iv) can be compared with a standard metric derived at least in part from the activation level or levels of the first activatable element in a second cell population in a culture comprising a plurality of discrete cell populations in communication and derived from a sample removed from a healthy individual and treated substantially as in steps (i)-(v). Additionally, the standard metric can be derived at least in part from the activation level or levels of the first activatable element in a second cell population in a plurality of cultures each comprising a plurality of discrete cell populations in communication, each culture being derived from samples removed from a plurality of healthy individuals and treated substantially as in steps (i)-(iv). Additionally, or alternatively, the standard metric can be derived or further derived, at least in part, from the activation level or levels of the first activatable element in a second cell population in a plurality of cultures comprising a plurality of discrete cell populations in communication, each derived from samples removed from a plurality of individuals having a status that is a status to be determined for the individual of step (i). The standard metric can comprises a threshold to which the individual metric is compared.

In cases where the status is a health condition, the health condition may be any health condition as described herein, such as a cancer or an autoimmune disease.

The method may further include preparing a report based on the status of the individual, communicating the report to the individual and/or to a healthcare provider for the individual, and/or determining a course of treatment for the individual. The course of treatment may include administering an agent to the individual.

One embodiment of the present invention involves the classification, diagnosis, prognosis of a condition or outcome after administering a therapeutic to treat a condition. Another embodiment of the invention involves monitoring and predicting outcome of a condition (e.g. cancer or an autoimmune disease). Another embodiment is drug screening using some of the methods of the invention, to determine which drugs may be useful in particular conditions. In some embodiments, an analysis method involves evaluating cell signals and/or expression markers in different discrete cell populations in performing these processes. One embodiment of cell signal analysis involves the analysis of one or more phosphorylated proteins (e.g. by flow cytometry) in different discrete cell populations. One embodiment of cell signal analysis involves the coordinated analysis of activatable protein phosphorylation with total protein levels (including intracellular cytokines, enzymes, transcription factors, and/or surface markers) evoked by modulation in different discrete cell populations. The classification, diagnosis, prognosis of a condition and/or outcome after administering a therapeutic to treat the condition is then determined based in the analysis of the one or more phosphorylated proteins in different discrete cell populations. In one embodiment, a signal transduction-based classification of a condition can be performed using clustering of phospho-protein patterns or biosignatures of the different cell discrete populations.

In some embodiments, a treatment is chosen based on the characterization of a plurality of discrete cell populations. In some embodiments, characterizing a plurality of discrete cell populations comprises determining the activation state of one or more activatable elements in the plurality of cell populations. The activatable element(s) analyzed among the plurality of discrete cell populations can be the same or can be different.

In some embodiments, the present invention provides methods for classification, diagnosis, and/or prognosis of a condition or outcome after administering a therapeutic to treat the condition by characterizing one or more pathways in different discrete cell populations. In some embodiments, a treatment is chosen based on the characterization of the pathway(s) simultaneously in the different discrete cell populations. In some embodiments, characterizing one or more pathways in discrete cell populations comprises determining whether one or more of: apoptosis pathways, cell cycle pathways, signaling pathways, immune-regulatory pathways, or DNA damage pathways are functional in the different discrete cell populations based on the activation levels of one or more activatable elements within the pathways, where a pathway is functional if it is permissive for a response to a treatment.

In some embodiments, the characterization of one or more different discrete cell populations in a condition (e.g. cancer or autoimmune disease) shows disruptions in cellular networks that are reflective of disregulated immune-suppressive function, proliferation, survival, evasion of apoptosis, sensitivity to anti-growth signals and other mechanisms. In some embodiments, the disruption in these networks can be revealed by exposing a plurality of discrete cell populations to one or more modulators that mimic one or more environmental cues.

The determination of the status (e.g. health status, disease status and/or any status indicating the pathophysiology of an individual) may also indicate response of an individual to treatment for a condition. Such information allows for ongoing monitoring of the condition and/or additional treatment. In one embodiment, the invention provides for the detection of the presence of disease-associated cells or the absence or reduction of cells necessary for normal physiology in an individual that is being treated, or was previously treated, for the disease or condition. In some embodiments, the status may also indicate predicted response to a treatment. For example, the activation or other state of one or more specific cell types (such as a Treg) can indicate a disease state. Also, the specific activation or other state may indicate an appropriate treatment for the disease state.

In some embodiments, the determination of the status of an individual may be used to ascertain whether a previous condition or treatment has induced a new pre-pathological or pathological condition that requires monitoring and/or treatment. For example, treatment for many forms of cancers (e.g. lymphomas and childhood leukemias) can induce certain adult leukemias, and the methods of the present invention allow for the early detection and treatment of such leukemias.

In one embodiment of the invention, the present method employs single cell network profiling (SCNP). It enables the determination of the short term signaling competence of peripheral blood mononuclear cells (PBMCs) among other things. It can also provide the determination of long term signaling competency to understand if signaling is properly turned off in disease and if there is normal communication between cells in disease. The SCNP embodiment can show an ex vivo model of the immune system and can discover aberrant cell cross-talk in a disease state and can test drug activity in drug screening.

In a further embodiment, the status of an individual may indicate an individual's immunologic status and may reflect a general immunologic status, an organ or tissue specific status, or a disease related status.

The subject invention also provides kits (described in detail below in the section entitled "Kits") for use in determining the status of an individual, the kit comprising one or more specific binding elements for signaling molecules, and may additionally comprise one or more therapeutic agents. These binding elements can also be called "stains" which can include an antibody and a label. The kit may further comprise a software package for data analysis of the different populations of cells, which may include reference profiles for comparison with the test profile.

In one embodiment of the present invention, one or more superantigens (SAgs) are used as modulators to stimulate signaling pathway responses in which cells communicate with one another as shown in FIG. 1. These modulators have been known to stimulate T cells, but we have found that they can broadly stimulate multiple cell types, such as monocytes, T cells and B cells. One embodiment of the present invention is capable of detecting "cross-talk" between multiple cell types in response to the use of a stimulus, such as SAgs.

The ability to examine cell-cell cross-talk in healthy cells would enable the analysis of the same in disease states, such as RA and SLE, such that aberrant or absent "talking" could be identified. The ability to detect monocyte down-regulation over time after stimulation in healthy samples enables the examination of the same in disease states, such as RA, where down-regulation may be absent and immune signaling continue to fire. Similar analyses can be applied to the lymphocytes. In one embodiment, targeted biologics may be employed on these cell-cell "conversations", including the blockade of TNFα, IL-6, IL-17, and IFNs. Typical blocking agents can include antibodies, or their fragments, directed to the above compounds (and others shown in FIG. 1). The ability to examine the effects of antibodies which block target cytokines enables the analysis of cell-cell cross-talk and the effects of inhibiting one pathway on the social network of the cells in the well. It also enables examination of the potency/affinity/specificity of one biologic over another.

The targeting of specific pathways by small molecules can also be examined for analogous effects.

In one embodiment of the invention, the invention can be used for drug discovery, patient stratification, diagnosis or prognosis of a disease. Exemplary diseases are cancer and autoimmune diseases. In one embodiment of the invention, cells from an individual patient can be tested and matched to a response profile for a particular disease state. In another embodiment, cells from the individual can be tested and cross talk between cells may be detected. This communication may be interrupted if appropriate to address the disease state. Blocking agents may be administered for cytokines or other molecules that are involved in this cross talk (see FIG. 1). For example, blocking agents can include antibodies to the cytokines, such as anti-TNFα therapeutic agents, such as infliximab (Remicade), adalimumab (Humira), certolizumab pegol (Cimzia), and golimumab (Simponi), or with a circulating receptor fusion protein such as etanercept (Enbrel). Other embodiments include the use of the invention to detect the robustness of a vaccine response from the immune system. Other potential blocking agents include an anti-IL-6 chimeric monoclonal antibody (CNTO 328), ALD518/BMS-945429, CNTO 136, CPSI-2364, and CDP6038. An anti-IL-17 compound includes ixekizumab (Lilly) and an anti-CTLA-4 includes Abatacept.

D. Methods of Evaluating a Condition that Affects a Group of Individuals

The invention also provides methods of evaluating a condition that affects a group of individuals, such as health condition, e.g., an autoimmune disease or a cancer. The methods may include determining intercellular communication pathways and constituents of the pathways that are involved in susceptibility to, genesis of, progression of, or resistance to the condition. The methods may utilize samples taken from individuals, e.g., healthy individuals, and/or individuals in various stages of the condition or treatment for the condition, who are followed and sampled over time for the appearance, progression, remission, or response to treatment of the condition (longitudinal samples). The methods may utilize samples taken from individuals in the past whose present condition is now known, and in some cases samples from the individuals at later time points, where the individuals may be healthy individuals who developed the condition, individuals suffering from the condition (in some cases and preferably whose course of progression and/or remission of the condition is known), or individuals suffering from the condition and treated for the condition whose outcome of treatment is known (retrospective samples).

In certain embodiments, the invention provides a method of evaluating a condition that affects a group of individuals comprising (i) obtaining samples from individuals suffering from the condition; (ii) contacting cultures comprising a plurality of discrete cell populations in communication with a modulator, wherein the cultures are derived from the samples, and wherein the modulator interacts with a first discrete cell population in the culture but does not substantially interact with a second discrete cell population in the culture; (iii) incubating the cultures for a period of time; (iv) after the incubation, determining the activation level of an activatable element in single cells in the second cell population in the cultures; and (v) based at least in part on the activation level or information derived from the activation level, evaluating the condition.

The evaluation can further comprise performing steps (i)-(iv) on samples from individuals not suffering from the condition, and comparing the activation level, or information derived from the activation level, in cells from individuals suffering from the condition with the activation level, or information derived from the activation level, in cells from individuals not suffering from the condition. In certain cases, the samples from individuals not suffering from the condition are samples collected in the past from individuals who did not then suffer from the condition but who at a later time suffered from the condition.

In certain embodiments, the condition is an autoimmune condition or a cancer. Techniques and methods useful in performing the above method are described elsewhere herein, see, e.g., the section entitled "Comparison to Normal, unaffected Individuals"

E. Methods of Generating a Report

The invention also provides methods of generating reports. The report is in a form suitable for transport to an end user. The report may be in any suitable form, such as a hard (paper) copy or in electronic form, such as a data file or files stored in an electronically readable media, such as expressed and stored on computer readable medium in the form of magnetic fields on a hard drive or etchings on a CDROM. The transport may be physical transport or it may be electronic transport (i.e., through the Internet), or any other suitable transport so long as the report arrives at its destination in substantially the same form as it started, though it may be converted at its destination into other forms The report contains information generated by a method comprising
  (i) obtaining data or information obtained from data from an assay comprising
    (a) contacting a first cell from a first discrete cell population with a modulator in a culture containing a plurality of discrete cell populations in communication, wherein the modulator interacts with the first cell population but does not substantially interact with a second discrete cell population in the culture, and wherein the culture is derived from a sample that has been removed from an individual and placed in an artificial environment;
    (b) incubating the culture for a period of time; and
    (c) after the incubation, determining an activation level of a first activatable element on a cell-by-cell basis in single cells from the second cell population, The report may further, or alternatively, include data or information obtained from data, where step (c) additionally, or alternatively, includes determining the intracellular level of an intercellular communication messenger, such as a growth factor, hormone, cytokine, or exosome, e.g., an exosome. In certain embodiments, the report further, or alternatively, include data or information obtained from data, where step (c) additionally, or alternatively, includes contacting the culture with an agent that affects an intercellular communication messenger, or whose effect on such a messenger is desired to be known, or an agent that affects an intracellular pathway involved in intercellular communication, or whose effect on such a pathway or other pathways is desired to be known. In certain embodiments, the report includes information regarding the subject, who may be a subject suffering from, or suspected of suffering from, a condition. In certain embodiments in which an agent is used, the report may contain information regarding the agent.

The method utilizes raw data at one end of the process, or information derived from such raw data, and in its most basic form a report may contain just the raw data; one of the simplest reports is a report of raw data from detection of a specific form of one activatable element in one cell; one or more such reports may be transported together or separately to one or more end-users. There is virtually no limit to the number of such reports that may be generated by the methods of the invention, as each report may contain as little as the raw data for a single element in a single cell at a single time point, and hundreds of thousands or even millions or more such pieces of data may constitute their own report. In more sophisticated forms, the report may contain the results of manipulation of the raw data, such as control corrections, gating, calibrations, application of one or more statistical models, construction of a classifier, and the like. In the case of a report regarding a sample from an individual suffering from, or suspected of suffering from, a condition, the report may include diagnosis, prognosis, treatment, or other relevant information. The report may include recommendations for action, such as a recommendation regarding use, dosage, timing, and other aspects of treatment of a condition with a particular agent, e.g., drug. In addition the report can contain identifier information for the sample or samples on which the assay was run. At the other end of the spectrum from a report of raw data is a report that includes merely the final result, e.g., in the case of a report regarding a subject suffering from, or suspected of suffering from, a condition, such a report may contain a prognosis, diagnosis, treatment recommendation, etc., for the particular subject from whom a sample that was run in the assay was obtained. In the case of a drug screening report, the report may merely contain a prioritization of the agent, or a yes/no decision regarding the agent. However, a report of the invention may include any or all aspects from raw data to final recommendations In certain embodiments, the transportable report is a hard copy such as a paper report, and the conversion of the data is accomplished by methods well-known in the art for producing hard copies, such as printing the report at a printer connected to a computer. In certain embodiments, the transportable report is expressed and stored on computer-readable media in the form of magnetic fields, e.g., on a hard drive or etching on a CD. Methods for expressing and storing data on computer-readable media in the form of magnetic fields are also well-known in the art, see, e.g., U.S. Pat. Nos. 7,714,933 and 7,082,426, and U.S. Patent Applications Nos. 20130096948, 20050009078, and 20030100995, all of which are incorporated by reference herein in their entirety. In certain embodiments, the method includes obtaining identifying data for the identity of the subject from whom the sample was obtained and converting the data into the transportable report. Such identifying data does not necessarily need to identify the personal identity of the subject, e.g., name, but does need to convey enough information so that the data in the report can be matched to a subject from whom the sample on which the report is based was obtained. In certain embodiments in which the report concerns a chemical or biological agent, the method includes obtaining identifying data for the agent and converting the data into the transportable report.

In certain embodiments, the data further comprises data regarding the activation level of a second activatable element determined on a cell-by-cell basis in single cells from a third discrete cell population in the culture, data regarding the level of an intracellular communication molecule determined on a cell-by-cell basis in single cells from a fourth discrete cell population in the culture, data regarding the activation level of the first activatable element wherein the culture has also been treated with an agent that affects an intercellular communication messenger, or data regarding the activation level of the first activatable element wherein the culture has also been treated with an agent that affects an intracellular pathway involved in production of an intercellular communication messenger, or a combination thereof.

The invention also provides compositions comprising a report as described above in electronically readable medium, in addition to the methods of producing them.

XIII. Compositions

A. Reports

In certain embodiments, the invention provides a report comprising data regarding an activation level of an activatable element in a single cell in a culture comprising a plurality of discrete cell populations, wherein the cell is a member of a first discrete cell population and wherein the culture has been contacted for a period of time with a modulator that interacts with a second cell population in the culture, but does not substantially interact with the first cell population, or information derived at least in part from the data.

The report may further comprise data, or information derived from data regarding an activation level of an activatable element in a plurality of single cells, obtained on a cell-by-cell basis, in a culture comprising a plurality of discrete cell populations, wherein the cells are members of the first discrete cell population and wherein the culture has been contacted for a period of time with a modulator that interacts with a second cell population in the culture but does not substantially interact with the first cell population In certain embodiments, the report is an electronic report. In certain embodiments, the report is a hard copy.

Methods of preparing such reports are described elsewhere herein.

B. Kits

The invention also provides kits.

In certain embodiments, the invention provides a kit for analysis of a culture comprising a plurality of discrete cell populations in communication, comprising (i) a modulator that interacts with a first discrete cell population in the culture but does not substantially interact with a second cell population in the culture; and (ii) a state-specific detectable binding element that binds to an state of an activatable element found in cells in the second cell population. The kit may further include a detectable binding element that binds to an element that is not state-specific, e.g., a detectable binding element specific for an intercellular communication messenger. The kit may provide, in addition to, or as an alternative to the detectable binding element for an activated form of an activated element of (b), a detectable binding element for an intercellular communication messenger. In certain cases the intercellular communication messenger is growth factor, hormone, exosome, or cytokine. In certain embodiments, the intercellular growth factor to which the binding element binds is a cytokine, e.g., a cytokine that is IL1, IL2, IL3, IL4, IL5, IL6, IL8, IL9, IL10, IL12, IL15, IL17A, IL17F, IL21, IL23, TNF☐, TNF☐, IFN☐, IFN☐, or IFN☐☐☐☐ The kit may include one or more chemical or biological agents that may be used in certain instances instead of, or in addition to, the modulator. The chemical or biological agent may be an agent that affects an intercellular communication messenger. The chemical or biological agent may be an agent that affects an intracellular pathway involved in intracellular communication. The chemical or biological agent may be a modulator of a kinase, e.g., a kinase inhibitor.

The kit may be packaged as separate units that are shipped either together or separately, so longer as it is clear to the end user that the separate units are to be assembled and used as a kit, e.g., through knowledge generally available in the art, instructions from a third party, instructions or information from the maker or seller, and the like.

The state-specific detectable binding element may be an antibody, such as a phospho-specific antibody. Kits provided by the invention may comprise one or more of the state-specific binding elements described herein, such as phospho-specific antibodies.

A kit may also include other reagents that are useful in carrying out the procedures for which the kit is intended, such as permeabilizing agents, fixatives, containers, plates, buffers, therapeutic agents, instructions, and the like.

In some embodiments, the kit comprises one or more of the phospho-specific antibodies specific for the proteins selected from the group consisting of PI3-Kinase (p85, p110a, p110b, p110d), Jak1, Jak2, SOCs, Rac, Rho, Cdc42, Ras-GAP, Vav, Tiam, Sos, Dbl, Nck, Gab, PRK, SHP1, and SHP2, SHIP1, SHIP2, sSHIP, PTEN, Shc, Grb2, PDK1, SGK, Akt1, Akt2, Akt3, TSC1,2, Rheb, mTor, 4EBP-1, p70S6Kinase, S6, LKB-1, AMPK, PFK, Acetyl-CoAa Carboxylase, DokS, Rafs, Mos, Tp12, MEK1/2, MLK3, TAK, DLK, MKK3/6, MEKK1,4, MLK3, ASK1, MKK4/7, SAPK/JNK1,2,3, p38s, Erk1/2, Syk, Btk, BLNK, LAT, ZAP70, Lck, Cbl, SLP-76, PLCγ1, PLCγ2, STAT1, STAT 3, STAT 4, STAT 5, STAT 6, FAK, p130CAS, PAKs, LIMK1/2, Hsp90, Hsp70, Hsp27, SMADs, Rel-A (p65-NFKB), CREB, Histone H2B, HATs, HDACs, PKR, Rb, Cyclin D, Cyclin E, Cyclin A, Cyclin B, P16, p14Arf, p27KIP, p21CIP, Cdk4, Cdk6, Cdk7, Cdk1, Cdk2, Cdk9, Cdc25, A/B/C, Abl, E2F, FADD, TRADD, TRAF2, RIP, Myd88, BAD, Bcl-2, Mcl-1, Bcl-XL, Caspase 2, Caspase 3, Caspase 6, Caspase 7, Caspase 8, Caspase 9, IAPs, Smac, Fodrin, Actin, Src, Lyn, Fyn, Lck, NIK, I☐B, p65(RelA), IKKα, PKA, PKC☐, PKC☐, PKC☐, PKC☐, CAMK, Elk, AFT, Myc, Egr-1, NFAT, ATF-2, Mdm2, p53, DNA-PK, Chk1, Chk2, ATM, ATR, ☐☐catenin, CrkL, GSK3α, GSK3β, and FOXO. In some embodiments, the kit comprises one or more of the phospho-specific antibodies specific for the proteins selected from the group consisting of Erk, Syk, Zap70, Lck, Btk, BLNK, Cbl, PLCγ2, Akt, RelA, p38, S6. In some embodiments, the kit comprises one or more of the phospho-specific antibodies specific for the proteins selected from the group consisting of Akt1, Akt2, Akt3, SAPK/JNK1,2,3, p38s, Erk1/2, Syk, ZAP70, Btk, BLNK, Lck, PLCγ, PLCγ2, STAT1, STAT 3, STAT 4, STAT 5, STAT 6, CREB, Lyn, p-S6, Cbl, NF-☐B, GSK3β, CARMA/Bcl10 and Tcl-1. In some embodiments, the kit comprises one or more of phospho-specific antibodies specific for one or more of the proteins AKT, s6, ERK, p38, STAT1, STAT3, or STAT5. Here, as elsewhere herein, a protein may be specified in a general term, e.g., AKT, or specifically as an activated form, e.g., a phosphorylated form, e.g., pAKT. In general, when the form is referred to in the context of a binding element, it is meant a binding element specific for the activated form, e.g., phosphorylated form or cleaved form, whether or not the general or specific term is used. Thus, for example, when a term is used regarding a "binding element [e.g., antibody] for AKT," it is intended to mean "binding element [e.g. antibody]

The state-specific binding element of the kit can be conjugated to a solid support and to detectable groups directly or indirectly. The reagents may also include ancillary agents such as buffering agents and stabilizing agents, e.g., polysaccharides and the like. The kit may further include, where necessary, other members of the signal-producing system of which system the detectable group is a member (e.g., enzyme substrates), agents for reducing background interference in a test, control reagents, apparatus for conducting a test, and the like. The kit may be packaged in any suitable manner, typically with all elements in a single container along with a sheet of printed instructions for carrying out the test.

Such kits enable the detection of activatable elements by sensitive cellular assay methods, such as mass spectrometry and flow cytometry, which are suitable for many uses, such as the clinical detection, prognosis, and screening of cells and tissue from patients, such as leukemia patients, having a disease involving altered pathway signaling.

Such kits may additionally comprise one or more therapeutic agents. The kit may further comprise a software package for data analysis of the physiological status, which may include reference profiles for comparison with the test profile.

Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the end-user, e.g., health care provider. Such information may be based on the results of various studies, for example, studies using experimental animals involving in vivo models and studies based on human clinical trials. Kits described herein can be provided, marketed and/or promoted to health providers, including physicians, nurses, pharmacists, formulary officials, and the like. Kits may also, in some embodiments, be marketed directly to the consumer.

XIV. Systems

The invention also provides systems.

A. System for Informing a Decision by a Subject and/or Healthcare Provider for the Subject In certain embodiments, the invention provides a system for informing a decision by a subject and/or healthcare provider for the subject involving diagnosing, prognosing, evaluating status of, or determining a method of treatment for a condition from which the subject is suffering or is suspected of suffering, wherein the system comprises
  (i) the subject and the healthcare provider;
  (ii) a sample removed from the subject;
  (ii) a unit configured to analyze a culture derived from the sample, wherein the culture comprises a plurality of discrete cell populations in communication, wherein the unit is configured to
    (a) contact a first cell from a first discrete cell population in the culture with a modulator, wherein the modulator interacts with the first cell population but does not substantially interact with a second discrete cell population in the culture;
    (b) incubate the culture for a period of time; and
    (c) after the incubation, determine an activation level of a first activatable element in single cells from the second cell population, in the form of raw data;
  (iii) a unit configured to communicate the raw data or information derived at least in part from the raw data to the subject and/or healthcare provider so that a decision may be made regarding diagnosis, prognosis, state of, or treatment of the condition that the subject suffers from or is suspected of suffering from. The system may further comprise a unit for treating and transporting the sample from the patient to the analysis unit, or transporting a second sample or culture derived from the sample, to the analysis unit. In certain instances, the sample or second sample or culture may be treated, e.g., to enhance preservation, such as by cryopreservation.

The subject can be an individual, e.g., a human who suffers from, or is suspected of suffering from, a condition, where the condition can be any condition as described herein. In some cases, the condition is an autoimmune condition or a cancer. In some cases, the condition is a pathological condition such as a neoplastic, hematopoietic, or autoimmune condition, such as Non-Hodgkin Lymphoma, Hodgkin or other lymphomas, acute or chronic leukemias, polycythemias, thrombocythemias, multiple myeloma or plasma cell disorders, e.g., amyloidosis and Waldenstrom's macroglobulinemia, myelodysplastic disorders, myeloproliferative disorders, myelofibrosis, or atypical immune lymphoproliferation, systemic lupus erythematosis (SLE), rheumatoid arthritis (RA).

The sample may be any sample as described herein. In certain embodiments, the sample is a blood sample. In certain embodiments, the sample is a bone marrow aspirate sample. The sample may be a sample obtained previously, or it may be a sample that the subject or healthcare provider requests to be made based on information that makes one or both suspect the presence of a condition, or on diagnosis of the condition and the desire to obtain relevant information regarding prognosis, course of treatment or progression of the condition, prediction of effectiveness of a particular treatment for this subject. Thus, in general, the subject and/or healthcare provider order the obtaining of the sample and the use of the system to obtain the desired information.

In certain embodiments, the system also includes a unit for treating the sample and transporting the sample to the analysis unit Treatment includes any necessary treatment to allow the sample to be transported to the analysis unit without significant degradation of relevant characteristics. Various methods of treatment which may be used in this unit are as described herein. In certain embodiments, the treatment includes cryopreservation.

The modulator or modulators can be any modulator or modulators as described herein. In certain embodiments, no modulator is used (e.g. embodiments in which the analysis determines basal levels of activatable or other elements in cells). In certain embodiments, only modulators are used.

In the methods for which the analytical unit is configured a form of an activatable element is detected by exposing the cell to a detectable binding element and detecting the element. Activatable elements are described herein. In certain embodiments, the activated form is the form detected. Activated forms may be, e.g., phosphorylated or cleaved. In certain embodiments the element is a protein and the form detected is a phosphorylated form or a cleaved form. Detectable binding elements are as described herein, for example antibodies specific to a specific form of an activatable element, e.g., antibodies specific to a phosphorylated form or antibodies specific to a cleaved form. The component of the analytical unit for detection may be any suitable component as described herein, such as flow cytometer or mass spectrometer. In certain additional or alternative embodiments the element detected does not exist as activated and non-activated forms, in which case the total level of the element is detected using a detectable binding element specific to the element to be detected. Such elements include intercellular communication messengers such as cytokines.

The analytical unit may also be configured to analyze the raw data obtained from the detection of the detectable binding elements in single cells, or it may transmit the data to a separate data manipulation unit or units.

The analytical unit may also be configured to gate data from healthy cells vs unhealthy cells, also as described herein, e.g., by scatter, Amine Aqua staining, and/or cPARP determinations. The analytical unit may be manually controlled or automated or a combination thereof, also as described herein.

The unit for communicating the results of the analysis of the sample to the subject and/or healthcare provider so that a decision may be made regarding diagnosis, prognosis, state of, or treatment of the condition that the subject suffers from or is suspected of suffering from, may be any suitable unit. For example, the unit may generate a hard copy of a report of the results which may be physically transported to the patient and/or healthcare provider. Alternatively, the results may be electronically communicated, and displayed in a format suitable for communicating the results to the subject and/or healthcare provider, e.g., on a screen, or as a printed report.

The system allows the subject and/or the healthcare provider to receive information to assist in the diagnosis, prognosis, evaluation of status, or determining a method of treatment for the condition. For the patient, the additional information and the extra certainty it provides can provide emotional comfort and the greater probability of a successful outcome. For the healthcare provider, the system allows for greater ability to diagnose, prognose, evaluate, or determine treatment for the patient, and to subsequently receive payment. For the subject, the system allows greater certainty as to the presence or absence of a condition, the probable course of the condition and/or a more informed choice of, e.g., intervals for subsequent testing, as well as evaluation of subsequent samples. For subjects in whom the condition has progressed to the point of treatment, the system allows greater certainty for the patient and provider in knowing whether or not to pursue a particular treatment, such as treatment with a particular drug.

In certain embodiments, the condition is a pathological condition selected from the group consisting of cancer and autoimmune conditions.

In certain embodiments, the analysis unit comprises a flow cytometer or mass spectrometer configured to determine on a single cell basis the levels of a detectable binding element in the cell, wherein the detectable binding element is an element that binds to a form of the activatable element. The form of the activatable element may be an activated form, for example the activatable element is activated by cleavage or phosphorylation.

B. System for Informing a Decision by a Decision-Making Entity Regarding a Chemical or Biological Agent In certain embodiments, the invention provides a system for informing a decision by a decision-making entity, wherein the system comprises 1) the decision-making entity; 2) a unit configured to analyze a biological sample obtained from an individual by a method of analysis comprising a) exposing cells from the sample to one or modulators, or no modulator, in the presence or absence of a chemical or biological agent that potentially affects one or more intracellular elements of the cells or one or more extracellular elements secreted by the cells; b) exposing the cells to a detectable binding element that binds to a form of an activatable element in the cell, and c) determining on a single cell basis the levels of the detectable binding element in the cells and 3) a unit for communicating the results of the analysis of the sample to the decision-making entity so that a decision may be made regarding the chemical or biological agent. In certain embodiments, the decision is a decision as to whether or not to pursue additional studies of the agent, and/or the priority of such studies relative to studies for other agents. The system may further comprise a unit for treating and transporting the sample from the patient to the analysis unit. The chemical or biological agent may be any agent for which the effect on one or more intracellular elements or one or more extracellular elements is desired to be known, or an agent whose potential efficacy in a use, e.g., in treatment of a condition, is desired to be known. In certain embodiments, the agent is a potential therapeutic agent for a condition. The decision-making entity may include a computer that uses algorithms to select or prioritize agents for further investigation. The decision-making entity may include a person or collection of persons who are, e.g., pursuing further development of the agents, and who benefit from the information provided by the analysis unit because the information, in some cases in association with other information, allows prioritization of further investigation or further use of the agents, and/or helps identify desired (e.g. drug target) and/or undesired (e.g. off target) effects of the agent. Thus in certain embodiments the system allows drug screening for biological or chemical agents of potential usefulness in treating a condition.

In certain embodiments, the system also includes a unit for treating the sample and transporting the sample to the analysis unit. Treatment includes any necessary treatment to allow the sample to be transported to the analysis unit without significant degradation of relevant characteristics. Various methods of treatment which may be used in this unit are as described herein. In certain embodiments, the treatment includes cryopreservation.

The analytical unit may also be configured to analyze the raw data obtained from the detection of the detectable binding elements in single cells, or it may transmit the data to a separate data manipulation unit or units.

The analytical unit may also be configured to gate data from healthy cells vs unhealthy cells, also as described herein, e.g., by scatter, Amine Aqua staining, and/or cPARP determinations. The analytical unit may be manually controlled or automated or a combination thereof, also as described herein.

The unit for communicating the results of the analysis of the sample to the decision-making entity so that a decision may be made regarding the agent, may be any suitable unit. For example, the unit may generate a hard copy of a report of the results which may be physically transported to the decision-making entity. Alternatively, the results may be electronically communicated, and displayed in a format suitable for communicating the results to the decision-making entity, e.g., on a screen, or as a printed report.

In certain embodiments, the invention provides a system for informing a decision by a decision-making entity regarding a chemical or biological agent comprising
  (i) the decision-making entity;
  (ii) a unit configured to analyze a culture derived from a sample obtained from an individual wherein the culture comprises a plurality of discrete cell populations in communication, wherein the unit is configured to
    (a) contact a first cell from a first discrete cell population in the culture with a modulator, wherein the modulator interacts with the first cell population but does not substantially interact with a second discrete cell population in the culture;
    (b) contact the culture with the agent, (c) incubate the culture for a period of time; and
(d) after the incubation, determine an activation level of a first activatable element in single cells from the second cell population, in the form of raw data;
(iii) a unit configured to communicate the raw data, or information derived at least in part from the raw data, to the decision-making entity so that a decision may be made regarding the agent. In certain embodiments, step (d) includes additionally, or alternatively, determine the intracellular level of an intercellular communication messenger, e.g., a cytokine, in single cells from the second population, in the form of raw data.

In certain embodiments, the decision is a decision as to whether or not to pursue additional studies of the agent, and/or the priority of such studies relative to studies for other agents. The system may further comprise a unit for treating and transporting the sample from the patient to the analysis unit. The chemical or biological agent may be any agent for which the effect on one or more intracellular elements or one or more extracellular elements is desired to be known, or an agent whose potential efficacy in a use, e.g., in treatment of a condition, is desired to be known. In certain embodiments, the agent is a potential therapeutic agent for a condition. The decision-making entity may include a computer that uses algorithms to select or prioritize agents for further investigation. The decision-making entity may include a person or collection of persons who are, e.g., pursuing further development of the agents, and who benefit from the information provided by the analysis unit because the information, in some cases in association with other information, allows prioritization of further investigation or further use of the agents, and/or helps identify desired (e.g. drug target) and/or undesired (e.g. off target) effects of the agent. Thus in certain embodiments the system allows drug screening for biological or chemical agents of potential usefulness in treating a condition.

In certain of these embodiments, the system further comprises a unit configured to treat the sample, or a culture derived from the sample, for transport to the analysis unit. Such treatment can include treatments intended to preserve the sample, or a culture derived from the sample, e.g., cryopreservation.

In certain of these embodiments, the agent is an agent to be evaluated for efficacy in affecting an intercellular communication messenger such as a growth factor, hormone, cytokine, or exosome; e.g., a cytokine. In certain of these embodiments, the agent is an agent to be evaluated for efficacy in affecting an intracellular pathway involved in intercellular communication. The agent may be evaluated for effects on particular intracellular or extracellular components thought to be involved in the mechanism of a condition (e.g., drug targets) and/or effects on intracellular or extracellular components not thought to be involved in the mechanism of a condition (e.g., off-target effects).

In certain of these embodiments, the system further comprises a unit configured to treat the sample, or a culture derived from the sample, for transport to the analysis unit. Such treatment can include treatments intended to preserve the sample, or a culture derived from the sample, e.g., cryopreservation.

In certain of these embodiments, the analysis unit comprises a flow cytometer or mass spectrometer configured to determine on a single cell basis the levels of a detectable binding element in the cell, wherein the detectable binding element is an element that binds to a form of the activatable element. The activatable element may be an activated form, activated by cleavage or phosphorylation. The analytical unit may be configured to gate data from healthy vs. unhealthy cells, such gating may include determining cPARP levels in cells and gating the cells at least in part based on their cPARP levels.

In some embodiments, this invention is directed to methods and compositions, and kits that allow for the determination of the status of an individual and/or the state of a cellular network comprised of at least two discrete cell populations. The methods and compositions, and kits described herein for any condition for which a correlation between the condition, its prognosis, course of treatment, or other relevant characteristic, and the state of a cellular network and/or activation state data of a plurality of cell populations, e.g., activation level of one or more activatable elements in the populations, in samples from individuals may be ascertained. In some embodiments, this invention is directed to methods and compositions, and kits for analysis, drug screening, diagnosis, prognosis, for methods of disease treatment and prediction. In some embodiments, the present invention involves methods of analyzing experimental data. In some embodiments, the activation state data of different discrete cell populations in a sample (e.g. clinical sample) is used, e.g., in diagnosis or prognosis of a condition, patient selection for therapy using some of the agents identified above, to monitor treatment, modify therapeutic regimens, and/or to further optimize the selection of therapeutic agents which may be administered as one or a combination of agents. Hence, therapeutic regimens can be individualized and tailored according to the data obtained prior to, and at different times over the course of treatment, thereby providing a regimen that is individually appropriate. In some embodiments, a compound is contacted with cells to analyze the response to the compound. The activation state data of a discrete cell population can be generated by quantifying the activation level of at least one activatable element in response to at least one modulator in one or more cells belonging to the cell population.

The invention allows for the determination of the state of a cellular network comprising two or more discrete cell populations. The methods of the invention provide tools useful in the treatment of an individual afflicted with a condition, including but not limited to: diagnosis, methods for assigning a risk group, methods of predicting an increased risk of relapse, methods of predicting an increased risk of developing secondary complications, methods of choosing a therapy for an individual, methods of predicting duration of response, response to a therapy for an individual, methods of determining the efficacy of a therapy in an individual, and methods of determining the prognosis for an individual. The state of a cellular network can serve as a prognostic indicator to predict the course of a condition, e.g. whether the course of a neoplastic or a hematopoietic condition in an individual will be aggressive or indolent, thereby aiding the clinician in managing the patient and evaluating the modality of treatment to be used. In another embodiment, the present invention provides information to a physician to aid in the clinical management of a patient so that the information may be translated into action, including treatment, prognosis or prediction.

In some embodiments, the methods described herein are used to screen candidate compounds useful in the treatment of a condition or to identify new drug targets.

In some embodiments, the status of the individual or the state of the cellular network can be used to confirm or refute the presence of a suspected genetic or physiologic abnormality associated with increased risk of disease. Such testing methodologies can replace other confirmatory techniques like cytogenetic analysis or fluorescent in situ histochemistry (FISH). In still another embodiment, the status of the individual or the state of the cellular network can be used to confirm or refute a diagnosis of a pre-pathological or pathological condition.

In instances where an individual has a known pre-pathologic or pathologic condition, the status of the individual or the state of the cellular network can be used to predict the response of the individual to available treatment options. In one embodiment, an individual treated with the intent to reduce in number or ablate cells that are causative or associated with a pre-pathological or pathological condition can be monitored to assess the decrease in such cells and the state of a cellular network over time. A reduction in causative or associated cells may or may not be associated with the disappearance or lessening of disease symptoms, e.g. depending of the state of the cellular network. If the anticipated decrease in cell number and/or improvement in the state of a cellular network do not occur, further treatment with the same or a different treatment regiment may be warranted.

In another embodiment, an individual treated to reverse or arrest the progression of a pre-pathological condition can be monitored to assess the reversion rate or percentage of cells arrested at the pre-pathological status point. If the anticipated reversion rate is not seen or cells do not arrest at the desired pre-pathological status point further treatment with the same or a different treatment regiment can be considered.

In a further embodiment, cells of an individual can be analyzed to see if treatment with a differentiating agent has pushed a cell type along a specific tissue lineage and to terminally differentiate with subsequent loss of proliferative or renewal capacity. Such treatment may be used preventively to keep the number of dedifferentiated cells associated with disease at a low level thereby preventing the development of overt disease. Alternatively, such treatment may be used in regenerative medicine to coax or direct pluripotent or multipotent stem cells down a desired tissue or organ specific lineage and thereby accelerate or improve the healing process.

Individuals may also be monitored for the appearance or increase in cell number of a discrete cell population(s) that are associated with a good prognosis. If a beneficial discrete population of cells is observed, measures can be taken to further increase their numbers, such as the administration of growth factors. Alternatively, individuals may be monitored for the appearance or increase in cell number of a discrete cells population(s) associated with a poor prognosis. In such a situation, renewed therapy can be considered including continuing, modifying the present therapy or initiating another type of therapy.

In some embodiments, the determination of the status of an individual may be used to ascertain whether a previous condition or treatment has induced a new pre-pathological or pathological condition that requires monitoring and/or treatment. For example, treatment for many forms of cancers (e.g. lymphomas and childhood leukemias) can induce certain adult leukemias, and the methods of the present invention allow for the early detection and treatment of such leukemias.

The invention provides methods for determining characteristics such as the disease status of an individual by analyzing different discrete cell populations in said individual. In some embodiments, the disease status of an individual is determined by a method comprising contacting a first cell from a first discrete cell population from said individual with at least a first modulator, determining an activation level of at least one activatable element in said first cell, creating a response panel for said individual comprising said determined activation levels of said activatable element, and making a decision regarding the disease status of said individual, wherein said decision is based on said response panel.

In some embodiments, one or more samples containing the different discrete cell populations may be taken from the individual, and subjected to a modulator, as described herein. In some embodiments, the sample is divided into subsamples that are each subjected to a different modulator. After treatment with the modulator, different discrete populations of cells in the sample or subsample are analyzed to determine their activation level(s). In some embodiments, single cells in the different discrete cell populations are analyzed. Any suitable form of analysis that allows a determination of activation level(s) may be used. In some embodiments, the analysis includes the determination of the activation level of an intracellular element, e.g., a protein. In some embodiments, the analysis includes the determination of the activation level of an activatable element, e.g., an intracellular activatable element such as a protein, e.g., a phosphoprotein. Determination of the activation level may be achieved by the use of activation state-specific binding elements, such as antibodies, as described herein. A plurality of activatable elements may be examined in one or more of the different discrete cell populations.

In some embodiments, the invention provides methods for determining the status of a cellular network in an individual by analyzing different discrete cell populations in said individual. The analysis of different discrete cell populations allows for the determination of directionality (e.g. vectors) within the different discrete cell populations participating in a cellular network. The analysis of the different discrete cell populations can be performed by determining the activation level of at least one activatable element in the different discrete cell populations in response to a modulator. In some embodiments, the analysis of the different discrete cell populations is performed by dividing each discrete cell population into a plurality of samples and determining the activation level of at least one activatable element in the samples in response to a modulator.

In some embodiments, the invention is directed to methods of determining the presence or absence of a condition in an individual by subjecting one or more discrete cell populations from the individual to a modulator, determining the activation level of an activatable element in one or more different discrete cell populations, and determining the presence or absence of the condition based on the activation level upon treatment with a modulator. In some embodiments, each discrete cell population is contacted with a different modulator in separate cultures. In some embodiments, each discrete cell population is contacted with the same modulator in the same or separate cultures. The term "same modulator" as described herein in relation to a modulator encompasses active fragment or portion of the modulator, a modulator that binds the same target as the modulator and/or a modulator that modulates the same signaling pathway as the modulator. For example, when a discrete cell population is treated with a modulator as described herein, another discrete cell population treated with the same modulator can be treated with an active fragment or portion of the modulator, a modulator that binds the same target and/or a modulator that modulates the same signaling pathway. In some embodiments, some discrete cell populations are contacted with the same modulator in the same or separate cultures, while other discrete cell populations are contacted with a different modulator. In some embodiments, the contacting of discrete cell population is before isolation of said first cell and said second cell from said individual, for example, when the modulator such as a chemical is in the cell environment inside of the individual. Thus, in some embodiments the modulator is present inside the individual and the discrete cell populations are contacted by the modulator in a cell environment inside the individual.

In some embodiments, the determination of status of a cellular network comprises the detection and determination of the activation state of immune cells specifically related to the pathogenesis of autoimmune diseases. Specific immune cells can be monitored over time while they are under therapeutic pressure either in vitro or in vivo to provide information to guide patient management. For immune cells, see generally FIG. 1.

In some embodiments, the invention provides methods for determining a status of an individual such a disease status, therapeutic response, and/or clinical responses wherein the positive predictive value (PPV) is higher than 60, 70, 80, 90, 95, or 99.9%. In some embodiments, the invention provides methods for determining a status of an individual such a disease status, therapeutic response, and/or clinical responses, wherein the PPV is equal or higher than 95%. In some embodiments, the invention provides methods determining a status of an individual such a disease status, therapeutic response, and/or clinical responses, wherein the negative predictive value (NPV) is higher than 60, 70, 80, 90, 95, or 99.9%. In some embodiments, the invention provides methods for determining a status of an individual such a disease status, therapeutic response, and/or clinical responses, wherein the NPV is higher than 85%.

In some embodiments, the p value in the analysis of the methods described herein is below 0.05, 0.04, 0.03, 0.02, 0.01, 0.009, 0.005, or 0.001. In some embodiments, the invention provides methods for determining a status of an individual such a disease status, therapeutic response, and/or clinical responses, wherein the AUC value is higher than 0.5, 0.6, 07, 0.8 or 0.9.

In some embodiments, a discrete population of cells is a population of cells wherein every cell has the same or substantially the same of a set of phenotypic markers or range of phenotypic markers that are used to identify the discrete cell population. Phenotypic markers are generally extracellular markers, but may include intracellular markers including but not limited to transcription factors, cytokines, and cleaved PARP and Ki67. Cells may also be labeled with fluorescent dyes. The set of phenotypic markers can be one phenotypic marker. For example, "stem cell populations" are characterized by CD34+ CD38− or CD34+ CD33− expressing cells, regulatory CD4 T lymphocytes by CD4+CD25+ Foxp3+ cells, and multiple leukemic subclones can be identified based on CD33, CD45, HLA-DR, CD11b. In addition to extracellular markers, expression levels of intracellular biomolecules, e.g., proteins, may be used alone or in combination with the extracellular markers to identify a cell population. Further, additional cellular elements, e.g., biomolecules or molecular complexes such as RNA, DNA, carbohydrates, metabolites, and the like, may be used in conjunction with extracellular markers and/or expression levels in the identification of cell populations encompassed here.

In some embodiments, other biological processes that affect the status of a cellular constituent may also be used to identify a cell population. Examples include the translocation of biomolecules or changes in their turnover rates and the formation and disassociation of complexes of biomolecule. Such complexes can include multi-protein complexes, multi-lipid complexes, homo- or hetero-dimers or oligomers, and combinations thereof. Other characteristics include proteolytic cleavage, e.g. from exposure of a cell to an extracellular protease or from the intracellular proteolytic cleavage of a biomolecule.

The absence of a discrete subpopulation of cells is itself activation state data that is useful in understanding the pathophysiology of a discrete population of cells. This is useful, for example, when it is desired to determine what the percentage of the total number of a discrete population of cells belongs to one particular subpopulation of cells.

The discrete populations of cells may be identified based on empirical characteristics derived from individuals that indicate the status of individuals, e.g., health status. For example, blood samples from the clinic and/or from clinical trials may be analyzed retrospectively to identify discrete populations of cells; the activation state data of certain populations or quantitative features of the discrete cell populations may be associated with certain known outcomes for the patients.

For example, blood samples may be obtained from cancer patients over the course of treatment. Various outcomes, from complete remission for a number of years, to death from cancer or cancer recurrence after treatment, may be recorded. Profiles of the states of activatable elements in a plurality of discrete cell populations, with or without modulator, may be obtained from retrospective samples to determine discrete populations of cells present in the samples, activation state data in each discrete population of cells, numbers of cells in each discrete population of cells, relative numbers or proportions of cells in different discrete populations and/or subpopulations of cells, and the like. These discrete populations of cells together with their predictive value for various health status, may be placed in a database that is then used for analysis of further samples. As more samples are obtained and correlated health status determined, the database may be modified.

In some embodiments the different discrete cell populations are hematopoietic cell populations. Examples of hematopoietic populations include, but are not limited to, pluripotent hematopoietic stem cells, B-lymphocyte lineage progenitor or derived cells, T-lymphocyte lineage progenitor or derived cells, NK cell lineage progenitor or derived cells, granulocyte lineage progenitor or derived cells, monocyte lineage progenitor or derived cells, megakaryocyte lineage progenitor or derived cells and erythroid lineage progenitor or derived cells. Thus, for example, in some embodiments, the status of an individual is determined by analyzing the activation level of an activatable element in a B-lymphocyte-derived discrete cell population and a T-lymphocyte-derived discrete cell population in response to a modulator, wherein the modulator for the different discrete cell populations can be the same or different.

In some embodiments, the status of an individual or the state of cellular network is determined by creating a response panel by analyzing one or more activatable elements in different discrete cell populations in response to one or more modulators. In some embodiments, a response panel is created by contacting each of the different discrete cell populations with at least one modulator and determining an activation level of at least one activatable element in each of the discrete cell populations. In some embodiments, a response panel is created by dividing each discrete cell population into a plurality of samples and contacting the samples with at least one modulator and determining an activation level of at least one activatable element in the samples. In some embodiments, each discrete cell population is contacted with a different modulator in separate cultures. In some embodiments, each discrete cell population is contacted with the same modulator in the same or separate cultures. In some embodiments, some discrete cell populations are contacted with the same modulator in the same or separate cultures, while other cell populations are contacted with a different modulator. For example, if the different discrete populations being analyzed are naive CD4 T cells, memory CD4 T cells, naive CD8 T cells and memory CD8 T cells, naive CD4 and memory CD4 can be contacted with the same first modulator in the same culture, while naive CD8 T cells and memory CD8 T cells are contacted with a second and third modulator, respectively, in separate cultures. The different discrete cells populations can be analyzed for the same activatable element or a different activatable element. The different discrete cells populations can be analyzed simultaneously or sequentially.

In some embodiments, the activatable element analyzed in each discrete cell population is different. In some embodiments, the activatable element analyzed in each discrete cell population is the same. In some embodiments, a plurality of activatable elements are analyzed in the discrete cell populations, where the activatable elements can be the same or different among the different discrete cell populations. In some embodiments, the number of activatable elements analyzed in each cell population is different. For example, in some embodiments only one activatable element is analyzed in one cell population, while a plurality (e.g. two or more) of activatable elements are analyzed in the other cell populations. When a plurality of activatable elements is analyzed in a discrete cell population, the activatable elements can be analyzed sequentially or simultaneously.

In some embodiments, the methods of the invention provide methods for generating activation state data for different discrete populations of cells by exposing each discrete population of cells to a plurality of modulators (recited herein) in separate cultures, determining the presence or absence of an increase in activation level of an activatable element in the discrete cell population from each of the separate cultures and classifying the discrete cell population based on the presence or absence of the increase in the activation of the activatable element from each of the separate culture. In some embodiments, activation state data is used to characterize multiple pathways in each of the population of cells. The activation state data of the different populations of cells can be used to determine the status of an individual or the state a cellular network.

The status of an individual or of a cellular network can be used in selecting a method of treatment. Example of methods of treatments include, but are not limited to immunotherapy, chemotherapy, biological therapy, radiation therapy, bone marrow transplantation, Peripheral stem cell transplantation, umbilical cord blood transplantation, autologous stem cell transplantation, allogeneic stem cell transplantation, syngeneic stem cell transplantation, surgery, induction therapy, maintenance therapy, watchful waiting, and other therapy.

In addition to activation levels of activatable elements, expression levels of intracellular or extracellular biomolecules, e.g., proteins may be used alone or in combination with activation states of activatable elements to determine the status of an individual or a cellular network. Further, additional cellular elements, e.g., biomolecules or molecular complexes such as RNA, DNA, carbohydrates, metabolites, and the like, may be used in conjunction with activatable states or expression levels in the analysis of different discrete population of cells encompassed here. In some embodiments, expression markers are also measured in the different discrete cell populations. In some embodiments, expression markers or drug transporters, such as CD34, CD33, CD45, HLADR, CD11B FLT3 Ligand, c-KIT, ABCG2, MDR1, BCRP, MRP1, LRP, and others noted below, can also be used in the methods described herein. The expression markers may be detected using many different techniques, for example using nodes from flow cytometry data. Other common techniques employ expression arrays (commercially available from Affymetrix, Santa Clara Calif.), taqman (commercially available from ABI, Foster City Calif.), SAGE (commercially available from Genzyme, Cambridge Mass.), sequencing techniques (see the commercial products from Helicos, 454, US Genomics, and ABI) and other commonly know assays. See Golub et al., Science 286: 531-537 (1999). In some embodiments, the expression markers include epitope-based markers, RNA, mRNA, siRNA, or metabolomic markers.

In some embodiments, the invention provides methods to carry out multiparameter flow cytometry for monitoring phospho-protein responses to various factors in different discrete cell populations. Phospho-protein members of signaling cascades and the kinases and phosphatases that interact with them are required to initiate and regulate proliferative signals in cells. Flow cytometry is useful in a clinical setting, since relatively small sample sizes, as few as 10,000 cells, can produce a considerable amount of statistically tractable multidimensional signaling data. (See U.S. Pat. Nos. 7,381,535 and 7,393,656. See also Krutzik et al, 2004).

In the determination of a characteristic such as a prognostic or disease status of an individual, other factors can be considered. Any factor that gives additional predictive or diagnostic power to the analyses of different discrete cell populations described herein may be used. Such factors are well-known in the art. These include an individual's gender; race; current age; age at the time of disease presentation; age at the time of treatment; clinical stage of disease; genetic results, number of previous therapies; type of previous therapies; response to previous therapy or therapies; time from last treatment; blood cell count; bone marrow reserves; and performance status, patient's past medical history, family history of any medical problems, patient's social history, as well as any current medical history termed "review of systems", and physical exam findings. Other factors are more specific to the specific condition being evaluated, e.g., percentage of blasts in bone marrow as an indicator of certain leukemias. Such factors are well-known in the art for particular diseases and conditions. Examples of tests that can be performed together with the methods described herein include, but are not limited to, immunophenotyping, morphology, conventional cytogenetics, molecular cytogenetics, molecular genetics and HLA typing.

Conditions

The methods of the invention are applicable to any condition in an individual involving, indicated by, and/or arising from, in whole or in part, altered physiological status in cells. The term "physiological status" includes mechanical, physical, and biochemical functions in a cell. In some embodiments, the physiological status of a cell is determined by measuring characteristics of at least one cellular component of a cellular pathway in cells from different populations (e.g. different cell networks). Cellular pathways are well known in the art. In some embodiments the cellular pathway is a signaling pathway. Signaling pathways are also well known in the art (see, e.g., Hunter T., Cell 100(1):

113-27 (2000); Cell Signaling Technology, Inc., 2002 Catalogue, Pathway Diagrams pgs. 232-253; Weinberg, Chapter 6, The biology of Cancer, 2007; Blume-Jensen and Hunter, Nature, vol 411, 17 May 2001, p 355-365) and U.S. Pat. No. 8,227,202. A condition involving or characterized by altered physiological status may be readily identified, for example, by determining the state of one or more activatable elements in cells from different populations, as taught herein.

In certain embodiments of the invention, the condition is a neoplastic, immunologic or hematopoietic condition. In some embodiments, the neoplastic, immunologic or hematopoietic condition is selected from the group consisting of solid tumors such as head and neck cancer including brain, thyroid cancer, breast cancer, lung cancer, mesothelioma, germ cell tumors, ovarian cancer, liver cancer, gastric carcinoma, colon cancer, prostate cancer, pancreatic cancer, melanoma, bladder cancer, renal cancer, prostate cancer, testicular cancer, cervical cancer, endometrial cancer, myosarcoma, leiomyosarcoma and other soft tissue sarcomas, osteosarcoma, Ewing's sarcoma, retinoblastoma, rhabdomyosarcoma, Wilm's tumor, and neuroblastoma, sepsis, allergic diseases and disorders that include but are not limited to allergic rhinitis, allergic conjunctivitis, allergic asthma, atopic eczema, atopic dermatitis, and food allergy, immunodeficiencies including but not limited to severe combined immunodeficiency (SCID), hypereosiniphic syndrome, chronic granulomatous disease, leukocyte adhesion deficiency I and II, hyper IgE syndrome, Chediak Higashi, neutrophilias, neutropenias, aplasias, agammaglobulinemia, hyper-IgM syndromes, DiGeorge/Velocardial-facial syndromes and Interferon gamma-TH1 pathway defects, autoimmune and immune dysregulation disorders that include but are not limited to rheumatoid arthritis, diabetes, systemic lupus erythematosus, Graves' disease, Graves ophthalmopathy, Crohn's disease, multiple sclerosis, psoriasis, systemic sclerosis, goiter and struma lymphomatosa (Hashimoto's thyroiditis, lymphadenoid goiter), alopecia aerata, autoimmune myocarditis, lichen sclerosis, autoimmune uveitis, Addison's disease, atrophic gastritis, myasthenia gravis, idiopathic thrombocytopenic purpura, hemolytic anemia, primary biliary cirrhosis, Wegener's granulomatosis, polyarteritis nodosa, and inflammatory bowel disease, allograft rejection and tissue destructive from allergic reactions to infectious microorganisms or to environmental antigens, and hematopoietic conditions that include but are not limited to Non-Hodgkin Lymphoma, Hodgkin or other lymphomas, acute or chronic leukemias, polycythemias, thrombocythemias, multiple myeloma or plasma cell disorders, e.g., amyloidosis and Waldenstrom's macroglobulinemia, myelodysplastic disorders, myeloproliferative disorders, myelo fibroses, or atypical immune lymphoproliferations. In some embodiments, the neoplastic or hematopoietic condition is non-B lineage derived, such as Acute myeloid leukemia (AML), Chronic Myeloid Leukemia (CML), non-B cell Acute lymphocytic leukemia (ALL), non-B cell lymphomas, myelodysplastic disorders, myeloproliferative disorders, myelo fibroses, polycythemias, thrombocythemias, or non-B atypical immune lymphoproliferations, Chronic Lymphocytic Leukemia (CLL), B lymphocyte lineage leukemia, B lymphocyte lineage lymphoma, Multiple Myeloma, or plasma cell disorders, e.g., amyloidosis or Waldenstrom's macroglobulinemia.

In some embodiments, the neoplastic or hematopoietic condition is non-B lineage derived. Examples of non-B lineage derived neoplastic or hematopoietic condition include, but are not limited to, Acute myeloid leukemia (AML), Chronic Myeloid Leukemia (CML), non-B cell Acute lymphocytic leukemia (ALL), non-B cell lymphomas, myelodysplastic disorders, myeloproliferative disorders, myelofibroses, polycythemias, thrombocythemias, and non-B atypical immune lymphoproliferations.

In some embodiments, the neoplastic or hematopoietic condition is a B-Cell or B cell lineage derived disorder. Examples of B-Cell or B cell lineage derived neoplastic or hematopoietic condition include but are not limited to Chronic Lymphocytic Leukemia (CLL), B lymphocyte lineage leukemia, B lymphocyte lineage lymphoma, Multiple Myeloma, and plasma cell disorders, including amyloidosis and Waldenstrom's macroglobulinemia.

Other conditions within the scope of the present invention include, but are not limited to, cancers such as gliomas, lung cancer, colon cancer and prostate cancer. Specific signaling pathway alterations have been described for many cancers, including loss of PTEN and resulting activation of Akt signaling in prostate cancer (Whang Y E. Proc Natl Acad Sci USA Apr. 28, 1998; 95(9):5246-50), increased IGF-1 expression in prostate cancer (Schaefer et al., Science Oct. 9, 1998, 282: 199a), EGFR overexpression and resulting ERK activation in glioma cancer (Thomas C Y. Int J Cancer Mar. 10, 2003; 104(1):19-27), expression of HER2 in breast cancers (Menard et al. Oncogene. Sep. 29, 2003, 22(42): 6570-8), and APC mutation and activated Wnt signaling in colon cancer (Bienz M. Curr Opin Genet Dev 1999 October, 9(5):595-603).

Diseases other than cancer involving altered physiological status are also encompassed by the present invention. For example, it has been shown that diabetes involves underlying signaling changes, namely resistance to insulin and failure to activate downstream signaling through IRS (Burks D J, White M F. Diabetes 2001 February; 50 Suppl 1:S140-5). Similarly, cardiovascular disease has been shown to involve hypertrophy of the cardiac cells involving multiple pathways such as the PKC family (Malhotra A. Mol Cell Biochem 2001 September; 225 (1-):97-107). Inflammatory diseases, such as rheumatoid arthritis, are known to involve the chemokine receptors and disrupted downstream signaling (D'Ambrosio D. J Immunol Methods 2003 February; 273 (1-2):3-13) and are also encompassed herein. Transplant rejection, infections (e.g. viral or bacterial), and vaccines state responses are also encompassed in the invention. Examples of vaccine state responses that can be measured by the methods described herein are described in U.S. provisional application No. 61/327,347 incorporate by reference herein in its entirety for all purposes. The invention is not limited to diseases presently known to involve altered cellular function, but includes diseases subsequently shown to involve physiological alterations or anomalies.

EXAMPLES

Example 1

Single Cell Network Profiling

This Example presents a general protocol that can be used in Single Cell Network Profiling. Subsequent Examples utilize techniques substantially similar to these techniques.

Cell thawing, ficoll density gradient separation, and live/dead staining: Cells are thawed in a 37° C. water bath in cryovials. Once the cells are thawed, 1 mL of pre-warmed thaw buffer (RPMI+60% FBS) is added dropwise to the cryovials and then the entire contents of the cryovials are transferred to a 15 mL conical tube. The volume of each sample is brought up to 12 mL by adding the appropriate volume of thaw buffer. The 15 mL tubes are then capped and inverted 3 times.

A ficoll density gradient separation is then performed by underlaying 2 mL of ambient temperature ficoll using a Pasteur pipette on the samples. Next, the tubes are centrifuged at 400×g for 30 minutes at room temperature, the "buffy coat" aspirated, and the mononuclear cell layer transferred to a new 15 mL conical tube containing 9 mL thaw buffer. The cell layers are centrifuged at 400×g for 5 minutes, the liquid aspirated, the cell pellet gently resuspended. Subsequently, 10 mLs ambient temperature RPMI+ 1% FBS is added to the cell pellets and the cells centrifuged at 400×g for 5 minutes. The cell pellet is resuspended in 1 mL PBS and, if necessary, cell clumps removed by filtering (Celltrics filters) or by pipetting.

1 mL of PBS/Amine Aqua solution is added to the samples, the samples are mixed thoroughly by pipetting, and are incubated in a 37° C. water bath for 15 minutes.

After 15 minute incubation, 1 ml RPMI+10% FBS is added to the samples, a 150 µL aliquot removed from each sample and is placed in a 12×75 mm FACSTube. A cell count is performed on the AcT10 hematology analyzer. 5 mL RPMI+10% FBS are added to the samples, the cells are centrifuged at 400×g for 5 minutes, the liquid is aspirated, and the cells are resuspended at $1.25 \times 10^6$ cells/mL in RPMI+10% FCS. The cells are kept in a 37° C. water bath until ready to array in deep-well plates.

Treatment of Cells with Modulators: A concentration for each modulator (e.g., stimulant) that is five fold (5×) more than the final concentration is prepared using Media A as diluents. The 5× modulators (e.g., stimulants) are arrayed in a standard 96 well v-bottom plate that corresponds to the well on the plate with the cells to be stimulated. Fixative is prepared by dilution of stock 16% paraformaldehyde with PBS to a concentration that is 2.4%, then placed in a 37° C. water bath. Once the plated cells have completed their incubation, the plate(s) are taken out of the incubator and placed in a 37° C. water bath next to the pipette apparatus. Prior to addition of stimulant, each plate of cells is taken from the water bath and gently swirled to resuspend any settled cells. The stimulant is pipetted into the cell plate, which is then held over a vortexer set to "7" and mixed for 5 seconds, and followed by the return of the deep well plate to the water bath. Modulation times can include 5, 10, and 15 minutes in a 37° C. water bath. For longer incubation times, or for assays measuring induced apoptosis, cells are modulated for 6-72 h and restained with Amine Aqua viability dye prior to the fixation steps below.

Fixing Cells and Cell Permeabilzation: Fixation is performed using approximately 2.4% paraformaldehyde (Electron Microscopy Sciences, Hatfield, Pa.) diluted in PBS and is added to cells for a final concentration of 1.6%. The cells are pipetted up and down three times to mix and incubated for 10 minutes at 37° C. Next, the plates are centrifuged at 1000×g for 5 minutes at room temperature, the liquid aspirated from the cell pellets, and cell pellets are resuspended and the cells are permeabilized with 200 µL/well 100% ice cold methanol (SigmaAldrich), is added while vortexing. Cell plates are then covered with a foil seal and stored overnight at −80° C.

Surface and intracellular cell staining: Plates from −80° C. storage are centrifuged at 1000×g for 5 minutes at room temperature, the supernatant is aspirated, and the cell pellet is disrupted by vortexing for 10 seconds and a speed of "3000." Then, the cell pellets are washed two times with 1 mL FACS Buffer (PBS 0.5% BSA, 0.05% NaN3), and are incubated at room temperature at room temperature, centrifuged at 1000×g for 5 minutes at room temperature, supernatant aspirated, and the cell disrupted by vortexing as above.

Next, 20 µL of antibody cocktail is added to each well in the cell plate, the mixture is pipetted up and down 3 times to mix, and the cells are incubated at 25° C. for 1 hr or 4° C. overnight (16 hours). After incubation, cells are washed twice by the same procedure as above.

Subsequently, 10 µl of secondary antibody mix is added the cells, the mixture is pipetted up and down three times to mix, the plate covered, and the cells incubated at 25° C. for 30 minutes. After incubation, cells are washed twice by the same procedure as above.

Cell fixation and preparation for flow cytometry: The cells are then fixed by addition 1 mL of 1.6% PFA, the cells are covered and incubated at room temperature for 5 minutes. The cells are then centrifuged at 1000×g for 5 minutes, the supernatant is aspirated, the cell pellet is disrupted by vortexing as above, the cells are resuspended in 100 µL FACS Buffer, and are mixed by pipetting up and down 4 times. The mixed cells are transferred to a 96-well u-bottom plate and 100 µL of pre-diluted (40 µL into 1 mL of FACS Buffer) Sphero Rainbow 8-peak fluorescent beads to all wells. The plates are sealed with foil and placed at 4° C. in the dark until ready for acquisition on the flow cytometer.

Example 2

Analysis of AML Patients

Patient samples: Sets of fresh or cryopreserved samples from patients can be analyzed. The sets can consist of peripheral blood mononuclear cell (PBMC) samples or bone marrow mononuclear cell (BMMC) samples derived from the blood of AML patients. All patients will be asked for consent for the collection and use of their samples for institutional review board (IRB)-approved research purposes. All clinical data is de-identified in compliance with Health Insurance Portability and Accountability Act (HIPAA) regulations. Sample inclusion criteria can require collection at a time point prior to initiation of induction chemotherapy, AML classification by the French-American-British (FAB) criteria as M0 through M7 (excluding M3), and availability of appropriate clinical annotations (e.g., disease response after one or two cycles of induction chemotherapy). Induction chemotherapy can consist of at least one cycle of standard cytarabine-based induction therapy (i.e., daunorubicin 60 mg/m2×3 days, cytarabine 100-200 mg/m2 continuous infusion×7 days); responses are measured after one cycle of induction therapy. Standard clinical and laboratory criteria can be used for defining complete responders (CR) in the patient samples. Leukemia samples obtained from patients who do not meet the criteria for CR or samples obtained from those who died during induction therapy are considered non-complete response (NR) for the primary analyses.

Cell network profiling assays: Cell network profiling assays involved measuring the expression of protein levels and their post-translational modification by phosphorylation in different populations of cells at baseline and after perturbation with various modulators. The populations that can be analyzed include myeloid leukemic cells, B cells, T cells, dendritic cells, monocytes, macrophages, neutrophils, eosinophils, and basophils. Other cells such as epithelial cells can also be analyzed.

A pathway "node" is defined as a combination of a specific proteomic readout in the presence or absence of a specific modulator. Levels of signaling proteins, as well as expression of cell surface markers (including cell lineage markers, membrane receptors and drug transporters), are detected by multiparameter flow cytometry using fluorochrome-conjugated antibodies to the target proteins. Multiple nodes (including surface receptors and transporters), using multiple modulators can be assessed in the two studies.

A minimum yield of 100,000 viable cells and 500 cells per gated sample in gate of interest can be used for each patient sample to be classified as evaluable.

Cyropreserved samples are thawed at 37° C., washed, and centrifuged in PBS, 10% FBS, and 2 mM EDTA. The cells are resuspended, filtered, and are washed in RPMI cell culture media, 1% FBS, then are stained with Live/Dead Fixable Aqua Viability Dye (Invitrogen, Carlsbad, Calif.) to distinguish non-viable cells. The viable cells are resuspended in RPMI, 1% FBS, aliquoted to 100,000 cells/condition, and are rested for 1-2 hours at 37° C. prior to cell-based functional assays or staining for phenotypic markers. Each condition can include 2 to 5 phenotypic markers (e.g., CD45, CD33), up to 3 intracellular stains, or up to 3 additional surface markers.

Cells are incubated with modulators, at 37° C. for 3-15 minutes, then fixed with 1.6% paraformaldehyde (final concentration) for 10 minutes at 37° C., pelleted, and permeabilized with 100% ice-cold methanol and stored at −20° C. For functional apoptosis assays, cells are incubated for 24 hours with cytotoxic drugs (i.e. Etoposide or Ara-C and daunorubicin), then re-stained with Live/Dead Fixable Aqua Viability Dye to distinguish non-viable cells before fixation and permeabilization, washed with FACS Buffer (PBS, 0.5% BSA, 0.05% NaN3), pelleted, and stained with fluorescent dye-conjugated antibodies (Becton Dickenson-Pharmingen, San Diego, Calif.) to both surface antigens (CD33, CD45) and the signaling protein targets.

Data acquisition and cytometry analysis: Data is acquired using FACS DIVA software on both LSR II and CANTO II Flow Cytometers (BD). For all analyses, dead cells and debris are excluded by FSC (forward scatter), SSC (side scatter), and Amine Aqua Viability Dye measurement. Leukemic cells are identified as cells that lacked the characteristics of mature lymphocytes (CD45++, CD33−), and that fit the CD45 and CD33 versus right-angle light-scatter characteristics consistent with myeloid leukemia cells. Other cell populations are identified using markers known in the art.

Statistical Analysis and Stratifying Node Selection a) Metrics:

The median fluorescence intensity (MFI) is computed for each node from the intensity levels for the cells in the gate of interest. The MFI values are then used to compute a variety of metrics by comparing them to the various baseline or background values, i.e. the unstimulated condition, autofluorescence, and isotype control. The following metricscan be computed in these studies: (1) Basal MFI=log 2(MFI-Unmodulated Stained)−log 2(MFIGated Unstained (Autofluoresence)), designed to measure the basal levels of a certain protein under unmodulated conditions; (2) Fold Change MFI=log 2(MFIModulated Stained)−log 2(MFIUnmodulated Stained), a measure of the change in the activation state of a protein under modulated conditions; (3) Total Phospho MFI=log 2(MFIModulated Stained)−log 2(MFI-Gated Unstained (Autofluorescence)), a measure of the total levels of a protein under modulated conditions; (4) Fold over Control MFI=log 2(MFIStain)−log 2(MFIControl), a measure of the levels of surface marker staining relative to control antibody staining; (5) Percent Cell Positivity=a measure of the frequency of cells that have surface markers staining at an intensity level greater than the 95th percentile for control antibody staining An additional metric is designed to measure the levels of cellular apoptosis in response to cytotoxic drugs: (6) Quadrant=a measure of the percentage of cells expressing high levels of apoptosis molecules (e.g. cleaved PARP and low levels of p-Chk2).

A low signaling node is defined as a node having a fold change metric or total phosphoprotein signal equal to I log 2(Fold) I>0.15. However, it is not necessary to use this as an exclusion criterion in this study.

b) Reproducibility Analysis

Two or more cryopreserved vials or fresh samples for each evaluable patient sample are obtained. All the vials are processessed separately to access the assay reproducibility. Pearson and Spearman rank correlations were computed for each node/metric combination between the two data sets.

c) Univariate Analysis

All cell population/node/metric combinations are analyzed and compared across samples for their ability to distinguish between CR and NR samples. For each cell population/node/metric combination student t-test and Wilcoxon test p-Values are computed. In addition, the area under the receiver operator characteristic (ROC) (Hanley and McNeil, Radiology, 1982, Hanley and McNeil, Radiology, 1983, Bewick, et al, Critical Care, 2004) curve is also computed to access the diagnostic accuracy of each node for a given metric. The sensitivity (proportion of patients for whom a CR is correctly identified) and specificity (proportion of patients for whom a NR is correctly identified) data are plotted as ROC curves. A random result would produce an AUC value of 0.5. A (bio)marker with 100% specificity and selectivity would result in an AUC of 1.0. The cell population/node/metric combinations are independently tested for differences between patient samples whose response to standard induction therapy was CR vs NR. No corrections are applied to the p-values to correct for multiple testing. Instead, simulations are performed by randomly permuting the clinical variable to estimate the number of cell population/node/metric combinations that might appear to be significant by chance. For each permutation, nine donors are randomly chosen (without replacement) and assigned to the CR category and the remaining are assigned to the NR category. By comparing each cell population/node/metric combination to the permuted clinical variable, the student t-test p-values are computed. This process is repeated. The results from these simulations are then used to estimate the number of cell population/node/metric combinations that are expected to be significant by chance at the various p-values and compared with the empirical p-values for the number of cell population/node/metric combinations that were found to be significant from the real data.

The statistical analyses can be performed with the statistical software package R, version 2.7.0.

d) Correlations Between Node:

Correlations between all pairs of cell population/node/metric combinations are accessed by computing Pearson and Spearman rank correlation.

e) Combinations of Nodes

Nodes that can potentially complement each other in combination to improve the accuracy of prediction of response to therapy are also explored. With a small size of the data set, a straightforward "corner classifier" approach for picking combinations can be adopted. Combinations that seem promising are also tested for their stability via a bootstrapping approach described below.

The corners classifier is a rules-based algorithm for dividing subjects into two classes (in this case the dichotomized response to induction therapy) using one or more numeric variables (defined in our study as a node/metric combination). This method works by setting a threshold on each variable, and then combining the resulting intervals (e.g., X<10, or Y>50) with the conjunction (and) operator (reference). This creates a rectangular region that is expected to hold most members of the class previously identified as the target (in this study CR or NR samples). Threshold values are chosen by minimizing an error criterion based on the logit-transformed misclassification rate within each class. The method assumes only that the two classes (i.e. response or lack of response to induction therapy) tend to have different locations along the variables used, and is invariant under monotone transformations of those variables.

A bagging, also known as bootstrapped aggregation, is used i to internally cross-validate the results of the above statistical model. Bootstrap re-samples are drawn from the original data. Each classifier, i.e. combination of cell population/node/metric, is fit to the resample, and then used to predict the class membership of those patients who were excluded from the resample. After repeating the re-sampling operation sufficiently, each patient acquires a list of predicted class memberships based on classifiers that are fit using other patients. Each patient's list is reduced to the fraction of target class predictions; members of the target class should have fractions near 1, unlike members of the other class. The set of such fractions, along with the patient's true class membership, is used to create an ROC curve and to calculate its AUC.

Example 3

Analysis of Rheumatoid Arthritis Patients

Patient samples: Sets of fresh or cryopreserved samples from patients can be analyzed. The sets can consist of cells samples derived from the lymph nodes, synovium and/or synovial fluid of rheumatoid patients. All patients will be asked for consent for the collection and use of their samples for institutional review board (IRB)-approved research purposes. All clinical data is de-identified in compliance with Health Insurance Portability and Accountability Act (HIPAA) regulations.

Sample inclusion criteria can include: (i) A diagnosis of rheumatoid arthritis by the 1987 ACR criteria, (ii) Definite bony erosions, (iii) Age of disease onset greater than 18 years. (iv) Patient does not have psoriasis, inflammatory bowel disease, or systemic lupus erythematosus.

Standard clinical and laboratory criteria can be used for defining RA patients that are able to respond to a treatment in the patient samples. RA samples obtained from patients who do not meet the criteria for patients that are able to respond are considered non-complete responders for the primary analyses. Examples of possible treatments include nonsteroidal antiinflammatory drugs (NSAIDs) such as Acetylsalicylate (aspirin), naproxen (Naprosyn), ibuprofen (Advil, Medipren, Motrin), and etodolac (Lodine); Corticosteroid; Hydroxychloroquine; Sulfasalazine (Azulfidine); Gold salts such as Gold thioglucose (Solganal), gold thiomalate (Myochrysine), and auranofin (Ridaura); D-penicillamine (Depen, Cuprimine); Immunosuppressive medicines such as methotrexate (Rheumatrex, Trexall), azathioprine (Imuran), cyclophosphamide (Cytoxan), chlorambucil (Leukeran), and cyclosporine (Sandimmune).

Populations of cells that can be analyzed using the methods described in Example 1 include B cells, T cells, dendritic cells, monocytes, macrophages, neutrophils, eosinophils, and basophils. Other cells such as mesechymal cells and epithelial cells can also be analyzed.

Example 4

Cellular and Intracellular Network Characterization of Cytokine JAK/STAT Signaling in Whole Blood Across Multiple Healthy Individuals: Defining "Normal"

Aberrant JAK/STAT signaling in hematopoietic cells has shown to be involved in certain hematological and immune diseases; thus, the regulation of JAK/STAT signaling is an important research area. Signaling pathway- and cell type-specific responses to various cytokines in the immune system signaling network can elicit a wide range of biological outcomes due to the combinatorial use of a limited set of kinases and STAT proteins. Although advances have been made in uncovering the intracellular mechanisms relating to cytokine signaling, the biological outcome may vary depending on composition and activation state of the cellular network. Single Cell Network Profiling (SCNP) by flow cytometry allows the interrogation of intracellular signaling networks within a heterogeneous cellular network, such as in unfractionated whole blood. We applied SCNP to investigate cytokine-induced JAK/STAT signaling in whole blood across healthy human donors (n=11) to 1) measure the relative contribution of signaling across multiple cell subsets; 2) measure the kinetics of signaling activation and resolution across cytokines and cell subsets; 3) measure the variation among donors in their overall signaling characteristics. Our aim was to better characterize "normal" cytokine responses across healthy individuals as a basis to eventually describe abnormal states.

Method: Whole blood from 11 healthy donors (20-65 yrs, 7 males, 4 females, 8 Caucasians, 2 Hispanics, 1 East Asian) was stimulated at 37° C. in 96-well plates with a low, medium, and high dose of GM-CSF, IFN-α, IL-27 and IL-6, each added separately, as described in Example 5. For each dose, a stimulation time course was run with 6 time points between 3 and 45 minutes. Each well had a final concentration of 90% whole blood. The SCNP assay was performed using a fluorophore-labeled antibody cocktail to simultaneously measure signaling in six distinct cell populations, including: neutrophils, CD20+ B cells, CD3+CD4+T cells, CD3+CD4− T cells (CD8 enriched), CD3-CD20-lymphocytes (NK cell enriched), and CD14+ monocytes. The median fluorescent intensity of phospho (p)-STAT1(Y701), p-STAT3(Y705), and p-STAT5(Y694) were measured in each defined cell population for each experimental condition.

Results: This SCNP assay was relatively high-throughput and provided high-content data, that equates to 19,000 gel lanes if attempted by Western analysis (11 donors×4 cytokines×4 concentrations×6 time points×6 cell subsets×3 p-readouts). In general, each cytokine demonstrated unique dose-dependent signaling characteristics (e.g., activation/termination kinetics, magnitude of response) for each cell type analyzed, and in some cases, the kinetics differed between p-STAT readouts within the same cell subset for the same cytokine. For instance, IL-6 induced signaling was only observed in CD4+ T cells and monocytes with peak p-STAT3 levels at 3 minutes followed by p-STAT1 and p-STAT5 at 10-15 minutes. In addition, signal resolution fell to baseline levels at 45 minutes in monocytes, while the CD4+ T cells showed sustained elevated signaling, suggesting a cell-type specific regulation. In contrast to IL-6, IFN-□□ stimulation activated all 3 STAT proteins, peaking at 10 minutes with similar kinetics in all cell subsets. However, IFN-□□ signaling resolution was faster and almost complete at 45 minutes in monocytes, while in the all other subsets the signal was sustained. This efficient signal termination in monocytes was also observed with GM-CSF→p-STAT5, while neutrophils maintained persistent p-STAT5 levels. IL-27 induced p-STAT1 and p-STAT3 in T cell subsets, B cells, and monocytes with peak activation at 30 minutes. In general, signaling characteristics were remarkably uniform across the healthy donors. IL-6→p-STAT3 was particularly consistent across time points and ligand concentrations, while p-STAT1 and p-STAT5 showed more variation. More results are provided in Example 5.

Approaching cell signaling from the perspective of the cellular network under physiological conditions (whole blood) allows for a more comprehensive and clinically relevant view of the signaling state of complex tissues. As many JAK/STAT targeting small molecule compounds enter the clinic, this study provides an important reference point for comparison with signaling networks that have become altered either by the pathological disease state or by therapy.

Example 5

Single Cell Network Profiling (SCNP) of IFN-α Signaling Pathways in Peripheral Blood Mononuclear Cells from Healthy Donors: Implications for Disease Characterization, Treatment Selection, and Drug Discovery The antiviral and antitumor effects of IFN-α, have been exploited for the treatment of viral infections such as hepatitis C (HCV) as well as for various malignancies, such as hairy cell leukemia and melanoma. However, widespread use of IFN-α for these and other indications is severely hampered by significant side effects which can have a major impact on patient quality of life. Thus, a greater understanding of intracellular signaling pathways regulated by IFN-α may guide in the selection of patients whose disease will have an optimal response with tolerable side effects to this cytokine. Specifically, the Signal Transducer and Activation of Transcription (Stat) transcription factors are known to play a critical role in transducing IFN-α mediated signals. Single cell network profiling (SCNP) is a multiparameter flow-cytometry based approach that can be used to simultaneously measure extracellular surface makers and intracellular signaling proteins in individual cells in response to externally added modulators. Here, we use SCNP to interrogate IFN-α signaling pathways in multiple cell subsets within peripheral blood mononuclear cells (PBMCs) from healthy donors.

This study was designed to apply SCNP to generate a map of IFN-□-mediated signaling responses, with emphasis on Stat proteins, in PBMCs from healthy donors. The data provides a reference for future studies using PBMCs from patient samples in which IFN□□-mediated signaling is aberrantly regulated.

Methods: IFN-α-mediated signaling responses were measured by SCNP in PBMC samples from 12 healthy donors. PBMCs were processed for flow cytometry by fixation and permeabilization followed by incubation with fluorochrome-conjugated antibodies that recognize extracellular lineage markers and intracellular signaling molecules. The levels of several phospho-proteins (p-Stat1, p-Stat3, p-Stat4, p-Stat5, p-Stat6, and p-p38) were measured in multiple cell populations (CD14+ monocytes, CD20+ B cells, CD4+ CD3+ T cells, and CD4− CD3+ T cells) at 15 minutes, 1, 2 and 4 hours post IFN-α exposure as described in Example 6.

Results: The data revealed distinct phospho-protein activation patterns in different cell subsets within PBMCs in response to IFN-α exposure. For example, activation of p-Stat4 was detected in T cell subsets (both CD4+ and CD4− T cells), but not in monocytes or B cells. Such cell-type specific activation patterns likely play a key role in mediating specific functions within different cell types in response to IFN-α. Differences in the kinetics of activation by IFN-α for different phospho-proteins were also observed. The peak response for activation of p-Stat1, p-Stat3, and p-Stat5 was at 15 minutes in most of the cell types interrogated in this study, whereas for the activation of p-Stat4, p-Stat6, and p-p38 it was at 1 hr in the majority of cell types tested. The relationships between phospho-protein readouts in each cell subset were determined by calculating the Pearson correlation coefficients. For example, the activation of p-Stat1 and p-Stat5 at 15 minutes was positively correlated in both B cells and T cells. More results are provided in Example 6.

The activation of intracellular signaling proteins was measured with emphasis on Stat transcription factors in PBMC subsets from healthy donors. We have analyzed the relationships between the activation states of phospho-proteins in the IFN-α signaling network. Characterization of IFN-α signaling pathways in samples from healthy donors has provided a network map that can be used as a reference for identifying alterations in IFN-α signaling that are the consequence of disease and/or therapeutic intervention. Future studies using SCNP to characterize IFN-α signaling pathways in PBMCs from patients with diseases such as viral infections or cancer may enable the optimization of IFN-α dosing and the identification of patient stratification biomarkers as well as the discovery of novel therapeutic agents.

Example 6

Normal Cell Response to Erythropoietin (EPO) and Granulocyte Colony Stimulating Factor (G-CSF)

Normal cell signaling response to EPO and G-CSF was characterized through comparison to signaling response observed in samples from a subclass of patients with myelodysplastic syndrome (MDS) referred to herein as "low risk" patients. 15 samples of healthy BMMCs (from patients with no known diagnosis of disease) and 14 samples of BMMCs from patients who belonged to a subclass of patients with myelodysplastic syndrome were used to characterize normal cell response. The 14 samples of low risk patients were obtained from MD Anderson Cancer Center in Texas. The low risk patients were diagnosed as per standard of care at MD Anderson Cancer Center. The 15 samples of healthy BMMCs were obtained through Williamson Medical Center and from a commercial source (AllCells, Emeryville, Calif.). The samples obtained through Williamson Medical Center were collected with informed consent from patients undergoing surgeries such as knee or hip replacements.

Each of the normal and the low risk samples were separated in aliquots. The aliquots were treated with a 3

IU/ml concentration of Erythropoietin, a 50 ng/ml concentration of G-CSF and both a 3 IU/ml concentration of Erythropoietin and a 50 ng/ml concentration of G-CSF. Activation levels of pStat1, pStat3 and pStat5 were measured using flow cytometry at 15 minutes after treatment with the modulators. In addition to the Stat proteins measured, several other elements were measured in order to separate the cells into discrete populations according to cell type. These markers included CD45, CD34, CD71 and CD235ab. CD45 was used to segregate Lymphocytes, Myeloid(p1) cells and nRBCs. The nRBCs were further segregated into 4 distinct cell populations based on expression of CD71 and CD235ab: m1, m2, m3 and m4. These cell populations correspond to RBC maturity and are illustrated in FIG. 2.

Distinct signaling responses were observed in the different discrete cell populations. FIG. 2 of U.S. Ser. No. 12/877,998 illustrates the different activation levels of pStat1, pStat3 and pStat5 observed in EPO, G-CSF and EPO+G-CSF treated Lymphocytes, nRBC1 cells, Myeloid (p1) cells and stem cells. Activation levels observed in different samples from the normal and low risk populations are plotted as dots. As shown in FIG. 2, different cell discrete populations demonstrated different induced activation levels. Although this was true in both the healthy and the low risk patients, the different discrete cell populations exhibited a narrower range of induced activation levels in then normal samples than in the low risk samples. These observations accord with the common understanding that diseased cells exhibit a wider range of different signaling phenotypes than normal cells.

Additionally, cell differentiation in disease may be inhibited or stunted, causing cells to exhibit characteristics that are different from other cells of the same type.

Example 7

Normal Cell Response to Varying Concentrations of GM-CSF, IL-27, IFN☐ and IL-6

Kinetic response to varying concentrations of modulators was investigated in normal samples (i.e. samples from persons who have no diagnosis of disease). 11 normal samples were donated with informed consent by Nodality Inc. employees and processed at Nodality Inc. in South San Francisco, Calif. The samples were treated with 4 different modulators (GM-CSF, IL-27, IFN☐ and IL-6) at 4 different concentrations of the modulator and activation levels of pStat1, pStat3 and pStat5 were measured at different time points. Activation levels were measured at 3, 5, 10, 15, 30 and 45 minutes using flow cytometry-based single cell network profiling. The concentrations of the stimulators are tabulated below:

TABLE 2

Stimulator Concentrations

| | low | med | hi |
|---|---|---|---|
| GM-CSF | 0.1 ng/ml | 1 ng/ml | 10 ng/ml |
| IL-27 | 1 ng/ml | 10 ng/ml | 100 ng/ml |
| IFNα | 1000 IU | 4000 IU | 100000 IU |
| IL-6 | 1 ng/ml | 10 ng/ml | 100/ml |

Activation levels of different cell surface markers were also profiled using single cell network profiling and used in conjunction with gating to segregate the cells into discrete cell populations. In the gating analysis, SSC-A and FSC-A were first used to segregate lymphocytes from non-lymphocytes. CD14 and CD4 were then used to segregate the non-lymphocytes into populations of neutrophils and CD14+ cells (monocytes). CD3 and CD20 were then used to segregate the lymphocytes into populations of CD20+ (B Cells), CD3+ (T Cells) and CD20-CD3-cells. CD4 was used to segregate the CD3+ T cells into populations of CD3+ CD4– and CD3+CD4+ T cells.

FIG. 3 of U.S. Ser. No. 12/877,998 illustrates the kinetic responses of different discrete cell populations in the normal samples. The line graphs contained in FIG. 3 of U.S. Ser. No. 12/877,998 plot the activation levels observed in all of the donors over the time intervals at which they were measured. The different concentrations of IL-6 tabulated above are represented by solid and dashed lines. Generally, the normal samples demonstrated similar activation profiles over time according to the concentration of sample given. Different concentrations of the modulator IL-6 yielded dramatically different activation profiles for some of the Stat phosphoproteins measured. For example, IL-6-induced pStat3 response varied at early time points (5-15 minutes) for the different concentrations of IL-6 but became more uniform at later time points. This uniformity of response supports the idea that normal cells exhibit a narrow range of activation.

Different discrete cell populations demonstrated unique responses to modulation. The neutrophils exhibited very low IL-6 induced activation as compared to the CD4+ T cells and monocytes. Between the CD4+ T cells and monocytes, several differences in activation profiles were observed. Monocytes showed a peak activation of IL-6-induced pStat1 activity at a different time point than the CD4+ T cells. Although both the monocytes and the CD4+ T cells demonstrated a drop-off in pStat3 activity after 15 minutes, the drop-off was much more dramatic in the monocytes. The difference in the slopes is illustrated in FIG. 3 of U.S. Ser. No. 12/877,998 by the use of boxes. This observation confirms the utility of using additional metrics which describe the dynamic response such as 'slope' and liner equations to represent dynamic response to induced activation.

Example 8

PBMC without Subset Isolation

The present example analyzes PBMC without subset isolation, enabling the analysis of cell-cell communication in response to modulator (triple SAg=SEA+SEB+TSST, or LPS).

The results were consistent with intercellular communication in response to modulator, including negative feedback loops. In monocytes, signaling increased from 45 minutes to 2 hours, then a down-regulation of this signaling (p38, pERK, pS6). We see B and CD4+/– T lymphocyte signaling coming up at 6 hours to 24 hours, presumably in response to the production and release of cytokines from the monocytes. We see evidence of NFκB pathway down-regulation at 24 hours in the B cells.

The present example was conducted in a manner similar to that shown in the above examples and the disclosure related to the process details of the general method. PMBCs from normal healthy patients (CON 402 and CON 403) were collected and cryopreserved. PMBCs were thawed and 100,000 cells were placed in wells of microplates. The cells rested for 2 hours at 370 C. SEA, SEB and TSST-1 (in 1:1:1 combination at 0.02, 0.1, 0.5, 2.5 ug/mL) (there were 4 concentrations, but only 3 constituents) were added to the PBMCs and the mixture was incubated at 370 C for 45 minutes, 2 hours, 6 hours and 24 hours. An LPS control was included (1 ug/mL) and pZap70 is added as an IC readout. The cells were fixed and permeabilized following standard procedures and the cells were processed, stained and acquired using a flow cytometer as shown above.

The following cells were analyzed: CD4+ T cells, CD4− T cells, B cells, monocytes (CD4/CD20, CD3, CD14). The following intracellular signaling cocktails to detect intracellular activatable elements were used (labeled antibodies to the following intracellular activatable elements, or readouts): Cocktail #1: p-Lck, p-Zap70, p-NFκB p105; Cocktail #2: pS6, pERK, p-p38; Cocktail #3: p-Src, CD25, pAKT; and Cocktail #4: IkB, CD27, pIKK.

Generally, the triple SAg-induced signaling is detectable predominantly in monocytes at 45 minutes and 2 hours, with lymphocyte signaling detectable across intracellular readouts at 6 and 24 hours. B cell signaling is greater than T cell signaling in breadth of activated elements, population shift (Uu metric) and magnitude (Log 2Fold). T cell subsets show no consistent IkB signaling, in contrast with B cells which show IkB degradation at 6 hours and stabilization at 24 hours. Dose-dependent triple SAg-modulated signaling is more evident below 6 hours and not evident at 24 hours. There is evidence for down-regulation of monocyte signaling at 6 and 24 hours. Also, there is evidence of IkB stabilization and decreased pERK. We also saw some donor variation in signaling with CON402 (32 year old male) greater than that of CON 403 (33 year old female).

Figure 4:
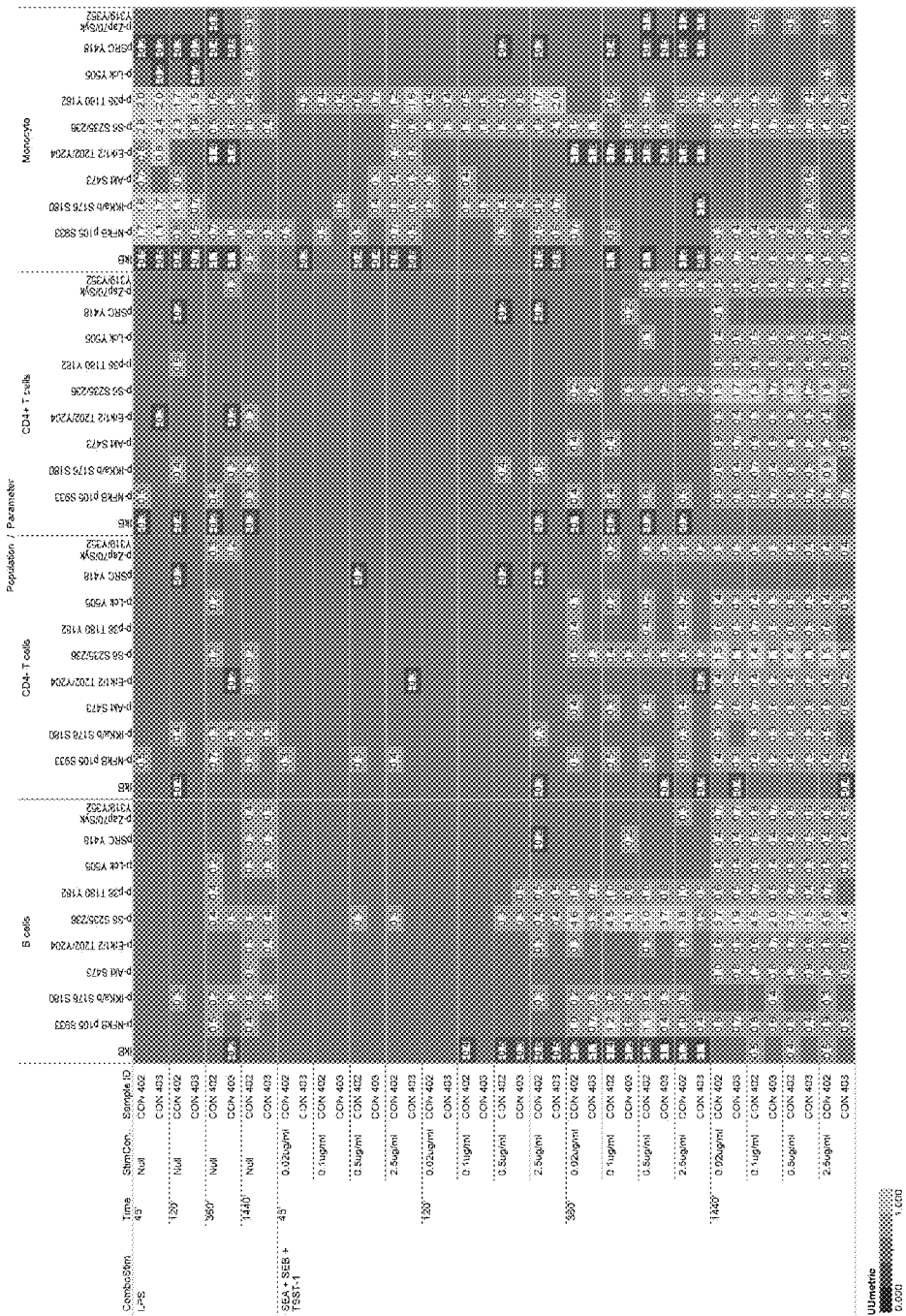
FIG. 4 shows a five shade heat map for the full data set for one set of experiments described in Example 8.

FIG. 4 shows the full data set in a 5 shade heat map.

Figure 5:
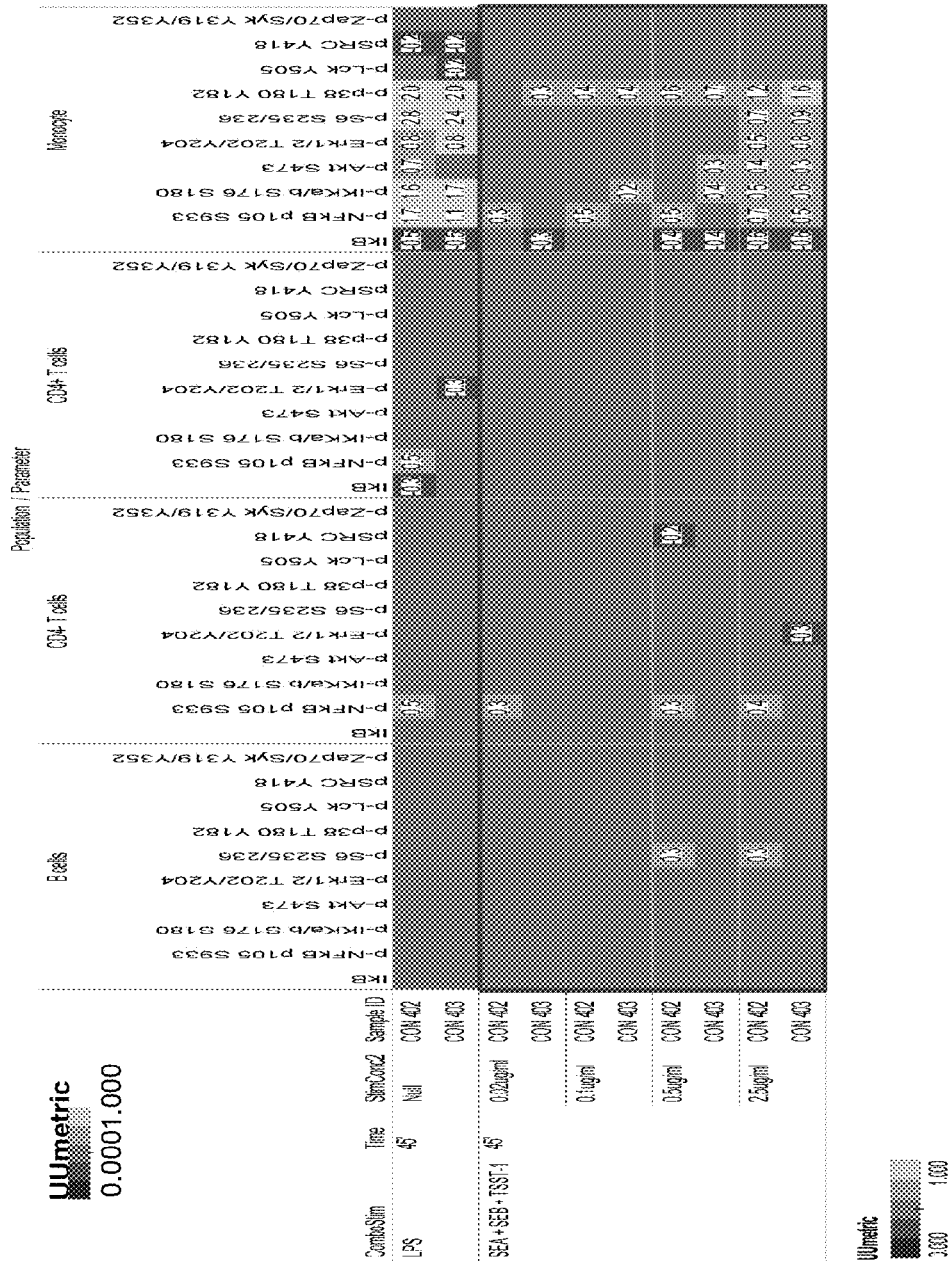
FIG. 5 shows a five shade heat map for signaling at 45 minutes in monocytes.

FIGS. 4 and 5 shows that intracellular signaling in response to modulator at 45 minutes was predominantly in monocytes. This was true in both SAg- and LPS-modulated samples. In SAg-modulated samples, there was signaling across all intracellular readouts tested except pLck, pSrc, pZAP-70 and some dose-dependence. B cell signaling in pS6 in CON 402 was dose-dependent. CD4− T cell signaling in pNFκB p105 in CON 402 was dose-dependent.

Figure 6:
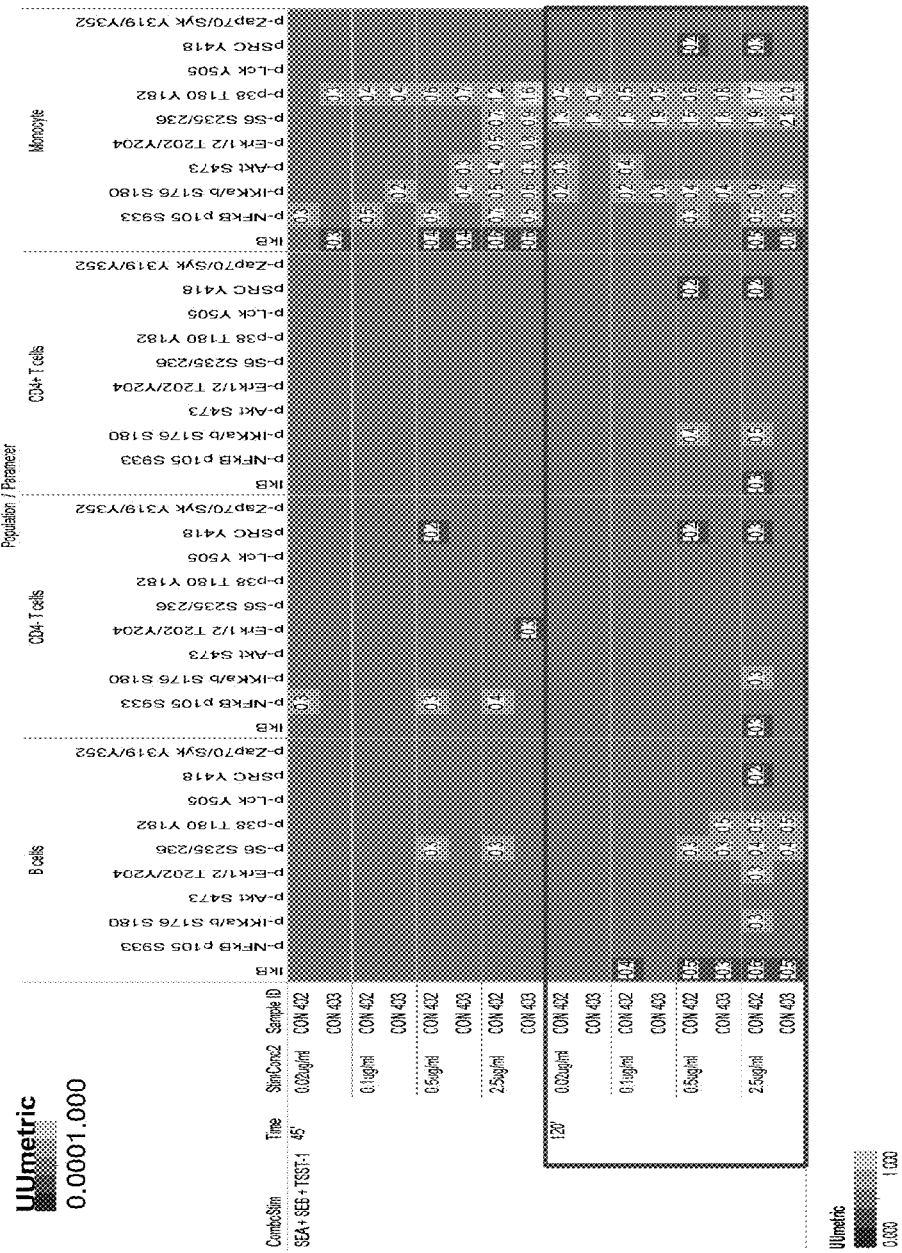
FIG. 6 shows a five shade heat map for signaling at 2 hours for B and T cells.

FIGS. 4 and 6 shows signaling at 2 hours includes B and T cell intracellular readouts. Monocytes remained the predominant signaling population at 2 hours. B cell signaling was detectable through IkB, pS6 and p38; both donors, with dose-dependence. In CON 402 only—pERK, pIKK showed dose-dependence. CD4+/− T cell signaling through IkB, pIKK, in CON 402 was dose-dependent. There was down-regulation of pSrc in all subsets for CON402, with dose-dependence.

Figure 7:
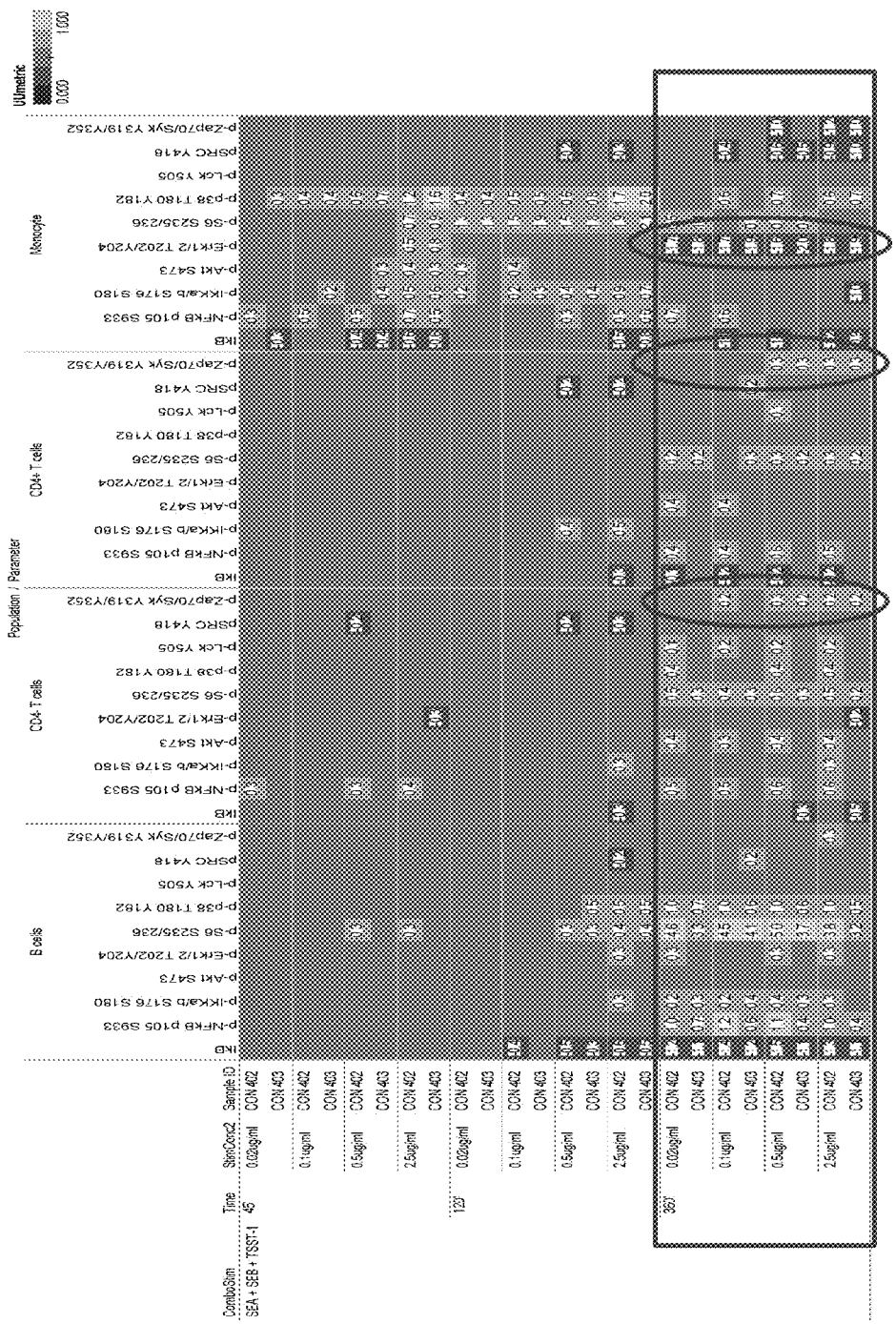
FIG. 7 shows a five shade heat map that indicates that lymphocyte signaling is activated at 6 hours.

FIGS. 4 and 7 show Lymphocyte signaling was activated at 6 Hours. Monocytes show that pERK is down-regulated in both donors at all doses, and P38 and pS6 signaling reduced from 6 hours. B cell signaling was increased across intracellular readouts, in both donors at all concentrations. Signaling was greater in T cells for IkB, pNFκB p105 (high), pIKK, pS6 (very high), and p38. There was dose-dependent T cell signaling through ZAP-70 (positive control) in both donors. pS6 was also detected in both subpopulations at all concentrations. CD4− T cell signaling increased across intracellular readouts. In CON 402 only—pNFκB p105, pIKK (dose-dependent) pAKT, p38, and pLck, In CON 403 only there was IkB dose-dependent signaling, and pERK down-regulation which was dose-dependent. CD4+ T cell signaling was increased across intracellular readouts. In CON 402 only—IkB, pNFκB p105, pAKT showed inverse dose-dependence.

Figure 8:
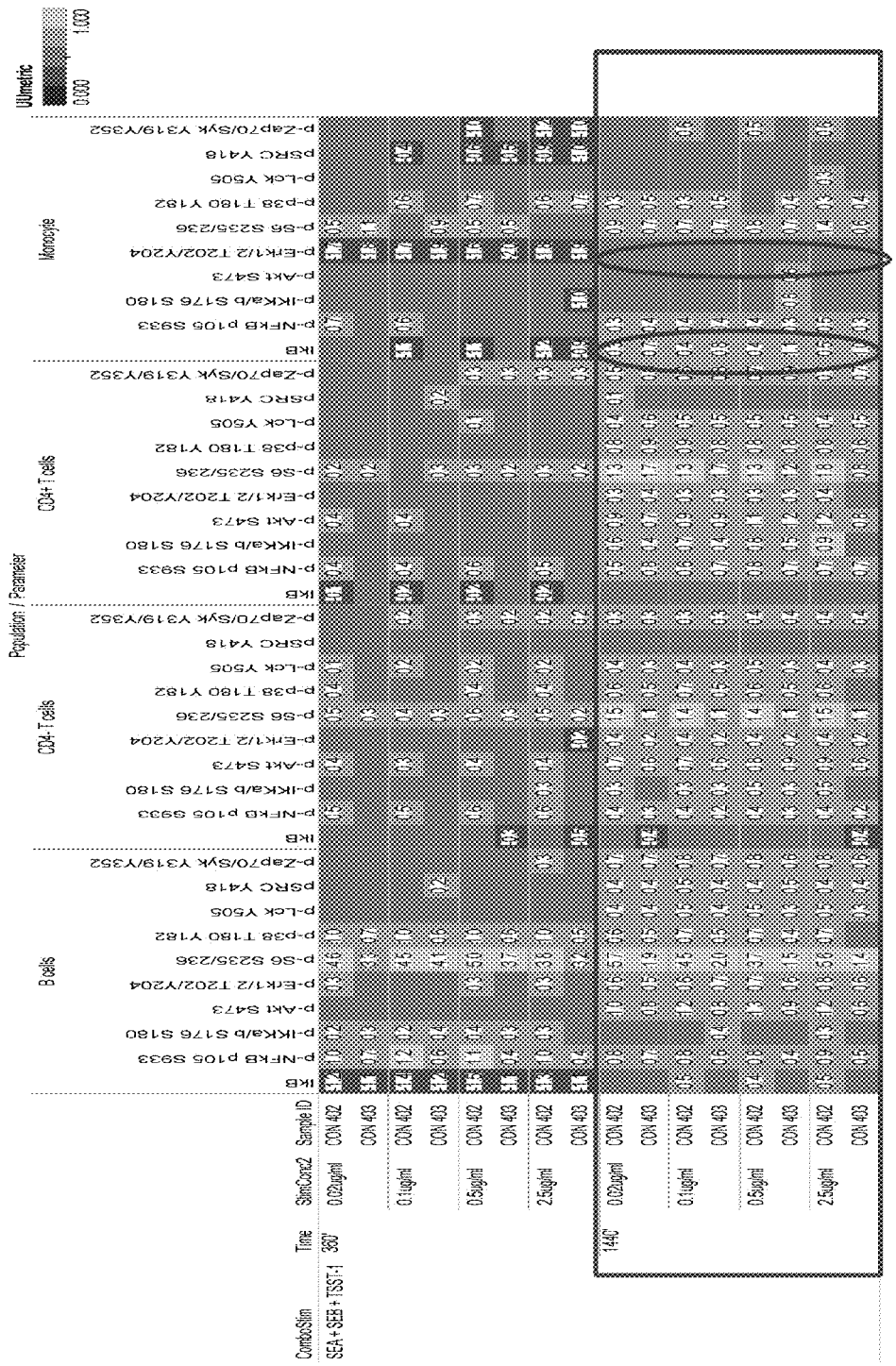
FIG. 8 shows a five shade heat map for 24 hour signaling in B cells, T cells, and monocytes, and indicates negative feedback on monocytes and high B cell proliferation/survival signaling.

FIGS. 4 and 8 show that 24 hour signaling suggests negative feedback on monocytes and high B cell proliferation/survival signaling. Monocytes show IkB induction (switching pathway off) and pNFκB p105 induction, but lacking pIKK. pERK was not induced and it returned to its basal state. Monocytes lacked pAKT, pERK induction, contrasting with lymphocytes. B cell signaling was seen in both donors (no dose-dependence) detectable through: pNFκB p105, pAKT, pERK, pS6 (high), p38, pLck, pSYK, pSrc, pSYK. In CON 402 only—IkB stabilization (switch pathway off). T cell signaling in both donors (no dose-dependence) was detectable through pNFκB p105, pIKK, pAKT, pERK, pS6 (high) p38, pLck, and pZAP70, but there was no consistent IkB modulation.

Figure 9:
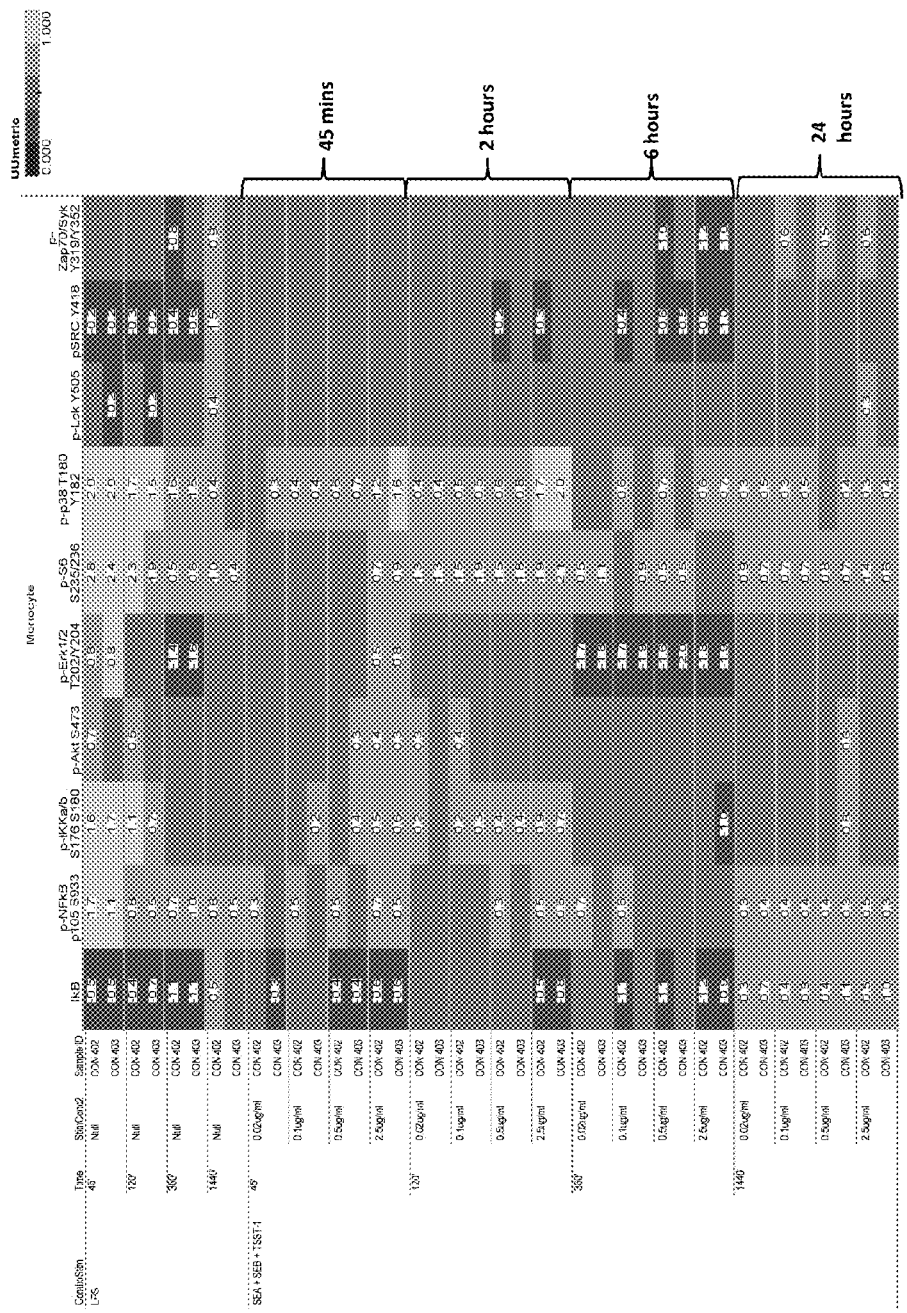
FIG. 9 shows a five shade heat map indicating monocyte signaling is detectable from 45 minutes and is downregulated thereafter. 45 mins: Signaling cross all nodes except pLCK, pSRC, pZAP. 6 hours: Evidence for down-regulation of signaling: pERK down-regulated in both donors at all doses; P38 and pS6 signaling reduced 24 hours: Additional evidence for down-regulation of signaling: Negative feedback regulation of pERK and IkB Lack pAKT, pERK induction, contrasting with lymphocytes. LPS (positive control, 1 ug/mL) stimulation induces monocyte signaling as predicted
Figure 10:
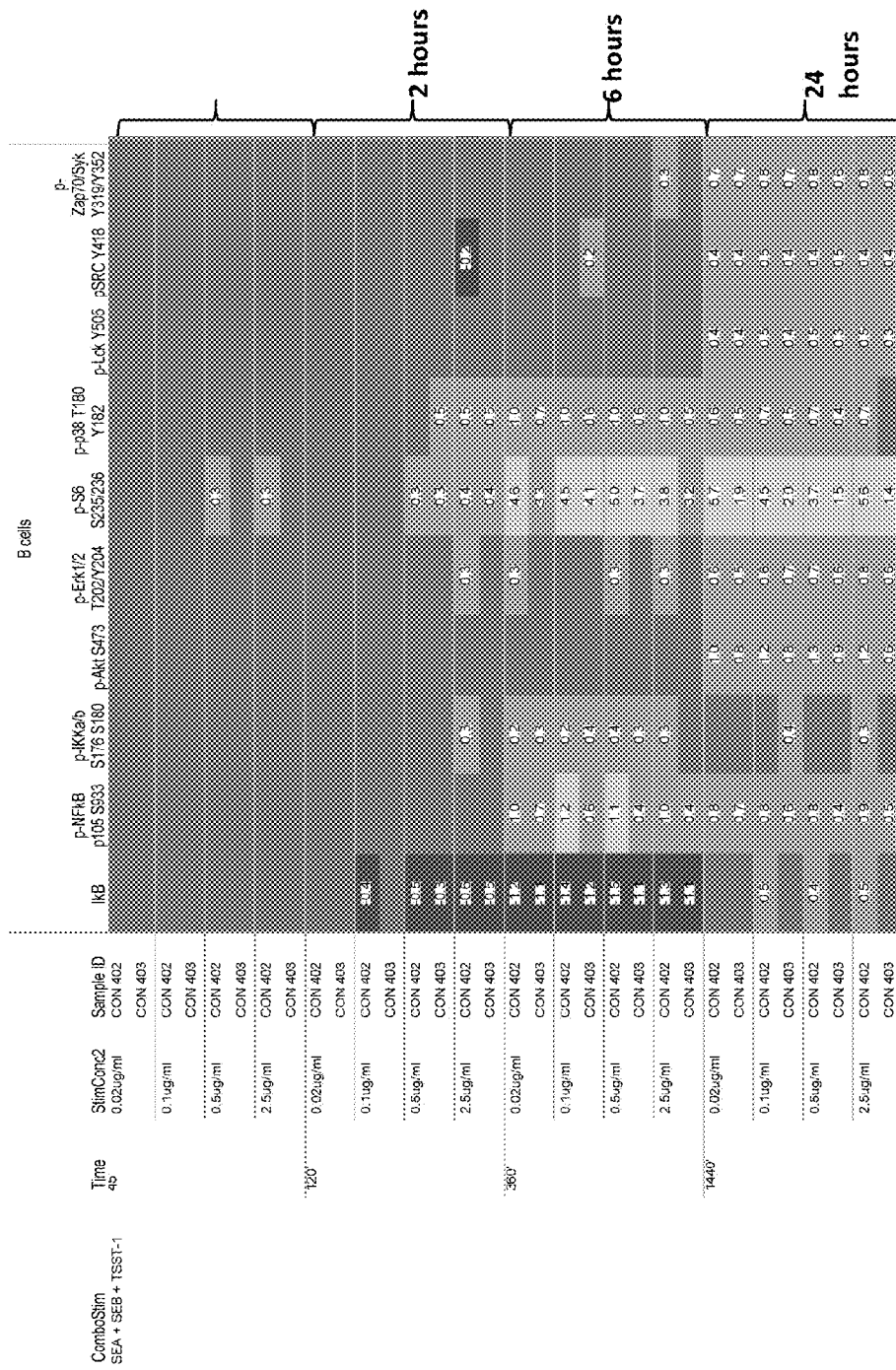
FIG. 10 shows a five shade heat map that indicates that B cell signaling is detectable at 2 hours and increases to 24 hours.
Figure 11:
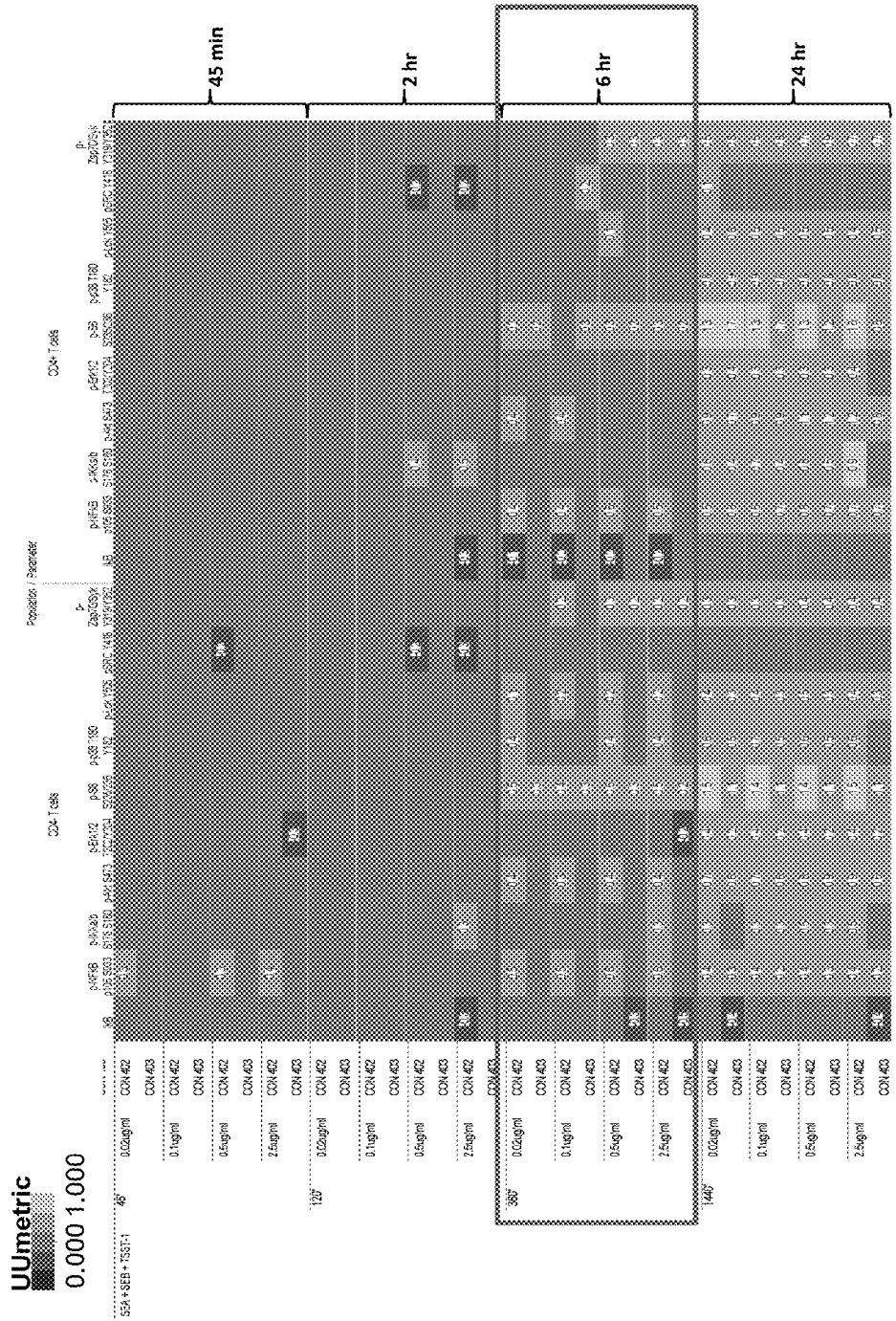
FIG. 11 shows a five shade heat map indicating that T cell signaling is detectable at 6 hours and increases to 24 hours.
Figure 14:
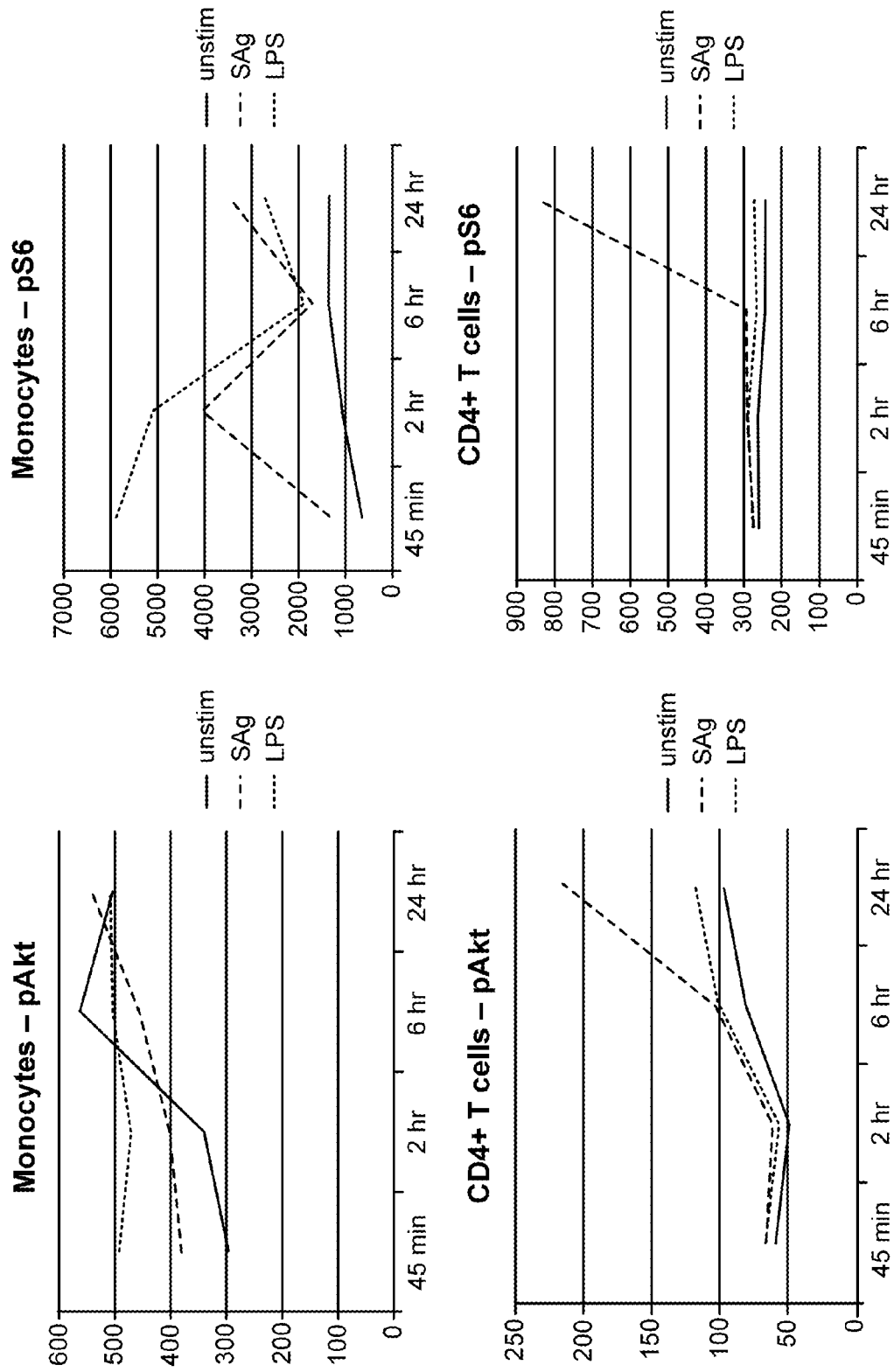
FIG. 14 shows PI3k pathway signaling in response to SAg (SEA+SEB+TSST) or LPS in monocytes and T cells. SAg activation is early in monocytes and late in T cells. In Monocytes-pAKT, the lower line at 45 min is unstimulated, middle is SAg stimulated, and top is LPS stimulated. In Monocytes-p56, the lower line at 45 min is unstimulated, middle is SAg stimulated, and top is LPS stimulated. In CD4+ T cells-pAKT, the lower line at 24 hr is unstimulated, middle is LPS stimulated, and top is SAg stimulated. In CD4+ T cells-pS6, the lower line at 24 hr is unstimulated, middle is LPS stimulated, and top is SAg stimulated.
Figure 15:
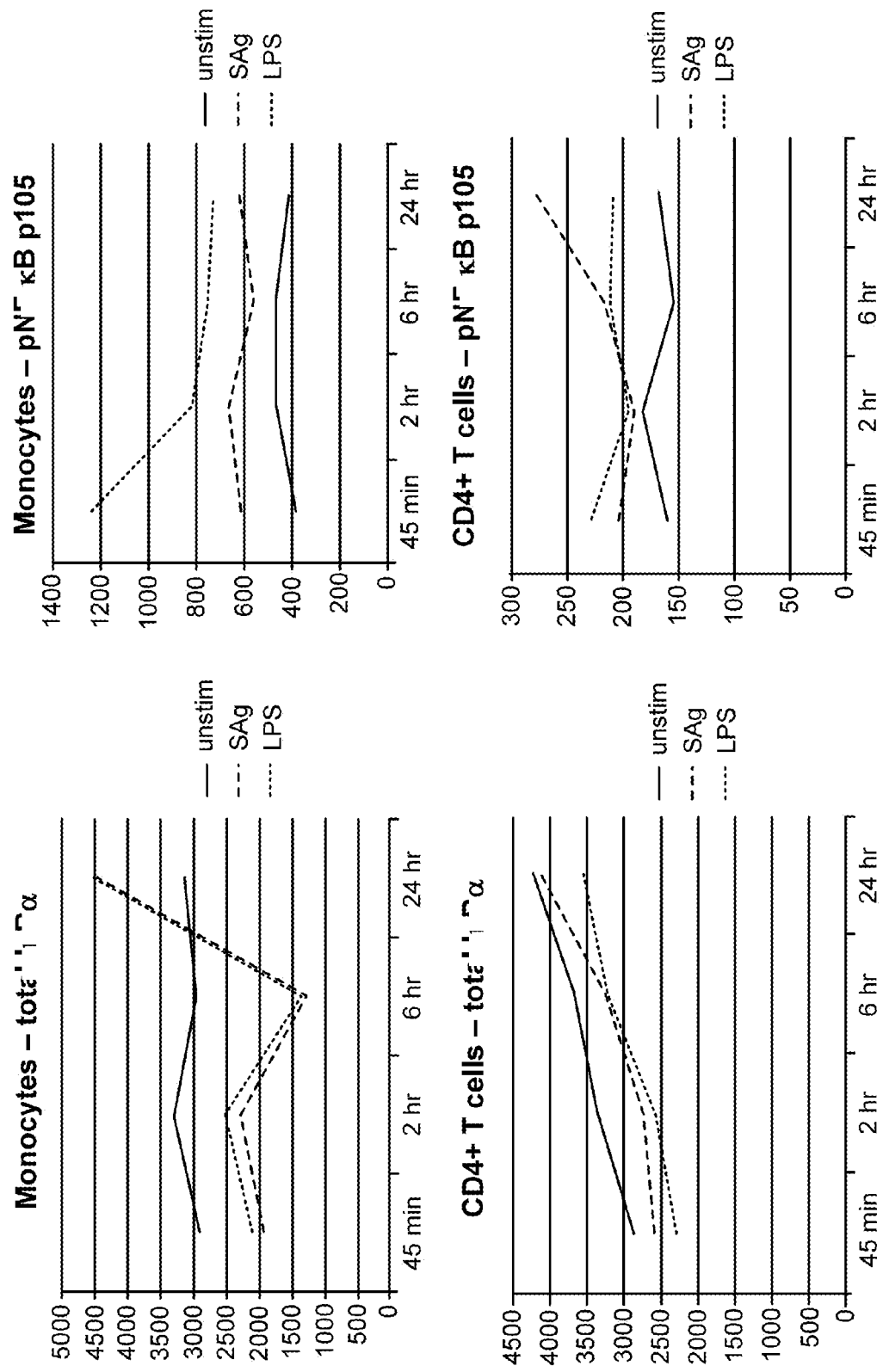
FIG. 15 shows NFκB pathway signaling in response to SAg (SEA+SEB+TSST) or LPS in monocytes and T cells. SAg activation is early in monocytes and minimal in T cells. In Monocytes-total IκBα, the lower line at 45 min is SAg stimulated, middle is LPS stimulated, and top is unstimulated. In Monocytes-pNFκB p105, the lower line at 45 min is unstimulated, middle is SAg stimulated, and top is LPS stimulated In CD4+ T cells—total IκBα, the lower line at 24 hr is LPS stimulated, middle is SAg stimulated, and top is SAg stimulated In CD4+ T cells-pNFκB p105, the lower line at 24 hr is unstimulated, middle is LPS stimulated, and top is SAg stimulated.
Figure 16:
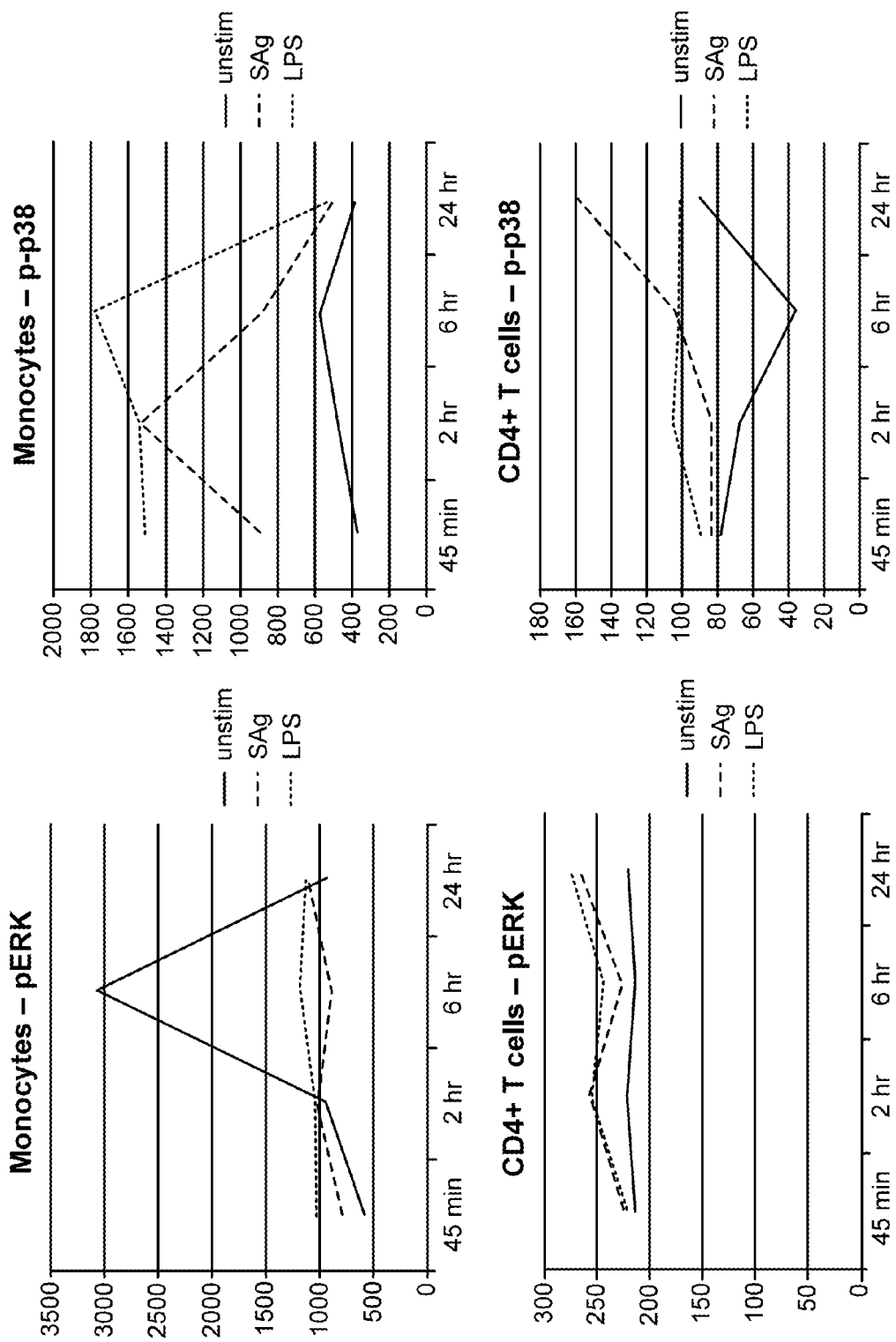
FIG. 16 shows p38 pathway signaling in response to SAg (SEA+SEB+TSST) or LPS in monocytes and T cells. Sag activation is early in monocytes and late in T cells. Monocyte-pERK: the lower line at 45 min is unstimulated, middle is SAg stimulated, and top is LPS stimulated Monocytes-pp38: the lower line at 45 min is unstimulated, middle is SAg stimulated, and top is LPS stimulated CD4+ T cells-pERK: the lower line at 24 hr is unstimulated, middle is SAg stimulated, and top is LPS stimulated. CD4+ T cells-pp38 the lower line at 24 hr is unstimulated, middle is LPS stimulated, and top is SAg stimulated.

FIGS. 9, 10 and 11 show the data by cell subsets, such as monocytes, B cells and T cells respectively. SAg acts rapidly and directly on monocytes whereas T cell activation is delayed and sustained. Without being bound by theory, T cell activation is dependent on modulator-induced intercellular communication, either via direct interaction with monocytes or through secreted factors. FIGS. 14, 15 and 16 show that SAg activation is early in monocytes and late in T cells.

Example 9

The present example is conducted in a manner similar to that shown in the above examples and the details of the general method.

PMBCs from normal healthy patients (CON 402 and CON 403) were collected and cryopreserved in a manner similar to that shown above. The PBMCs were treated for 24 hours with a modulator, such as SAg or LPS, plus an inhibitor. The inhibitor was added to analyze the communication between discrete cell types.

TABLE 3

| Inhibitor | Reason |
| --- | --- |
| Anti IL-2 | Neutralize secreted IL-2 |
| Anti IL-6 | Neutralize secreted IL-6 |
| Anti TNFα | Neutralize secreted TNFα |
| Anti IL-2, anti IL-6, anti TNFα | In case these cytokines have redundant signaling activation |
| CAL-101 (PI3K delta inhibitor) | PI3K pathway induced both directly by modulators and via cross-talk mechanisms |
| Tofacitinib (JAK inhibitor) | Block cytokine signaling through JAKs |

We measured 9 intracellular readouts and 3 cytokines. FIG. 17 show the results from the experiment. The Figure should be read in groups of 3—Unstim, SAg & LPS for a given cell type/cytokine. A higher number indicated increased percentage of a cell type positive for cytokine expression (darker shading). The results show that LPS induced monocytes to produce IL-6. Tofacitinib also induced IL-6 production by monocytes, and TNF☐ neutralization resulted in increased LPS mediated TNF production by monocytes. Without being limited by theory, this could be due to inhibition of negative feedback. CAL-101 and Tofacitinib both blocked TNFα production (but not IL-6). SAg induced B cells to produce IL-6. CAL-101 and Tofacitinib both blocked B cell IL-6 production. CD4+ cells produced IL-2 and TNF and SAg condition. CAL-101 and Tofacitinib both blocked T cell cytokine production.

These inhibitors perturbed cytokine secretion. T cell cytokine secretion was dependent on both a functional PI3K pathway and JAK/STAT signaling. Monocyte TNF was not detected at 24 hours. IL-6 production was independent of PI3K and JAK/STAT. TNF a production was dependent on PI3K and JAK/STAT. Extracellular TNFα inhibited further TNFα production.

Figure 18:
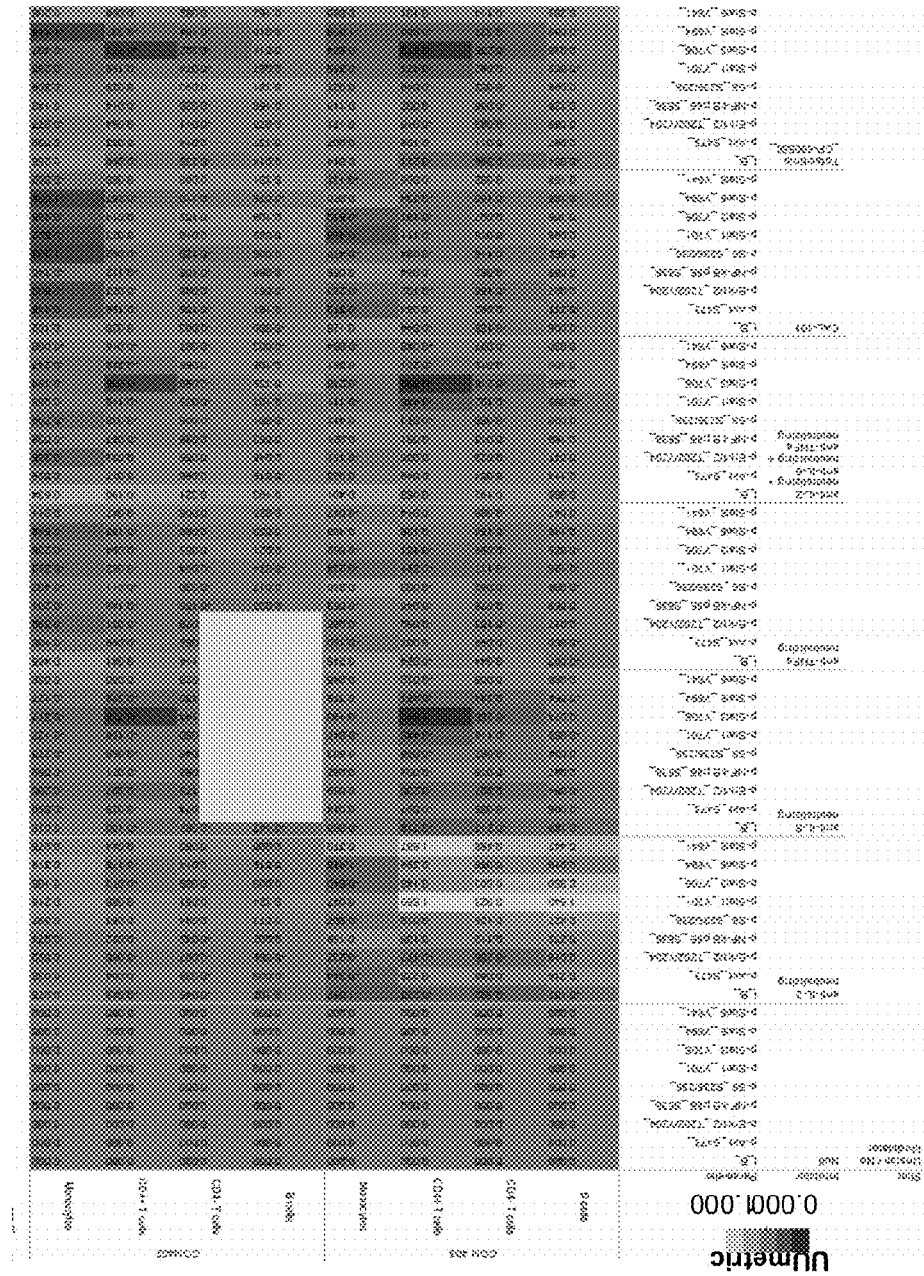
FIG. 18 shows the effects of inhibitors on cell signaling. 7 inhibitor conditions (6 inhibitors and one null) were characterized by 9 intracellular readouts each, in 4 cell types from 2 donors. Shading is proportional to Uu (5-shade heat map). Numbers are log 2 (fold change)

FIG. 18 shows the effects of inhibitors on cell signaling. It was observed that tonic STAT 3 signaling was induced by IL-6. Tonic IκBα degradation was induced by TNFα. It was also observed that basal PI3K activity is present in monocytes and there was inhibitable JAK/STAT activity.

Figure 19:
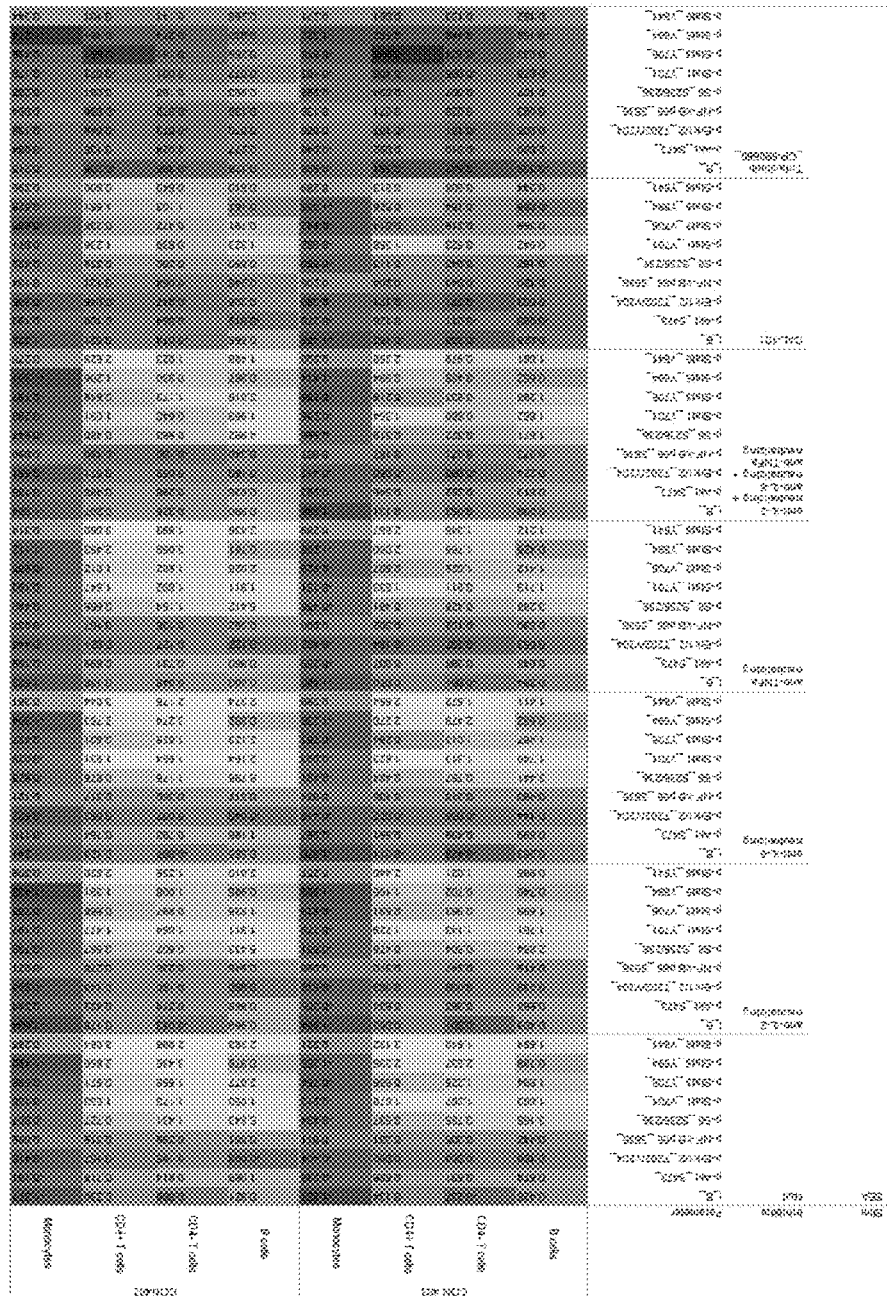
FIG. 19 shows inhibitor effects on SAg modulation, 5-shade heat map.

FIG. 19 shows the inhibitor effects on SAg modulation. The reference well was unmodulated, so there was no inhibitor. The top heatmap reveals effect of SAg on signaling without inhibitors (null). The bottom heatmap compares SAg with inhibitor to SAg alone. It was a 24 hour experiment which showed that monocyte signaling was down and T cell signaling was up in samples modulated with SAg but with no inhibitor. This is consistent with the results observed at 24 hours in Example 8. Using SAg alone, the PI3K and STAT pathways were active in lymphocytes. All measured signaling was resolved in monocytes except for p-STAT6. CAL-101 showed that the PI3K pathway (p-Akt and p-S6) was inhibited and that there was a partial inhibition of STAT signaling. Tofacitinib inhibited all signaling except for monocyte p-STAT6. There was some STAT signaling when using CAL-101.

Figure 20:
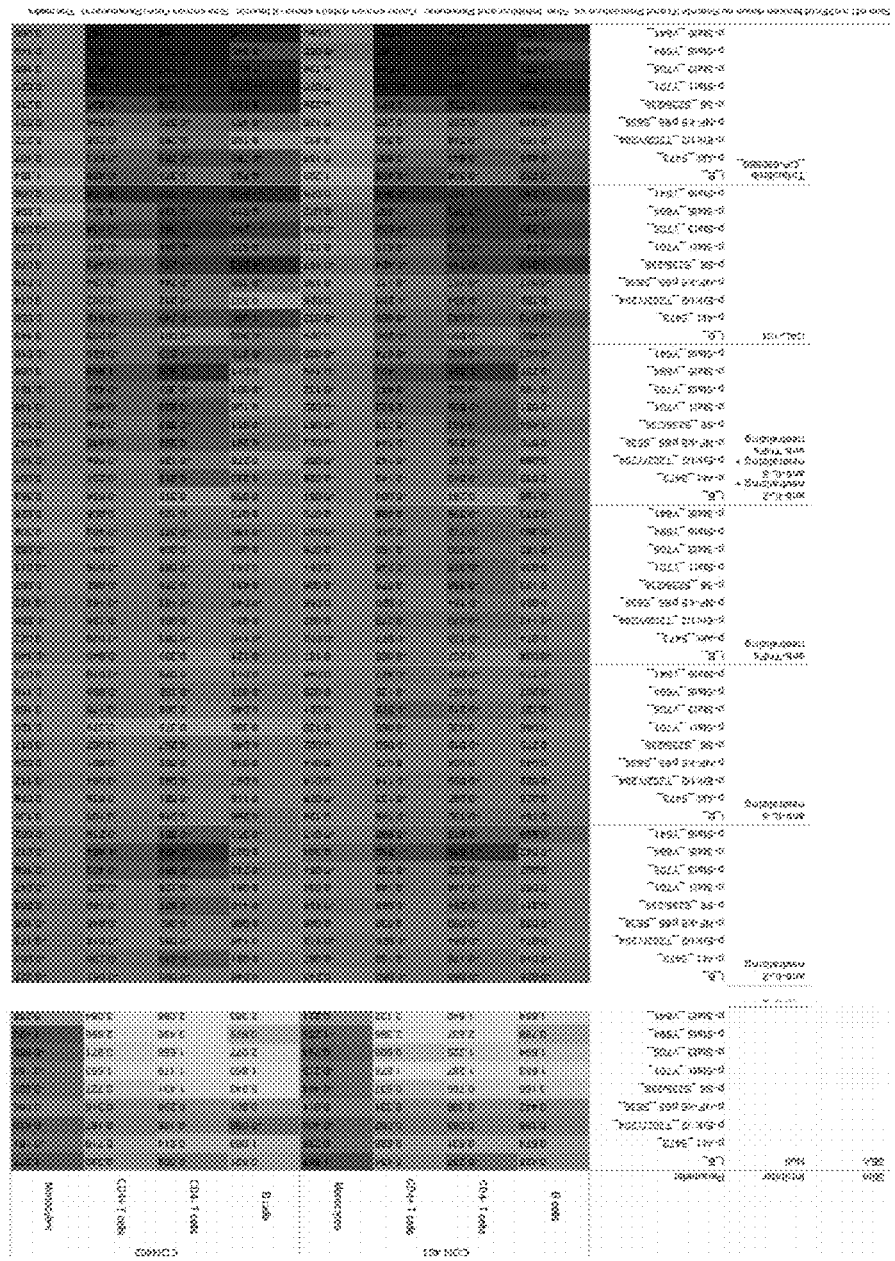
FIG. 20 shows inhibitor effects on SAg modulation, 5-shade heat map. A comparison is not made to untreated cells as in FIG. 25, but to cells without the drug. 5-shade heat map.

FIG. 20 shows IL-2 neutralization resulted in partial inhibition of PI3K pathway & STAT5 in T cells. Inhibition of IκBα degradation in CD4– T cells resulted from TNFα neutralization. Triple cytokine neutralization showed individual cytokine effects and partial inhibition of STAT1 and STAT3 signaling. CAL-101 and Tofacitinib inhibited lymphocyte signaling.

Figure 21:
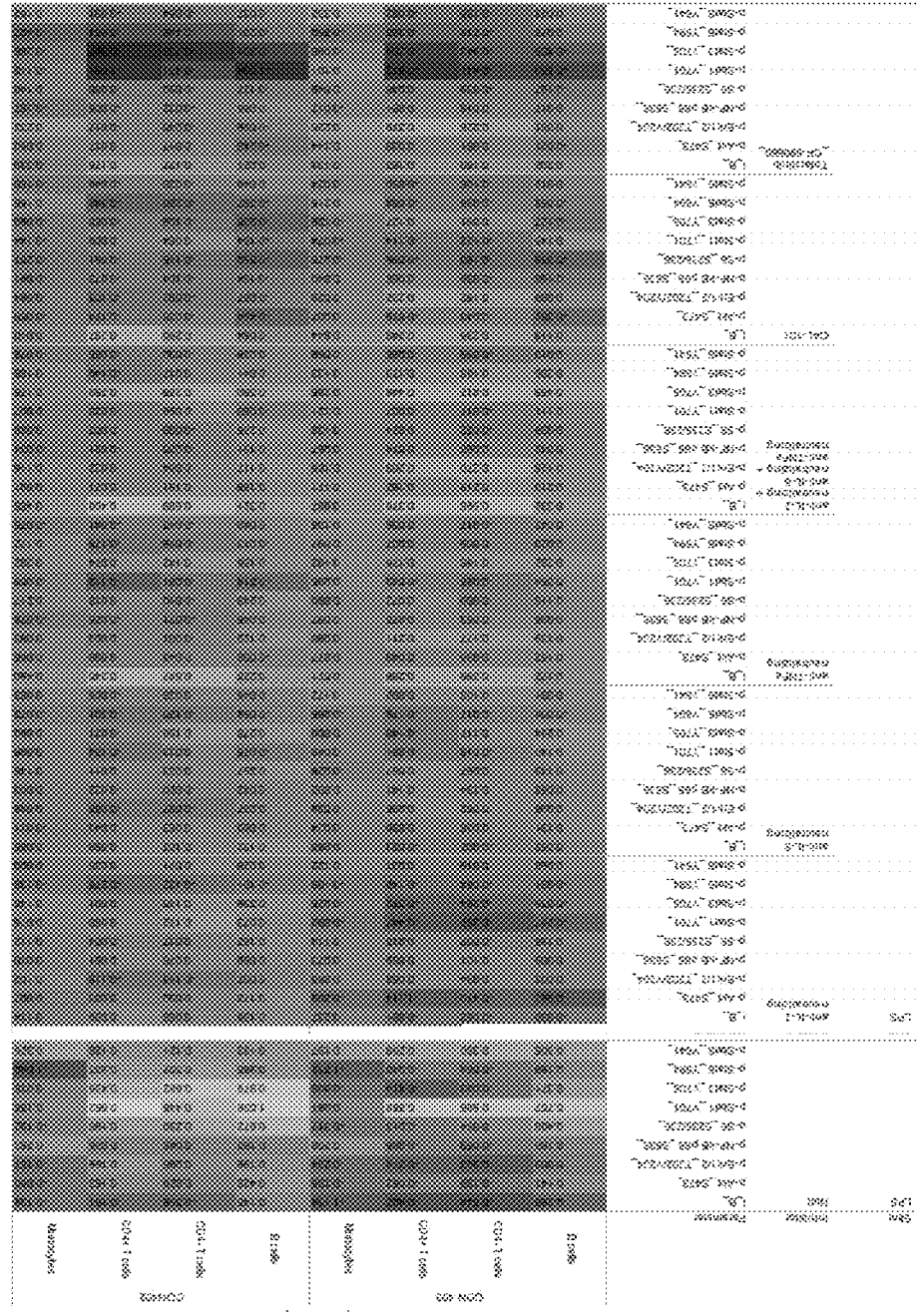
FIG. 21 shows inhibitor effects on LPS modulation, 5-shade heat map. The top heat map reveals effect of LPS on signaling without inhibitors. Bottom heat map is comparison of LPS with inhibitor to LPS alone.

FIG. 21 shows the inhibitor effects on LPS modulation. The top heatmap reveals effect of LPS on signaling without inhibitors (null). The bottom heatmap compares LPS with inhibitor to LPS alone. Effects of LPS were T cell degradation of IκBα, Lymphocyte activation of STAT1 and Monocyte inhibition of STAT5. IL-2 neutralization showed partial inhibition of STAT5 which was not observed in triple neutralization. IL-6 neutralization showed partial inhibition of STAT1 activation in T cells. TNFα neutralization showed inhibition of IκBα degradation in T cells. Triple cytokine neutralization showed inhibition of IκBα degradation maintained and that STAT signaling inhibition was reduced. CAL-101 blocked B cell PI3K pathway and showed a partial reduction in STAT phosphorylation. Tofacitinib inhibited STAT signaling.

It was observed that in SAg mediated cell cross talk, complete activation of T cells was dependent on both PI3K and JAK/STAT pathways. LPS mediated cross talk was dependent on the PI3K pathway. Akt, S6 and partial STAT phosphorylation were observed. LPS mediated cross talk was also dependent on JAK/STAT pathway as STAT signaling was observed. IL-6 production was independent of PI3K and JAK/STAT. Whereas, TNFα production was dependent on PI3K and JAK/STAT.

This Example illustrates that the use of inhibitors that interact with cytokines involved in cell-cell communication, or that modulate intracellular pathways involved in cell-cell communication, when used in conjunction with a modulator that induces cell-cell communication, cause changes in cytokine expression and changes in intracellular readouts downstream from the initial modulation.

Example 10

This Example demonstrates the use of SCNP to follow intracellular events in different discrete cell populations in communication, after stimulation with a modulator (SAg) that affects only certain populations.

The recent advent of biological inhibitors of cytokine signaling as therapeutics for auto-immunity represents an important development in patient treatment strategy. However, tools for patient stratification are still needed to identify sub-populations for which a specific drug is efficacious. By determining both the ability of specific cell subsets to produce a cytokine of interest, as well as the potential for bystander cells to respond to that cytokine, a more complete picture of cytokine activity within a patient sample may be formed. Single Cell Network Profiling (SCNP) provides a unique platform to derive this information. In this assay, cell samples are activated with a modulator to evoke cell signaling, then flow cytometry is used to quantify the level of the activated, e.g., phosphorylated form of intracellular signaling proteins at the single cell level. Thus, the activation state of the intracellular signaling network in lineage-specific cell subsets is revealed. Furthermore, kinetic studies identify the activation and resolution of evoked signaling, as well as delayed signaling events potentially mediated through an induced secondary factor.

SCNP has demonstrated predictive ability for the likelihood of response to standard induction therapy in acute myeloid leukemia (AML) patients, and time to first treatment for patients with B cell chronic lymphocytic leukemia (CLL). In both instances, this ability relied on interrogation of signaling specific to the leukemic cell population, such as the FLT3 pathway in AML or B cell receptor activation in CLL. In contrast to leukemia, multiple cell types drive pathology in auto-immune disease. Thus, the interplay between cell subsets is crucial in this context. Herein, SCNP is used to identify intracellular events that are occurring presumably in response to intercellular signaling among different discrete cell populations in communication in a culture, where the signaling is induced by a modulator that acts on one cell type, but the "downstream" response can also be measured in a different cell type at a later time. The use of inhibitors that block a particular signaling molecule (e.g., anti-TNF□□ or anti-IL6), or that modulate a particular intracellular signaling pathway (e.g., Tofacitinib) provides further information as to cell-cell communication in response to modulator, and also offers a means of screening potential drug candidates, e.g., biologics or small molecule modulators (see Model in FIG. 3). The use of samples that are modified from natural blood by removal of cells so that the samples can be frozen and thawed and remain viable (e.g., PBMC samples), allows the extension to retrospective studies in normal and diseased individuals for whom such samples have been collected.

Materials and Methods

Cells: Peripheral blood mononuclear cells (PBMCs) from two healthy subjects were isolated from whole blood by a ficoll (Histopaque-1077, Sigma) gradient purification and cryopreserved in FBS+10% DMSO. Results from two subjects were averaged.

SCNP Assay: PBMCs were thawed and debris removed by a ficoll gradient purification. Cells were plated in 96-well plates at 100,000 cells in 100 uL per well, and rested for 2 hours at 37 C. For experiments described herein, superantigen (SAg) is defined as a combination of staphylococcal enterotoxin A (SEA), staphylococcal enterotoxin B (SEB), and toxic shock syndrome toxin 1 (TSST-1) (Toxin Technologies, Srasota, Fla.) at equal concentrations. In Examples 10-14, cells were treated with SAg, LPS (Sigma) or media, in some instances in in combinations with the inhibitors Tofacitinib (Selleck), anti-IL-6, anti-IL2, or anti-TNFα

(R&D Systems). Neutralizing antibodies were applied at saturating levels (10 ug/mL) and Tofacitinib was used at 500 nM, which is clinically achievable (http://www.ncbi.nlm.nih.gov/pmc/articles/PMC3585773/) and exceeds the IC50 for p-STAT5 inhibition. Following sample activation, cells were fixed with 1.6% paraformaldehyde at 37 C for 10 minutes, at the deisired time point, then resuspended in cold methanol and stored at −80 C.

Flow Cytometry: For cell staining, cells were washed with fluorescence-activated cell sorting buffer (PBS/0.5% bovine serum albumin/0.05% NaN3), pelleted, and stained with cocktails of fluorochrome-conjugated antibodies. These cocktails included antibodies against cell surface markers for monocytes (CD14), B cells (CD20) and T cell subsets (CD3 and CD4), the apoptotic marker cleaved PARP (cPARP), and antibodies against intracellular signaling molecules and cytokines. Flow cytometry data were acquired on a LSRII flow cytometer using FACSDiva software (BD Biosciences) and analyzed with FlowJo (TreeStar Software) or Winlist (Verity House Software). Cells were gated by light scatter properties and cPARP expression to identify non-apoptotic cells, and then surface markers to identify specific cell lineages. The 24 hr SAg condition caused a decrease of CD14 expression on monocytes, so the CD14 gate was lowered exclusively in that condition.

Results

Activation Kinetics

In order to evaluate the activation kinetics of unique cell subsets treated with super antigen (SAg: SEA+SEB+TSST-1), peripheral blood mononuclear cells (PBMC) were modulated with SAg and assayed for cell signaling at 45 minutes and 2, 6, and 24 hours. Evoked signaling was measured across four biological pathways: NF$\Box$B (total I$\kappa$B$\alpha$, p-NF$\kappa$B p105), PI3K (p-AKT, p-S6), MAPK (p-ERK, p-p38), and JAK/STAT (p-STAT1, p-STAT3, p-STAT5). The cell subsets analyzed consisted of CD20+ B cells, CD4+ T cells, CD4− T cells, and CD14+ monocytes; all cells were gated for viability by exclusion of cPARP+ apoptotic events.

Figure 12:
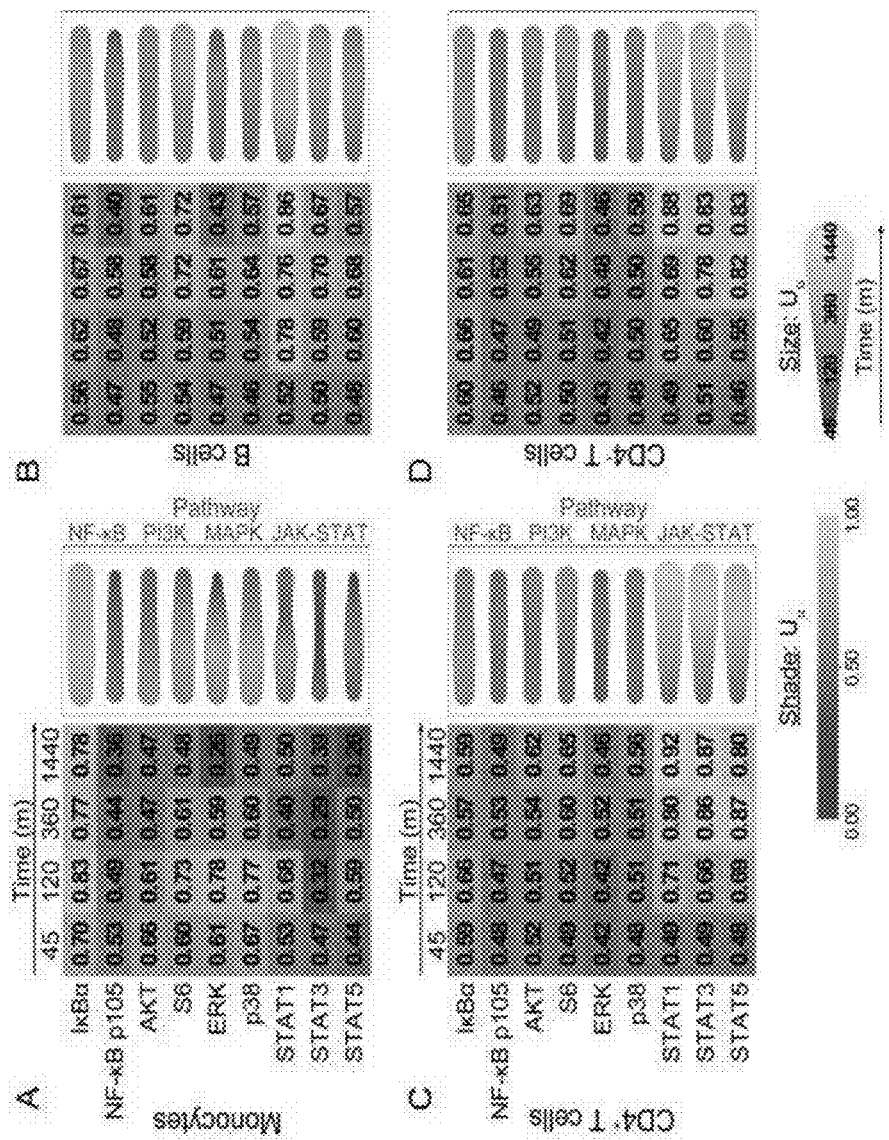
FIG. 12 shows results for another experiment (Example 10) in which PBMC from 2 healthy volunteers were stimulated with SEA+SEB+TSST. Results for two subjects were averaged. Results are shown as a five color heat map with Uu numbers, and as bars where the width of the bar indicates Uu as does the shading, while the length of the bar indicates time (left side=45 min, right side=24 hrs). A. Monocytes; B. CD4+ T cells; C. CD4− T cells; D. B cells

Rapid and transient signaling was detected in monocytes, whereas the lymphocyte subsets demonstrated delayed and sustained cellular activation. See FIG. 12A. In monocytes NF$\kappa$B (readouts: I$\Box$B$\Box$, NF$\Box$B p105), PI3K (readouts: pAKT, also designated AKT, and pS6, also designated S6) and MAPK (readouts: pERK, also designated ERK, and p-p38, also designated p38) pathway activity was detected following 45 minutes of SAg modulation. Monocyte signaling peaked at 2 hours post-modulation and was resolved by 24 hours.

In contrast, onset of PI3K pathway activation in lymphocytes occurred between 2 to 6 hours and continued through 24 hours. See FIGS. 12B-D. Similarly, lymphocyte signaling through the JAK/STAT pathway (readouts: pSTAT1, also designated STAT1, pSTAT3, also designated STAT3, and pSTAT5, also designated STAT5) was detected 2 hours after modulation and continued to escalate through the 24 hour time course. SAg-mediated signaling kinetics are described as early and short-lived activation of monocytes, followed by lymphocyte activation first through the JAK/STAT pathway and then PI3K pathway.

In the context of SAg modulation, monocyte cytokine production both enhanced T cell activation and suppressed maximal monocyte signaling via feedback inhibition.

This example shows that a modulator affecting one group of cells, SAg, can be used to obtain information on those and other cells in kinetic analysis to show differential activation and potential feedback inhibition of various discrete cell populations on a single cell level using SCNP.

Example 11

This example demonstrates the use of SCNP to follow intracellular events in different discrete cell populations in communication, after stimulation with a modulator that affects only certain populations, and in the presence of an agent, in this case an inhibitor, that affects the intercellular communication, either by inhibiting an intercellular communication messenger (e.g., anti-TNFα or anti-IL6), or by inhibiting an intracellular pathway involved in intercellular communication (e.g., Tofacitinib). Materials and methods were as described in Example 10 regarding SAg stimulation and inhibitors.

Blockade of TNF$\Box\Box$ and IL-6 signaling is currently used in the clinic for treatment of auto-immune disease. One strategy to evaluate biological inhibitor activity is to measure their effects in an ex vivo model of immune cell signaling. Activating the system induces a signaling cascade, potentially informing on drug activity upon dysregulated signaling that underlies clinical disease. Superantigens (SAgs) are potent activators of the immune system that induce cell-cell crosstalk through both direct interactions and secreted factors. For example, staphylococcal enterotoxin A (SEA) binds MHC II, which induces signaling and cytokine production by the host cell. In turn, the SEA::MHC II complex is capable of binding the b-chain of the T cell receptor (TCR), thus mimicking antigen presentation and causing T cell activation and proliferation. Therefore, SAg provides a mechanism to study intercellular communication that is mediated in part by cytokine signaling through IL-6 and TNF$\Box$.

PBMC were treated with modulator and compared to untreated cells (Uu). PBMC cells also were treated simultaneously with SAg modulation and one of three cytokine pathway inhibitors: anti-IL-6, anti-TNF$\Box$, or the JAK inhibitor Tofacitinib, and compared to SAg treatment with no inhibition (Uim). For an explanation of Uu and Uim see FIG. 27. Materials, conditions, and SCNP assays were as in Example 10.

Tofacitinib exhibited broad and potent inhibition of the JAK/STAT pathway and down-stream signaling, whereas IL-6 and TNFα neutralization yielded specific inhibition of targeted signaling nodes.

SAg modulation of PBMC without inhibitor resulted in monocyte activation prior to T cells, a finding consistent with monocyte-mediated paracrine signaling causal of elements of T cell activation. See FIG. 25A (size of circle corresponds to Uu, a measure of activation without inhibitor, monocytes show activation at 120 min, while B cells and T cells show activation at 6 hrs). PBMC were treated simultaneously with SAg modulation and one of three cytokine pathway inhibitors: anti-IL-6, anti-TNF$\Box$, or the JAK inhibitor Tofacitinib. Tofacitinib exhibited broad and potent inhibition of the JAK/STAT pathway and down-stream signaling, whereas IL-6 and TNFα neutralization yielded specific inhibition of targeted signaling nodes.

Tofacitinib is a JAK3 inhibitor that demonstrates pan-JAK promiscuity in the SCNP assay at elevated concentrations (unpublished data). In agreement with this, Tofacitinib completely abrogated STAT induction evoked by SAg modulation. See FIG. 25A (dark shading of circles of the JAK/STAT pathway, which is the right grouping, indicates drug inhibition compared to no drug, i.e., high Uim). For example, STAT activation in CD4− T cells was detected at 2 hours and intensified during the time course, and Tofacitinib treatment restored p-STAT levels to the unmodulated condition (FIG. 25D, left graph). In addition, Tofacitinib blocked PI3K pathway activation in lymphocytes at 24 hours (FIG. 25A).

Following 6 hours of SAg modulation, p-STAT3 was induced in CD4+ T cells to a log 2fold of 1.8 and IL-6 neutralization inhibited this by 33% (FIG. 25D middle graph). Anti-IL-6 also inhibited p-STAT5 in monocytes by 36% at the 2 hour time point. Neutralization of TNFα robustly inhibited SAg-mediated I☐B☐ degradation in CD4− T cells at 24 hours, suggesting TNFα activation of the expected target (FIG. 25D, right graph). Interestingly, anti-TNFα treatment augmented PI3K and MAPK pathway activity in monocytes at 2 hours post-SAg modulation. This finding implies that TNFα partially inhibits induction of these pathways.

Figure 25C:
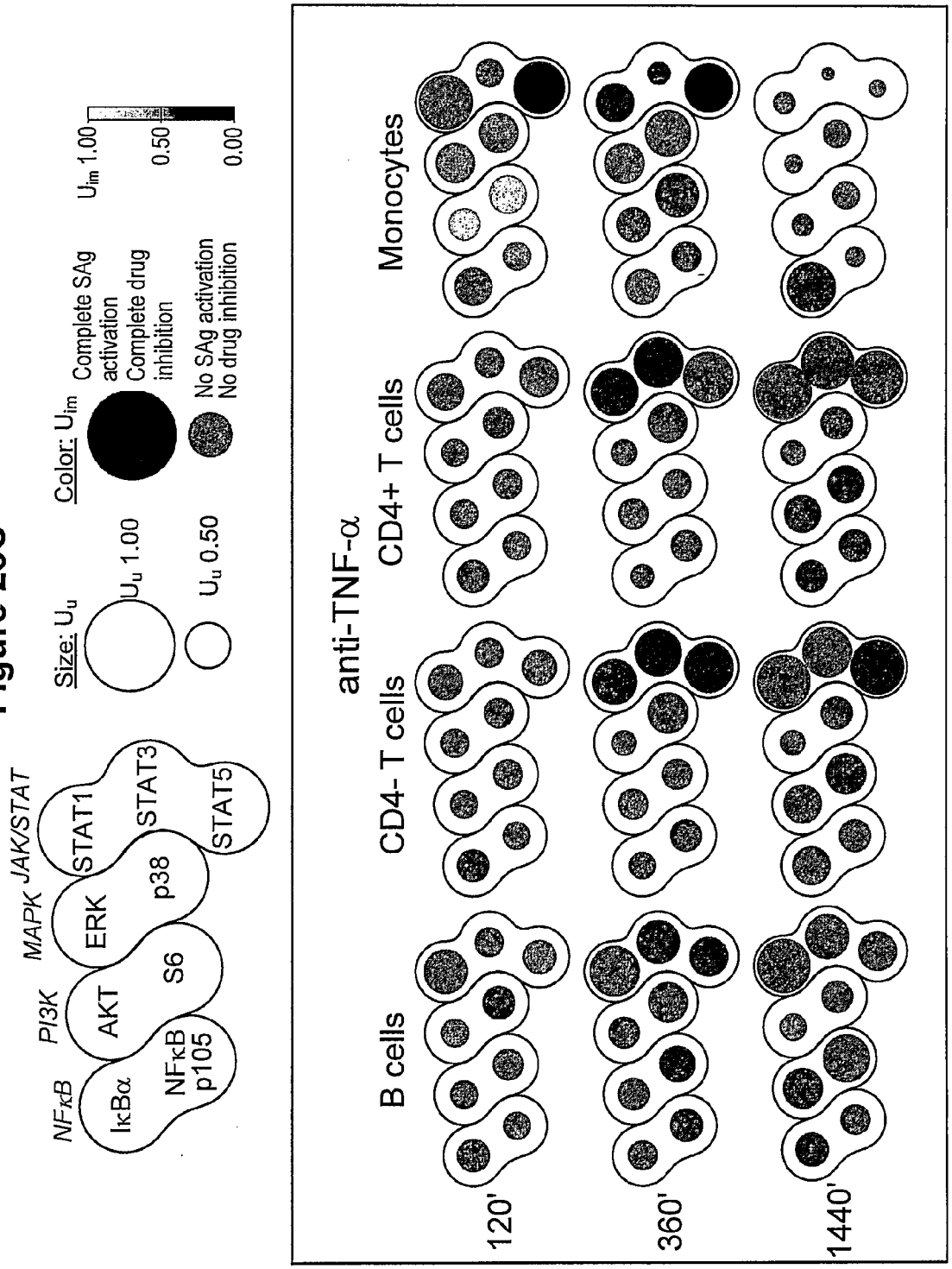
FIG. 25C shows the effects of treatment with anti-TNFα on intracellular readouts in B cells, CD4– T cells, CD4+ T cells and B cells modulated with SAg (SEA+SEB+TSST) over time. Readouts corresponding to a given pathway are grouped together. Size of the circle corresponds to the size of the effect of the SAg compared to unmodulated, in the absence of inhibitor (Uu). Shade of the circle corresponds to the magnitude of the effect of the inhibitor, SAg–inhibitor compared to SAg+inhibitor (Uim). See FIG. 27 for an explanation of how Uim is calculated.
Figure 25D:
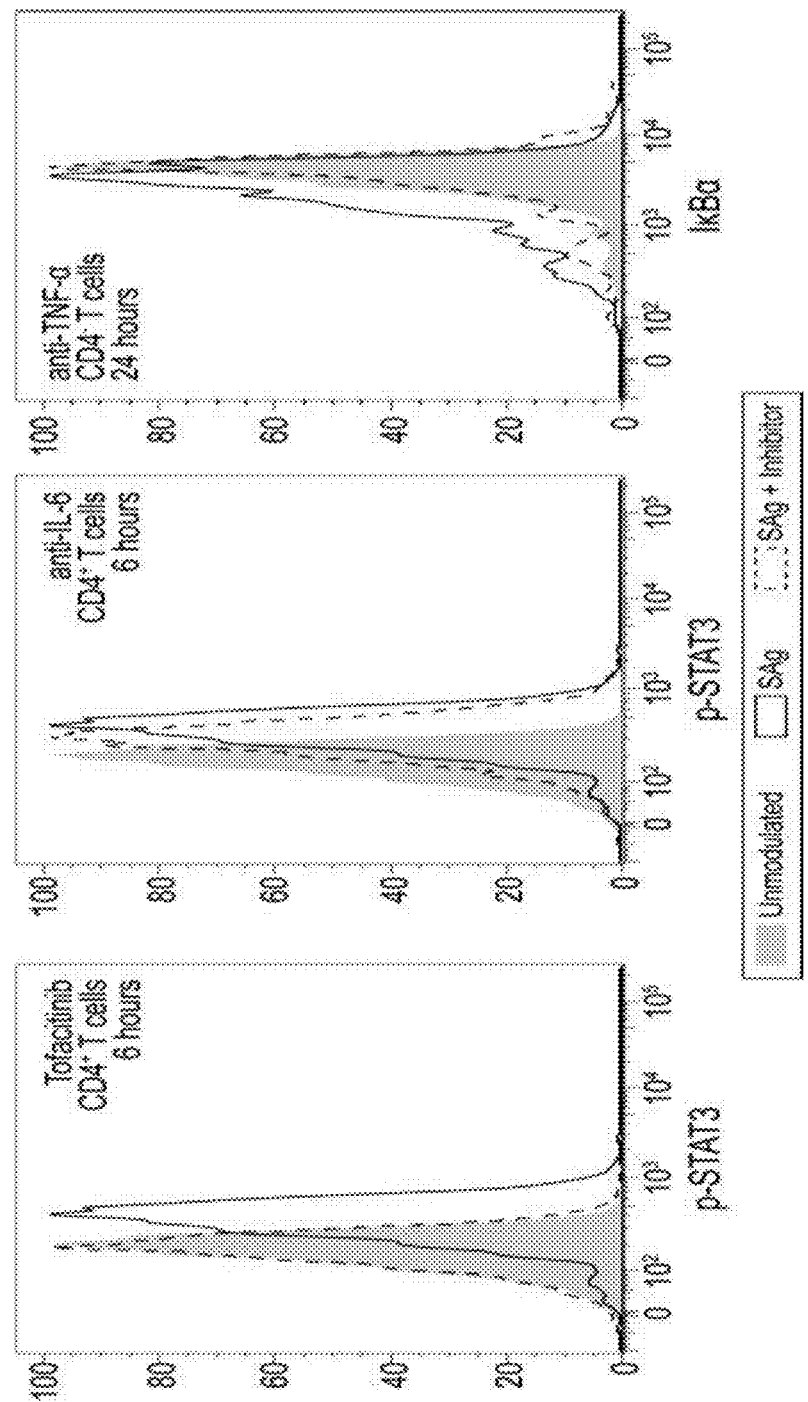
FIG. 25A shows the effects of treatment with Tofacitinib on intracellular readouts in B cells, CD4− T cells, CD4+ T cells and monocytes modulated with SAg (SEA+SEB+TSST) over time. Readouts corresponding to a given pathway are grouped together. Size of the circle corresponds to the size of the effect of the SAg compared to unmodulated, in the absence of inhibitor (Uu). Shade of the circle corresponds to the magnitude of the effect of the inhibitor, SAg−inhibitor compared to SAg+inhibitor (Uim). See FIG. 27 for an explanation of how Uim is calculated
FIG. 25B shows the effects of treatment with anti-IL6 on intracellular readouts in B cells, CD4− T cells, CD4+ T cells and B cells modulated with SAg (SEA+SEB+TSST) over time. Readouts corresponding to a given pathway are grouped together. Size of the circle corresponds to the size of the effect of the SAg compared to unmodulated, in the absence of inhibitor (Uu). Shade of the circle corresponds to the magnitude of the effect of the inhibitor, SAg−inhibitor compared to SAg+inhibitor (Uim). See FIG. 27 for an explanation of how Uim is calculated
FIG. 25 D shows raw data for various points in FIGS. 25A-C. Left: CD4+ T cells, Tofacitinib treatment, 6 hours, p-STAT3 readout. Middle: CD4+ T cells, anti-IL6 treatment, 6 hours, p-STAT3 readout. Right: CD4+ T cells, anti-TNFα treatment, 6 hours, p-STAT3 readout. For all, shaded peak is unmodulated, solid line peak is modulated with SAg, dashed line peak is modulated with SAg in the presence of inhibitor. See FIG. 27 for explanation of how Uim is calculated from these three peaks.

Both Tofacitinib and anti-TNFα inhibited p-STAT5 and PI3K pathway signaling in CD4− T cells at 24 hours (FIGS. 25A and 25C); this inhibition pattern extended to CD4+ T cells treated with Tofacitinib (FIG. 25A). Given that TNFα does not directly activate p-STAT5, these findings suggested that TNFα-dependent secondary cytokine signaling via STAT5 (i.e. IL-2, IL-7, IL-15) was essential for complete PI3K pathway activation.

The inhibitors showed only slight effects on unmodulated PBMCs, likely reflecting minimal tonic signaling for inhibitors to act upon. Tofacitinib weakly reduced phosphorylation of STAT1 and STAT5 at 2 hours, with diminishing effects at later time points (data not shown).

Blockade of TNFα and JAK signaling augmented PI3K and MAPK pathway activation in monocytes, indicating that cytokines serve to dampen signaling in these cells. In concordance, these inhibitors increased production of TNFα and IL-6 by monocytes. Therefore, inhibition of autocrine cytokine signaling in monocytes promotes activation of cell signaling events with ensuing consequences of increased cytokine production.

SAg induced delayed and sustained activation of T cells, which was also mediated in part by cytokines. Unexpectedly, TNFα neutralization dampened off-target PI3K pathway and STAT5 activation in CD4− T cells. This finding is likely explained by a role for TNFα in driving production of an intermediate cytokine. For example, activated T cells produced IL-2 which in turn promoted PI3K and STAT5 signaling. In these studies, inhibition of TNFα did not significantly affect IL-2 production (data not shown), so the specific intermediary between TNFα and off-target pathways remains unknown. Altogether, this highlights the utility of SCNP to discover unexpected effects of inhibitors acting upon sequential cytokine signaling events between cells.

This example shows that SCNP reveals the biology of multiple modulated signaling pathways across immune cell subsets. Here, kinetic differences in evoked signaling between specific cell lineages were leveraged to target points of cell crosstalk. Biologic and small molecule inhibitors were utilized to identify the systems level contribution of specific cytokines towards activation of the immune signaling network. This application enables more holistic in vitro analysis of targeted inhibitors and their disruption of cell-to-cell communication. This analysis enables identification of feedback loops and their possible absence and/or dysregulation in the context of disease, as well as being useful in screening agents that affect the intracellular communication, e.g., for their potential usefulness in treatment of disease in which the pathways are involved, such as autoimmune disease and cancer. Along the drug discovery pathway the interrogation of drug potency, selectivity, mechanism of action, and potential unexpected effects on cell signaling in both healthy and disease-associated context is enabled.

Example 12

This example demonstrates the use of flow cytometry to follow intracellular events, in this case expression levels of cytokines, in a discrete cell population, after stimulation with a modulator that affects only certain populations, and in the presence of an agent, in this case an inhibitor, that affects the intercellular communication, either by inhibiting an intercellular communication messenger (e.g., anti-TNFα or anti-IL6), or by inhibiting an intracellular pathway involved in intercellular communication (e.g., Tofacitinib).

Experimental conditions were as described in Example 10 regarding modulation with SAg and use of inhibitors.

Figure 13:
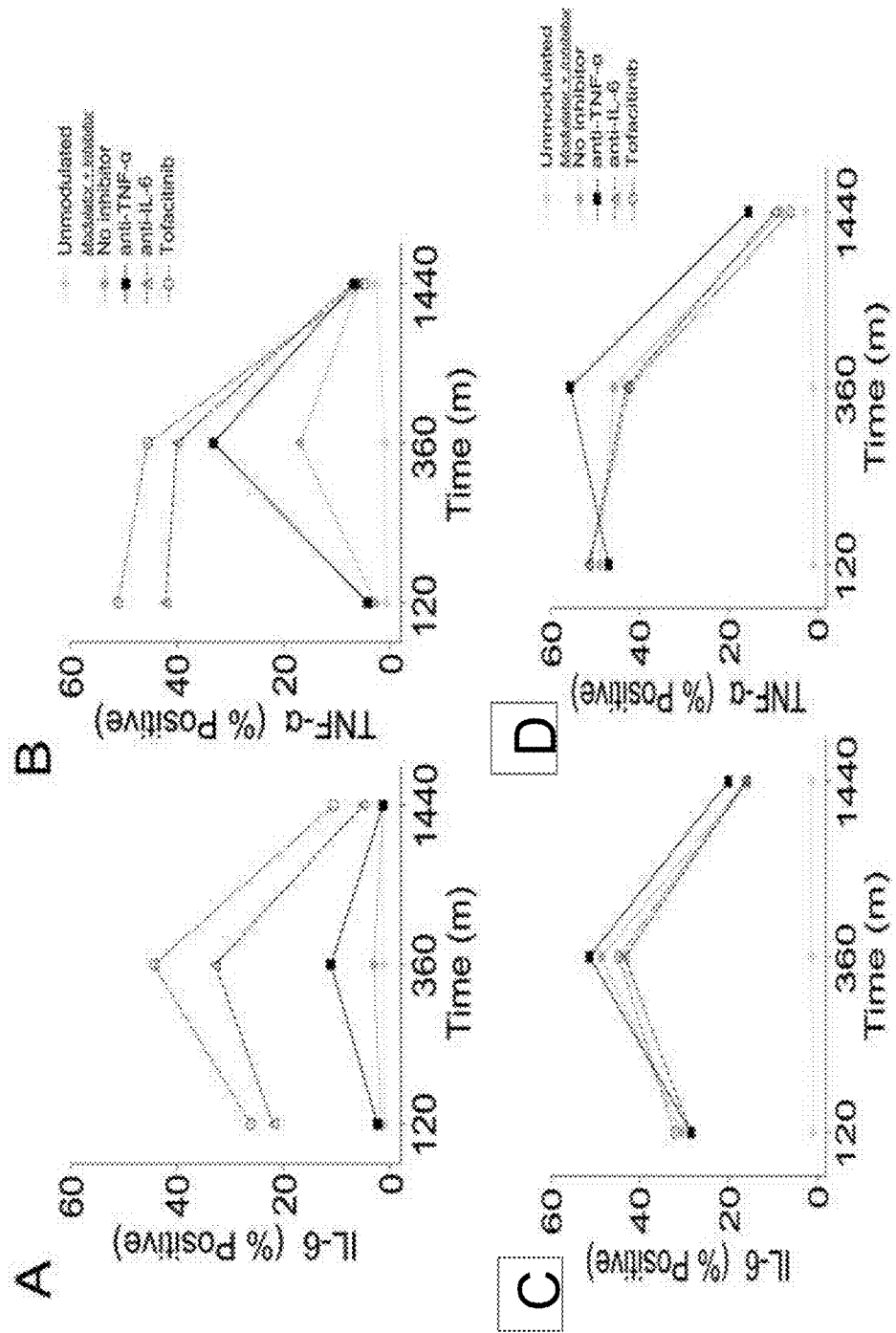
FIG. 13 shows results for an experiment in which PBMC from 2 healthy volunteers were stimulated with modulator, in the presence or absence of the inhibitors anti-TNF☐, anti-IL6, or Tofacitinib, and cytokine content of monocytes followed over time. The intracellular cytokines measured were TNF☐ and IL6. Results for two subjects were averaged. A. Modulator=(SEA+SEB+TSST), cytokine followed=IL-6. Unmodulated: solid grey diamond, solid line; Modulated, no inhibitor: solid grey circle, solid line; Modulated+anti-TNF☐: solid black square, solid line Modulated+anti-IL-6: empty triangle, dashed line Modulated+Tofacitinib: empty circle, dashed line B. Modulator=(SEA+SEB+TSST), cytokine followed=TNF☐ Unmodulated: solid grey diamond, solid line; Modulated, no inhibitor: solid grey circle, solid line; Modulated+anti-TNF☐: solid black square, solid line Modulated+anti-IL-6: empty triangle, dashed line Modulated+Tofacitinib: empty circle, dashed line C. Modulator=LPS, cytokine followed=IL-6. Unmodulated: solid grey diamond, solid line; Modulated, no inhibitor: solid grey circle, solid line; Modulated+anti-TNF☐: solid black square, solid line Modulated+anti-IL-6: empty triangle, dashed line Modulated+Tofacitinib: empty circle, dashed line D. Modulator=LPS, cytokine followed=TNF☐. Unmodulated: solid grey diamond, solid line; Modulated, no inhibitor: solid grey circle, solid line; Modulated+anti-TNF☐: solid black square, solid line Modulated+anti-IL-6: empty triangle, dashed line Modulated+Tofacitinib: empty circle, dashed line

The effects of cytokine signaling inhibition on intracellular cytokine induction were measured. Tofacitinib, anti-IL-6 and anti-TNFα were each combined with SAg modulation, and intracellular IL-2, IL-6, and TNFα were measured by flow cytometry. SAg modulation induced nominal IL-6 production in monocytes, but the examined inhibitors greatly augmented this response. See FIG. 13 A. For example, at 6 hours following SAg treatment 3% of monocytes expressed IL-6, compared to 1% of untreated monocytes. However, Tofacitinib (44% IL-6+), anti-IL-6 (33% IL-6+) and anti-TNFα (11% IL-6+) all potentiated IL-6 production by monocytes. FIG. 13A. Tofacitinib also induced IL-6 at the 2 hour and 24 hour time points. Similarly, after 6 hours of SAg modulation the frequency of monocytes expressing TNFα increased from 17% without inhibitor to 33% with anti-TNFα, 40% with anti-IL-6, and 46% with Tofacitinib. FIG. 25B. Importantly, the inhibitors showed little effect on unmodulated cells, indicating that the observed elevated cytokine production required the synergistic effects of SAg modulation and cytokine blockade. This suggests that cytokine neutralization relieves a negative feedback mechanism that functions to dampen cytokine production by monocytes.

Example 13

This example further demonstrates the use of SCNP to follow intracellular events in different discrete cell populations in communication, after stimulation with a modulator that affects only certain populations, and in the presence of an agent, in this case an inhibitor, that affects the intercellular communication by inhibiting an intercellular communication messenger. In this Example, the intercellular communication messenger is IL2 and the agent is anti-IL2.

Experimental conditions were as described in Example 10 regarding modulation with SAg and use of inhibitors.

Figure 24:
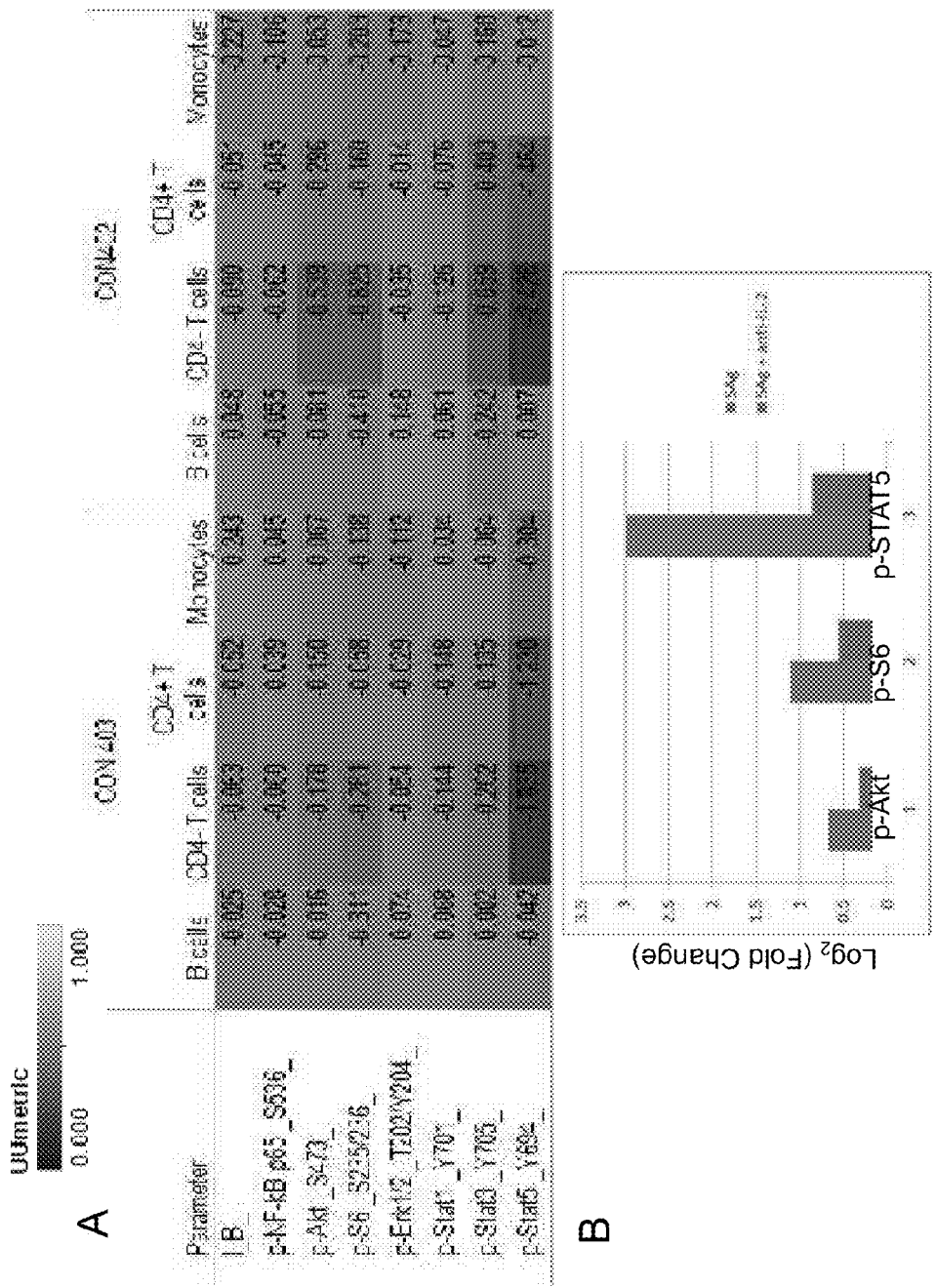
FIG. 24 shows the effects of IL-2 inhibition on various cell types modulated with SAg. A. Samples from 2 subjects, effects on various cell types at 24 hours. B. Effect of anti-IL2 in combination with SAg stimulation on various intracellular readouts in CD4+ T cells, left bar SAg alone, right bar SAg+anti-IL2.
Figure 26:
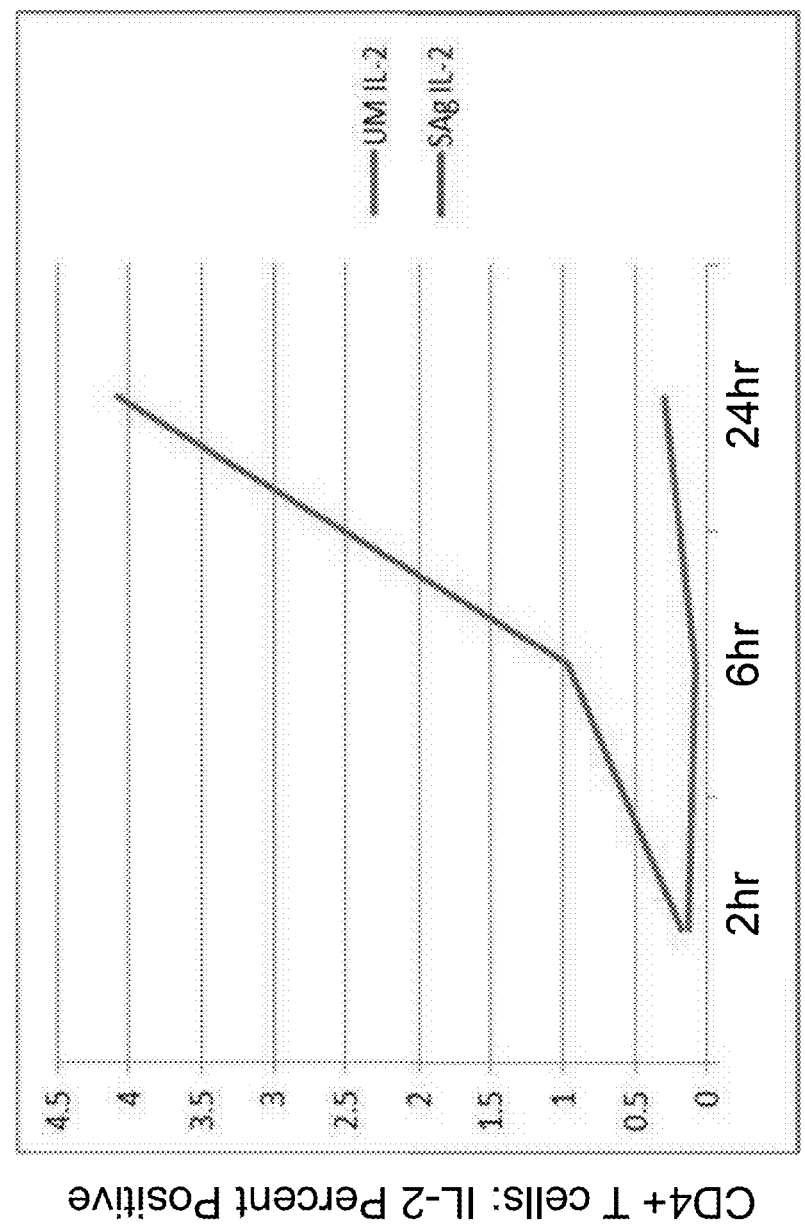
FIG. 26 SAg induces IL-2 production by CD4+ T cells. Bottom line: unmodulated. Top line: Modulated with SAg

It has been reported that IL-2 promotes PI3K activation in T cells, so SAg-modulated PBMCs were co-treated with anti-IL-2 for 24 hours for analysis of intracellular signaling. IL-2 neutralization resulted in dampened p-STAT5 and PI3K signaling preferentially in CD4− T cells. See FIG. 24; in 24B left bar is SAg−inhibitor, right bar is SAg+inhibitor. In concurrence, CD4+ T cells produced IL-2 between 6 and 24 hours post-SAg, in the absence of inhibitor. See FIG. 26, lower line unmodulated, upper line SAg modulated. Taken together, these data demonstrate the sequential contribution of individual cytokines towards cell subset specific pathway activation.

Example 14

Having observed inhibitor effects on SAg-induced signaling and cytokine production, similar analyses were extended to PBMCs treated with LPS. Experimental conditions were as described in Example 10, for LPS and for various inhibitors.

LPS activates monocytes, but not T cells, causing cytokine secretion that directs downstream signaling events in bystander cells.

As expected, LPS induced IL-6 and TNFα production by monocytes. See FIG. 13C,D. Addition of anti-TNFα enhanced the frequency of TNFα-producing monocytes compared to no inhibition at 6 hours (56% vs. 46%) and 24 hours (16% vs 8%). FIG. 13D. This finding supports the presence of a negative feedback loop, whereby TNFα autocrine signaling blocks further production of the cytokine. In comparison, anti-IL-6 did not enhance IL-6 production in monocytes. FIG. 13C.

Figure 22:
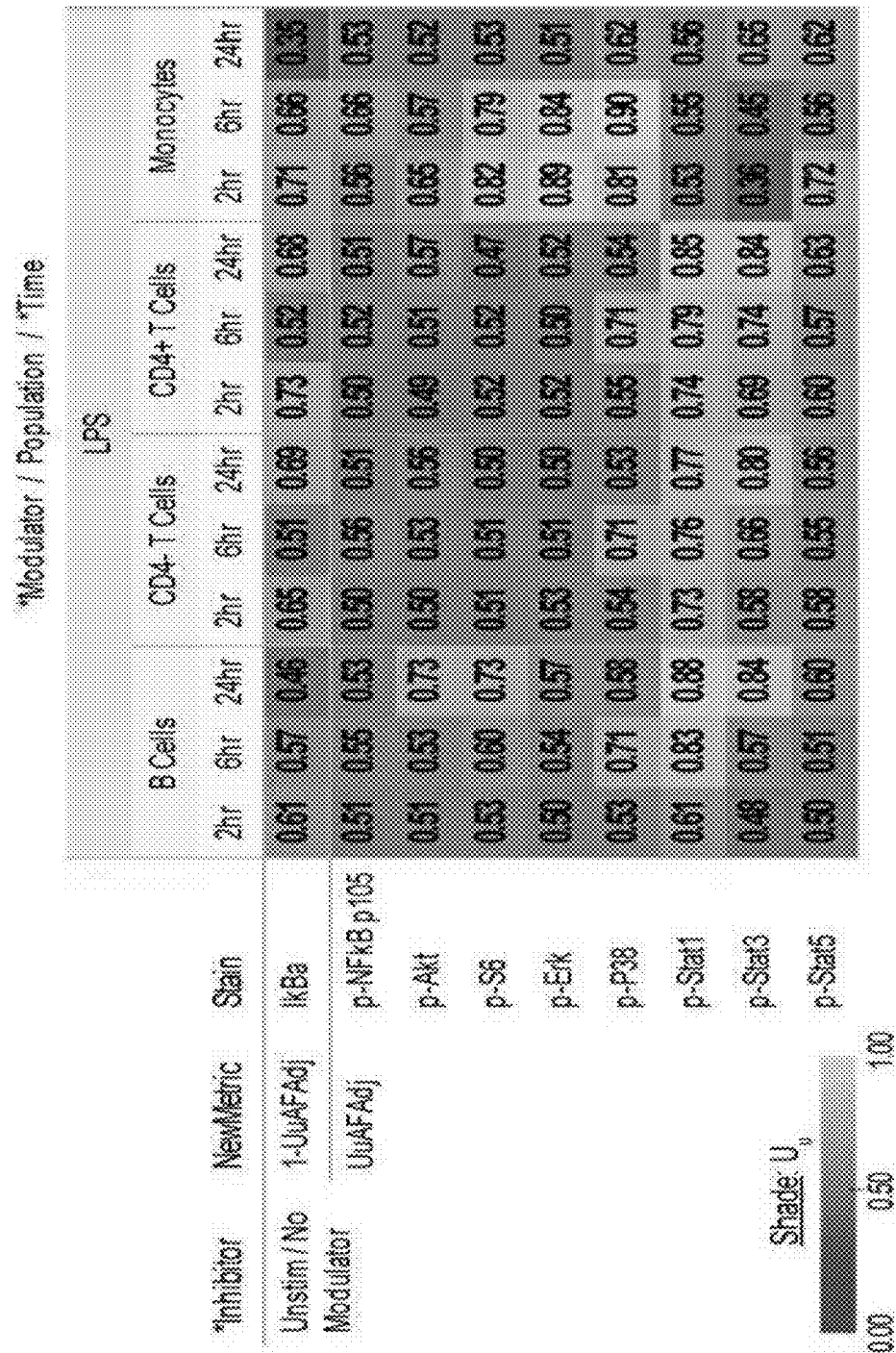
FIG. 22 shows the effects of LPS modulation (10 ug/ml) on intracellular readouts at various time points in B cells, CD4− cells, CD4+ cells, and monocytes. Metric is Uu, shown as 5-color heat map and as numbers within cells. PBMC from two healthy volunteers, values averaged.

As expected, LPS induced robust signaling in monocytes. In this cell subset, activity of NFκB, PI3K, and MAPK pathways ensued after 2 and 6 hours of LPS treatment, and this signaling was resolved by 24 hours. See FIG. 22. In accordance with the observed induction of IL-6 and TNFα in monocytes, LPS-treated PBMCs demonstrated a signaling profile consistent with these cytokines. STAT3 phosphorylation was induced in lymphocytes with sustained intensity through progression of the time course, potentially via IL-6. Likewise, the TNFα target IκBα was degraded in both monocytes and lymphocytes. In addition, p-STAT1 was induced in lymphocytes, and B cells exhibited PI3K pathway activity at 24 hours.

Figure 23:
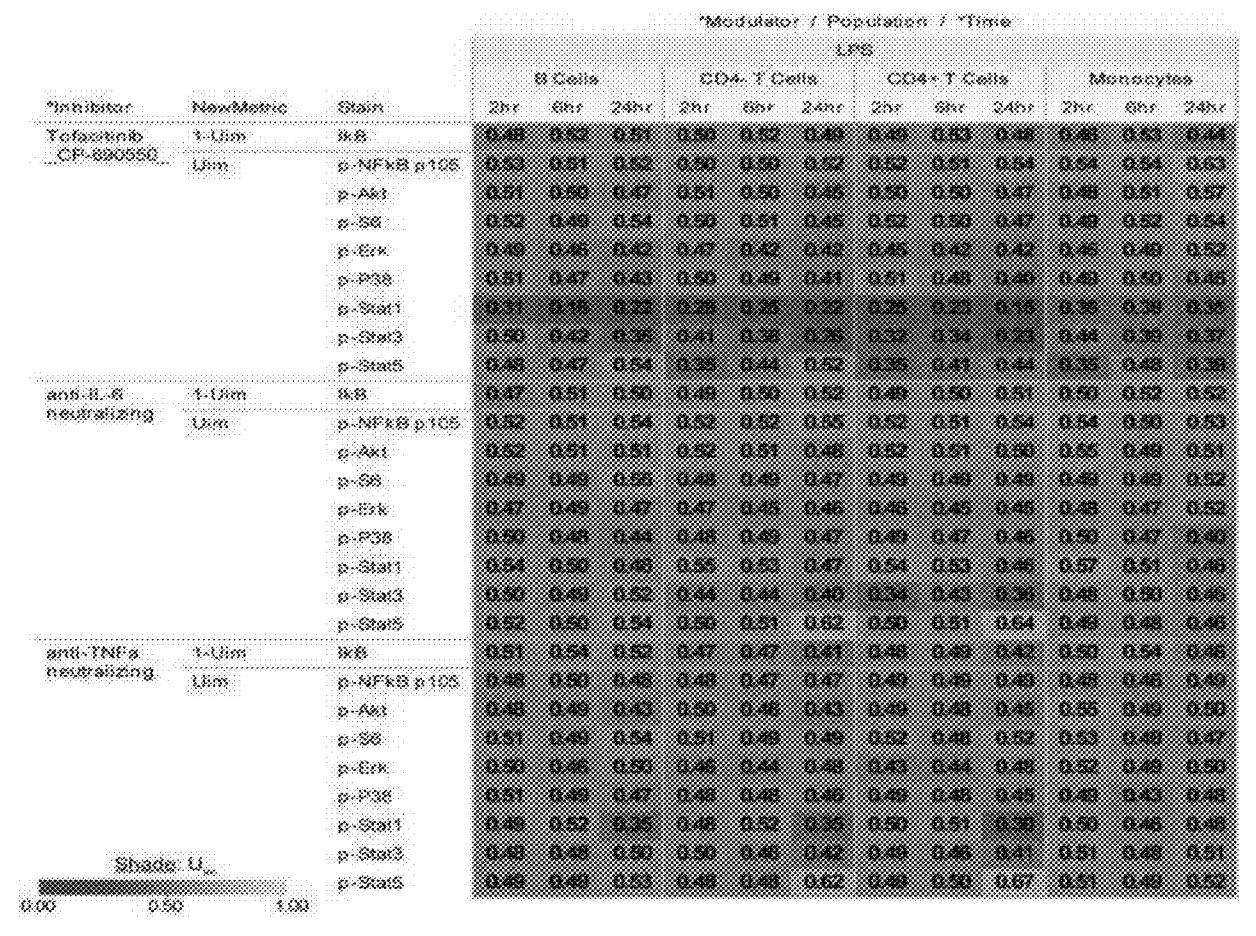

In order to examine the dependence of the observed signaling on IL-6 and TNFα, LPS-treated PBMCs were inhibited with neutralizing antibodies of these two cytokines, as well as with Tofacitinib. See FIG. 23. Tofacitinib completed abrogated p-STAT1 and p-STAT3 induction in lymphocytes at 2 hours, and partially inhibited p-STAT3 at later time points. For example, in CD4+ T cells p-STAT1 was inhibited by 102% and p-STAT3 by 99% at 2 hours, while at 24 hours p-STAT1 was inhibited 102% and p-STAT3 by 79%. This p-STAT3 induction was largely mediated through IL-6, as IL-6 neutralization resulted in 90% inhibition an 2 hours and 46% inhibition at 24 hours. Anti-TNFα predominantly exerted inhibitory effects in lymphocytes following 24 hours of LPS treatment. In CD4+ T cells, IκBα degradation was inhibited by 45% and p-STAT1 induction was inhibited by 58%. In contrast, no consistent inhibition was observed in monocytes (FIGS. 13 C,D)

Example 15

This example demonstrates Single Cell Network Profiling (SCNP) of IFN-α Signaling Pathways in Peripheral Blood Mononuclear Cells from Healthy Donors and its Implications for Disease Characterization, Treatment Selection, and Drug Discovery The antiviral and antitumor effects of IFN-α, have been exploited for the treatment of viral infections such as hepatitis C (HCV) as well as for various malignancies, such as hairy cell leukemia and melanoma. However, widespread use of IFN-α for these and other indications is severely hampered by significant side effects which can have a major impact on patient quality of life. Thus, a greater understanding of intracellular signaling pathways regulated by IFN-α may guide in the selection of patients whose disease will have an optimal response with tolerable side effects to this cytokine. Specifically, the Signal Transducer and Activation of Transcription (Stat) transcription factors are known to play a critical role in transducing IFN-α mediated signals. Single cell network profiling (SCNP) is a multiparameter flow-cytometry based approach that can be used to simultaneously measure extracellular surface makers and intracellular signaling proteins in individual cells in response to externally added modulators. Here, we use SCNP to interrogate IFN-α signaling pathways in multiple cell subsets within peripheral blood mononuclear cells (PBMCs) from healthy donors.

This study was designed to apply SCNP to generate a map of IFN-□-mediated signaling responses, with emphasis on Stat proteins, in PBMCs from healthy donors. The data provides a reference for future studies using PBMCs from patient samples in which IFN□□-mediated signaling is aberrantly regulated.

Methods:

IFN-α-mediated signaling responses were measured by SCNP in PBMC samples from 12 healthy donors. PBMCs were processed for flow cytometry by fixation and permeabilization followed by incubation with fluorochrome-conjugated antibodies that recognize extracellular lineage markers and intracellular signaling molecules. The levels of several phospho-proteins (p-Stat1, p-Stat3, p-Stat4, p-Stat5, p-Stat6, and p-p38) were measured in multiple cell populations (CD14+ monocytes, CD20+ B cells, CD4+ CD3+ T cells, and CD4− CD3+ T cells) at 15 minutes, 1, 2 and 4 hours post IFN-α exposure as described in Example 6.

Results:

The data revealed distinct phospho-protein activation patterns in different cell subsets within PBMCs in response to IFN-α exposure. For example, activation of p-Stat4 was detected in T cell subsets (both CD4+ and CD4− T cells), but not in monocytes or B cells. Such cell-type specific activation patterns likely play a key role in mediating specific functions within different cell types in response to IFN-α. Differences in the kinetics of activation by IFN-α for different phospho-proteins were also observed. The peak response for activation of p-Stat1, p-Stat3, and p-Stat5 was at 15 minutes in most of the cell types interrogated in this study, whereas for the activation of p-Stat4, p-Stat6, and p-p38 it was at 1 hr in the majority of cell types tested. The relationships between phospho-protein readouts in each cell subset were determined by calculating the Pearson correlation coefficients. For example, the activation of p-Stat1 and p-Stat5 at 15 minutes was positively correlated in both B cells and T cells. More results are provided in Example 6.

The activation of intracellular signaling proteins was measured with emphasis on Stat transcription factors in PBMC subsets from healthy donors. We have analyzed the relationships between the activation states of phospho-proteins in the IFN-α signaling network. Characterization of IFN-α signaling pathways in samples from healthy donors has provided a network map that can be used as a reference for identifying alterations in IFN-α signaling that are the consequence of disease and/or therapeutic intervention. Future studies using SCNP to characterize IFN-α signaling pathways in PBMCs from patients with diseases such as viral infections or cancer may enable the optimization of IFN-α dosing and the identification of patient stratification biomarkers as well as the discovery of novel therapeutic agents.

Example 16

A greater understanding of the function of the human immune system at the single cell level in healthy individuals can play a role in discerning aberrant cellular behavior that can occur in settings such as autoimmunity, immunosenescence, and cancer. To achieve this goal, a systems-level approach capable of capturing responses of interdependent immune cell types to external stimuli can be used. In this study, an extensive characterization of signaling responses in multiple immune cell subpopulations within PBMCs from a cohort of 60 healthy donors was performed using single cell network profiling (SCNP). SCNP can be a multiparametric flow-cytometry based approach that can enable the simultaneous measurement of basal and evoked signaling in multiple cell subsets within heterogeneous populations. In addition to establishing the inter-individual degree of variation within immune signaling responses, the possible association of any observed variation with demographic variables including age and race was investigated. Using half of the donors as a training set, multiple age- and race-associated variations in signaling responses in discrete cell subsets were identified, and several were subsequently confirmed in the remaining samples (test set). Such associations can provide insight into age-related immune alterations associated with high infection rates and diminished protection following vaccination and into the basis for ethnic differences in autoimmune disease incidence and treatment response. SCNP allowed for the generation of a functional map of healthy immune cell network responses that can provide clinically relevant information regarding both the mechanisms underlying immune pathological conditions and the selection and effect of therapeutics.

A systems-level approach can be used to provide a comprehensive understanding of how the function of the human immune system arises from the interactions among numerous inter-connected components, pathways, and cell types. Reductionist approaches that analyze individual components within the immune system have dominated in the past several decades primarily due to technological limitations. The recent development of high-throughput technologies is beginning to change the landscape of immunological studies and researchers are ushering in the new field of systems immunology (1). Here, a novel technology is described that can have an enormous impact on this burgeoning field because it can allow for simultaneous functional measurements from multiple cell subpopulations without the need for prior cell separation. This capability can enable a more integrated description of immune function than traditional studies which often focus on the behavior of specific cell types that have been physically isolated from heterogeneous tissues such as peripheral blood, spleen, or lymph nodes. This technology was applied to the characterization of immune cell signaling in healthy individuals to establish a reference functional map in the context of an immune cell signaling network, which can be used to elucidate aberrant network-level behaviors underlying the pathogenesis of immune-based diseases.

SCNP can be a multiparametric flow-cytometry based analysis that can simultaneously measure, at the single cell level, both extracellular surface markers and changes in intracellular signaling proteins in response to extracellular modulators. Measuring changes in signaling proteins following the application of an external stimulus informs on the functional capacity of the signaling network which cannot be assessed by the measurement of basal signaling alone (2). In addition, the simultaneous analysis of multiple pathways in multiple cell subsets can provide insight into the connectivity of both cell signaling networks and immune cell subtypes (3). SCNP technology can be used to investigate signaling activity within the many interdependent cell types that make up the immune system because it can allow for the simultaneous interrogation of modulated signaling network responses in multiple cell subtypes within heterogeneous populations, such as PBMCs, without the additional cellular manipulation that can be used for the isolation of specific cell types.

Summarized below are the results of an extensive characterization of immune cell signaling responses utilizing SCNP technology to quantify phospho-protein levels (pStat1, pStat3, pStat5, pStat6, pAkt, pS6, pNFκB, and pErk) within pathways downstream of a broad panel of immunomodulators (including IFNα, IFNγ, IL2, IL4, IL6, IL10, IL27, α-IgD, LPS, R848, PMA, and CD40L) in seven distinct immune cell subpopulations within PBMC samples from 60 healthy adults. This systems-level approach enabled the generation of a functional map of immune cell network responses in healthy individuals which serves as a reference for understanding signaling variations that occur in pathological conditions such as autoimmunity and to inform clinical decision-making in vaccination and other immunotherapeutic settings. In addition, inter-subject variation in immune signaling responses associated with demographic characteristics of the healthy donors such as age or race was identified.

Materials and Methods

PBMC Samples

Cryopreserved PBMC samples taken from 60 healthy donors within the Department of Transfusion Medicine, Clinical Center, National Institutes of Health with Institutional Review Board approval were used in this study (Table 4). Blood donations from healthy donors, donated for research purposes with informed consent, were collected and processed as described previously (4).

TABLE 4

Summary of donor numbers, age, race, and gender in the master, training, and test sample sets

| | Master | Training | Test |
|---|---|---|---|
| Number of Donors | 60 | 30 | 30 |
| Mean Age (Range) | 48.9 (19-73) yrs | 47.9 (22-73) yrs | 49.8 (19-73) yrs |
| Gender | 12 Female<br>48 Male | 5 Female<br>25 Male | 7 Female<br>23 Male |
| Race | 25 African American<br>34 European American<br>1 Hispanic | 10 African American<br>19 European American<br>1 Hispanic | 15 African American<br>15 European American<br>0 Hispanic |

SCNP Assay

Cryopreserved PBMC samples were thawed at 37° C. and resuspended in RPMI 1% FBS before staining with amine aqua viability dye (Invitrogen, Carlsbad, Calif.). Cells were resuspended in RPMI 10% FBS, aliquoted to 100,000 cells per well of 96-well plates, and rested for 2 h at 37° C. prior to 15 min 37° C. incubation with the following modulators: 1000 IU/ml IFNα (PBL, Piscataqay, N.J.); 250 ng/ml IFNγ, 50 ng/ml IL4, 50 ng/ml IL10, α-IgD 5 m/ml (BD, San Jose, Calif.); 50 ng/ml IL2, 50 ng/ml IL6, 50 ng/ml IL27, CD40L 0.5 μg/ml (R&D, Minneapolis, Minn.); R848 5 μg/ml (Invivogen, San Diego, Calif.); LPS 1 μg/ml, PMA 40 nM (Sigma Aldrich, St. Louis, Mo.). After exposure to modulators, cells were fixed with paraformaldehyde and permeabilized with 100% ice-cold methanol as previously described (5). Methanol permeabilized cells were washed with FACS buffer (PBS, 0.5% BSA, 0.05% NaN$_3$), pelleted, and stained with fluorochrome-conjugated Abs. Abs used include α-CD3 (clone UCHT1), α-CD4 (clone RPA-T4), α-CD45RA (clone HI100), α-CD20 (clone H1), α-pNFκB (clone K10-

895.12.50), α-cPARP (clone F21-852), α-pStat1 (clone 4a), α-pStat3 (clone 4/p-Stat3), α-pStat5 (clone 47), α-pStat6 (clone 18/p-Stat6), α-pErk (clone 20A) [BD, San Jose Calif.]; α-pAtk (clone D9E), α-pS6 (clone 2F9) [CST, Danvers, Mass.]; and α-CD14 (clone RMO52) [Beckman Coulter, Brea, Calif.].

Flow Cytometry Data Acquisition and Analysis

Flow cytometry data was acquired using FACS DIVA software (BD, San Jose, Calif.) on two LSRII Flow Cytometers (BD, San Jose, Calif.). All flow cytometry data were analyzed with WinList (Verity House Software, Topsham, Me.). For all analyses, dead cells and debris were excluded by forward scatter (FSC), side scatter (SSC), and amine aqua viability dye. PBMC subpopulations were delineated according to an immunophenotypic gating scheme (not shown).

SCNP Terminology and Metrics

The term "signaling node" can refer to a specific protein readout in the presence or absence of a specific modulator. For example, a response to IFNα stimulation can be measured using pStat1 as a readout. This signaling node can be designated "IFNα→pStat1". Each signaling node can be measured in each cell subpopulation. The cell subpopulation can be noted following the node, e.g., "IFNα→pStat1|B cells". Two different metrics are utilized in this study to measure the levels of intracellular signaling proteins in either the unmodulated state or in response to modulation. The "Basal" metric is used to measure basal levels of signaling in the resting, unmodulated state. The "Fold" metric is applied to measure the level of a signaling molecule after modulation compared to its level in the basal state. The Equivalent Number of Reference Fluorophores (ERFs), fluorescence measurements calibrated by rainbow calibration particles on each 96-well plate, serve as a basis for all metric calculations (6, 7).

The "Basal" and "Fold" metrics were calculated as follows:

Basal: $\log_2 [\text{ERF(Unmodulated)}/\text{ERF(Autofluorescence)}]$
Fold: $(\log_2 [\text{ERF(Modulated)}/\text{ERF(Unmodulated)}]+\text{Ph}-1)/\text{Ph}$ Where Ph is the percentage of healthy [cleaved PARP (poly ADP-ribose polymerase) negative] cells Statistical Analysis The high dimensionality of the SCNP data for individual nodes (i.e., combination of cell populations, modulators, and protein readouts) greatly increases the probability of finding chance associations in the data (i.e., false discovery). To address this issue, a multi-step analysis strategy designed to reduce the chance of false discoveries, by accounting for multiple testing and therefore reducing the chance of a Type 1 Error (incorrectly rejecting the null hypothesis) was followed. First, the data was split into training (30 samples) and test sets (30 samples) stratified randomly on race and age (Table 4). Multivariate linear regression was then used to find associations between individual immune signaling nodes and age and/or race in the training set. Associations with immune signaling were found by controlling for age and race. The exact form of the linear model used to test for significant associations between age, race and node signaling in the training data set was:

$$\text{SignalingNode}|\text{Population}=\alpha_1+\text{Age}^*\beta_1+\text{Race}^*\beta_2$$

Where Race was coded as (1=African American, 0=European American). Linear models were built for each signaling node in each of the following cell subpopulations: monocytes, B cells, naïve helper T cells, naïve cytotoxic T cells, memory helper T cells, and memory cytotoxic T cells. In the training data set, signaling nodes were considered to have a significant association with age for models in which $\beta_1$ has a significant p-value (<0.05) and a significant association for race for models in which $\beta_2$ has a significant p-value (<0.05). Discovering groups of signaling nodes rather than individual nodes can guard against finding chance associations. To create groupings of nodes, a principal component analysis (PCA, (8)) was performed both on the set of immune signaling nodes found to be significantly associated with age and also with the set of immune signaling nodes found to be significantly associated with race from the linear models in the training data. The PCA analysis accounted for correlation among signaling nodes, which can carry redundant information, by creating linear combinations of signaling nodes associated with age and/or race. In addition, to confirm the age and race associations in the test set a Gatekeeper strategy was used to control the Type 1 Error rate (9). In this strategy, each hypothesis to be validated in the test set can be pre-specified and sequentially ordered and subsequently tested in that order. A hypothesis can be considered validated if it is significant in the test set and all other hypotheses tested prior to it are significant. For this study, models using the first principal component from the age PCA and the first principal component from the race PCA were tested in the test set. The principal component PCA models for age and race which were locked (i.e., the model coefficients and PCA loadings matrices were locked) in the training set before being tested on the test set (in order) were of the form:

$$\text{Race}=\alpha_1+\text{NodePC}_1^*\beta_1+\text{Age}^*\beta_2$$

$$\text{NodePC}_1=\alpha_1+\text{Age}^*\beta_1+\text{Race}^*\beta_2$$

Only the first principal components were tested since both first principal components for both the age and race PCA both accounted for approximately 50% of the variance in training data. Only after the confirmation of the principal components in the test set were the contributions of the individual signaling nodes to the principal components for age and race associations examined, to understand the biology associated with age and/or race.

Correlations Between Signaling Nodes.

R software (version 2.12.1) was used to compute Pearson correlation coefficients between all pairs of signaling nodes within and between each of the seven distinct cell subpopulations. Heatmaps were generated in Excel 2007 (Microsoft, Redmond, Wash.).

Results

Cell-Type-Specific Patterns of Immune Signaling Responses in PBMCs from Healthy Donors Thirty eight signaling nodes, or specific protein readouts in the presence or absence of a specific modulator (Table 5), were measured in 12 cell populations defined by their surface phenotypes including 7 distinct immune cell subpopulations (monocytes, B cells, CD3-CD20-lymphocytes (NK cell-enriched subpopulation), naïve helper T cells, memory helper T cells, naïve cytotoxic T cells, and memory cytotoxic T cells, (data not shown)) within unsorted PBMC samples from 60 healthy donors (3) using two different metrics [Basal and Fold (Materials and Methods).

Table 5 shows the thirty-eight signaling nodes measured in the study. All signaling nodes were measured in each immune cell subpopulation.

TABLE 5

| | Signaling Node |
|---|---|
| 1 | IFNα → pStat1 |
| 2 | IFNα → pStat3 |
| 3 | IFNα → pStat5 |
| 4 | IFNα → pStat6 |
| 5 | IFNγ → pStat1 |
| 6 | IFNγ → pStat3 |
| 7 | IFNγ → pStat5 |
| 8 | IFNγ → pStat6 |
| 9 | IL2 → pStat5 |
| 10 | IL2 → pStat6 |
| 11 | IL4 → pStat5 |
| 12 | IL4 → pStat6 |
| 13 | IL6 → pStat1 |
| 14 | IL6 → pStat3 |
| 15 | IL10 → pStat1 |
| 16 | IL10 → pStat3 |
| 17 | IL27 → pStat1 |
| 18 | IL27 → pStat3 |
| 19 | IL27 → pStat5 |
| 20 | IL27 → pStat6 |
| 21 | α-IgD/LPS → pS6 |
| 22 | α-IgD/LPS → pAkt |
| 23 | R848 → pErk |
| 24 | R848 → pNFκB |
| 25 | CD40L → pErk |
| 26 | CD40L → pNFκB |
| 27 | PMA → pS6 |
| 28 | PMA → pErk |
| 29 | Unmodulated → pStat1 |
| 30 | Unmodulated → pStat3 |
| 31 | Unmodulated → pStat5 |
| 32 | Unmodulated → pStat6 |
| 33 | Unmodulated → pS6 |
| 34 | Unmodulated → pAkt |
| 35 | Unmodulated → pErk |
| 36 | Unmodulated → pNFκB |
| 37 | Unmodulated (DMSO) → pS6 |
| 38 | Unmodulated (DMSO) → pErk |

When gating on the viable cells (defined by scatter properties and amine aqua as described in Materials and Methods) only 15 of the 28 modulated signaling nodes showed a signaling response above the threshold level of Fold >0.25 representing an approximately 1.2 fold change in modulated levels relative to basal (see Materials and Methods), and a level of signaling that is very reproducible (data not shown). In contrast, when gating separately in the same samples on the 7 distinct immune cell subpopulations, 23 of these nodes showed induced signaling in at least one of the 7 subpopulations (data not shown), exemplifying the utility of SCNP in the identification of heterogeneous functionality in complex tissues and rare cell populations.

Other examples support this conclusion (data not shown). The TLR ligand R848 (Resiquimod) can be an immunomodulator that can portray cell-type specificity, and consistent with this induced pErk and pNFκB only in B cells and monocytes, immune cell subpopulations known to express the receptors (TLR7/8) for this ligand. In contrast to R848, IFNα can be a globally active immunomodulator due to the ubiquitous expression of the IFNα receptor on immune cells. As expected, at least one pStat protein was activated in response to IFNα in all of the immune cell subpopulations (data not shown) and this global responsiveness was reflected in the data from the Viable Cell population. Due to the generally reduced signaling responses from the more heterogeneous parental populations, in the sections below, data is reported primarily for the 7 distinct immune cell subpopulations.

Since the SCNP assay allows for an actual quantification of signaling responses, by measuring the degree of pathway activity for each node in each cell subpopulation, differential levels of activation in the different immune cell subtypes was observed. For example, as expected, modulation of PBMCs with IFNγ produced the highest level of pStat1 in monocytes, lower levels in B cells, and a much weaker pStat1 response in T cells (with differential levels of activation among the latter, i.e., naïve T cell subsets showing a higher level of response than their memory counterparts (data not shown). In contrast to IFNγ treatment, IL2 modulation of PBMCs led to pStat5 activation primarily in CD3-CD20-lymphocytes and T cells, again with differential activation levels seen among the T cell subsets and no effects on monocytes and B cells (data not shown).

Variation in Immune Signaling Responses in PBMCs from Healthy Individuals

For each of the 38 signaling nodes tested in the assay (listed in Table 5), the range of signaling responses in each immune cell subset across the 60 samples was quantified (data not shown). A comparison of the data obtained from the analysis of the training set and the test set revealed that, as expected, the distributions in the training and test set did not differ significantly for a majority of the signaling responses (p>0.05 for 98.9% of the 38 signaling nodes measured within each of the 7 distinct cell subsets). Although there was a narrow range of responses for the majority of the signaling nodes measured within the 7 distinct cell subsets, considerable inter-donor variation was observed for a subset of the modulated nodes (data not shown).

Immune Cell Signaling Network Map in PBMCs from Healthy Individuals

A functional map of the healthy immune cell signaling network was generated by calculating the Pearson correlation coefficients between pairs of nodes within and between each of the 7 distinct immune cell subpopulations. Overall, visualization of the healthy immune cell signaling network map revealed a high frequency of positively correlated signaling responses (data not shown). Cytokine-induced signaling responses within each subpopulation were highly positively correlated, with a no exception occurring for the naïve cytotoxic T cell subset for which IL10 and IL2 signaling responses were uncorrelated or weakly inversely correlated with responses to other cytokines (data not shown). Positive correlations among cytokine signaling responses were also present across different cell subpopulations with the strongest inter-subpopulation correlations generally occurring between pairs of nodes within the different T cell subsets. Intra-subpopulation correlations among cytokine-induced signaling responses and among PMA-induced signaling responses were weakest within the B cell subset, although strong positive correlations were present for signaling responses downstream of CD40L and between responses downstream of IgD crosslinking in this subpopulation.

Age and/or Race as Variables Associated with Immune Signaling Responses

Both age and race are known to be relevant to clinical outcomes in immune based disorders (10-12). Demographic heterogeneity of the 60 donor cohort (Table 4) allowed us to assess the association between immune signaling responses and age and/or race. Given the large dimensionality of the SCNP data for individual nodes (i.e., combination of cell populations, modulators, and protein readouts) the possibility of chance association (i.e., false discovery) is high. To address this issue, we followed a multi-step analysis strategy. First, the data was split into training (30 samples) and test sets (30 samples) randomly stratified on race and age. Multivariate linear regression was then used to find associations between individual immune signaling nodes and age and/or race in the training set. Because discovering groups of signaling nodes can guard against chance associations, a principal component analysis (PCA) was performed both on the set of immune signaling nodes associated with age and the set of signaling nodes associated with race. The PCA analysis accounted for the previously observed correlation among signaling nodes by combining the correlated signaling nodes associated with age or race in the training set. For confirmation of associations in the test set, a Gatekeeper strategy was used. The first principal component for both the age and race PCAs in the training set were locked and applied to the test set in a pre-specified order and significance level ($p<0.05$). Only after the confirmation of the principal components in the test set were the contributions of the individual signaling nodes to the principal components for age and race associations examined, to understand the biology associated with age and/or race.

The PCA for age-associated immune signaling was performed on 19 signaling responses found to be associated with age, controlled for race, in the training set ($p<0.05$, Table 6).

TABLE 6

Summary of age-associated signaling nodes identified in the training set. All age-associated responses identified in the training set are shown, and nodes which were confirmed in the test set are highlighted in gray. A negative slope indicates a negative correlation with age.

| | Training | | | Test | | |
|---|---|---|---|---|---|---|
| Node \| Population | $R^2$ | Age slope | Age p-Value | $R^2$ | Age slope | Age p-Value |
| IFNα → pStat1 \| Naive cytotoxic T cells | 0.434 | −0.014 | 0.000 | 0.129 | −0.012 | 0.069 |
| IFNα → pStat3 \| Naive cytotoxic T cells | 0.249 | −0.006 | 0.013 | 0.043 | −0.003 | 0.399 |
| IFNα → pStat5 \| Naive cytotoxic T cells | 0.325 | −0.013 | 0.002 | 0.206 | −0.016 | 0.017 |
| IFNα → pStat6 \| Memory helper T cells | 0.644 | −0.002 | 0.031 | 0.003 | 0.000 | 0.875 |
| IFNγ → pStat1 \| Naive cytotoxic T cells | 0.422 | −0.007 | 0.000 | 0.131 | −0.005 | 0.074 |
| IL10 → pStat3 \| Naive cytotoxic T cells | 0.201 | 0.010 | 0.022 | 0.059 | 0.005 | 0.368 |
| IL2 → pStat5 \| Naive helper T cells | 0.539 | 0.027 | 0.000 | 0.201 | 0.023 | 0.022 |
| IL2 → pStat6 \| Naive helper T cells | 0.291 | −0.007 | 0.011 | 0.122 | 0.004 | 0.176 |
| IL27 → pStat1 \| Naive cytotoxic T cells | 0.310 | −0.026 | 0.010 | 0.076 | −0.017 | 0.168 |
| IL27 → pStat5 \| Naive cytotoxic T cells | 0.234 | −0.010 | 0.011 | 0.222 | −0.009 | 0.016 |
| IL27 → pStat6 \| Naive cytotoxic T cells | 0.278 | −0.003 | 0.049 | 0.009 | −0.001 | 0.678 |
| IL4 → pStat6 \| Naive cytotoxic T cells | 0.187 | −0.012 | 0.026 | 0.234 | −0.013 | 0.020 |
| IL6 → pStat1 \| Naive cytotoxic T cells | 0.342 | −0.009 | 0.002 | 0.129 | −0.008 | 0.074 |
| IL6 → pStat3 \| Naive cytotoxic T cells | 0.340 | −0.016 | 0.003 | 0.082 | −0.014 | 0.148 |
| PMA → pErk \| B cells | 0.201 | 0.009 | 0.040 | 0.005 | −0.001 | 0.816 |
| PMA → pErk \| Naive helper T cells | 0.331 | 0.012 | 0.026 | 0.005 | −0.001 | 0.816 |
| Unmodulated → pS6 \| Memory cytotoxic T cells | 0.199 | −0.002 | 0.020 | 0.028 | −0.001 | 0.519 |
| Unmodulated (DMSO) → pS6 \| Memory cytotoxic T cells | 0.167 | −0.002 | 0.036 | 0.064 | −0.001 | 0.208 |
| Unmodulated → pStat1 \| Memory cytotoxic T cells | 0.201 | 0.002 | 0.038 | 0.114 | 0.001 | 0.245 |

The first principal component for age accounted for 45% of the variance. Examination of the 19 individual signaling nodes revealed that one of these responses (PMA→pErk|B cells) was within the B cell subpopulation, while all of the remaining responses were within T cell subsets with the highest number occurring within the naïve cytotoxic T cell subset. Only 3 unmodulated nodes (Unmodulated→pS6|Memory cytotoxic T cells, Unmodulated (DMSO)→pS6|Memory cytotoxic T cells, and Unmodulated→pStat1|Memory cytotoxic T cells, Table 6) were found to be associated with age in the training set.

The PCA for race-associated immune signaling included 18 signaling responses found to be associated with race, controlled for age, in the training set ($p<0.05$, Table 7).

TABLE 7

Summary of race-associated signaling nodes identified in the training set. All of the race-associated responses identified in the training set are shown, and nodes which were confirmed in the test set are highlighted in gray. A positive slope indicates nodes that were more responsive in AAs than in EAs.

| Node | Population | Training $R^2$ | Race slope | Race p-Value | Test $R^2$ | Race slope | Race p-Value |
|---|---|---|---|---|---|---|
| IFNα → pStat3 | Memory cytotoxic T cells | 0.224 | 0.140 | 0.016 | 0.133 | −0.054 | 0.314 |
| IFNα → pStat3 | Memory helper T cells | 0.198 | 0.110 | 0.030 | 0.111 | −0.018 | 0.751 |
| IFNα → pStat5 | Monocytes | 0.343 | 0.100 | 0.025 | 0.015 | −0.038 | 0.534 |
| IFNα → pStat5 | Naïve helper T cells | 0.293 | 0.170 | 0.047 | 0.182 | −0.117 | 0.280 |
| IFNγ → pStat1 | Memory helper T cells | 0.234 | 0.060 | 0.048 | 0.032 | −0.015 | 0.699 |
| α-IgD + LPS → pAkt | B cells | 0.386 | −0.390 | 0.001 | 0.265 | −0.347 | 0.006 |
| α-IgD + LPS → pS6 | B cells | 0.277 | −0.680 | 0.008 | 0.228 | −0.617 | 0.018 |
| IL10 → pStat1 | Memory helper T cells | 0.187 | 0.050 | 0.024 | 0.097 | −0.038 | 0.126 |
| IL10 → pStat3 | Memory cytotoxic T cells | 0.244 | 0.280 | 0.018 | 0.034 | −0.084 | 0.439 |
| IL10 → pStat3 | Memory helper T cells | 0.174 | 0.200 | 0.047 | 0.003 | −0.026 | 0.816 |
| IL27 → pStat1 | Memory cytotoxic T cells | 0.288 | 0.350 | 0.008 | 0.028 | −0.004 | 0.975 |
| IL27 → pStat3 | Memory cytotoxic T cells | 0.357 | 0.240 | 0.003 | 0.008 | −0.026 | 0.671 |
| IL6 → pStat1 | Memory cytotoxic T cells | 0.335 | 0.080 | 0.002 | 0.044 | −0.030 | 0.278 |
| IL6 → pStat3 | Memory cytotoxic T cells | 0.297 | 0.290 | 0.006 | 0.031 | −0.051 | 0.406 |
| IL6 → pStat3 | Memory helper T cells | 0.182 | 0.280 | 0.031 | 0.014 | −0.057 | 0.717 |
| R848 → pNFκB | Memory B cells | 0.279 | −0.090 | 0.021 | 0.040 | −0.027 | 0.579 |
| R848 → pNFκB | Memory helper T cells | 0.258 | 0.030 | 0.016 | 0.121 | 0.008 | 0.603 |
| Unmodulated → pStat5 | Memory cytotoxic T cells | 0.568 | 0.039 | 0.043 | 0.017 | −0.002 | 0.881 |

The first principal component for race accounted for 54% of the variance. The 18 race-associated signaling responses consisted of a slightly more diverse set of cell subpopulations than the age-associated responses and included responses to several cytokines, the TLR ligand R848, and IgD crosslinking. Only one unmodulated node (Unmodulated→pStat5|Memory cytotoxic T cells) was associated with race in the training set.

The first principal component for age (locked from the training set) was significant in the test set (p<0.05), confirming that age can explain some of the observed inter-donor variation in immune signaling responses. After confirmation, this first principal component was dissected by inspecting the loadings matrix and whether or not the node was significant in both the test and training set, to further examine the underlying biology. Four individual signaling responses (IFNα→pStat5|Naïve cytotoxic T cells, IL27→pStat5|Naive cytotoxic T cells, IL4→pStat6|Naive cytotoxic T cells, IL2→pStat5|Naive helper T cells, Table 6) were found to have high loadings and were significantly associated with signaling in the test set as well. Of note, none of the unmodulated nodes with age-associations in the training set were individually significant in the test set. Exemplifying the SCNP assay advantage of subpopulation analysis, we confirmed that the IL4→pStat6 signaling node demonstrated a statistically significant decrease with age specifically within naïve cytotoxic T cells (data not shown; Table 6). A trend of decreasing signaling response with age was seen one level up the population hierarchy in the overall cytotoxic T cells, but this association was dampened by the memory cytotoxic T cells whose IL4→pStat6 signaling response showed no association with age and thus did not reach statistical significance in the overall cytotoxic T cell subset (data not shown). All 3 signaling nodes within the naïve cytotoxic T cell compartment (IFNα→pStat5, IL27→pStat5, and IL4→pStat6) were positively correlated with each other and all showed decreased responsiveness with age (Table 6, data not shown), while IL2→pStat5 activation within naive helper T cells increased with age and was uncorrelated with the three naïve cytotoxic T cell signaling nodes (Table 6, data not shown).

The race model, based on the first principal component for race (locked from the training set), was also significant in the test set (p<0.05), confirming that race is associated with differences in immune signaling responses (data not shown). After confirmation, this first principal component was also dissected to further examine the underlying biology. Two individual race-associated responses had high loadings and were significant in both the test and training sets. Both of these were within the B cell population (α-IgD/LPS→pAkt and α-IgD/LPS→pS6 nodes, data not shown, Table 7) and both showed greater levels of responsiveness in the European American (EA) donors than in the African American (AA) donors (data not shown), and they were highly correlated (r=0.81).

Defining the range of immune signaling activity in multiple immune cell subsets and establishing an overall map of the immune cell signaling network in healthy individuals can be used as a first step in providing a baseline for the characterization of aberrant signaling responses and changes in the immune signaling network architecture that occur in diseases such as cancer and autoimmune disorders. Because the immune system consists of multiple interdependent cell types whose behavior is mediated by complex intra- and inter-cellular regulatory networks, a comprehensive description of healthy immune function can use a systems-level approach capable of integrating information from multiple cell types, signaling pathways, and networks. In this Example, SCNP was used to perform a broad functional characterization of the healthy immune cell signaling network. As expected, many of the immunomodulators included in this study evoked cell-type specific responses (data not shown), highlighting the complexity of the regulation of biological function during immune responses. For a subset of the modulators and specific cell types investigated in this study, differential receptor expression and/or differential activation patterns have been previously reported. In instances where such data is available, the cell-type specific signaling responses described here are generally consistent with those reports (13-15).

To gain insight into the connectivity of the immune cell signaling network, node-to-node correlations within and between each of the distinct immune cell subpopulations were mapped. A high-level analysis of this map revealed an abundance of positively correlated nodes, with a higher frequency of positive correlations for node-to-node pairs within the same immune cell subset than for pairs of nodes spanning different cell types (data not shown). Very few nodes were inversely correlated with the most notable exceptions occurring for IL10- and IL2-induced responses which showed weak inverse correlations with other cytokine-induced signaling responses specifically within the naïve cytotoxic T cell subset. This map can be compared with those generated using samples from patients with immune-based disorders to identify changes in the network architecture that occur under pathological conditions, and can be applied to the analysis of samples obtained longitudinally from treated patients to monitor individual responses to therapeutics.

Aging is often accompanied by a deterioration of the immune system, resulting in a higher susceptibility to infections and lower efficacy of vaccination in the elderly population (16-18). Given the multitude of age-associated alterations in the function of the immune system, with some of the most profound occurring in T cells subsets (18, 19), it was hypothesized that age may have an impact on the cell signaling responses measured in this study.

The results shown here demonstrate that some of the variation in healthy immune signaling responses can in fact be attributed to donor demographic characteristics such as age or race. Specifically, the analysis provided herein of the impact of age on immune signaling responses has revealed 4 individual signaling nodes with significant associations with age. Strikingly, all 4 of the individual age-associated immune signaling responses identified here were within naïve T cells, a cell type which has been previously reported to undergo age-related functional changes such as reduced proliferation and cytokine production (18).

The majority (3 of 4) of the individual age-associated signaling nodes confirmed in the PCA analysis and with statistical significance in both training and test sets occurred within the naïve cytotoxic T cell subset, while only 1 of the 4 resided in the naive helper T cell subset. One of the most dramatic age-related changes in the cytotoxic T cell subset is a decrease in the frequency of naïve cytotoxic T cells with age (19, 20), and this was also observed in the samples analyzed in this study (data not shown). Additionally, we have observed an age-related decline in JAK-STAT signaling activity in the naïve cytotoxic T cell subset in response to multiple cytokines including IFNα, IL4, and IL27 (Table 6). Signaling elicited by these cytokines plays a role in cytotoxic T cell survival, proliferation and differentiation (21-24). Thus, the observed age-related decrease in responsiveness to these cytokines may underly some of the functional changes within the cytotoxic T cell compartment. For example, loss of the costimulatory receptor CD28 occurs frequently with increasing age (19) and the resultant CD28− cytotoxic T cells show reduced proliferation, resistance to apoptosis, and higher expression of effector proteins. In addition, a high frequency of CD28− cytotoxic T cells has been shown to correlate with decreased responses to vaccination (25).

The single naïve helper T cell age-associated signaling node was an increased IL2-induced activation of Stat5 (Table 6). This signaling pathway is required for T cell proliferation and activation (26, 27), and both the production of IL2 and the proliferation of naïve helper T cells have been shown to decrease with age (28). The data reported here suggest that the use of IL2 can be an effective strategy for rescuing naïve helper T cell proliferation in the elderly.

Overall, the results reported here provide evidence of age-associated alterations in T cell cytokine signaling responses, with the most striking differences occurring specifically within the naïve cytotoxic T cell subset. While age-associated differences in T cell signaling through the TCR have been widely reported (29), relatively few studies have documented age-related differences in human T cell cytokine signaling (30). Further, much of the work that has been conducted to examine associations between T cell cytokine signaling responses and age has been performed using isolated T cells with techniques such as Western blot analysis that allow for only population-level measurements of pathway activation. Analyses performed at the level of total T cells may fail to capture age-associated alterations specific to a given T cell subset.

The age-associated naïve T cell cytokine signaling responses identified here can play a role in age-related increase in susceptibility to infection, decline in vaccine responsiveness, and the prevalence of certain autoimmune diseases.

Differences in signaling between AAs and EAs, the two major ethnic groups with sufficient representation in this study cohort for statistical analysis, were examined. Because ethnic-related differences have been reported in the prevalence of autoimmune diseases such as systemic lupus erythematosus (31) and multiple sclerosis (32) and in response rates to immunotherapies such as IFNα (10), Benlysta/belimumab (11), and stem cell transplantation (12), it was hypothesized that some of the variation in immune signaling responses may be attributable to racial differences among the study donors. Our assessment of race-associated signaling responses revealed that BCR-(α-IgD) induced PI3K pathway activity was significantly higher in EAs than in AAs. While BCR crosslinking can lead to the activation of multiple signaling pathways, BCR-mediated activation of the PI3K pathway has been shown to provide signaling that plays a role in B cell survival (33). Thus, the differences in PI3K pathway activity observed here can result in racial differences in B cell fate in response to BCR stimulation.

Controlling for ethnicity is emerging as a key component in assuring the accuracy of clinical diagnostics (34) and in selecting treatments (11). For example, AAs and EAs infected with hepatitis C virus have been shown to differ in their response rates to IFNα-based therapy (35) and this has been shown to correlate with in vitro IFNα response profiles (36).

This work demonstrated the utility of the SCNP technology in providing a systems-level description of immune signaling responses within interdependent immune cell subpopulations. Applying this approach to the characterization of immune cell signaling in a cohort of healthy donors allowed for the quantification of the range of signaling across donors and revealed tight ranges for the immune signaling responses measured suggesting that the activation of these signaling nodes can be highly regulated in healthy individuals. Although inter-subject differences in immune signaling responses were generally quite low, within the subset of nodes that displayed the most substantial inter-donor variation some of the variation in immune signaling pathway activation could be attributed to differences in demographic factors such as age or race. Overall, the healthy immune cell signaling network map generated here provides a reference for comparison with network maps generated under disease-associated conditions, using samples from patients at baseline or over the course of therapeutic intervention to identify immune network restructuring that is thought to occur under therapeutic pressure and to guide therapeutic selection.

Example 17

Overview

Given the biologic and clinical heterogeneity inherent to AML, an unmet medical need exists for tools to guide the choice of drugs most relevant to the underlying biology of the individual AML. Single Cell Network Profiling (SCNP) can be used as a tool to inform biology-based clinical decision making including therapy selection and disease monitoring. Previous studies have provided preliminary proof-of-concept on the utility of SCNP to dissect the pathophysiologic heterogeneity of hematologic tumors and assess their differential response to single agent and combination therapies. This study characterizes the signal transduction networks implicated in the growth and survival of AML cells and how those are affected by in vitro exposure to various FDA-approved and investigational therapeutic agents. Compounds were selected based on their ability to disrupt key mechanisms of AML tumor cell growth and survival.

Design:

This study used peripheral blood or bone marrow samples (n=9), which had been previously ficoll separated and cryopreserved. Patient characteristics are shown Table 8. One cryovial per patient was used. Samples were thawed and centrifuged over ficoll to remove dead cells and debris.

TABLE 8

Patient Characterisics

| Reference | Disease | Sample Timepoint | Receipt date | Age | Usage |
|---|---|---|---|---|---|
| 1910-006 | AML | Pre-induction | Dec. 2, 2010 | 36 | 1 vial (10 million cells) |
| 1910-008 | AML | Post-induction Resistant | Dec. 2, 2010 | 47 | 1 vial (10 million cells) |
| 1910-011 | AML | Post-induction Resistant | Feb. 18, 2011 | 52 | 1 vial (10 million cells) |
| 1910-013 | AML | Relapse On Therapy | Jan. 15, 2011 | 60 | 1 vial (10 million cells) |
| 1910-015 | AML | Pre-induction | Jan. 19, 2011 | 83 | 1 vial (10 million cells) |
| 1910-016 | AML | Post-induction Resistant | Feb. 23, 2011 | 37 | 1 vial (10 million cells) |
| 1910-017 | AML | Pre-induction | Feb. 9, 2011 | 71 | 1 vial (10 million cells) |
| 1910-018 | AML | Relapse Off Therapy | Feb. 10, 2011 | 66 | 1 vial (10 million cells) |
| 1910-019 | AML | Pre-Induction | Apr. 13, 2011 | 24 | 1 vial (10 million cells) |

Samples were split to perform the following: Arm #1 assessed basal and modulated signaling in the JAK/STAT, PI3K/mTor, and MEK/ERK pathways in the presence and absence of specific kinase inhibitors. Kinase inhibitors were added 1 hr before the addition of the signaling stimulus. Signaling was induced by individual addition of stem cell factor, Flt3 ligand, G-CSF, IL-3, or thrombopoietin (TPO) for a short period of time (5-15 min). Cells were then fixed, permeabilized, and stained with a cocktail of cell surface and phospho-specific antibodies to measure signaling in multiple cell types. Signaling data is calculated in each cell type using a fold-change metric comparing each condition to its basal state: example: (stimulated$^{+/-inhibitor}$)/(unstimulated). Also, cells with an apoptotic phenotype were excluded from the signaling analysis by gating.

Arm #2 assessed the cytotoxic and cytostatic impact of various drugs as single agents and in combinations (including the specific kinase inhibitors tested in arm #1). Here the cells from each donor were cultured in the presence of TPO, IL-3, SCF, and FLT3L for 2 days to drive proliferation. After 2 days the cells were then distributed into wells containing various drugs, wherein the cells were cultured for 48 hours. The cultures were fixed, permeabilized, and stained with a cocktail of antibodies to measure complete cell death, apoptosis, S/G2 phase, M-Phase, and DNA damage. These readouts were also obstained from samples cultured separately with individual growth factors (no drugs) for 4 days.

A schematic of the experiment is shown in FIG. 3. (NOTE: All figures referenced in this Example are to U.S. patent application Ser. No. 13/750,700, filed Jan. 25, 2013, and PCT Application No. US2011/01565, filed Sep. 8, 2011, which are incorporated by reference)

Examples of reports for a subject (#1910-017) are shown in FIGS. 8, 9, and 10. In FIG. 8A, a cell lineage diagram is depicted. Percentages of cell types are show for subject #1910-017 (circle on graph, e.g., see FIG. 8B) and for healthy or normal cells (bar on graph). The report depicts fold activation of activatable elements relative to a basal state in radar plot form to allow comparison of the subject sample with fold activation ranges for normal samples (see e.g., FIG. 8B). Fold activation is indicated for samples that were or were not contacted with a kinase inhibitor. FIGS. 8B, 8C, 8D, and 8E show information for different cell types.

Another form of a report is depicted in FIG. 9. FIG. 9A indicates percentages of cells in a ring diagram. The outer circle corresponds to cells in the #1910-017 AML sample of PBMCs pre-induction. The inner circle corresponds to percentages of cells in healthy bone marrow. The percentages do not add up to 100%, as some types cells are not included. Fold change from basal state of cell signaling is indicated as a heat map.

For CD34+ cells, patient #1910-017 has high basal p-AKT level that is attenuated by PI3K/mTor inhibitor, but not FLT3 inhibitor. This suggests that the high basal level is not a function of high FLT3 activity. There is also a high p-STAT5 basal level. There is no FLT3L or G-CSF responses, which are observed in healthy CD34+ cells. The CD34-CD117+ cell population has a similar signaling phenotype as the CD34+ cells. The CD34-CD117- cells respond strongly to TPO, but not to G-CSF. The lymphocytes have no signaling. High basal level of p-STAT5 signaling is inhibited by CP-690550.

The report indicates drug responses. The response to AC220 is not known due to no FLT3L induced signaling in #1910-017. With respect to GDC-0941, there is partial inhibition of SCF-pAKT and pS6. With respect to AZD-6244, there is complete inhibition of SCF-pERK, partial inhibition of pS6, and no inhibition of pAKT. With respect to BEZ235, there is complete inhibition of SCF induced pAKT, and partial inhibition of pS6. With respect to CP-690550, there is complete inhibition of IL-3 signaling, and partial inhibition of TPO signaling.

FIG. 9D shows growth factor dependent effects on cell growth and survival. Survival and cell growth appear independent of growth factor stimulation.

FIGS. 9D and 9E show drug induced apoptosis and cytostasis. In general, this patient's myeloid cells resisted apoptosis for most drugs, including AraC. However, inhibition of cell cycle (M-phase) was observed for many drugs. Proteosome inhibition (bortezomib) induced considerable levels of cell death and cytostasis. HSP90 inhibitor also induced apoptosis.

FIG. 10 shows another example of a report for a subject (#1910-017). FIG. 10 illustrates information on percentage of cell types (based on surface phenotype) in a sample from the subject and percentages of cell types in normal or healthy cells (see e.g., FIG. 10G). FIG. 10 contains biological information on the cell types (see e.g., FIG. 10B). Information on signaling phenotypes are illustrated as radar plots (see e.g., FIGS. 10C, 10D, 10E, and 10F). The report in FIG. 10 also contains information on cell growth and cell survival and cytostasis after drug exposure.

Example 18

This Example demonstrates the use of various modulators, e.g., TLR modulators and T cell modulators, and a time course analysis for responses of various discrete cell populations SCNP Assay PBMCs were thawed and debris removed by a ficoll gradient purification. Cells were plated in 96-well plates at 100,000 cells in 100 uL per well, and rested for 2 hours at 37 C. Cells were either untreated or treated for 5 hr, 24 hr, or 48 hrs with 10 ug/ml LPS (Sigma), 5 ug/ml R848 (invitrogen), 10 ug/ml CpG-B (invivogen), 100 ng/ml Pam3Cys, 100 ng/ml IL-23 (R&D systems), a combination of 1 ug/ml biotinylated anti-CD3 Ab, 1.25 ug/ml biotinylated anti-CD28 Ab, 50 ug/ml avidin (eBioscience), or a combination of LPS, anti-CD3, anti-CD28, and avidin. Following sample activation, cells were fixed with 1.6% paraformaldehyde at 37 C for 10 minutes, then resuspended in cold methanol and stored at −80 C.

Flow Cytometry

For cell staining, cells were washed with fluorescence-activated cell sorting buffer (PBS/0.5% bovine serum albumin/0.05% NaN3), pelleted, and stained with cocktails of fluorochrome-conjugated antibodies. These cocktails included antibodies against cell surface markers for monocytes (CD14), B cells (CD20) and T cell subsets (CD3, CD8, and CD4), the apoptotic marker cleaved PARP (cPARP), and antibodies against intracellular signaling molecules and cytokines. Flow cytometry data were acquired on a LSRII flow cytometer using FACSDiva software (BD Biosciences) and analyzed with FlowJo (TreeStar Software) or Winlist (Verity House Software). Cells were gated by light scatter properties and cPARP expression to identify non-apoptotic cells, and then surface markers to identify specific cell lineages.

Intracellular readouts assayed were as described in Examples 8-15.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

We claim:

1. A method of evaluating the effects of a modulator on a plurality of discrete cell populations in communication, comprising (i) preparing a culture from a sample that has been removed from an individual, wherein the culture comprises a plurality of discrete cell populations derived from the sample in communication, and wherein the plurality of discrete cell populations comprises a first discrete cell population comprising monocyte cells and a second discrete cell population comprising a T-lymphocyte cells; (ii) contacting a first cell from the first discrete cell population in the culture with a modulator, wherein the modulator interacts with the first cell population but does not interact with the second discrete cell population in the culture, wherein the modulator comprises a toll-like receptor (TLR) activator; (iii) incubating the culture for a period of time; and (iv) after the incubation, determining an activation level of a first activatable element in single cells from the second cell population, wherein the activatable element is p-ERK or p-AKT.

2. The method of claim 1, wherein potential communication between the first and second cell populations is evaluated based, at least in part, on the activation level of the first activatable element in single cells from the second cell population.

3. The method of claim 1 further comprising determining an intracellular level of an intercellular communication messenger in single cells from the second discrete cell population, wherein the intercellular communication messenger is a cytokine.

4. The method of claim 3 wherein the cytokine is selected from the group consisting of IL1, IL2, IL3, IL4, IL5, IL6, IL8, IL9, IL10, IL12, IL15, IL17A, IL17F, IL21, IL23, TNFα, TNFβ, IFNα, IFNβ, and IFNγ.

5. The method of claim 1 wherein either the culture is sampled at a plurality of time periods and step (iv) is performed on a sample from each of the time periods, or steps (i)-(iv) are performed on a plurality of cell cultures under substantially the same conditions except the cell cultures are incubated for different periods of time.

6. The method of claim 5 wherein the activation levels of the first activatable element in cultures incubated for different periods of time are compared in a kinetic analysis.

7. The method of claim 6 wherein the kinetic analysis is used to produce an intercellular communication profile for the second discrete cell type.

8. The method of claim 1 wherein steps (i)-(iv) are performed on a second cell culture under substantially the same conditions except that no modulator is added to the second cell culture, and the activation level of the first activatable element in the first cell culture is compared to the activation level of the first activatable element in the second cell culture.

9. The method of claim 1 wherein activation levels of the first activatable element are determined on a single cell-by-cell basis in a plurality of cells in the second cell population.

10. The method of claim 1 further comprising adding an agent that affects one or more intercellular communication messengers to the culture.

11. The method of claim 1 further comprising adding an agent that affects one or more intracellular pathways involved in intercellular communication to the cell culture.

12. The method of claim 10 wherein the agent is added at the same time as the modulator, or at substantially the same time as the modulator.

13. The method of claim 1 further comprising determining a status for the individual, based at least in part on a metric for the individual derived at least in part from the result of step (iv).

14. The method of claim 13 wherein the status is a health status.

15. The method of claim 14, wherein the health status comprises presence or absence of a condition, status of a condition, prognosis of a condition, or responsiveness to therapy for a condition, or a combination thereof.

16. The method of claim 13 wherein the determination of the status of the individual, is based at least in part on a comparison of the individual metric with a standard metric, wherein the standard metric is derived, at least in part, from the activation level or levels of the first activatable element in a second cell population in a plurality of cultures each comprising a plurality of discrete cell populations in communication, each culture being derived from samples removed from a plurality of healthy individuals and treated substantially as in steps (i)-(iv).

17. The method of claim 16 wherein the standard metric is further derived, at least in part, from the activation level or levels of the first activatable element in a second cell population in a plurality of cultures comprising a plurality of discrete cell populations in communication, each derived from samples removed from a plurality of individuals having a status that is a status to be determined for the individual of step (i).

18. The method of claim 15 wherein the condition is an autoimmune condition or cancer.

19. The method of claim 1 wherein the sample is a blood sample.

20. The method of claim 19 wherein the blood sample is treated to remove certain classes of cells before being used for the culture, to create a modified sample not found in the individual.

21. The method of claim 20 wherein the modified sample not found in the individual is a peripheral blood mononuclear cell (PBMC) sample.

22. The method of claim 1 wherein the activatable element is an activatable element in a signaling pathway.

23. The method of claim 22 wherein the pathway is selected from the group consisting of a NFkB pathway, a PI3K/Akt pathway, a MAPK pathway, a JAK/STAT pathway, a DNA damage repair pathway, an apoptosis pathway, a PKC pathway, a cell cycle pathway, a phosphatase regulation pathway, a FLT3L signaling pathway, a TCR pathway, a BCR pathway, or a combination thereof.

24. The method of claim 23 wherein the pathway is selected from the group consisting of an NFkB pathway, a PI3K/Akt pathway, a MAPK pathway, a JAK/STAT pathway, or a combination thereof.

25. The method of claim 1 wherein the single cells of the second cell population are gated to remove unhealthy cells by applying a threshold level for an apoptosis element, wherein the apoptosis element is cleaved PARP (cPARP).

26. A method for evaluating a chemical or biological agent comprising (i) contacting a first cell from a first discrete cell population with a modulator in a first culture containing a plurality of discrete cell populations in communication, wherein the modulator interacts with the first discrete cell population in the culture but does not interact with a second discrete cell population in the culture, wherein the first discrete cell population comprises monocyte cells and the second discrete cell population comprises a T-lymphocyte cells, and the modulator comprises a toll-like receptor (TLR) activator; (ii) contacting the culture with the agent; (iii) incubating the first culture for a period of time; (iv) after the incubation, determining an activation level of a first activatable element in single cells from the second cell population, wherein the activatable element comprises P-ERK or p-AKT; and (v) evaluating the effect of the agent based at least in part on the activation level of the first activatable element determined in (iv).

27. The method of claim 26 wherein the culture has been prepared from a sample that has been removed from an individual.

28. The method of claim 26 further comprising comparing the activation level of the first activatable element with an activation level of the same element obtained in a second culture to which the agent has not been added but which is otherwise treated substantially the same as the first culture.

29. The method of claim 26 wherein either the first culture is sampled at a plurality of time periods and step (v) is performed on a sample from each of the time periods, or steps (i)-(v) are performed on a plurality of cell cultures under substantially the same conditions except the cell cultures are incubated for different periods of time.

30. The method of claim 26 further comprising determining a level of an intercellular communication messenger in single cells from a discrete cell population in the culture.

31. The method of claim 30 wherein the intercellular communication messenger is a cytokine.

32. The method of claim 31 wherein the cytokine is selected from the group consisting of IL1, IL2, IL3, IL4, IL5, IL6, IL8, IL9, IL10, IL12, IL15, IL17A, IL17F, IL21, IL23, TNFα, TNFβ, IFNα, IFNβ, and IFNγ.

33. The method of claim 26 wherein the agent comprises an agent that affects one or more intercellular communication messengers.

34. The method of claim 33 wherein the agent affects a cytokine.

35. The method of claim 34 wherein the cytokine is selected from the group consisting of IL1, IL2, IL3, IL4, IL5, IL6, IL8, IL9, IL10, IL12, IL15, IL17A, IL17F, IL21, IL23, TNFα, TNFβ, IFNα, IFNβ, and IFNγ.

36. The method of claim 26 wherein the agent is an agent that affects an intracellular pathway involved in intercellular communication.

37. The method of claim 36 wherein the agent is an inhibitor of the intracellular pathway.

38. The method of claim 36 wherein the pathway is selected from the group consisting of JAK/STAT pathway, PI3K pathway, and BCR pathway.

* * * * *